US012509671B2

(12) United States Patent
Rao et al.

(10) Patent No.: US 12,509,671 B2
(45) **Date of Patent: *Dec. 30, 2025**

(54) MANNANASE VARIANTS AND POLYNUCLEOTIDES ENCODING SAME

(71) Applicant: Novozymes A/S, Bagsvaerd (DK)

(72) Inventors: Vasudeva Prahlada Rao, Bangalore (IN); Geetha Hiremath Mendez, Bangalore (IN); Christian Isak Joergensen, Bagsvaerd (DK); Akshatha Venugopalan, Shornur (IN); Naveen Shivanand Raikar, Davangere (IN); Silja Poulose, Bangalore (IN); Lars Olsen, Valby (DK); Allan Svendsen, Hoersholm (DK); Jonatan Ulrik Fangel, Copenhagen (DK); Subith Krishna, Bangalore (IN); Pengfei Tian, Copenhagen (DK); Rajendra Kulothungan Sainathan, Bangalore (IN)

(73) Assignee: Novozymes A/S, Bagsvaerd (DK)

( * ) Notice: Subject to any disclaimer, the term of this patent is extended or adjusted under 35 U.S.C. 154(b) by 133 days.

This patent is subject to a terminal disclaimer.

(21) Appl. No.: 17/796,518

(22) PCT Filed: Jan. 29, 2021

(86) PCT No.: PCT/EP2021/052155

§ 371 (c)(1),
(2) Date: Jul. 29, 2022

(87) PCT Pub. No.: WO2021/152123

PCT Pub. Date: Aug. 5, 2021

(65) Prior Publication Data

US 2025/0002889 A1 Jan. 2, 2025

(30) Foreign Application Priority Data

Jan. 31, 2020 (IN) ............................ 202041004432

(51) Int. Cl.

*C12N 9/24* (2006.01)
*C11D 3/386* (2006.01)

(52) U.S. Cl.

CPC ........ *C12N 9/2494* (2013.01); *C11D 3/38636* (2013.01)

(58) Field of Classification Search

None

See application file for complete search history.

(56) References Cited

FOREIGN PATENT DOCUMENTS

| | | | | |
|---|---|---|---|---|
| WO | 1999064619 A2 | 12/1999 | | |
| WO | WO-0042146 A1 * | 7/2000 | ........... | C11D 3/1273 |
| WO | 2016054176 A1 | 4/2016 | | |
| WO | 2019068713 A1 | 4/2019 | | |
| WO | 2019068715 A1 | 4/2019 | | |
| WO | 2019081515 A1 | 5/2019 | | |
| WO | 2020201403 A1 | 10/2020 | | |

OTHER PUBLICATIONS

Uniprot Accession No. A0A1R1FLI8, Apr. 2017.*
Beno, 2017, Accession No. A0A1R1FLI8_9BACL.
Cai et al, 2011, J Biosci Bioeng 112(6), 551-557.
Jorgensen et al, 2010, Appl Biochem Biotechnol 161, 318-332.
Nunes et al, 2006, J Agric Food Chem 54, 3428-3439.
Varnai et al, 2011, Bioresource Technology 102(19), 9096-9104.
Anonymous, 2017, NCBI Reference Sequence WP_083657038.

* cited by examiner

*Primary Examiner* — Richard G Hutson
(74) *Attorney, Agent, or Firm* — Elias Lambiris

(57) ABSTRACT

The present invention relates to mannanase variants. The present invention also relates to polynucleotides encoding the variants; nucleic acid constructs, vectors, and host cells comprising the polynucleotides; and detergent compositions and methods of using the variants.

17 Claims, No Drawings

Specification includes a Sequence Listing.

SEQUENCE LISTING

```
<160> NUMBER OF SEQ ID NOS: 45

<210> SEQ ID NO 1
<211> LENGTH: 491
<212> TYPE: PRT
<213> ORGANISM: Paenibacillus illinoisensis

<400> SEQUENCE: 1

Ala Ile Thr Val Pro Gly Phe Val Val Glu Pro His Thr Ser Ser Asp
1               5                   10                  15

Gln Asn Gln Ala Ile Ile Ala Thr Phe Lys Asp Ala Ser Ile Glu Gly
            20                  25                  30

Tyr Gly Ile Lys Lys Arg Asp Glu Ala Thr Ala Lys Ala Glu Asp Asp
        35                  40                  45

Leu Tyr Asp Gly Thr Gly Tyr Ile Ser Tyr Phe Phe Glu Glu Asp Glu
    50                  55                  60

Lys Ala Thr Val Gln Lys Gly Ser Ala Thr Phe Gln Val Lys Ala Pro
65                  70                  75                  80

Glu Asn Gly Leu Tyr Glu Leu Ser Leu Gly Tyr Tyr Ile Pro Glu Gly
                85                  90                  95

Asn Gly Asp Lys Ala Thr Ser Ile Gln Val Asn Gly Ser Gly Ala Gly
            100                 105                 110

Glu Leu Thr Leu Ser Ala Pro Lys Pro Gly Thr Val Arg Ala Glu Lys
        115                 120                 125

Lys Met Thr Lys Val Leu Leu Asn Ser Gly Asn Asn Ser Ile Gln Ile
    130                 135                 140

Leu Arg Gly Trp Gly Tyr Tyr Gly Ile Glu Tyr Ile Lys Leu Glu Arg
145                 150                 155                 160

Val Glu Pro Arg Ile Thr Thr Gln Lys Thr Met Met Asp Pro Leu Ser
                165                 170                 175

Asn Ser Lys Ala Ser Pro Gln Ala Lys Ala Leu Met Lys Phe Met Thr
            180                 185                 190

Asn Gln Tyr Gly Lys Lys Ile Ile Ser Gly Gln Gln Thr Leu Glu Asp
        195                 200                 205

Ala Ala Trp Ile Tyr Gln Gln Thr Gly Lys Tyr Pro Ala Leu Val Ser
    210                 215                 220

Ser Asp Leu Met Asp Tyr Ser Pro Ser Arg Val Glu Asn Gly Ser Thr
225                 230                 235                 240

Ser Asn Glu Val Glu Lys Met Met Glu Trp Tyr Lys Arg Gly Gly Ile
                245                 250                 255

Val Ser Leu Ser Trp His Trp Asn Ala Pro Lys Gly Ile Gly Ser Asn
            260                 265                 270

Glu Pro Gly His Glu Trp Trp Arg Gly Phe Asn Thr Glu Phe Thr Thr
        275                 280                 285

Phe Asp Val Glu Tyr Ala Leu Asn His Pro Glu Ser Glu Asp Tyr Lys
    290                 295                 300

Leu Leu Ile Arg Asp Ile Asp Ala Ile Ala Thr Gln Leu Lys Arg Leu
305                 310                 315                 320

Gln Glu His His Ile Pro Val Leu Trp Arg Pro Leu His Glu Ala Glu
```

```
                325                 330                 335

Gly Gly Trp Phe Trp Trp Gly Ala Lys Gly Pro Glu Pro Ala Lys Lys
            340                 345                 350

Leu Tyr Arg Leu Met Tyr Glu Arg Leu Thr Glu Lys His Gly Leu Asn
        355                 360                 365

Asn Leu Ile Trp Val Trp Asn Ser Val Lys Glu Glu Trp Tyr Pro Gly
    370                 375                 380

Asp Asp Val Val Asp Met Val Ser Val Asp Ile Tyr Asn Pro Pro Gly
385                 390                 395                 400

Asp Tyr Ser Pro Asn Ile Ala Lys Tyr Asp Glu Leu Leu Phe Leu Ser
                405                 410                 415

Lys His Lys Lys Leu Val Ala Leu Ala Glu Asn Gly Pro Ile Pro Asp
            420                 425                 430

Pro Asp Leu Leu Gln Thr Tyr Gly Ala His Trp Ser Tyr Phe Asn Thr
        435                 440                 445

Trp Thr Gly Asp Val Leu Arg Asp Gly Lys Thr Asn Thr Lys Glu His
    450                 455                 460

Leu Lys Lys Val Tyr Asn His Asp Asn Val Ile Thr Leu Asp Glu Leu
465                 470                 475                 480

Pro Lys Gly Leu Tyr Asp Ser Pro Arg Trp Lys
                485                 490


<210> SEQ ID NO 2
<211> LENGTH: 491
<212> TYPE: PRT
<213> ORGANISM: Paenibacillus illinoisensis

<400> SEQUENCE: 2

Ala Ile Thr Val Pro Gly Phe Val Val Glu Pro His Thr Ser Ser Asp
1               5                   10                  15

Gln Asn Gln Ala Ile Ile Ala Thr Phe Lys Asp Ala Ser Ile Glu Gly
            20                  25                  30

Tyr Gly Ile Lys Lys Arg Asp Glu Ala Thr Ala Lys Ala Glu Asp Asp
        35                  40                  45

Leu Tyr Asp Gly Thr Gly Tyr Ile Ser Tyr Phe Phe Glu Glu Asp Glu
    50                  55                  60

Lys Ala Thr Val Gln Lys Gly Ser Ala Thr Phe Gln Val Lys Ala Pro
65                  70                  75                  80

Glu Asn Gly Leu Tyr Glu Leu Ser Leu Gly Tyr Tyr Ile Pro Glu Gly
                85                  90                  95

Asn Gly Asp Lys Ala Thr Ser Ile Gln Val Asn Gly Ser Gly Ala Gly
            100                 105                 110

Glu Leu Thr Leu Ser Ala Pro Lys Pro Gly Thr Val Arg Ala Glu Lys
        115                 120                 125

Lys Met Thr Lys Val Leu Leu Asn Ser Gly Asn Asn Ser Ile Gln Ile
    130                 135                 140

Leu Arg Gly Trp Gly Tyr Tyr Gly Ile Glu Tyr Ile Lys Leu Glu Arg
145                 150                 155                 160

Val Glu Pro Arg Ile Thr Thr Asp Lys Thr Met Met Asp Pro Leu Ser
                165                 170                 175

Asn Ser Lys Ala Ser Pro Gln Ala Lys Ala Leu Met Lys Phe Met Thr
            180                 185                 190

Asn Gln Tyr Gly Lys Lys Ile Ile Ser Gly Gln Gln Thr Leu Glu Asp
        195                 200                 205
```

```
Ala Ala Trp Ile Tyr Gln Gln Thr Gly Lys Tyr Pro Ala Leu Val Ser
    210                 215                 220

Ser Asp Leu Met Asp Tyr Ser Pro Ser Arg Val Glu Asn Gly Ser Thr
225                 230                 235                 240

Ser Asn Glu Val Glu Lys Met Met Glu Trp Tyr Lys Arg Gly Gly Ile
                245                 250                 255

Val Ser Leu Ser Trp His Trp Asn Ala Pro Lys Gly Ile Gly Ser Asn
            260                 265                 270

Glu Pro Gly His Glu Trp Trp Arg Gly Phe Asn Thr Glu Phe Thr Thr
        275                 280                 285

Phe Asp Val Glu Tyr Ala Leu Asn His Pro Glu Ser Glu Asp Tyr Lys
    290                 295                 300

Leu Leu Ile Arg Asp Ile Asp Ala Ile Ala Thr Gln Leu Lys Arg Leu
305                 310                 315                 320

Gln Glu His His Ile Pro Val Leu Trp Arg Pro Leu His Glu Ala Glu
                325                 330                 335

Gly Gly Trp Phe Trp Trp Gly Ala Lys Gly Pro Glu Pro Ala Lys Lys
            340                 345                 350

Leu Tyr Arg Leu Met Tyr Glu Arg Leu Thr Glu Lys His Gly Leu Asn
        355                 360                 365

Asn Leu Ile Trp Val Trp Asn Ser Val Lys Glu Glu Trp Tyr Pro Gly
    370                 375                 380

Asp Asp Val Val Asp Met Val Ser Val Asp Ile Tyr Asn Pro Pro Gly
385                 390                 395                 400

Asp Tyr Ser Pro Asn Ile Ala Lys Tyr Asp Glu Leu Leu Phe Leu Ser
                405                 410                 415

Lys His Lys Lys Leu Val Ala Leu Ala Glu Asn Gly Pro Ile Pro Asp
            420                 425                 430

Pro Asp Leu Leu Gln Thr Tyr Gly Ala His Trp Ser Tyr Phe Asn Thr
        435                 440                 445

Trp Thr Gly Asp Val Leu Arg Asp Gly Lys Thr Asn Thr Lys Glu His
    450                 455                 460

Leu Lys Lys Val Tyr Asn His Asp Asn Val Ile Thr Leu Asp Glu Leu
465                 470                 475                 480

Pro Lys Gly Leu Tyr Asp Ser Pro Arg Trp Lys
                485                 490


<210> SEQ ID NO 3
<211> LENGTH: 312
<212> TYPE: PRT
<213> ORGANISM: Paenibacillus illinoisensis

<400> SEQUENCE: 3

Ala Ser Pro Gln Ala Lys Ala Leu Met Lys Phe Met Thr Asn Gln Tyr
1               5                   10                  15

Gly Lys Lys Ile Ile Ser Gly Gln Gln Thr Leu Glu Asp Ala Ala Trp
            20                  25                  30

Ile Tyr Gln Gln Thr Gly Lys Tyr Pro Ala Leu Val Ser Ser Asp Leu
        35                  40                  45

Met Asp Tyr Ser Pro Ser Arg Val Glu Asn Gly Ser Thr Ser Asn Glu
    50                  55                  60

Val Glu Lys Met Met Glu Trp Tyr Lys Arg Gly Gly Ile Val Ser Leu
65                  70                  75                  80

Ser Trp His Trp Asn Ala Pro Lys Gly Ile Gly Ser Asn Glu Pro Gly
                85                  90                  95
```

His Glu Trp Trp Arg Gly Phe Asn Thr Glu Phe Thr Thr Phe Asp Val
100 105 110

Glu Tyr Ala Leu Asn His Pro Glu Ser Glu Asp Tyr Lys Leu Leu Ile
115 120 125

Arg Asp Ile Asp Ala Ile Ala Thr Gln Leu Lys Arg Leu Gln Glu His
130 135 140

His Ile Pro Val Leu Trp Arg Pro Leu His Glu Ala Glu Gly Gly Trp
145 150 155 160

Phe Trp Trp Gly Ala Lys Gly Pro Glu Pro Ala Lys Lys Leu Tyr Arg
165 170 175

Leu Met Tyr Glu Arg Leu Thr Glu Lys His Gly Leu Asn Asn Leu Ile
180 185 190

Trp Val Trp Asn Ser Val Lys Glu Glu Trp Tyr Pro Gly Asp Asp Val
195 200 205

Val Asp Met Val Ser Val Asp Ile Tyr Asn Pro Pro Gly Asp Tyr Ser
210 215 220

Pro Asn Ile Ala Lys Tyr Asp Glu Leu Leu Phe Leu Ser Lys His Lys
225 230 235 240

Lys Leu Val Ala Leu Ala Glu Asn Gly Pro Ile Pro Asp Pro Asp Leu
245 250 255

Leu Gln Thr Tyr Gly Ala His Trp Ser Tyr Phe Asn Thr Trp Thr Gly
260 265 270

Asp Val Leu Arg Asp Gly Lys Thr Asn Thr Lys Glu His Leu Lys Lys
275 280 285

Val Tyr Asn His Asp Asn Val Ile Thr Leu Asp Glu Leu Pro Lys Gly
290 295 300

Leu Tyr Asp Ser Pro Arg Trp Lys
305 310

<210> SEQ ID NO 4
<211> LENGTH: 342
<212> TYPE: PRT
<213> ORGANISM: Paenibacillus illinoisensis

<400> SEQUENCE: 4

Ala Ile Thr Val Pro Gly Phe Val Val Glu Arg Val Glu Pro Arg Ile
1 5 10 15

Pro Thr Asp Lys Thr Met Met Asp Pro Leu Ser Asn Ser Lys Ala Ser
20 25 30

Pro Gln Thr Lys Ala Leu Met Lys Phe Met Thr Asn Gln Tyr Gly Asp
35 40 45

Lys Ile Ile Ser Gly Gln Gln Thr Leu Glu Asp Ala Ala Trp Ile Tyr
50 55 60

Gln Gln Thr Gly Lys Tyr Pro Ala Leu Val Ser Ser Asp Leu Met Asp
65 70 75 80

Tyr Ser Pro Ser Arg Val Glu Asn Gly Ser Thr Ser Asn Glu Val Glu
85 90 95

Lys Met Ile Glu Trp Tyr Lys Arg Gly Gly Ile Val Ser Leu Ser Trp
100 105 110

His Trp Asn Ala Pro Lys Gly Ile Gly Gly Asn Glu Pro Gly His Glu
115 120 125

Trp Trp Arg Gly Phe Tyr Thr Glu Phe Thr Thr Phe Asp Val Glu Tyr
130 135 140

Ala Leu Asn His Pro Glu Ser Glu Asp Tyr Lys Leu Leu Ile Arg Asp

```
145                 150                 155                 160

Ile Asp Ala Ile Ala Thr Gln Leu Lys Arg Leu Gln Glu His His Ile
                165                 170                 175

Pro Val Leu Trp Arg Pro Leu His Glu Ala Glu Gly Gly Trp Phe Trp
            180                 185                 190

Trp Gly Ala Lys Gly Pro Glu Pro Ala Lys Lys Leu Tyr Arg Leu Met
        195                 200                 205

Tyr Glu Arg Leu Thr Glu Lys His Gly Leu Asn Asn Leu Ile Trp Val
    210                 215                 220

Trp Asn Ser Val Lys Glu Glu Trp Tyr Pro Gly Ala Asp Val Val Asp
225                 230                 235                 240

Met Val Ser Val Asp Ile Tyr Asn Pro Pro Gly Asp Tyr Ser Pro Asn
                245                 250                 255

Ile Ala Met Tyr Met Glu Leu Thr Phe Leu Ser Lys His Lys Lys Leu
            260                 265                 270

Val Ala Leu Ala Glu Asn Gly Pro Ile Pro Asp Pro Asp Leu Leu Gln
        275                 280                 285

Thr Tyr Gly Ala His Trp Ser Tyr Phe Asn Thr Trp Thr Gly Asp Val
    290                 295                 300

Leu Arg Asp Gly Lys Thr Asn Thr Lys Glu His Leu Lys Lys Val Tyr
305                 310                 315                 320

Asn His Asp Asn Val Ile Thr Leu Asp Glu Leu Pro Lys Gly Leu Tyr
                325                 330                 335

Asp Ser Pro Arg Trp Lys
            340


<210> SEQ ID NO 5
<211> LENGTH: 583
<212> TYPE: PRT
<213> ORGANISM: Bacillus sp

<400> SEQUENCE: 5

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175
```

```
Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
        515                 520                 525

Pro Thr Trp Lys Ala Thr Ile Ala Leu Pro Gln Gly Lys Ala Ile Glu
    530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580
```

<210> SEQ ID NO 6
<211> LENGTH: 484
<212> TYPE: PRT
<213> ORGANISM: Bacillus species

<400> SEQUENCE: 6

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380
```

```
Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys


<210> SEQ ID NO 7
<211> LENGTH: 485
<212> TYPE: PRT
<213> ORGANISM: Cytophaga species

<400> SEQUENCE: 7

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270
```

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
                485

<210> SEQ ID NO 8
<211> LENGTH: 485
<212> TYPE: PRT
<213> ORGANISM: Bacillus species

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

```
His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485


<210> SEQ ID NO 9
<211> LENGTH: 485
<212> TYPE: PRT
<213> ORGANISM: Bacillus species

<400> SEQUENCE: 9

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
```

```
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460
```

Asn Ala Asp Gly Trp Ala Asn Phe Ser Val Asn Gly Gly Ser Val Ser
465 470 475 480

Ile Trp Val Lys Arg
485

<210> SEQ ID NO 10
<211> LENGTH: 485
<212> TYPE: PRT
<213> ORGANISM: Bacillus species

<400> SEQUENCE: 10

His His Asn Gly Thr Asn Gly Thr Met Met Gln Tyr Phe Glu Trp Tyr
1 5 10 15

Leu Pro Asn Asp Gly Asn His Trp Asn Arg Leu Arg Ser Asp Ala Ser
20 25 30

Asn Leu Lys Asp Lys Gly Ile Ser Ala Val Trp Ile Pro Pro Ala Trp
35 40 45

Lys Gly Ala Ser Gln Asn Asp Val Gly Tyr Gly Ala Tyr Asp Leu Tyr
50 55 60

Asp Leu Gly Glu Phe Asn Gln Lys Gly Thr Ile Arg Thr Lys Tyr Gly
65 70 75 80

Thr Arg Asn Gln Leu Gln Ala Ala Val Asn Ala Leu Lys Ser Asn Gly
85 90 95

Ile Gln Val Tyr Gly Asp Val Val Met Asn His Lys Gly Gly Ala Asp
100 105 110

Ala Thr Glu Met Val Arg Ala Val Glu Val Asn Pro Asn Asn Arg Asn
115 120 125

Gln Glu Val Ser Gly Glu Tyr Thr Ile Glu Ala Trp Thr Lys Phe Asp
130 135 140

Phe Pro Gly Arg Gly Asn Thr His Ser Asn Phe Lys Trp Arg Trp Tyr
145 150 155 160

His Phe Asp Gly Val Asp Trp Asp Gln Ser Arg Lys Leu Asn Asn Arg
165 170 175

Ile Tyr Lys Phe Arg Gly Asp Gly Lys Gly Trp Asp Trp Glu Val Asp
180 185 190

Thr Glu Asn Gly Asn Tyr Asp Tyr Leu Met Tyr Ala Asp Ile Asp Met
195 200 205

Asp His Pro Glu Val Val Asn Glu Leu Arg Asn Trp Gly Val Trp Tyr
210 215 220

Thr Asn Thr Leu Gly Leu Asp Gly Phe Arg Ile Asp Ala Val Lys His
225 230 235 240

Ile Lys Tyr Ser Phe Thr Arg Asp Trp Ile Asn His Val Arg Ser Ala
245 250 255

Thr Gly Lys Asn Met Phe Ala Val Ala Glu Phe Trp Lys Asn Asp Leu
260 265 270

Gly Ala Ile Glu Asn Tyr Leu Asn Lys Thr Asn Trp Asn His Ser Val
275 280 285

Phe Asp Val Pro Leu His Tyr Asn Leu Tyr Asn Ala Ser Lys Ser Gly
290 295 300

Gly Asn Tyr Asp Met Arg Gln Ile Phe Asn Gly Thr Val Val Gln Arg
305 310 315 320

His Pro Met His Ala Val Thr Phe Val Asp Asn His Asp Ser Gln Pro
325 330 335

Glu Glu Ala Leu Glu Ser Phe Val Glu Glu Trp Phe Lys Pro Leu Ala

```
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485


<210> SEQ ID NO 11
<211> LENGTH: 485
<212> TYPE: PRT
<213> ORGANISM: Bacillus species

<400> SEQUENCE: 11

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220
```

```
Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Met Thr Gly Asn Arg Ser Gly Thr Val Thr Ile
    450                 455                 460

Asn Gln Asp Gly Trp Gly His Phe Phe Val Asn Gly Gly Ser Val Ser
465                 470                 475                 480

Val Trp Val Lys Arg
                485


<210> SEQ ID NO 12
<211> LENGTH: 485
<212> TYPE: PRT
<213> ORGANISM: Bacillus species

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110
```

```
Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Pro
385                 390                 395                 400

Gln His Asp Tyr Ile Asp His Pro Asp Val Ile Gly Trp Thr Arg Glu
                405                 410                 415

Gly Asp Ser Ser Ala Ala Lys Ser Gly Leu Ala Ala Leu Ile Thr Asp
            420                 425                 430

Gly Pro Gly Gly Ser Lys Arg Met Tyr Ala Gly Leu Lys Asn Ala Gly
        435                 440                 445

Glu Thr Trp Tyr Asp Ile Thr Gly Asn Arg Ser Asp Thr Val Lys Ile
    450                 455                 460

Gly Ser Asp Gly Trp Gly Glu Phe His Val Asn Asp Gly Ser Val Ser
465                 470                 475                 480

Ile Tyr Val Gln Lys
                485
```

<210> SEQ ID NO 13
<211> LENGTH: 485
<212> TYPE: PRT
<213> ORGANISM: Synthetic Construct

<400> SEQUENCE: 13

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Thr
385                 390                 395                 400

Gln His Asp Tyr Leu Asp Asn Gln Asp Val Ile Gly Trp Thr Arg Glu
                405                 410                 415

Gly Asp Ser Ala His Ala Gly Ser Gly Leu Ala Thr Val Met Ser Asp
420 425 430

Gly Pro Gly Gly Ser Lys Thr Met Tyr Val Gly Thr Ala His Ala Gly
435 440 445

Gln Val Phe Lys Asp Ile Thr Gly Asn Arg Thr Asp Thr Val Thr Ile
450 455 460

Asn Ser Ala Gly Asn Gly Thr Phe Pro Cys Asn Gly Gly Ser Val Ser
465 470 475 480

Ile Trp Val Lys Gln
485

<210> SEQ ID NO 14
<211> LENGTH: 269
<212> TYPE: PRT
<213> ORGANISM: Bacillus lentus

<400> SEQUENCE: 14

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 15
<211> LENGTH: 275
<212> TYPE: PRT

<213> ORGANISM: Bacillus amyloliquefaciens

<400> SEQUENCE: 15

Ala Gln Ser Val Pro Tyr Gly Val Ser Gln Ile Lys Ala Pro Ala Leu
1 5 10 15

His Ser Gln Gly Tyr Thr Gly Ser Asn Val Lys Val Ala Val Ile Asp
20 25 30

Ser Gly Ile Asp Ser Ser His Pro Asp Leu Lys Val Ala Gly Gly Ala
35 40 45

Ser Met Val Pro Ser Glu Thr Asn Pro Phe Gln Asp Asn Asn Ser His
50 55 60

Gly Thr His Val Ala Gly Thr Val Ala Ala Leu Asn Asn Ser Ile Gly
65 70 75 80

Val Leu Gly Val Ala Pro Ser Ala Ser Leu Tyr Ala Val Lys Val Leu
85 90 95

Gly Ala Asp Gly Ser Gly Gln Tyr Ser Trp Ile Ile Asn Gly Ile Glu
100 105 110

Trp Ala Ile Ala Asn Asn Met Asp Val Ile Asn Met Ser Leu Gly Gly
115 120 125

Pro Ser Gly Ser Ala Ala Leu Lys Ala Ala Val Asp Lys Ala Val Ala
130 135 140

Ser Gly Val Val Val Val Ala Ala Ala Gly Asn Glu Gly Thr Ser Gly
145 150 155 160

Ser Ser Ser Thr Val Gly Tyr Pro Gly Lys Tyr Pro Ser Val Ile Ala
165 170 175

Val Gly Ala Val Asp Ser Ser Asn Gln Arg Ala Ser Phe Ser Ser Val
180 185 190

Gly Pro Glu Leu Asp Val Met Ala Pro Gly Val Ser Ile Gln Ser Thr
195 200 205

Leu Pro Gly Asn Lys Tyr Gly Ala Tyr Asn Gly Thr Ser Met Ala Ser
210 215 220

Pro His Val Ala Gly Ala Ala Ala Leu Ile Leu Ser Lys His Pro Asn
225 230 235 240

Trp Thr Asn Thr Gln Val Arg Ser Ser Leu Glu Asn Thr Thr Thr Lys
245 250 255

Leu Gly Asp Ser Phe Tyr Tyr Gly Lys Gly Leu Ile Asn Val Gln Ala
260 265 270

Ala Ala Gln
275

<210> SEQ ID NO 16
<211> LENGTH: 311
<212> TYPE: PRT
<213> ORGANISM: Bacillus species

<400> SEQUENCE: 16

Ala Val Pro Ser Thr Gln Thr Pro Trp Gly Ile Lys Ser Ile Tyr Asn
1 5 10 15

Asp Gln Ser Ile Thr Lys Thr Thr Gly Gly Ser Gly Ile Lys Val Ala
20 25 30

Val Leu Asp Thr Gly Val Tyr Thr Ser His Leu Asp Leu Ala Gly Ser
35 40 45

Ala Glu Gln Cys Lys Asp Phe Thr Gln Ser Asn Pro Leu Val Asp Gly
50 55 60

Ser Cys Thr Asp Arg Gln Gly His Gly Thr His Val Ala Gly Thr Val

```
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
    290                 295                 300

Phe Gly Tyr Pro Arg Val Lys
305                 310


<210> SEQ ID NO 17
<211> LENGTH: 269
<212> TYPE: PRT
<213> ORGANISM: Bacillus gibsonii

<400> SEQUENCE: 17

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125
```

```
Pro Ser Ile Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 18
<211> LENGTH: 269
<212> TYPE: PRT
<213> ORGANISM: Bacillus lentus

<400> SEQUENCE: 18

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240
```

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 19
<211> LENGTH: 274
<212> TYPE: PRT
<213> ORGANISM: Bacillus licheniformis

<400> SEQUENCE: 19

Ala Gln Thr Val Pro Tyr Gly Ile Pro Leu Ile Lys Ala Asp Lys Val
1 5 10 15

Gln Ala Gln Gly Phe Lys Gly Ala Asn Val Lys Val Ala Val Leu Asp
20 25 30

Thr Gly Ile Gln Ala Ser His Pro Asp Leu Asn Val Val Gly Gly Ala
35 40 45

Ser Phe Val Ala Gly Glu Ala Tyr Asn Thr Asp Gly Asn Gly His Gly
50 55 60

Thr His Val Ala Gly Thr Val Ala Ala Leu Asp Asn Thr Thr Gly Val
65 70 75 80

Leu Gly Val Ala Pro Ser Val Ser Leu Tyr Ala Val Lys Val Leu Asn
85 90 95

Ser Ser Gly Ser Gly Ser Tyr Ser Gly Ile Val Ser Gly Ile Glu Trp
100 105 110

Ala Thr Thr Asn Gly Met Asp Val Ile Asn Met Ser Leu Gly Gly Ala
115 120 125

Ser Gly Ser Thr Ala Met Lys Gln Ala Val Asp Asn Ala Tyr Ala Arg
130 135 140

Gly Val Val Val Val Ala Ala Ala Gly Asn Ser Gly Ser Ser Gly Asn
145 150 155 160

Thr Asn Thr Ile Gly Tyr Pro Ala Lys Tyr Asp Ser Val Ile Ala Val
165 170 175

Gly Ala Val Asp Ser Asn Ser Asn Arg Ala Ser Phe Ser Ser Val Gly
180 185 190

Ala Glu Leu Glu Val Met Ala Pro Gly Ala Gly Val Tyr Ser Thr Tyr
195 200 205

Pro Thr Asn Thr Tyr Ala Thr Leu Asn Gly Thr Ser Met Ala Ser Pro
210 215 220

His Val Ala Gly Ala Ala Ala Leu Ile Leu Ser Lys His Pro Asn Leu
225 230 235 240

Ser Ala Ser Gln Val Arg Asn Arg Leu Ser Ser Thr Ala Thr Tyr Leu
245 250 255

Gly Ser Ser Phe Tyr Tyr Gly Lys Gly Leu Ile Asn Val Glu Ala Ala
260 265 270

Ala Gln

<210> SEQ ID NO 20
<211> LENGTH: 773
<212> TYPE: PRT
<213> ORGANISM: Bacillus species

<400> SEQUENCE: 20

Ala Glu Gly Asn Thr Arg Glu Asp Asn Phe Lys His Leu Leu Gly Asn
1 5 10 15

-continued

```
Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
    370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
            420                 425                 430

Asp Gly Trp Gly Lys Ser Val Asp Ile Leu Gly Ala Glu Lys Leu Thr
```

```
        435                 440                 445

Met Asp Val Ile Val Asp Glu Pro Thr Thr Val Ala Ile Ala Ala Ile
    450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
    530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Glu
    770


<210> SEQ ID NO 21
<211> LENGTH: 435
<212> TYPE: PRT
<213> ORGANISM: Humicola insolens

<400> SEQUENCE: 21

Met Ala Arg Gly Thr Ala Leu Leu Gly Leu Thr Ala Leu Leu Leu Gly
1               5                   10                  15

Leu Val Asn Gly Gln Lys Pro Gly Glu Thr Lys Glu Val His Pro Gln
            20                  25                  30
```

```
Leu Thr Thr Phe Arg Cys Thr Lys Arg Gly Gly Cys Lys Pro Ala Thr
        35                  40                  45

Asn Phe Ile Val Leu Asp Ser Leu Ser His Pro Ile His Arg Ala Glu
    50                  55                  60

Gly Leu Gly Pro Gly Gly Cys Gly Asp Trp Gly Asn Pro Pro Pro Lys
65                  70                  75                  80

Asp Val Cys Pro Asp Val Glu Ser Cys Ala Lys Asn Cys Ile Met Glu
                85                  90                  95

Gly Ile Pro Asp Tyr Ser Gln Tyr Gly Val Thr Thr Asn Gly Thr Ser
            100                 105                 110

Leu Arg Leu Gln His Ile Leu Pro Asp Gly Arg Val Pro Ser Pro Arg
        115                 120                 125

Val Tyr Leu Leu Asp Lys Thr Lys Arg Arg Tyr Glu Met Leu His Leu
    130                 135                 140

Thr Gly Phe Glu Phe Thr Phe Asp Val Asp Ala Thr Lys Leu Pro Cys
145                 150                 155                 160

Gly Met Asn Ser Ala Leu Tyr Leu Ser Glu Met His Pro Thr Gly Ala
                165                 170                 175

Lys Ser Lys Tyr Asn Pro Gly Gly Ala Tyr Tyr Gly Thr Gly Tyr Cys
            180                 185                 190

Asp Ala Gln Cys Phe Val Thr Pro Phe Ile Asn Gly Leu Gly Asn Ile
        195                 200                 205

Glu Gly Lys Gly Ser Cys Cys Asn Glu Met Asp Ile Trp Glu Ala Asn
    210                 215                 220

Ser Arg Ala Ser His Val Ala Pro His Thr Cys Asn Lys Lys Gly Leu
225                 230                 235                 240

Tyr Leu Cys Glu Gly Glu Glu Cys Ala Phe Glu Gly Val Cys Asp Lys
                245                 250                 255

Asn Gly Cys Gly Trp Asn Asn Tyr Arg Val Asn Val Thr Asp Tyr Tyr
            260                 265                 270

Gly Arg Gly Glu Glu Phe Lys Val Asn Thr Leu Lys Pro Phe Thr Val
        275                 280                 285

Val Thr Gln Phe Leu Ala Asn Arg Arg Gly Lys Leu Glu Lys Ile His
    290                 295                 300

Arg Phe Tyr Val Gln Asp Gly Lys Val Ile Glu Ser Phe Tyr Thr Asn
305                 310                 315                 320

Lys Glu Gly Val Pro Tyr Thr Asn Met Ile Asp Asp Glu Phe Cys Glu
                325                 330                 335

Ala Thr Gly Ser Arg Lys Tyr Met Glu Leu Gly Ala Thr Gln Gly Met
            340                 345                 350

Gly Glu Ala Leu Thr Arg Gly Met Val Leu Ala Met Ser Ile Trp Trp
        355                 360                 365

Asp Gln Gly Gly Asn Met Glu Trp Leu Asp His Gly Glu Ala Gly Pro
    370                 375                 380

Cys Ala Lys Gly Glu Gly Ala Pro Ser Asn Ile Val Gln Val Glu Pro
385                 390                 395                 400

Phe Pro Glu Val Thr Tyr Thr Asn Leu Arg Trp Gly Glu Ile Gly Ser
                405                 410                 415

Thr Tyr Gln Glu Val Gln Lys Pro Lys Pro Lys Pro Gly His Gly Pro
            420                 425                 430

Arg Ser Asp
        435
```

<210> SEQ ID NO 22
<211> LENGTH: 305
<212> TYPE: PRT
<213> ORGANISM: Humicola insolens

<400> SEQUENCE: 22

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 23
<211> LENGTH: 299
<212> TYPE: PRT
<213> ORGANISM: Thielavia terrestris

<400> SEQUENCE: 23

```
Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
```

```
            20                  25                  30

Asp Cys Cys Lys Pro Ser Cys Ala Trp Pro Gly Lys Ala Ala Val Ser
        35                  40                  45

Gln Pro Val Tyr Ala Cys Asp Ala Asn Phe Gln Arg Leu Ser Asp Phe
    50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
    130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
    210                 215                 220

Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
        275                 280                 285

Gln Lys Leu Asn Asp Tyr Tyr Ser Gln Cys Leu
    290                 295


<210> SEQ ID NO 24
<211> LENGTH: 524
<212> TYPE: PRT
<213> ORGANISM: Paenibacillus polymyxa

<400> SEQUENCE: 24

Val Val His Gly Gln Thr Ala Lys Thr Ile Thr Ile Lys Val Asp Thr
1               5                   10                  15

Phe Lys Asp Arg Lys Pro Ile Ser Pro Tyr Ile Tyr Gly Thr Asn Gln
            20                  25                  30

Asp Leu Ala Gly Asp Glu Asn Met Ala Ala Arg Arg Leu Gly Gly Asn
        35                  40                  45

Arg Met Thr Gly Tyr Asn Trp Glu Asn Asn Met Ser Asn Ala Gly Ser
    50                  55                  60

Asp Trp Gln His Ser Ser Asp Asn Tyr Leu Cys Ser Asn Gly Gly Leu
65                  70                  75                  80

Thr Gln Ala Glu Cys Glu Lys Pro Gly Ala Val Val Thr Ser Phe His
                85                  90                  95
```

```
Asp Gln Ser Leu Lys Leu Gly Thr Tyr Ser Leu Val Thr Leu Pro Met
            100                 105                 110

Ala Gly Tyr Val Ala Ala Asp Gly Asn Gly Ser Val Gln Glu Ser Glu
        115                 120                 125

Ala Ala Pro Ser Ala Arg Trp Asn Gln Val Val Asn Ala Lys Asn Ala
    130                 135                 140

Pro Phe Gln Leu Gln Pro Asp Leu Asn Asp Asn Tyr Val Tyr Val Asp
145                 150                 155                 160

Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Pro Glu Lys Val Gly Ala Lys Glu Leu
        195                 200                 205

Val Asp Arg Ser Val Ser Leu Ser Lys Ala Val Lys Ala Ile Asp Ala
    210                 215                 220

Gly Ala Glu Val Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Ser Gln Val
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
    290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Phe Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
        355                 360                 365

Gly Gly Ile Ala Met Thr Asp Val Leu Gly Ile Leu Gly Lys Asn Asp
    370                 375                 380

Val Tyr Met Ala Asn Tyr Trp Lys Leu Lys Asp Gly Val Asn Asn Tyr
385                 390                 395                 400

Val Ser Ala Ala Tyr Lys Leu Tyr Arg Asn Tyr Asp Gly Lys Asn Ser
                405                 410                 415

Thr Phe Gly Asp Thr Ser Val Ser Ala Gln Thr Ser Asp Ile Val Asn
            420                 425                 430

Ser Ser Val His Ala Ser Val Thr Asn Ala Ser Asp Lys Glu Leu His
        435                 440                 445

Leu Val Val Met Asn Lys Ser Met Asp Ser Ala Phe Asp Ala Gln Phe
    450                 455                 460

Asp Leu Ser Gly Ala Lys Thr Tyr Ile Ser Gly Lys Val Trp Gly Phe
465                 470                 475                 480

Asp Lys Asn Ser Ser Gln Ile Lys Glu Ala Ala Pro Ile Thr Gln Ile
                485                 490                 495

Ser Gly Asn Arg Phe Thr Tyr Thr Val Pro Pro Leu Thr Ala Tyr His
            500                 505                 510

Ile Val Leu Thr Thr Gly Asn Asp Thr Ser Pro Val
```

515 520

<210> SEQ ID NO 25
<211> LENGTH: 214
<212> TYPE: PRT
<213> ORGANISM: Melanocarpus albomyces

<400> SEQUENCE: 25

Ala Asn Gly Gln Ser Thr Arg Tyr Trp Asp Cys Cys Lys Pro Ser Cys
1 5 10 15

Gly Trp Arg Gly Lys Gly Pro Val Asn Gln Pro Val Tyr Ser Cys Asp
20 25 30

Ala Asn Phe Gln Arg Ile His Asp Phe Asp Ala Val Ser Gly Cys Glu
35 40 45

Gly Gly Pro Ala Phe Ser Cys Ala Asp His Ser Pro Trp Ala Ile Asn
50 55 60

Asp Asn Leu Ser Tyr Gly Phe Ala Ala Thr Ala Leu Ser Gly Gln Thr
65 70 75 80

Glu Glu Ser Trp Cys Cys Ala Cys Tyr Ala Leu Thr Phe Thr Ser Gly
85 90 95

Pro Val Ala Gly Lys Thr Met Val Val Gln Ser Thr Ser Thr Gly Gly
100 105 110

Asp Leu Gly Ser Asn His Phe Asp Leu Asn Ile Pro Gly Gly Gly Val
115 120 125

Gly Leu Phe Asp Gly Cys Thr Pro Gln Phe Gly Gly Leu Pro Gly Ala
130 135 140

Arg Tyr Gly Gly Ile Ser Ser Arg Gln Glu Cys Asp Ser Phe Pro Glu
145 150 155 160

Pro Leu Lys Pro Gly Cys Gln Trp Arg Phe Asp Trp Phe Gln Asn Ala
165 170 175

Asp Asn Pro Ser Phe Thr Phe Glu Arg Val Gln Cys Pro Glu Glu Leu
180 185 190

Val Ala Arg Thr Gly Cys Arg Arg His Asp Asp Gly Gly Phe Ala Val
195 200 205

Phe Lys Ala Pro Ser Ala
210

<210> SEQ ID NO 26
<211> LENGTH: 269
<212> TYPE: PRT
<213> ORGANISM: Thermomyces lanuginosus

<400> SEQUENCE: 26

Glu Val Ser Gln Asp Leu Phe Asn Gln Phe Asn Leu Phe Ala Gln Tyr
1 5 10 15

Ser Ala Ala Ala Tyr Cys Gly Lys Asn Asn Asp Ala Pro Ala Gly Thr
20 25 30

Asn Ile Thr Cys Thr Gly Asn Ala Cys Pro Glu Val Glu Lys Ala Asp
35 40 45

Ala Thr Phe Leu Tyr Ser Phe Glu Asp Ser Gly Val Gly Asp Val Thr
50 55 60

Gly Phe Leu Ala Leu Asp Asn Thr Asn Lys Leu Ile Val Leu Ser Phe
65 70 75 80

Arg Gly Ser Arg Ser Ile Glu Asn Trp Ile Gly Asn Leu Asn Phe Asp
85 90 95

Leu Lys Glu Ile Asn Asp Ile Cys Ser Gly Cys Arg Gly His Asp Gly

```
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 27
<211> LENGTH: 222
<212> TYPE: PRT
<213> ORGANISM: Bacillus agaradhaerens

<400> SEQUENCE: 27

```
His Asn Pro Val Thr Asp Glu Glu Val Tyr His Ser Phe Asn Ser His
1               5                   10                  15

Asp Trp Gln Asn Trp Asn Met Ser Asp Gly Trp Lys Asn Asp Asp Tyr
            20                  25                  30

Phe Phe Gly Cys His Trp Ser Gln Asn Arg Val Asn Phe Tyr Gly Gly
        35                  40                  45

Gln Met Glu Leu Ser Leu Arg Thr Asn Tyr Ser Tyr Ala Pro Pro Tyr
    50                  55                  60

Asn Tyr Glu Cys Ala Glu Tyr Thr Thr Asn Asn Phe Tyr Gly Tyr Gly
65                  70                  75                  80

Leu Tyr Glu Val Ser Met Lys Pro Ala Lys Val Ser Gly Val Ile Ser
                85                  90                  95

Ser Phe Phe Thr Tyr Thr Gly Pro Ser Tyr Asn Gly Ala Pro Trp Asp
            100                 105                 110

Glu Ile Asp Ile Glu Phe Leu Gly Asn Asp Thr Thr Lys Val Gln Phe
        115                 120                 125

Asn Tyr Tyr Thr Asp Gly Val Gly Gly Asn Glu Ile Leu Tyr Asp Leu
    130                 135                 140

Gly Phe Asp Ala Ala Asp Ser Tyr Asn Thr Tyr Ala Phe Asp Trp Gln
145                 150                 155                 160

Glu Asn Tyr Ile Asn Trp Tyr Val Asn Gly Gln Leu Val Ala Thr Ala
                165                 170                 175

Thr Glu Asn Ile Pro Ser Asn Pro Ser Lys Ile Met Met Asn Ile Trp
            180                 185                 190

Asn Thr Tyr Gly Ile Asp Glu Trp Ala Gly Arg Tyr Tyr Gly Glu Asp
        195                 200                 205
```

```
Ala Asn Ala Ser Tyr Asn Trp Val Arg Tyr Thr Pro Asn Arg
    210                 215                 220


<210> SEQ ID NO 28
<211> LENGTH: 351
<212> TYPE: PRT
<213> ORGANISM: Bacillus species

<400> SEQUENCE: 28

Tyr Asn Pro Val Thr Glu Asp Glu Leu Tyr His Ser Phe Asp Ser His
1               5                   10                  15

Asp Ala Arg Asn Trp Gln Ile Ser Asp Gly Trp Arg Asn Gly Asp Asp
            20                  25                  30

Phe Phe Gly Cys His Trp Ser Gln Asn Arg Val Asn Phe Asn Arg Gly
        35                  40                  45

Glu Met Glu Leu Ser Leu Arg Thr Asn Tyr Ser Tyr Ser Ala Pro Tyr
    50                  55                  60

Asn Tyr Glu Cys Ala Glu Tyr Ala Thr Ser Asn Phe Tyr Gly Tyr Gly
65                  70                  75                  80

Leu Tyr Glu Val Ser Met Lys Pro Ala Asn Val Ser Gly Val Ile Ser
                85                  90                  95

Ser Phe Phe Thr Tyr Thr Gly Pro Ser Tyr Asn Gly Ala Pro Trp Asp
            100                 105                 110

Glu Ile Asp Ile Glu Phe Leu Gly Asn Asp Thr Thr Lys Val Gln Phe
        115                 120                 125

Asn Tyr Tyr Thr Asn Gly Val Gly Gly Asn Glu Ile Ile Tyr Asp Leu
    130                 135                 140

Gly Phe Asp Ala Ala Asn Ser Phe Asn Thr Tyr Ala Phe Asp Trp Gln
145                 150                 155                 160

Glu Asn Tyr Ile Ser Trp Tyr Val Asn Gly Asn Leu Val Ala Thr Ala
                165                 170                 175

Thr Glu Asn Ile Pro Ser Asn Pro Ser Lys Ile Met Met Asn Val Trp
            180                 185                 190

Asn Thr Tyr Gly Ile Asp Glu Trp Ala Gly Ala Tyr Gly Gly Glu Ala
        195                 200                 205

Ala Asn Ala Thr Tyr Glu Trp Val Arg Tyr Thr Pro Asn Asn Gly Asn
    210                 215                 220

Thr Thr Pro Ser Thr Ala Pro Asp Phe Gln Leu Gln Ala Cys Asp Tyr
225                 230                 235                 240

Ser Asp Ser Ser Gly Ile Thr Ser Trp Ser Cys Gly Val Gly Thr Phe
                245                 250                 255

His Ser Ser Asn Trp Ile Lys Phe Asp Ser Val Asp Leu Ser Thr Gly
            260                 265                 270

Tyr Asn Ala Phe Ala Val Ser Tyr Thr Ser Pro Gly Ser Gly Ser Phe
        275                 280                 285

Asp Ile Arg Leu Gly Ser Pro His Gly Gln Arg Ile Gly Thr Val Asn
    290                 295                 300

Tyr Gly Ala Thr Gly Gly Trp Ser Asn Tyr Glu Trp Ser Gly Thr Pro
305                 310                 315                 320

Ser Leu Asp Val Thr Val Arg Gly Ala His Asp Ile Tyr Ile Val Ala
                325                 330                 335

Thr Ser Gly Ala Ala Asn Leu Arg Glu Phe Trp Phe Lys Asn Glu
            340                 345                 350


<210> SEQ ID NO 29
```

<211> LENGTH: 351
<212> TYPE: PRT
<213> ORGANISM: Bacillus species

<400> SEQUENCE: 29

Tyr Asn Pro Val Thr Glu Asp Glu Leu Tyr His Ser Phe Asp Ser His
1 5 10 15

Asp Ala Arg Asn Trp Gln Ile Ser Asp Gly Trp Arg Asn Gly Asp Asp
20 25 30

Phe Phe Gly Cys His Trp Ser Gln Asn Arg Val Asn Phe Asn Arg Gly
35 40 45

Glu Met Glu Leu Ser Leu Arg Thr Asn Tyr Ser Tyr Ser Ala Pro Tyr
50 55 60

Asn Tyr Glu Cys Ala Glu Tyr Ala Thr Ser Asn Phe Tyr Gly Tyr Gly
65 70 75 80

Leu Tyr Glu Val Ser Met Lys Pro Ala Asn Val Ser Gly Val Ile Ser
85 90 95

Ser Phe Phe Thr Tyr Thr Gly Pro Ser Tyr Asn Gly Ala Pro Trp Asp
100 105 110

Glu Ile Asp Ile Glu Phe Leu Gly Asn Asp Thr Thr Lys Val Gln Phe
115 120 125

Asn Tyr Tyr Thr Asn Gly Val Gly Gly Asn Glu Ile Ile Tyr Asp Leu
130 135 140

Gly Phe Asp Ala Ala Asn Ser Phe Asn Thr Tyr Ala Phe Asp Trp Gln
145 150 155 160

Glu Asn Tyr Ile Ser Trp Tyr Val Asn Gly Asn Leu Val Ala Thr Ala
165 170 175

Thr Glu Asn Ile Pro Ser Asn Pro Ser Lys Ile Met Met Asn Val Trp
180 185 190

Asn Thr Tyr Gly Ile Asp Glu Trp Ala Gly Ala Tyr Gly Gly Glu Ala
195 200 205

Ala Asn Ala Thr Tyr Glu Trp Val Arg Tyr Thr Pro Asn Asn Gly Asn
210 215 220

Thr Thr Pro Ser Thr Ala Pro Asp Phe Gln Leu Gln Ala Cys Asp Tyr
225 230 235 240

Ser Asp Ser Ser Gly Ile Thr Ser Trp Ser Cys Gly Val Gly Thr Phe
245 250 255

His Ser Ser Asn Trp Ile Lys Phe Asp Ser Val Asp Leu Ser Thr Gly
260 265 270

Tyr Asn Ala Phe Ala Val Ser Tyr Thr Ser Pro Gly Ser Gly Ser Phe
275 280 285

Asp Ile Arg Leu Gly Ser Pro His Gly Gln Arg Ile Gly Thr Val Asn
290 295 300

Tyr Gly Ala Thr Gly Gly Trp Ser Asn Tyr Glu Trp Ser Gly Thr Pro
305 310 315 320

Ser Leu Asp Val Thr Val Arg Gly Ala His Asp Ile Tyr Ile Val Ala
325 330 335

Thr Ser Gly Ala Ala Asn Leu Arg Glu Phe Trp Phe Lys Asn Glu
340 345 350

<210> SEQ ID NO 30
<211> LENGTH: 245
<212> TYPE: PRT
<213> ORGANISM: Bacillus akibai

<400> SEQUENCE: 30

Ala Glu Arg Pro Ile Gly Thr Thr Phe Val Glu Thr Phe Glu Ser Tyr
1 5 10 15

Asp Ser Glu Arg Trp Ser Lys Ala Gly Val Trp Thr Asn Gly Gln Met
20 25 30

Phe Asn Ala Thr Trp Tyr Pro Glu Gln Val Thr Phe Ser Asp Gly Lys
35 40 45

Met Lys Leu Gln Ile Asp Lys Glu Asp Asn Glu Thr Ala Ser Pro Pro
50 55 60

Tyr Lys Ala Gly Glu Leu Arg Thr Asn Asp Phe Tyr His Tyr Gly Leu
65 70 75 80

Phe Glu Val Ser Met Lys Pro Ala Lys Ser Thr Gly Thr Val Ser Ser
85 90 95

Phe Phe Thr Tyr Thr Gly Pro Trp Asp Trp Asp Asn Asp Pro Trp Asp
100 105 110

Glu Ile Asp Ile Glu Phe Leu Gly Lys Asp Thr Thr Lys Ile Gln Phe
115 120 125

Asn Tyr Phe Thr Asn Gly Val Gly Gly Asn Glu His Tyr His Glu Leu
130 135 140

Gly Phe Asp Ala Ala Asp Asp Phe Asn Thr Tyr Ala Phe Glu Trp Arg
145 150 155 160

Pro Glu Ser Ile Arg Trp Phe Val Asn Gly Glu Leu Val His Thr Ala
165 170 175

Thr Glu Asn Ile Pro Gln Thr Pro Gln Lys Ile Met Met Asn Leu Trp
180 185 190

Pro Gly Ile Gly Val Asp Gly Trp Thr Gly Arg Phe Asn Gly Glu Asp
195 200 205

Thr Pro Val Val Thr Gln Tyr Asp Trp Val Lys Tyr Thr Pro Leu Glu
210 215 220

Glu Leu Gly Cys Tyr Asn Glu Lys Asn Asn Lys Tyr Lys Lys Cys Lys
225 230 235 240

Lys Thr Lys Val Lys
245

<210> SEQ ID NO 31
<211> LENGTH: 214
<212> TYPE: PRT
<213> ORGANISM: Bacillus mojavensis

<400> SEQUENCE: 31

Gln Thr Gly Gly Ser Phe Phe Asp Pro Phe Asn Gly Tyr Asn Ser Gly
1 5 10 15

Phe Trp Gln Lys Ala Asn Gly Tyr Ser Asn Gly Asn Met Phe Asn Cys
20 25 30

Thr Trp Arg Ala Asn Asn Val Ser Met Thr Ser Leu Gly Glu Met Arg
35 40 45

Leu Ala Leu Thr Ser Pro Ser Tyr Asn Lys Phe Asp Cys Gly Glu Asn
50 55 60

Arg Ser Val Gln Thr Tyr Gly Tyr Gly Leu Tyr Glu Val Arg Met Lys
65 70 75 80

Pro Ala Lys Asn Val Gly Ile Val Ser Ser Phe Phe Thr Tyr Thr Gly
85 90 95

Pro Thr Asp Gly Thr Pro Trp Asp Glu Ile Asp Ile Glu Phe Leu Gly
100 105 110

Lys Asp Thr Thr Lys Val Gln Phe Asn Tyr Tyr Thr Asn Gly Val Gly

```
        115                 120                 125

Asn His Glu Lys Leu Val Asp Leu Gly Phe Asp Ala Ala Asn Ala Tyr
    130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Ser Gln Ile Pro Thr Thr Pro
                165                 170                 175

Gly Lys Ile Met Met Asn Leu Trp Asn Gly Thr Gly Val Asp Glu Trp
            180                 185                 190

Leu Gly Ser Tyr Asn Gly Val Thr Pro Leu Tyr Ala His Tyr Asp Trp
        195                 200                 205

Val Arg Tyr Thr Lys Lys
    210


<210> SEQ ID NO 32
<211> LENGTH: 480
<212> TYPE: PRT
<213> ORGANISM: Thermobacillus species

<400> SEQUENCE: 32

Ala Asp Leu Ser Gln Trp Arg Leu Val Trp Ser Asp Glu Phe Asp Gly
1               5                   10                  15

Pro Asn Gly Ser Ala Pro Asp Pro Asn Lys Trp Asn Leu Val His Ala
            20                  25                  30

Gly Gly Gly Phe Gly Asn Asn Glu Leu Gln Tyr Tyr Thr Asn Arg Arg
        35                  40                  45

Asp Asn Ser Tyr Leu Glu Asn Gly Ser Leu Val Ile Lys Ala Gln Lys
    50                  55                  60

Glu Thr Tyr Asn Gly His Ala Tyr Thr Ser Ala Lys Leu Thr Ser Gln
65                  70                  75                  80

Asn Lys Gly Asp Trp Lys Tyr Gly Arg Phe Glu Ile Arg Ala Lys Leu
                85                  90                  95

Pro Tyr Gly Arg Ser Val Trp Pro Ala Ile Trp Met Met Pro Thr Asp
            100                 105                 110

Ser Val Tyr Gly Gly Trp Pro Lys Ser Gly Glu Ile Asp Ile Met Glu
        115                 120                 125

Asn Arg Gly Asp Gln Met Asn Lys Ile Ser Gly Thr Ile His Tyr Gly
    130                 135                 140

Asn Asp Trp Pro Asn Asn Thr Trp Ser Gly Ala Ser Tyr Asn Leu Pro
145                 150                 155                 160

Gly Gly Gln Ser Phe Ala Asp Asp Phe His Thr Phe Ala Ile Glu Trp
                165                 170                 175

Glu Glu Gly Ile Ile Arg Trp Tyr Val Asp Asp Ile Leu Tyr Ser Thr
            180                 185                 190

Lys Thr Asp Trp Phe Thr Pro Ser Ala Pro Tyr Pro Ala Pro Phe Asp
        195                 200                 205

Gln Arg Phe Tyr Met Gln Leu Asn Val Ala Ile Gly Gly Pro Asn Thr
    210                 215                 220

Pro Phe Thr Gly Phe Gln Pro Pro Asp Asp Ser Val Leu Pro Gln Lys
225                 230                 235                 240

Met Tyr Val Asp Tyr Val Arg Val Tyr Glu Arg Ile Gly Ser Ser Ser
                245                 250                 255

Ser Thr Pro Ile Pro Gly Lys Ile Glu Ala Glu Asn Tyr Ser Ala Met
            260                 265                 270
```

```
Asn Gly Ile Gln Thr Glu Gln Thr Thr Asp Thr Gly Gly Gly Leu Asn
        275                 280                 285

Val Gly Trp Val Asp Ala Gly Asp Trp Leu Asp Tyr Ser Val Asn Val
    290                 295                 300

Gln Thr Ser Gly Thr Tyr Lys Val Gln Leu Arg Val Ala Asn Ala Leu
305                 310                 315                 320

Ser Thr Gly Gln Leu Gln Leu Arg Ser Gly Gly Thr Thr Leu Ala Thr
                325                 330                 335

Val Asn Val Pro Asn Thr Gly Gly Trp Gln Ser Trp Gln Thr Ile Glu
            340                 345                 350

Thr Thr Val Asn Leu Thr Ala Gly Gln Gln Thr Leu Arg Val Tyr Ala
        355                 360                 365

Thr Gln Arg Gly Phe Asn Leu Asn Trp Leu Asn Phe Ile Gln Asp Gly
    370                 375                 380

Gly Ser Gly Gly Gly Gly Glu His Val Thr Ala Asp Tyr Thr Ala Gly
385                 390                 395                 400

Val Ser Arg Val Ser Ala Ser Gln Ala Lys Ile Tyr Phe Thr Pro Val
                405                 410                 415

Thr Pro Ala Arg Tyr Val Asp Val His Tyr Thr Val Asn Ser Gly Gly
            420                 425                 430

Gln Leu Asn Val Arg Met Thr Asn Asn Asn Gly Thr Trp Glu Thr Ala
        435                 440                 445

Val Asn Asn Leu Lys Ser Gly Asp Val Ile Arg Tyr Trp Phe Thr Tyr
    450                 455                 460

Glu Lys Asn Gly Pro Gln Tyr Glu Ser Pro Glu Tyr Thr Tyr Thr His
465                 470                 475                 480


<210> SEQ ID NO 33
<211> LENGTH: 262
<212> TYPE: PRT
<213> ORGANISM: Paenibacillus species

<400> SEQUENCE: 33

Ala Pro Gln Gln Lys Asn Gly Trp Lys Leu Val Trp Asn Asp Glu Phe
1               5                   10                  15

Asp Gly Lys Glu Ile Asp Arg Thr Lys Trp Lys His Val Thr Gly Gly
            20                  25                  30

Ser Gly Phe Gly Asn Asn Glu Asp Gln Phe Tyr Thr Glu Asp Ala Ala
        35                  40                  45

Asn Ser Tyr Ile Glu Asp Gly Lys Leu Val Ile Lys Ala Leu Lys Gln
    50                  55                  60

Glu His Gly Gly Lys Pro Tyr Thr Ser Ala Lys Leu Ile Thr Glu Gly
65                  70                  75                  80

Tyr Ala Asp Trp Thr Tyr Gly Arg Phe Glu Phe Arg Ala Lys Met Pro
                85                  90                  95

Leu Gly Lys Gly Met Trp Pro Ala Ile Trp Met Met Pro Thr Asp Met
            100                 105                 110

Glu Lys Tyr Gly Gly Trp Pro Ser Ser Gly Glu Ile Asp Ile Met Glu
        115                 120                 125

Tyr Leu Gly His Glu Pro Glu Gln Val His Gly Thr Leu His Met Gly
    130                 135                 140

Asn Pro His Ile Tyr Arg Gly Gly Lys Val Ser Leu Glu Asp Gly Met
145                 150                 155                 160

Phe Ala Glu Ala Phe His Asp Phe Ala Leu Glu Trp Thr Pro Ser Gly
                165                 170                 175
```

Met Lys Trp Tyr Val Asp Asp Lys Glu Phe Tyr Gln Thr Thr Thr Trp
180 185 190

Phe Thr Arg Lys Asp Glu Ala Ala Asp Asn Glu Pro Phe Pro Ala Pro
195 200 205

Phe Asp Arg Ala Phe Phe Leu Gln Leu Asn Leu Ala Val Gly Gly Asn
210 215 220

Trp Pro Gly Tyr Pro Asp Glu Thr Thr Val Phe Pro Gln Thr Phe Glu
225 230 235 240

Leu Glu Tyr Val Arg Val Tyr Gln Pro Ala Asp Gly Asn Tyr Glu Thr
245 250 255

Ala Asn Asp Thr Ala Lys
260

<210> SEQ ID NO 34
<211> LENGTH: 385
<212> TYPE: PRT
<213> ORGANISM: Cohnella species

<400> SEQUENCE: 34

Ala Tyr Asn Leu Val Trp Ser Asp Glu Phe Asn Gly Thr Ser Ile Asp
1 5 10 15

Ser Asn Asn Trp Ser Phe Glu Val Gly Thr Gly Ser Gly Gly Trp Gly
20 25 30

Asn Asn Glu Leu Glu Tyr Tyr Thr Ser Arg Ser Glu Asn Ala Arg Ile
35 40 45

Glu Asn Gly Asn Leu Val Ile Glu Ala Arg Lys Glu Ser Tyr Gly Gly
50 55 60

Met Asn Tyr Thr Ser Ala Arg Leu Lys Thr Gln Gly Lys Lys Ser Phe
65 70 75 80

Gln Tyr Gly Arg Ile Glu Ala Arg Ile Lys Met Pro Asn Gly Gln Gly
85 90 95

Leu Trp Pro Ala Phe Trp Thr Leu Gly Ser Asp Ile Gly Thr Val Gly
100 105 110

Trp Pro Lys Ser Gly Glu Ile Asp Ile Met Glu His Val Asn Asn Asp
115 120 125

Asn Asn Thr Asn Gly Tyr Ile His Trp Asp Ala Asn Gly Gln Ala Asp
130 135 140

Tyr Gly Gly Pro Ser Gly Tyr Val Asp Val Thr Gln Tyr His Val Tyr
145 150 155 160

Ser Ile Glu Trp Thr Pro Ser Ala Ile Lys Trp Phe Ile Asp Gly Thr
165 170 175

Gln Phe Trp Glu Ala Asn Ile Ala Asn Asn Ile Asn Ser Thr Glu Glu
180 185 190

Phe His Lys Pro His Phe Ile Leu Leu Asn Met Ala Val Gly Gly Asn
195 200 205

Trp Pro Gly Ala Pro Asn Ala Gly Thr Ala Phe Pro Ala Lys Met Tyr
210 215 220

Val Asp Tyr Val Arg Val Tyr Gln Asp Asn Gly Thr Pro Gln Pro Ser
225 230 235 240

Asn Gly Ile Val Ser Gly Gly Thr Tyr Lys Leu Ile Asn Val Asn Ser
245 250 255

Gly Lys Ala Leu Asp Val Gln Ser Ala Gly Thr Thr Pro Gly Thr Asn
260 265 270

Val Gln Ile Trp Thr Asp Asn Gly Thr Gly Ala Gln Lys Trp Thr Ile

```
        275                 280                 285

Tyr Gln Asn Ala Asp Gly Ser Tyr Lys Leu Val Asn Val Asn Ser Ala
    290                 295                 300

Leu Ala Leu Asp Val Ala Ser Ser Gly Thr Ala Asp Gly Thr Asn Val
305                 310                 315                 320

Gln Ala Trp Thr Asp Asn Gly Thr Gly Ala Gln Lys Trp Asn Ile Ile
                325                 330                 335

Ala Asn Gly Asp Gly Ser Tyr Lys Leu Ile Asn Thr Asn Ser Gly Lys
            340                 345                 350

Ala Leu Asp Val Ser Gly Ser Gly Thr Ala Asp Gly Thr Asn Val Gln
        355                 360                 365

Ile Trp Asn Asp Asn Gly Thr Gly Ala Gln Lys Trp Asn Leu Ile Lys
    370                 375                 380

Leu
385


<210> SEQ ID NO 35
<211> LENGTH: 382
<212> TYPE: PRT
<213> ORGANISM: Paenibacillus elgii

<400> SEQUENCE: 35

Ala Pro Asn Trp Asn Leu Val Trp Ser Asp Glu Phe Asn Gly Asn Ala
1               5                   10                  15

Leu Asn Ser Ala Asn Trp Ser Ala Glu Ile Gly Thr Gly Gln Asn Gly
            20                  25                  30

Trp Gly Asn Asn Glu Leu Gln Tyr Tyr Thr Asn Arg Pro Glu Asn Val
        35                  40                  45

Arg Val Ala Asp Gly Asn Leu Val Ile Thr Ala Arg Lys Glu Ser Tyr
    50                  55                  60

Gly Gly Met Asn Tyr Thr Ser Ala Arg Ile Lys Thr Gln Asn Leu Lys
65                  70                  75                  80

Ser Phe Thr Tyr Gly Lys Ile Glu Ala Arg Ile Lys Leu Pro Ser Gly
                85                  90                  95

Gln Gly Leu Trp Pro Ala Phe Trp Met Leu Gly Ser Asn Ile Asn Ala
            100                 105                 110

Val Gly Trp Pro Gly Cys Gly Glu Ile Asp Ile Met Glu Arg Val Asn
        115                 120                 125

Asn Asn Pro His Val Asn Gly Thr Val His Trp Asp Ala Gly Gly His
    130                 135                 140

Ala Asp Tyr Gly Arg Val Ser Gly Asn Leu Asp Phe Ser Gln Tyr His
145                 150                 155                 160

Val Tyr Ser Ile Glu Trp Asp Ser Lys Tyr Ile Arg Trp Phe Val Asp
                165                 170                 175

Gly Gln Glu Tyr Asn Ala Phe Tyr Ile Glu Asn Gly Thr Gly Asn Thr
            180                 185                 190

Glu Glu Phe Gln Arg Pro Phe Phe Leu Leu Leu Asn Leu Ala Val Gly
        195                 200                 205

Gly Asn Trp Pro Gly Ser Pro Asp Pro Ser Thr Pro Phe Pro Ala Gln
    210                 215                 220

Met Leu Val Asp Tyr Val Arg Val Tyr Gln Ala Ser Pro Gly Ile Val
225                 230                 235                 240

Asn Gly Gly Ile Tyr Thr Ile Ala Ser Lys Ala Ser Gly Lys Val Met
                245                 250                 255
```

```
Asp Val Val Asp Val Ser Thr Gln Ser Gly Ala Lys Ile Gln Gln Trp
            260                 265                 270

Thr Asn Tyr Val Ala Asn Asn Gln Lys Phe Lys Val Glu Ser Ala Gly
        275                 280                 285

Asp Gly Tyr Tyr Lys Leu Thr Ala Val His Ser Gly Lys Val Leu Asp
    290                 295                 300

Val Pro Asn Ser Ser Thr Ser Ser Gly Val Gln Leu Gln Gln Trp Asp
305                 310                 315                 320

Asp Asn Gly Ser Ala Ala Gln Arg Trp Ser Ile Val Asp Ala Gly Gly
                325                 330                 335

Gly Tyr Tyr Lys Ile Val Ser Lys Thr Asn Gly Leu Val Val Asp Val
            340                 345                 350

Ser Gly Ser Ser Thr Ala Asp Gly Ala Thr Val Gln Gln Trp Ser Asp
        355                 360                 365

Asn Gly Thr Asp Ala Gln Lys Trp Ser Phe Val Lys Val Asn
    370                 375                 380


<210> SEQ ID NO 36
<211> LENGTH: 260
<212> TYPE: PRT
<213> ORGANISM: Bacillus species

<400> SEQUENCE: 36

Thr Glu Thr Glu Glu Gly Ile Ser Ile Glu Gln Glu Gly Trp Asn Leu
1               5                   10                  15

Val Trp Asn Asp Glu Phe Asp Gly Asp Ser Leu Asp Gln Ser Lys Trp
            20                  25                  30

Arg Tyr Asp Ile Gly Asn Gly Gln Pro Asn Leu Pro Gly Trp Gly Asn
        35                  40                  45

Glu Glu Leu Gln Tyr Tyr Asn Asp Asp Pro Lys Asn Val Arg Val Glu
    50                  55                  60

Asn Gly Glu Leu Ile Ile Glu Ala His Gln Glu Pro Ile Ser Asp Glu
65                  70                  75                  80

Phe Gly Ser Tyr Glu Tyr Thr Ser Gly Lys Val Leu Thr Glu Gly Leu
                85                  90                  95

Phe Ser Gln Thr Tyr Gly Arg Phe Glu Ala Arg Met Arg Leu Pro Ala
            100                 105                 110

Gly Gln Gly Phe Trp Pro Ala Phe Trp Met Met Pro Glu Asn Asp Gln
        115                 120                 125

Tyr Gly Gly Trp Ala Ala Ser Gly Glu Ile Asp Ile Met Glu Asn Ala
    130                 135                 140

Gly Gly Thr Pro Tyr Lys Val Gly Gly Ala Ile His Tyr Gly Gly Pro
145                 150                 155                 160

Trp Pro Glu Asn Gln Phe Gln Ala Gly Asp Tyr Phe Phe Pro Asp Gly
                165                 170                 175

Thr Asp Ala Thr Gly Tyr His Glu Tyr Ala Val Glu Trp Glu Pro Gly
            180                 185                 190

Glu Ile Arg Trp Tyr Val Asp Gly Asn Leu Tyr Gln Thr Ile Asn Asp
        195                 200                 205

Trp Tyr Ser Thr Gly Gly Ala Tyr Pro Ala Pro Phe Asp Gln Asp Phe
    210                 215                 220

His Leu Ile Leu Asn Leu Ala Val Gly Gly Trp Tyr Gly Gly Asn Pro
225                 230                 235                 240

Asp Gly Ser Thr Pro Phe Pro Ser Thr Met Ala Val Asp Tyr Val Arg
                245                 250                 255
```

Val Tyr Glu Arg
260

<210> SEQ ID NO 37
<211> LENGTH: 256
<212> TYPE: PRT
<213> ORGANISM: Bacillus species

<400> SEQUENCE: 37

Ala Thr Ala Pro Glu Pro Gln Asn Asp Trp Asn Leu Val Trp Ser Asp
1 5 10 15

Glu Phe Asp Gly Asn Ser Leu Asp Ser Ser Lys Trp Arg Tyr Asp Ile
20 25 30

Gly Asn Gly Gln Pro Asn Leu Pro Gly Trp Gly Asn Glu Glu Leu Gln
35 40 45

Tyr Tyr Ser Asp Asp Pro Lys Asn Val Arg Val Glu Asn Gly Glu Leu
50 55 60

Val Ile Glu Ala His Gln Glu Thr Val Ser Asp Pro Tyr Gly Thr Tyr
65 70 75 80

Pro Tyr Thr Ser Gly Lys Val Leu Thr Asp Gly Lys Phe Ser Gln Thr
85 90 95

Tyr Gly Arg Phe Glu Ala Arg Met Arg Leu Pro Ala Gly Gln Gly Phe
100 105 110

Trp Pro Ala Phe Trp Met Met Pro Glu Asn Asp Arg Tyr Gly Gly Trp
115 120 125

Ala Ala Ser Gly Glu Ile Asp Ile Met Glu Asn Ala Gly Ala Thr Pro
130 135 140

Tyr Lys Thr Gly Gly Ala Ile His Tyr Gly Gly Pro Trp Pro Glu Asn
145 150 155 160

Gln Phe Gln Ala Gly Asp Tyr Tyr Phe Pro Asp Trp Thr Asn Ala Thr
165 170 175

Asp Tyr His Glu Tyr Ala Val Glu Trp Glu Pro Gly Glu Ile Arg Trp
180 185 190

Tyr Val Asp Gly Asn Leu Tyr Gln Thr Ile Asn Asp Trp Tyr Ser Val
195 200 205

Gly Gly Ser Tyr Pro Ala Pro Phe Asp Gln Asp Phe His Leu Ile Leu
210 215 220

Asn Leu Ala Val Gly Gly Trp Tyr Gly Gly Asn Pro Asp Ala Thr Thr
225 230 235 240

Pro Phe Pro Ser Thr Met Ala Val Asp Tyr Val Arg Val Tyr Gln Arg
245 250 255

<210> SEQ ID NO 38
<211> LENGTH: 298
<212> TYPE: PRT
<213> ORGANISM: Bacillus bogoriensis

<400> SEQUENCE: 38

Ala Asn Ser Gly Phe Tyr Val Ser Gly Thr Thr Leu Tyr Asp Ala Asn
1 5 10 15

Gly Asn Pro Phe Val Met Arg Gly Ile Asn His Gly His Ala Trp Tyr
20 25 30

Lys Asp Gln Ala Thr Thr Ala Ile Glu Gly Ile Ala Asn Thr Gly Ala
35 40 45

Asn Thr Val Arg Ile Val Leu Ser Asp Gly Gly Gln Trp Thr Lys Asp
50 55 60

Asp Ile His Thr Val Arg Asn Leu Ile Ser Leu Ala Glu Asp Asn His
65 70 75 80

Leu Val Ala Val Leu Glu Val His Asp Ala Thr Gly Tyr Asp Ser Ile
85 90 95

Ala Ser Leu Asn Arg Ala Val Asp Tyr Trp Ile Glu Met Arg Ser Ala
100 105 110

Leu Ile Gly Lys Glu Asp Thr Val Ile Ile Asn Ile Ala Asn Glu Trp
115 120 125

Phe Gly Ser Trp Glu Gly Asp Ala Trp Ala Asp Gly Tyr Lys Gln Ala
130 135 140

Ile Pro Arg Leu Arg Asn Ala Gly Leu Asn His Thr Leu Met Val Asp
145 150 155 160

Ala Ala Gly Trp Gly Gln Phe Pro Gln Ser Ile His Asp Tyr Gly Arg
165 170 175

Glu Val Phe Asn Ala Asp Pro Gln Arg Asn Thr Met Phe Ser Ile His
180 185 190

Met Tyr Glu Tyr Ala Gly Gly Asn Ala Ser Gln Val Arg Thr Asn Ile
195 200 205

Asp Arg Val Leu Asn Gln Asp Leu Ala Leu Val Ile Gly Glu Phe Gly
210 215 220

His Arg His Thr Asn Gly Asp Val Asp Glu Ala Thr Ile Met Ser Tyr
225 230 235 240

Ser Glu Gln Arg Gly Val Gly Trp Leu Ala Trp Ser Trp Lys Gly Asn
245 250 255

Gly Pro Glu Trp Glu Tyr Leu Asp Leu Ser Asn Asp Trp Ala Gly Asn
260 265 270

Asn Leu Thr Ala Trp Gly Asn Thr Ile Val Asn Gly Pro Tyr Gly Leu
275 280 285

Arg Glu Thr Ser Arg Leu Ser Thr Val Phe
290 295

<210> SEQ ID NO 39
<211> LENGTH: 297
<212> TYPE: PRT
<213> ORGANISM: Paenibacillus species

<400> SEQUENCE: 39

Met Ala Thr Gly Phe Tyr Val Ser Gly Asn Lys Leu Tyr Asp Ser Thr
1 5 10 15

Gly Lys Pro Phe Val Met Arg Gly Val Asn His Gly His Ser Trp Phe
20 25 30

Lys Asn Asp Leu Asn Thr Ala Ile Pro Ala Ile Ala Lys Thr Gly Ala
35 40 45

Asn Thr Val Arg Ile Val Leu Ser Asn Gly Ser Leu Tyr Thr Lys Asp
50 55 60

Asp Leu Asn Ala Val Lys Asn Ile Ile Asn Val Val Asn Gln Asn Lys
65 70 75 80

Met Ile Ala Val Leu Glu Val His Asp Ala Thr Gly Lys Asp Asp Tyr
85 90 95

Asn Ser Leu Asp Ala Ala Val Asn Tyr Trp Ile Ser Ile Lys Glu Ala
100 105 110

Leu Ile Gly Lys Glu Asp Arg Val Ile Val Asn Ile Ala Asn Glu Trp
115 120 125

Tyr Gly Thr Trp Asn Gly Ser Ala Trp Ala Asp Gly Tyr Lys Lys Ala

```
    130                 135                 140

Ile Pro Lys Leu Arg Asn Ala Gly Ile Lys Asn Thr Leu Ile Val Asp
145                 150                 155                 160

Ala Ala Gly Trp Gly Gln Phe Pro Gln Ser Ile Val Asp Tyr Gly Gln
                165                 170                 175

Ser Val Phe Ala Ala Asp Ser Gln Lys Asn Thr Val Phe Ser Ile His
            180                 185                 190

Met Tyr Glu Tyr Ala Gly Lys Asp Ala Ala Thr Val Lys Ala Asn Met
        195                 200                 205

Glu Asn Val Leu Asn Lys Gly Leu Ala Leu Ile Ile Gly Glu Phe Gly
    210                 215                 220

Gly Tyr His Thr Asn Gly Asp Val Asp Glu Tyr Ala Ile Met Arg Tyr
225                 230                 235                 240

Gly Gln Glu Lys Gly Val Gly Trp Leu Ala Trp Ser Trp Tyr Gly Asn
                245                 250                 255

Ser Ser Gly Leu Asn Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
        275                 280                 285

Asn Thr Ser Gln Lys Ala Gly Ile Phe
    290                 295


<210> SEQ ID NO 40
<211> LENGTH: 464
<212> TYPE: PRT
<213> ORGANISM: Bacillus hemicellulosilyticus

<400> SEQUENCE: 40

Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ser Met Val Gln Ser Asn
        195                 200                 205
```

-continued

```
Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Thr Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
        275                 280                 285

Leu Leu Glu Thr Ser Ile Pro Ser Ser Ile Phe His Thr Ala Pro Asn
    290                 295                 300

Asn Gly Asp Pro Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365

Glu Asn Arg Asn Leu Ser Gly Tyr Ser Thr Leu Gln Ala Thr Val Arg
    370                 375                 380

His Ala His Trp Gly Asn Val Gly Asn Leu Thr Ala Arg Met Tyr Val
385                 390                 395                 400

Lys Thr Gly Ser Asn Tyr Ser Trp Phe Asn Gly Asp Pro Ile Pro Val
                405                 410                 415

Asn Ser Ala Asn Gly Thr Thr Val Thr Leu Pro Leu Ser Ser Ile Pro
            420                 425                 430

Asn Leu Asn Asp Val Lys Glu Ile Gly Val Glu Phe Ile Gly Ala Ser
        435                 440                 445

Asn Ser Asn Gly Gln Thr Ala Ile Tyr Leu Asp His Val Thr Ile Gln
    450                 455                 460


<210> SEQ ID NO 41
<211> LENGTH: 399
<212> TYPE: PRT
<213> ORGANISM: Bacillus subtilis

<400> SEQUENCE: 41

Ala Asp Leu Gly His Gln Thr Leu Glu Ser Asn Asp Gly Trp Gly Ala
1               5                   10                  15

Tyr Ser Thr Gly Thr Thr Gly Gly Ser Lys Ala Ser Ser Ser His Val
            20                  25                  30

Tyr Thr Val Ser Asn Arg Asn Gln Leu Val Ser Ala Leu Gly Lys Asp
        35                  40                  45

Thr Asn Thr Thr Pro Lys Ile Ile Tyr Ile Lys Gly Thr Ile Asp Met
    50                  55                  60

Asn Val Asp Asp Asn Leu Lys Pro Leu Gly Leu Asn Asp Tyr Lys Asp
65                  70                  75                  80

Pro Glu Tyr Asp Leu Asp Lys Tyr Leu Lys Ala Tyr Asp Pro Ser Thr
                85                  90                  95

Trp Gly Lys Lys Glu Pro Ser Gly Thr Leu Glu Glu Ala Arg Ala Arg
            100                 105                 110

Ser Gln Lys Asn Gln Lys Ala Arg Val Met Val Asp Ile Pro Ala Asn
        115                 120                 125
```

Thr Thr Ile Val Gly Ser Gly Thr Asn Ala Lys Ile Val Gly Gly Asn
    130                 135                 140

Phe Gln Ile Lys Ser Asp Asn Val Ile Ile Arg Asn Ile Glu Phe Gln
145                 150                 155                 160

Asp Ala Tyr Asp Tyr Phe Pro Gln Trp Asp Pro Thr Asp Gly Ser Ser
                165                 170                 175

Gly Asn Trp Asn Ser Gln Tyr Asp Asn Ile Thr Ile Asn Gly Gly Thr
            180                 185                 190

His Ile Trp Ile Asp His Cys Thr Phe Asn Asp Gly Ser Arg Pro Asp
        195                 200                 205

Ser Thr Ser Pro Lys Tyr Phe Gly Arg Lys Tyr Gln His His Asp Gly
    210                 215                 220

Gln Thr Asp Ala Ser Asn Gly Ala Asn Tyr Ile Thr Met Ser Tyr Asn
225                 230                 235                 240

Tyr Tyr His Asp His Asp Lys Ser Ser Ile Phe Gly Ser Ser Asp Ser
                245                 250                 255

Lys Thr Ser Asp Asp Gly Lys Leu Lys Ile Thr Leu His His Asn Arg
            260                 265                 270

Tyr Lys Asn Ile Val Gln Arg Ala Pro Arg Val Arg Phe Gly Gln Val
        275                 280                 285

His Val Tyr Asn Asn Tyr Tyr Glu Gly Ser Thr Ser Ser Ser Asp Tyr
    290                 295                 300

Ala Phe Ser Tyr Ala Trp Gly Ile Gly Lys Ser Ser Lys Ile Tyr Ala
305                 310                 315                 320

Gln Asn Asn Val Ile Asp Val Pro Gly Leu Ser Ala Ala Lys Thr Ile
                325                 330                 335

Ser Val Phe Ser Gly Gly Thr Ala Leu Tyr Asp Ser Gly Thr Leu Leu
            340                 345                 350

Asn Gly Thr Gln Ile Asn Ala Ser Ala Ala Asn Gly Leu Ser Ser Ser
        355                 360                 365

Val Gly Trp Thr Pro Ser Leu His Gly Thr Ile Asp Ala Ser Ala His
    370                 375                 380

Val Lys Ser Asn Val Ile Ser Gln Ala Gly Ala Gly Lys Leu Asn
385                 390                 395

<210> SEQ ID NO 42
<211> LENGTH: 182
<212> TYPE: PRT
<213> ORGANISM: Bacillus cibi

<400> SEQUENCE: 42

Thr Pro Pro Gly Thr Pro Ser Lys Ser Ala Ala Gln Ser Gln Leu Asn
1               5                   10                  15

Ala Leu Thr Val Lys Thr Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala

```
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180


<210> SEQ ID NO 43
<211> LENGTH: 221
<212> TYPE: PRT
<213> ORGANISM: Aspergillus oryzae

<400> SEQUENCE: 43

Val Pro Val Asn Pro Glu Pro Asp Ala Thr Ser Val Glu Asn Val Ala
1               5                   10                  15

Leu Lys Thr Gly Ser Gly Asp Ser Gln Ser Asp Pro Ile Lys Ala Asp
            20                  25                  30

Leu Glu Val Lys Gly Gln Ser Ala Leu Pro Phe Asp Val Asp Cys Trp
        35                  40                  45

Ala Ile Leu Cys Lys Gly Ala Pro Asn Val Leu Gln Arg Val Asn Glu
    50                  55                  60

Lys Thr Lys Asn Ser Asn Arg Asp Arg Ser Gly Ala Asn Lys Gly Pro
65                  70                  75                  80

Phe Lys Asp Pro Gln Lys Trp Gly Ile Lys Ala Leu Pro Pro Lys Asn
                85                  90                  95

Pro Ser Trp Ser Ala Gln Asp Phe Lys Ser Pro Glu Glu Tyr Ala Phe
            100                 105                 110

Ala Ser Ser Leu Gln Gly Gly Thr Asn Ala Ile Leu Ala Pro Val Asn
        115                 120                 125

Leu Ala Ser Gln Asn Ser Gln Gly Gly Val Leu Asn Gly Phe Tyr Ser
    130                 135                 140

Ala Asn Lys Val Ala Gln Phe Asp Pro Ser Lys Pro Gln Gln Thr Lys
145                 150                 155                 160

Gly Thr Trp Phe Gln Ile Thr Lys Phe Thr Gly Ala Ala Gly Pro Tyr
                165                 170                 175

Cys Lys Ala Leu Gly Ser Asn Asp Lys Ser Val Cys Asp Lys Asn Lys
            180                 185                 190

Asn Ile Ala Gly Asp Trp Gly Phe Asp Pro Ala Lys Trp Ala Tyr Gln
        195                 200                 205

Tyr Asp Glu Lys Asn Asn Lys Phe Asn Tyr Val Gly Lys
    210                 215                 220


<210> SEQ ID NO 44
<211> LENGTH: 1557
<212> TYPE: DNA
<213> ORGANISM: Paenibacillus illinoisensis

<400> SEQUENCE: 44

atgaagaaac cgttggggaa aattgtcgca agcaccgcac tactcatttc tgttgctttt      60

agttcatcga tagcatcagc agctattacg gtaccgggat ttgttgttga accccatact     120
```

```
tcttctgatc aaaaccaggc cataatagcc acattcaaag atgcttccat cgaagggtac    180
gggatcaaga aacgcgatga ggcaacagcc aaagcggagg acgatctata tgatggtaca    240
ggttatatct cttatttttt tgaagaggat gaaaaggcca cagttcagaa gggaagcgct    300
acattccagg ttaaagcacc ggaaaatggg ctttatgagt taagtttggg atactacatc    360
ccagaaggaa atggggataa agcgacttcc atccaagtaa atggttcggg agccggggag    420
ctgacgctca gtgcgccaaa gccagggacg gttcgagcag aaaaaaagat gacaaaggtg    480
cttctgaaca gcggtaacaa ctccattcaa atattaaggg ggtgggggta ctatggcatt    540
gagtatatca agcttgaacg tgtagaaccc cgcataacca cgcaaaaaac aatgatggat    600
cccttaagta actccaaagc atctccgcaa gccaaagcat taatgaaatt tatgaccaac    660
cagtatggaa aaaaaattat atcaggccag caaaccctag aggacgcagc gtggatctat    720
cagcagactg gaaagtaccc tgcactggtt tccagtgatt tgatggatta ttctccatcc    780
cgtgtggaaa acggaagcac ctcgaatgag gtagaaaaga tgatggagtg gtacaagcgt    840
ggaggcattg tctccttaag ctggcactgg aatgcgccga aagggatcgg cagcaatgaa    900
ccaggccatg agtggtggcg gggttcaat acagagttca caaccttcga tgtagaatat    960
gctctgaatc atccggaatc ggaagattac aagcttctaa ttcgggatat tgatgcgatc   1020
gctactcaat tgaagcggct gcaggagcac catattcccg tactttggag accactgcat   1080
gaagcggagg gtggctggtt ttggtgggga gccaaaggtc ctgaacctgc gaaaaaattg   1140
tatcgattaa tgtacgaacg attgacggag aagcatgggt taaacaatct catttgggtt   1200
tggaactctg ttaaggagga gtggtacccg ggagatgatg tggtggatat ggtaagtgtc   1260
gacatttata atccacccgg tgattacagc ccgaacattg ccaagtacga cgagctcttg   1320
tttctgagca agcataagaa acttgtggca ctcgccgaaa atgggccgat tcccgatcct   1380
gatctgctgc agacatacgg tgcacattgg agctatttta atacctggac tggcgatgtt   1440
ctgcgtgatg gaaaaacgaa tacaaaggaa catttgaaaa aagtctacaa tcatgacaac   1500
gtgatcacac tggatgaact tcccaaggga ttgtacgaca gtcctagatg gaaatga      1557
```

<210> SEQ ID NO 45
<211> LENGTH: 1557
<212> TYPE: DNA
<213> ORGANISM: Paenibacillus illinoisensis

<400> SEQUENCE: 45

```
atgaagaaac cgttggggaa aattgtcgca agcaccgcac tactcatttc tgttgctttt     60
agttcatcga tagcatcagc agctattacg gtaccgggat ttgttgttga accccatact    120
tcttctgatc aaaaccaggc cataatagcc acattcaaag atgcttccat cgaagggtac    180
gggatcaaga aacgcgatga ggcaacagcc aaagcggagg acgatctata tgatggtaca    240
ggttatatct cttatttttt tgaagaggat gaaaaggcca cagttcagaa gggaagcgct    300
acattccagg ttaaagcacc ggaaaatggg ctttatgagt taagtttggg atactacatc    360
ccagaaggaa atggggataa agcgacttcc atccaagtaa atggttcggg agccggggag    420
ctgacgctca gtgcgccaaa gccagggacg gttcgagcag aaaaaaagat gacaaaggtg    480
cttctgaaca gcggtaacaa ctccattcaa atattaaggg ggtgggggta ctatggcatt    540
gagtatatca agcttgaacg tgtagaaccc cgcataacca cggataaaac aatgatggat    600
cccttaagta actccaaagc atctccgcaa gccaaagcat taatgaaatt tatgaccaac    660
cagtatggaa aaaaaattat atcaggccag caaaccctag aggacgcagc gtggatctat    720
```

-continued

```
cagcagactg gaaagtaccc tgcactggtt tccagtgatt tgatggatta ttctccatcc    780
cgtgtggaaa acggaagcac ctcgaatgag gtagaaaaga tgatggagtg gtacaagcgt    840
ggaggcattg tctccttaag ctggcactgg aatgcgccga aagggatcgg cagcaatgaa    900
ccaggccatg agtggtggcg ggggttcaat acagagttca caaccttcga tgtagaatat    960
gctctgaatc atccggaatc ggaagattac aagcttctaa ttcgggatat tgatgcgatc   1020
gctactcaat tgaagcggct gcaggagcac catattcccg tactttggag accactgcat   1080
gaagcggagg gtggctggtt ttggtgggga gccaaaggtc ctgaacctgc gaaaaaattg   1140
tatcgattaa tgtacgaacg attgacggag aagcatgggt taaacaatct catttgggtt   1200
tggaactctg ttaaggagga gtggtacccg ggagatgatg tggtggatat ggtaagtgtc   1260
gacatttata atccacccgg tgattacagc ccgaacattg ccaagtacga cgagctcttg   1320
tttctgagca agcataagaa acttgtggca ctcgccgaaa atgggccgat tcccgatcct   1380
gatctgctgc agacatacgg tgcacattgg agctatttta atacctggac tggcgatgtt   1440
ctgcgtgatg gaaaaacgaa tacaaaggaa catttgaaaa aagtctacaa tcatgacaac   1500
gtgatcacac tggatgaact tcccaaggga ttgtacgaca gtcctagatg gaaatga      1557
```

MANNANASE VARIANTS AND POLYNUCLEOTIDES ENCODING SAME

CROSS-REFERENCE TO RELATED APPLICATIONS

This application is a 35 U.S.C. 371 national application of international application no. PCT/EP2021/052155 filed Jan. 29, 2021 and published on Aug. 5, 2021 as International Publication No. WO2021/152123, which application claims priority or the benefit under 35 U.S.C. 119 of Indian Application No. 202041004432 filed Jan. 31, 2020, the contents of which are fully incorporated herein by reference.

REFERENCE TO A SEQUENCE LISTING

This application contains a Sequence Listing in computer readable form. The contents of the electronic sequence listing created on Jan. 29, 2021, named 15047-WO-PCT SQ listing ST25.txt and 143 KB in size, is hereby incorporated by reference in its entirety.

BACKGROUND OF THE INVENTION

Field of the Invention

The present invention relates to mannanase variants exhibiting mannanase activity, compositions comprising the mannanase variants, polynucleotides encoding the variants, methods of producing the variants, and methods of using the variants.

Description of the Related Art

Mannans are polysaccharides with a backbone of β-1,4-linked D-mannopyranosyl residues, which can contain galactose or acetyl substitutions and may have glucose residues in the backbone. The main enzyme type participating in the degradation of mannans are endo-1,4-β-mannanases (EC 3.2.1.78), which hydrolyze the internal glycoside bonds in the mannan backbone.

Mannans are a type of hemicellulose representing up to 25% of wood dry weight in softwoods, but are also found in other plant material, especially in a variety of seeds. The mannan containing guar gum is used as a stabilizer in many food products.

Thus, it could be advantageous to use endomannanases in applications where mannan needs to be degraded. Examples of where mannanases could be used are in detergents to remove mannan containing stains, in the production of bioethanol from softwood (Várnai et al, (2011) "Synergistic action of xylanase and mannanase improves the total hydrolysis of softwood", *Bioresource tech.,* 102(19), pp. 9096-104) and palm kernel press cake (Jørgensen et al, (2010) "Production of ethanol and feed by high dry matter hydrolysis and fermentation of palm kernel press cake", *Applied Biochem. Biotech.,* 161(1-8), pp. 318-32), for the improvement of animal feed (Cai, et al, (2011), "Acidic β-mannanase from *Penicillium pinophilum* C1: Cloning, characterization and assessment of its potential for animal feed application", *J. Biosci. Bioeng.,* 112(6), pp. 551-557) and in the hydrolysis of coffee extract (Nunes et al, (2006), "Characterization of Galactomannan Derivatives in Roasted Coffee Beverages", *J. Agricultural Food Chem.,* 54(9), pp. 3428-3439).

Within the household care industry, it has been known to use mannanases in e.g. laundry detergents. In WO 1999/064619 an alkaline mannanase, which exhibits mannanase activity also in the alkaline pH range when applied in cleaning compositions, is disclosed.

According to CAZy (azy.org), endo-1,4-β-mannanases have been found in glycoside hydrolyase families 5, 26 and 113. In WO 2019/068715 and WO 2019/068713, mannanases of family GH 26 exhibiting beta-mannanase activity are disclosed.

However, alternative mannanases are desirable and industrially applicable for, e.g., the detergent producing industry. The present invention is directed to these and other important ends.

SUMMARY OF THE INVENTION

Described herein are variants of a parent mannanase, wherein said variant comprises at least two modifications, wherein (a) said first modification is a substitution or a deletion in a position selected from positions: 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein the variant has mannanase activity and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1, SEQ ID NO: 2, or a fragment thereof having mannanase activity.

The present invention also relates to a composition comprising a variant as herein disclosed, use of such a composition in a domestic or industrial cleaning process, an isolated polynucleotide encoding the variants; nucleic acid constructs, vectors, and host cells comprising the polynucleotides; and methods of producing the variants as well as methods of washing using a composition herein disclosed.

Overview of Sequence Listing

SEQ ID NO: 1 is the amino acid sequence of the mature GH26 mannanase from a strain of *Paenibacillus illinoisensis* with CBM35 domain.

SEQ ID NO: 2 is the mannanase of SEQ ID NO: 1, further including a stabilizing mutation.

SEQ ID NO: 3 is the amino acid sequence of a truncated mature GH26 mannanase from a strain of *Paenibacillus illinoisensis* missing the CBM35 domain.

SEQ ID NO: 4 is the amino acid sequence of a truncated mature GH26 mannanase from a strain of *Paenibacillus illinoisensis* missing the CBM35 domain.

SEQ ID NO: 5 mature polypeptide obtained from *Bacillus* sp.

SEQ ID NO: 6 mature polypeptide obtained from *Bacillus* sp.

SEQ ID NO: 7 mature polypeptide obtained from *Cytophaga* sp.

SEQ ID NO: 8 mature polypeptide obtained from *Bacillus* sp.

SEQ ID NO: 9 mature polypeptide obtained from *Bacillus* sp.

SEQ ID NO: 10 mature polypeptide obtained from *Bacillus subtilis*

SEQ ID NO: 11 mature polypeptide obtained from *Bacillus* sp.

SEQ ID NO: 12 mature polypeptide obtained from *Bacillus* sp.

SEQ ID NO: 13 Synthetic construct

SEQ ID NO: 14 mature polypeptide obtained from *Bacillus lentus*

SEQ ID NO: 15 mature polypeptide obtained from *Bacillus amyloliquefaciens*

SEQ ID NO: 16 mature polypeptide obtained from *Bacillus* sp.

SEQ ID NO: 17 mature polypeptide obtained from *Bacillus gibsonii*

SEQ ID NO: 18 mature polypeptide obtained from *Bacillus lentus*

SEQ ID NO: 19 mature polypeptide obtained from *Bacillus licheniformis*

SEQ ID NO: 20 mature polypeptide obtained from *Bacillus* sp.

SEQ ID NO: 21 mature polypeptide obtained from *Humicola insolens*

SEQ ID NO: 22 mature polypeptide obtained from *Humicola insolens*

SEQ ID NO: 23 mature polypeptide obtained from *Thielavia terrestris*

SEQ ID NO: 24 mature polypeptide obtained from *Paenibacillus polymyxa*

SEQ ID NO: 25 mature polypeptide obtained from *Melanocarpus albomyces*

SEQ ID NO: 26 mature polypeptide obtained from *Thermomyces lanuginosus*

SEQ ID NO: 27 mature polypeptide obtained from *Bacillus agaradhaerens*

SEQ ID NO: 28 mature polypeptide obtained from *Bacillus* sp

SEQ ID NO: 29 mature polypeptide obtained from *Bacillus* sp

SEQ ID NO: 30 mature polypeptide obtained from *Bacillus akibai*

SEQ ID NO: 31 mature polypeptide obtained from *Bacillus mojavensis*

SEQ ID NO: 32 mature polypeptide obtained from *Thermobacillus* species

SEQ ID NO: 33 mature polypeptide obtained from *Paenibacillus* species

SEQ ID NO: 34 mature polypeptide obtained from *Cohnella* species

SEQ ID NO: 35 mature polypeptide obtained from *Paenibacillus elgii*

SEQ ID NO: 36 mature polypeptide obtained from *Bacillus* species

SEQ ID NO: 37 mature polypeptide obtained from *Bacillus* species

SEQ ID NO: 38 mature polypeptide obtained from *Bacillus bogoriensis*

SEQ ID NO: 39 mature polypeptide obtained from *Paenibacillus* species

SEQ ID NO: 40 mature polypeptide obtained from *Bacillus hemicellulosilyticus*

SEQ ID NO: 41 mature polypeptide obtained from *Bacillus subtilis*

SEQ ID NO: 42 mature polypeptide obtained from *Bacillus cibi*

SEQ ID NO: 43 mature polypeptide obtained from *Aspergillus oryzae*

SEQ ID NO: 44 is a gene encoding the mature GH26 mannanase of SEQ ID NO: 1.

SEQ ID NO: 45 is a gene encoding the mature GH26 mannanase of SEQ ID NO: 2.

Definitions

In accordance with the detailed description, the following abbreviations and definitions apply. Note that the singular forms "a", "an", and "the" include plural referents unless the context clearly indicates otherwise. Thus, for example, reference to "an enzyme" includes a plurality of such enzymes, and reference to "the dosage" includes reference to one or more dosages and equivalents thereof known to those skilled in the art, and so forth.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Amylase: The term "amylase" (EC 3.2.1) refers to enzymes which catalyze the hydrolysis of starch, glycogen, and related polysaccharides to oligosaccharides, maltose, or glucose. Amylases are glycoside hydrolases and act on α-1,4-glycosidic bonds. The amylases suitable in the cleaning compositions of the invention are preferably alpha amylases. Alpha-amylases (EC 3.2.1.1) includes 1,4-α-D-glucan glucanohydrolase and glycogenase and are calcium metalloenzymes. By acting at random locations along the starch chain, alpha-amylase breaks down long-chain carbohydrates, ultimately yielding maltotriose and maltose from amylose, or maltose, glucose and "limit dextrin" from amylopectin. Suitable amylases of the present invention are preferably microbial e.g. obtained from bacterial or fungal sources. The term "alpha-amylase activity" means the activity of alpha 1,4-glucan 4 glucanohydrolases, E.C. 3.2.1.1, which constitute a group of enzymes, which catalyze hydrolysis of starch and other linear and branched 1,4 alpha-glucosidic oligo and poly-saccharides. Alpha-amylase activity may be determined by Assay II as described in the Examples herein.

Beta-glucanase: The term "beta-glucanase" as used herein means an endo-acting enzyme that catalyzes the hydrolysis of a beta-1,3-, beta-1,6- and/or beta-1,4-bonds connecting two glucosyl residues in a beta-glucan.

A subgroup of beta-glucanases as defined herein, also known as a licheninases (or lichenases) (e.g. EC 3.2.1.73), can also be used to catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1,4-bonds. As used herein the term "beta-glucanase activity" comprises licheninase (or lichenases) (e.g. EC 3.2.1.73) activity. Licheninase activity may be determined as in Assay VII herein.

Another further subgroup of beta-glucanases as defined herein, also known as a laminarinases (e.g. EC 3.2.1.6, EC 3.2.1.39, and/or EC 3.2.1.58), can also be used to catalyse the hydrolysis of the beta-1,3-glucosidic bonds, or beta-1, 4-glucosidic bonds when the glucose residue whose reducing group is involved in the linkage to be hydrolysed is substituted at C3 to release glucose or oligosaccharides. As used herein the term "beta-glucanase activity" also comprises laminarinase (e.g. EC 3.2.1.6, EC 3.2.1.39, and/or EC 3.2.1.58) activity. Laminarinase activity may be determined as in Assay VI herein.

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp.

Carbohydrate binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose. In one embodiment, the CBM is a family 35 CBM (Pfam PF16990) such as that disclosed in Tunnicliffe R B, Bolam D N, Pell G, Gilbert H J, Williamson M P; *J Mol Biol.* 2005; 347:287-296.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the *International Union of Pure and Applied Chemistry* (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, CA, USA), and as described in the Examples herein.

Chimeric polypeptide: The term "chimeric polypeptide" means a polypeptide having mannanase activity whose composition is generated by replacing a sequence of amino acids from one polypeptide having mannanase activity with those from homologous positions of one or more other polypeptides having mannanase activity.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: the term "deep cleaning" is defined herein to mean reduction, disruption or removal of components which may be comprised in organic matter, e.g. biofilm, such as polysaccharides, proteins, DNA, soil or other components present in the organic matter. The organic matter may be termed poly-organic stains comprising more than one organic component such as starch, grease, protein, DNA and mannan.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents).

In addition to containing the mannanase variant of the invention, the detergent composition may contain one or more additional enzymes (such as amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, licheninases, laminarinases, DNAses, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" or "dish wash composition" refers to compositions intended for cleaning dishes, table ware, pots, pans, cutlery and all forms of compositions for cleaning hard surfaces areas in kitchens. The present invention is not restricted to any particular type of dish wash composition or any particular detergent.

DNases: DNases are polypeptides with DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endo-deoxyribonucleases cleaves or cut within the DNA backbone. A DNase may cleave only double-stranded DNA or may cleave double stranded and single stranded DNA. The term "DNases" and the expression "a polypeptide with DNase activity" may be used interchangeably throughout the application. For purposes of the present invention, DNase activity may determined according to the procedure described in the Assay IV or Assay V of the Examples herein. Preferably the DNase is selected from any of the enzyme classes E.C.3.1, preferably E.C.3.1.21. Preferably, the polypeptide having DNase activity is obtained from a microorganism and the DNase is a microbial enzyme. The DNase is preferably of fungal or of bacterial origin.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has mannanase activity. In one aspect, the fragment comprises at least 90% of the length of the mature polypeptide, such as at least 441 amino acids of SEQ ID NO: 1, at least 441 amino acids of SEQ ID NO: 2, at least 280 amino acids of SEQ ID NO: 3, or at least 307 amino acids of SEQ ID NO: 4. In one aspect, the fragment comprises at least 92% of the length of the mature polypeptide, such as at least 451 amino acids of SEQ ID NO: 1, such as at least 451 amino acids of SEQ ID NO: 2, at least 287 amino acids of SEQ ID NO: 3, or at least 314 amino acids of SEQ ID NO: 4. In one aspect, the fragment comprises at least 94% of the length of the mature polypeptide, such as at least 461 amino acids of SEQ ID NO: 1, at least 461 amino acids of SEQ ID NO: 2, at least 293 amino acids of SEQ ID NO: 3, or at least 321 amino acids of SEQ ID NO: 3. In one aspect, the fragment comprises at least 96% of the length of the mature polypeptide, such as at least 471 amino acids of SEQ ID NO: 1, at least 471 amino acids of SEQ ID NO: 2, at least 299 amino acids of SEQ ID NO: 3, or at least 28 amino acids of SEQ ID NO: 4. In one aspect, the fragment comprises at least 98% of the length of the mature polypeptide, such as at least 481 amino acids of SEQ ID NO: 1, at least 481 amino acids of SEQ ID NO: 2, at least 305 amino acids of SEQ ID NO: 3, or at least 335 amino acids of SEQ ID NO: 4. In one aspect, the fragment comprises at least 99% of the length of the mature polypeptide, such as at least 486 amino acids of SEQ ID NO: 1, at least 486 amino acids of SEQ ID NO: 2, at least 308 amino acids of SEQ ID NO: 3, or at least 338 amino acids of SEQ ID NO: 4.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication, as well as a recombinant host cell, an isolated host cell (e.g., an isolated recombinant host cell), a heterologous host cell (e.g., a host cell that is not *Myrothecium roridum* host cell).

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Hybridization: The term "hybridization" means the pairing of substantially complementary strands of nucleic acids, using standard Southern blotting procedures. Hybridization may be performed under medium, medium-high, high or very high stringency conditions. Medium stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 55° C. Medium-high stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 60° C. High stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 65° C. Very high stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 70° C.

Improved property: The term "improved property" means a characteristic associated with a variant that is improved compared to the parent. Such improved properties include, but are not limited to, in-detergent stability, thermostability, protease stability, surfactant stability, pH stability.

In-detergent stability: The term "in-detergent stability" or "detergent stability" refers to the stability of a mannanase enzyme, whether a wild-type, parent, or variant, which has been incubated in detergent. For purposes of the present invention, in-detergent stability may be determined as shown in the Examples, particularly Example 6.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Lipase: The term lipase includes enzymes which catalyze the hydrolysis of fats (lipids). Lipases are a sub class of esterases. Lipases suitable in the present invention include phospholipases, acyltransferases or perhydrolases e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028). Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147). Lipase activity may be determined as described in Assay VIII in the Examples herein.

Mannanase: The term "mannanase" means a polypeptide having mannan endo-1,4-beta-mannosidase activity (EC 3.2.1.78) that catalyzes the hydrolysis of 1,4-β-D-mannosidic linkages in mannans, galactomannans and glucomannans. Alternative names of mannan endo-1,4-beta-mannosidase are 1,4-β-D-mannan mannanohydrolase; endo-1,4-β-mannanase; endo-β-1,4-mannase; β-mannanase B; β-1,4-mannan 4-mannanohydrolase; endo-β-mannanase; and β-D-mannanase. For purposes of the present invention, mannanase activity may be determined using the Reducing End Assay as described in Example 1 herein. In one aspect, the polypeptides of the present invention have at least 50%, e.g., at least 60%, at least 70%, at least 80%, at least 90%, at least 95%, or at least 100% of the mannanase activity of the polypeptide of SEQ ID NO: 1. In one aspect, the polypeptides of the present invention have at least 50%, e.g., at least 60%, at least 70%, at least 80%, at least 90%, at least 95%, or at least 100% of the mannanase activity of the polypeptide of SEQ ID NO: 2.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 491 of SEQ ID NO: 1. In one aspect, the mature polypeptide is amino acids 1 to 491 of SEQ ID NO: 2. In one aspect, the mature polypeptide is amino acids 1 to 312 of SEQ ID NO: 3. In one aspect, the mature polypeptide is amino acids 1 to 342 of SEQ ID NO: 4.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having mannanase activity.

Malodor: The term "malodor" is meant an odor which is not desired on clean items. The cleaned item should smell fresh and clean without malodors adhered to the item. One example of malodor is compounds with an unpleasant smell, which may be produced by microorganisms. Another example is sweat or body odor adheringed to an item which has been in contact with humans or animals. Another example of malodor can be the smell from spices, for example curry or other exotic spices adheringed to an item such as a piece of textile. One way of measuring the ability of an item to adhere malodor is by using the Malodor Assay.

Modification: The term "modification", in the context of the polypeptides of the invention, means that one or more amino acids within the reference amino acid sequence (i.e. SEQ ID NOs: 1 or 2) are altered by substitution with a different amino acid, by insertion of an amino acid or by deletion, preferably by at least one deletion. The terms "modification", "alteration", and "mutation" may be used interchangeably and constitute the same meaning and purpose.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent mannanase: The term "parent" or "parent mannanase" or "parent polypeptide" as used herein refers to any polypeptide with mannanase activity to which a modification is made to produce the enzyme variants of the present invention. In the present invention, it is to be understood, that a parent polypeptide refers to a naturally-occurring polypeptide that does not include a man-made substitution, insertion, or deletion at one or more amino acid positions. Similarly, the term "parent" with respect to a polynucleotide, refers to a naturally-occurring polynucleotide that does not include a man-made nucleoside change. However, a polynucleotide encoding a parent polypeptide is not limited to a naturally-occurring polynucleotide, but rather encompasses any polynucleotide encoding the parent polypeptide. The parent mannanase may be any mannanase having at least 60%, such as at least 62%, at least 65%, at least 70%, at least 75%, at least 80%, at least 85%, at least 90%, at least 95%, or 100% sequence identity to SEQ ID NO: 1 or SEQ ID NO: 2.

Pectinase: The term "pectinase" denotes a pectinase enzyme defined according to the art and includes an enzyme that cleaves poly- and/or oligosaccharide chains in pectic substances, e.g., poly(1,4-alpha-D-galacturonide) and its derivatives (see reference Sakai et al., Pectin, pectinase and protopectinase: production, properties and applications, pp 213-294 in: Advances in Applied Microbiology vol:39, 1993). Non-limiting examples of pectinases include hydrolase type pectinases (e.g. rhamnogalacturonan hydrolases) and lyase type pectinases (e.g., pectate lyases). Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase. Pectinase activity may be determined as described in Assay IX in the Examples herein.

Protease: The term "protease" includes enzymes that hydrolyze peptide bonds and the term incudes peptidase and proteinase. Serine proteases (or serine endopeptidases), E.C. 3.4.21 are enzymes that cleave peptide bonds in proteins, in which serine serves as the nucleophilic amino acid at the active site. Suitable proteases include those of bacterial, fungal, plant, viral or animal origin e.g. vegetable or microbial origin. Microbial origin is preferred. Chemically modified or protein engineered mutants are included. Most relevant proteases for laundry may be the alkaline proteases, such as a serine protease. A serine protease may for example be of the S1 family, such as trypsin, or the S8 family such as subtilisin. A metalloproteases protease may for example be a thermolysin from e.g. family M4 or other metalloproteases such as those from M5, M7 or M8 families. The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. Protease activity may be determined as described in Assay X in the Examples herein.

pH stability: The term "pH stability" refers to the stability of a mannanase enzyme, whether a wild-type, parent, or variant, which has been incubated at a particular pH, for example at an elevated pH (above pH 7), such as pH 8-8.5, pH 9-9.5, pH 10-10.5, as in a detergent composition. For purposes of the present invention, pH stability may be determined as shown in the Examples.

Polypeptide or enzyme: The terms "polypeptide" and "enzyme" may be used interchangeably to refer to polymers of any length comprising amino acid residues linked by peptide bonds. The conventional one-letter or three-letter codes for amino acid residues are used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.) as well as other modifications known in the art.

Protease stability: The term "protease stability" refers to the stability of a mannanase enzyme, whether a wild-type, parent, or variant, which has been incubated in the presence of a protease, for example in the presence of a protease in a detergent. For purposes of the present invention, protease stability may be determined as shown in the Examples. Exemplary protease are those described in detail below.

Purified: The term "purified" means a nucleic acid or polypeptide that is substantially free from other components as determined by analytical techniques well known in the art (e.g., a purified polypeptide or nucleic acid may form a discrete band in an electrophoretic gel, chromatographic eluate, and/or a media subjected to density gradient centrifugation). A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having mannanase activity.

Surfactant stability: The term "surfactant stability" refers to the stability of a mannanase enzyme, whether a wild-type, parent, or variant, which has been incubated in the presence of a surfactant, for example in the presence of a surfactant in a detergent. Exemplary surfactants are those described in detail below, and in a particular embodiment, surfactant stability refers to stability in the presence of an anionic surfactant, such as LAS. For purposes of the present invention, surfactant stability may be determined as shown in the Examples.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylene and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Thermostability: The term "thermostability" refers to the stability of a mannanase enzyme, whether a wild-type, parent, or variant, which has been incubated in the presence of a elevated temperature. For purposes of the present invention, thermostability may be determined using nDSF (Prometheus, Nanotemper) by measuring melting temperature (Tm) of variants in presence of detergent (for example, Model A). Samples are prepared to achieve Model A concentration of 10% and protein concentration of 200 ppm. Samples after brief mixing are loaded into capillaries and placed in nDSF sample tray. Samples are run in Tm estimation mode with temperature range of 25-85° C. with 1° C./min ramp. After completion of run, Tm is estimated using 350 nm signal in the software.

Variant: The term "variant" means a polypeptide having mannanase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 50%, e.g., at least 60%, at least 70%, at least 80%, at least 90%, at least 95%, or at least 100% of the mannanase activity of the polypeptide of SEQ ID NO: 1 or SEQ ID NO: 2.

Wild-type: The term "wild-type" in reference to an amino acid sequence or nucleic acid sequence means that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

Conventions for Designation of Variants

For purposes of the present invention, the polypeptide disclosed in SEQ ID NO: 1 is used to determine the corresponding amino acid position in another mannanase. The amino acid sequence of another mannanase is aligned with the polypeptide disclosed in SEQ ID NO: 1, and based on the alignment, the amino acid position number corresponding to any amino acid residue in the polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to A variant of a parent mannanase, wherein said variant comprises at least two substitutions, wherein (a) said first substitution is in a position selected from positions: 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second substitution is in any other position of said variant, wherein the variant has mannanase activity and wherein the variant has at least 60%, e.g., at least 65%, at least 70%, at least 75%, at least 80%, at least 85%, at least 90%, at least 95%, at least 96%, at least 97%, at least 98%, or at least 99% sequence identity, but less than 100% sequence identity, to the polypeptide of SEQ ID NO: 1, SEQ ID NO: 2, SEQ ID NO: 3, SEQ ID NO: 4, or a fragment thereof having mannanase activity.

Variants

The inventors of the present invention have found that a modification in one of the above listed positions provides mannanase variants which have an improved stability compared to the parent mannanase, i.e. a mannanase not comprising a modification in any one of the listed positions. In particular, the stability may be observed as stability in detergent compositions, thermostability, protease stability, surfactant stability, and/or pH stability.

The stability in detergent compositions may herein be referred to a "in detergent stability" and falls under the definition elsewhere described herein. The terms may be used interchangeably, but constitute the same meaning and purpose for the present invention. The stability has been determined as described in the Examples.

Thus, the improvement of the mannanase variants is observed when the variant has at least one of the (a) listed positions. When combining (a) listed positions with any other modification, it has been observed that the stability is maintained. Thus, these positions are believed to be important for stability of mannanases. In particular, the stability may be observed as stability in detergent compositions. Such detergent stability may be determined as described in the Examples 3, i.e. by incubating the variants in detergent, and then measuring the residual activity. The residual activity is correlated/compared to the residual activity of a parent mannanase incubated at 4° C. for the equal amount of hours. The improvement of the mannanase variants are given as half-life improvement factor (HIF).

Thus, the present invention provides variants of a parent mannanase, wherein the variant comprises at least one substitution in one or more of the positions: 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491, wherein numbering is according to SEQ ID NO: 1, and at least one second (or further) modification in a position which is in any other position in the amino acid sequence. The term "second modification" or "further modification" as used herein, are to be understood as being a substitution or a deletion which is in addition to, and not in, any of the following positions: 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491. However, the variant according to the invention may comprise more than one substitution in any one of the positions: 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491. Furthermore, the term "second substitution" is to be understood as "at least one second substitution", i.e. the second substitution may be in one or more positions.

As can be seen from the Examples, all the disclosed variants have an improved stability, in particular when tested under stress. Such stress in according to the present invention may be increased by altering (i.e. raising the pH), incubating for a longer/extended time period, altered (i.e raised) temperature and/or in the presence of a protease.

It is to be understood that the variants of the present invention comprises at least two modifications, such as substitutions, which means that the variants may comprise a substitution in one of the positions listed in (a) and then the second/further substitution(s) is in any other positions herein disclosed. However, it is also to be understood that variants of the present invention may be variants that comprise a substitution in more than one of the listed positions in (a), i.e. in two, three, four, five, six, seven, eight, nine, ten, 11, 12, or even all 13 of these positions.

The invention also relates to variants having multiple modifications, e.g., at least 19 mutations, such as at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or even 75 mutations compared to the parent mannanase, such that the resultant variant has at least 85% but less than 96%, e.g., 86-96%, 87-96%, 88-96%, 89-96%, 90-96%, 91-96%, 92-96%, 93-96%, 94-96% such as 95-96%, or has at least 85% but less than 95%, e.g., 86-95%, 87-95%, 88-95%, 89-95%, 90-95%, 91-95%, 92-95%, 93-95%, such as 94-95%, or has at least 85% but less than 94%, e.g., 86-94%, 87-94%, 88-94%, 89-94%, 90-94%, 91-94%, 92-94%, such as 93-94% sequence identity or has at least 85% but less than 93%, e.g., 86-93%, 87-93%, 88-93%, 89-93%, 90-93%, 91-93%, such as 92-93%, or has at least 85% but less than 92%, e.g., 86-92%, 87-92%, 88-92%, 89-92%, 90-92%, such as 91-92%, or has at least 85% but less than 91%, e.g., 86-91%, 87-91%, 88-91%, 89-91%, such as 90-91%, or has at least 85% but less than 90%, e.g., 86-90%, 87-90%, 88-90%, such as 89-90% sequence identity to the polypeptide of SEQ ID NO: 1, SEQ ID NO: 2, or a fragment thereof having mannanase activity.

In another embodiment, the variant comprises or consists of a deletion or a substitution in the position corresponding to position 7 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 7*, 7A, 7D, 7G, 7I, 7P. In an embodiment, the deletion or substitution is F7*, F7A, F7D, F7G, F7I, F7P, preferably F7G.

In another embodiment, the variant comprises or consists of a substitution in the position corresponding to position 13 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 13I, 13M, 13N, 13W, 13Y, 13E. In an embodiment, the substitution is T13I, T13M, T13N, T13W, T13Y, T13E, preferably T13I.

In another embodiment, the variant comprises or consists of a substitution in the position corresponding to position 15 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 15K, 15C, 15D, 15M, 15Q, 15T. In an embodiment, the substitution is S15K, S15C, S15D, S15M, S15Q, S15T, preferably S15Q.

In another embodiment, the variant comprises or consists of a substitution in the position corresponding to position 20 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 20S, 20P, 20T, 20G, 20V. In an embodiment, the substitution is A20S, A20P, A20T, A20G, A20V, preferably A20P.

In another embodiment, the variant comprises or consists of a substitution in the position corresponding to position 26 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 26D, 26E, 26H. In an embodiment, the substitution is K26D, K26E, K26H, preferably K26E.

In another embodiment, the variant comprises or consists of a substitution in the position corresponding to position 36 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 36A, 36C, 36D, 36E, 36M, 36T. In an embodiment, the substitution is K36A, K36C, K36D, K36E, K36M, K36T, preferably K36E.

In another embodiment, the variant comprises or consists of a substitution in the position corresponding to position 46 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 46I, 46F, 46M, 46Y. In an embodiment, the substitution is E46I, E46F, E46M, E46Y, preferably E46M or E46Y.

In another embodiment, the variant comprises or consists of a substitution in the position corresponding to position 64 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 64P. In an embodiment, the substitution is E64P.

In another embodiment, the variant comprises or consists of a substitution in the position corresponding to position 69 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 69P, 69R, 69S, 69T. In an embodiment, the substitution is Q69P, Q69R, Q69S, Q69T, preferably Q69P.

In another embodiment, the variant comprises or consists of a substitution in the position corresponding to position 70 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 70A, 70E, 70I, 70M, 70P, 70T. In an embodiment, the substitution is K70A, K70E, K70I, K70M, K70P, K70T, preferably K70P.

In another embodiment, the variant comprises or consists of a substitution in the position corresponding to position 82 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 82T, 82A. In an embodiment, the substitution is N82T, N82A.

In another embodiment, the variant comprises or consists of a substitution in the position corresponding to position 101 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 101R, 101C, 101E, 101I, 101L, 101N, 101Q, 101V. In an embodiment, the substitution is A101R, A101C, A101E, A101I, A101L, A101N, A101Q, A101V, preferably A101R or A101L.

In another embodiment, the variant comprises or consists of a substitution in the position corresponding to position 103 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 103R, 103A, 103C, 103D, 103E, 103I, 103L, 103N, 103Q, 103V, 103Y. In an embodiment, the substitution is S103R, S103A, S103C, S103D, S103E, S103I, S103L, S103N, S103Q, S103V, S103Y, preferably 103V.

In another embodiment, the variant comprises or consists of a substitution in the position corresponding to position 109 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 109E, 109D. In an embodiment, the substitution is S109E, S109D.

In another embodiment, the variant comprises or consists of a substitution in the position corresponding to position 120 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 120S, 120A, 120G, 120I, 120P. In an embodiment, the substitution is K120S, K120A, K120G, K120I, K120P, preferably K120A or K120P.

In another embodiment, the variant comprises or consists of a substitution in the position corresponding to position 141 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 141R, 141I, 141Q, 141A. In an embodiment, the substitution is S141R, S141I, S141Q, S141A, preferably 141R.

In another embodiment, the variant comprises or consists of a substitution in the position corresponding to position 155 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 155H. In an embodiment, the substitution is Y155H.

In another embodiment, the variant comprises or consists of a substitution in the position corresponding to position 162 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 162D, 162G, 162Q. In an embodiment, the substitution is E162D, E162G, E162Q, preferably E162D.

In another embodiment, the variant comprises or consists of a substitution in the position corresponding to position 163 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 163*, 163A, 163E, 163T, 163N. In an embodiment, the substitution is P163*, P163T, P163A, P163E, P163N, preferably P163A.

In another embodiment, the variant comprises or consists of a substitution in the position corresponding to position 166 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 166E, 166G, 166I, 166L, 166N, 166P, 166Q, 166R, 166V, 166W. In an embodiment, the substitution is T166E, T166G, T166I, T166L, T166N, T166P, T166Q, T166R, T166V, T166W, preferably T166P.

In another embodiment, the variant comprises or consists of a substitution in the position corresponding to position 167 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 167P, 167A, 167R, 167K. In an embodiment, the substitution is T167P, T167A, T167R, T167K, preferably T167P.

In another embodiment, the variant comprises or consists of a substitution in the position corresponding to position 168 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 168D, 168F, 168M, 168P. In an embodiment, the substitution is Q168D, Q168F, Q168M, Q168P, preferably 168D.

In another embodiment, the variant comprises or consists of a substitution in the position corresponding to position 172 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 172I. In an embodiment, the substitution is M172I.

In another embodiment, the variant comprises or consists of a substitution in the position corresponding to position 176 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 176N. In an embodiment, the substitution is S176N.

In another embodiment, the variant comprises or consists of a substitution in the position corresponding to position 178 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 178R, 178E, 178H, 178P, 178T. In an embodiment, the substitution is S178R, S178E, S178H, S178P, S178T, preferably S178P.

In another embodiment, the variant comprises or consists of a substitution in the position corresponding to position 182 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 182R, 182E. In an embodiment, the substitution is P182R, P182E.

In another embodiment, the variant comprises or consists of a substitution in the position corresponding to position 190 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 190Y. In an embodiment, the substitution is F190Y.

In another embodiment, the variant comprises or consists of a substitution in the position corresponding to position 197 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 197A, 197D, 197F, 197M, 197N, 197Y. In an embodiment, the substitution is K197A, K197D, K197F, K197M, K197N, K197Y, preferably K197D.

In another embodiment, the variant comprises or consists of a substitution in the position corresponding to position 214 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 214R, 214W. In an embodiment, the substitution is Q214R, Q214W, preferably Q214R.

In another embodiment, the variant comprises or consists of a substitution in the position corresponding to position 215 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 215E. In an embodiment, the substitution is Q215E.

In another embodiment, the variant comprises or consists of a substitution in the position corresponding to position 219 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 219W. In an embodiment, the substitution is Y219W.

In another embodiment, the variant comprises or consists of a substitution in the position corresponding to position 239 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 239A. In an embodiment, the substitution is S239A.

In another embodiment, the variant comprises or consists of a substitution in the position corresponding to position 248 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 248I. In an embodiment, the substitution is M248I.

In another embodiment, the variant comprises or consists of a substitution in the position corresponding to position 253 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 253A, 253W. In an embodiment, the substitution is R253A, R253W, preferably R253A.

In another embodiment, the variant comprises or consists of a substitution in the position corresponding to position 258 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 258G. In an embodiment, the substitution is S258G.

In another embodiment, the variant comprises or consists of a substitution in the position corresponding to position 271 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 271G, 271Y. In an embodiment, the substitution is S271G, S271Y, preferably S271G.

In another embodiment, the variant comprises or consists of a substitution in the position corresponding to position 276 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 276C, 276N, 276Y. In an embodiment, the substitution is H276C, H276N, H276Y preferably H276C.

In another embodiment, the variant comprises or consists of a substitution in the position corresponding to position 280 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 280L, 280K. In an embodiment, the substitution is R280L, R280K, preferably R280K.

In another embodiment, the variant comprises or consists of a substitution in the position corresponding to position 283 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 283M, 283Y. In an embodiment, the substitution is N283M, N283Y.

In another embodiment, the variant comprises or consists of a substitution in the position corresponding to position 286 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 285C. In an embodiment, the substitution is F286C.

In another embodiment, the variant comprises or consists of a substitution in the position corresponding to position 299 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 299K, 299D, 299W. In an embodiment, the substitution is E299K, E299D, E299W, preferably E299W.

In another embodiment, the variant comprises or consists of a substitution in the position corresponding to position 366 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 366N, 366H, 366I. In an embodiment, the substitution is G366N, G366H, G366I, preferably G366N.

In another embodiment, the variant comprises or consists of a substitution in the position corresponding to position 378 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 378D, 378H, 378Q, 378R. In an embodiment, the substitution is K378D, K378H, K378Q, K378R, preferably K378Q.

In another embodiment, the variant comprises or consists of a substitution in the position corresponding to position 385 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 385A, 385F, 385H, 385P, 385S. In an embodiment, the substitution is D385A, D385F, D385H, D385P, D385S, preferably D385H.

In another embodiment, the variant comprises or consists of a substitution in the position corresponding to position 408 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 408A, 408C, 408D, 408E, 408Q, 408S, 408T, 408V. In an embodiment, the substitution is K408A, K408C, K408D, K408E, K408M, K408Q, K408S, K408T, K408V, preferably K408M.

In another embodiment, the variant comprises or consists of a substitution in the position corresponding to position 410 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 410L, 410M. In an embodiment, the substitution is D410L, D410M, preferably D410M.

In another embodiment, the variant comprises or consists of a substitution in the position corresponding to position 413 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 413Q, 413A, 413T, 413V. In an embodiment, the substitution is L413Q, L413A, L413T, L413V, preferably L413T.

In another embodiment, the variant comprises or consists of a substitution in the position corresponding to position 473 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 473Y. In an embodiment, the substitution is N473Y.

In another embodiment, the variant comprises or consists of a substitution in the position corresponding to position 486 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 486E, 486K, 486V. In an embodiment, the substitution is D486E, D486K, D486V, preferably D486E.

In another embodiment, the variant comprises or consists of a substitution in the position corresponding to position 491 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 491E, 491P, 491R. In an embodiment, the substitution is K491E, K491P, K491R, preferably K491R.

In one embodiment, the modification is a substitution.

In one embodiment, the modification is a deletion.

In an embodiment, the modification is a substitution, wherein said substitution of the naturally-occurring amino acid residue at the one position for a different amino acid residue produces a mannanase variant having an Improvement Factor of >1.0 for a measure of stability.

When the Improvement Factor (IF) is more than 1.0, it means that the variant tested has an improved property, such as improved stability, compared to a reference enzyme, e.g., the parent mannanase or a wild type mannanase.

In one embodiment, the improved stability is in-detergent stability or thermostability.

Unless specifically disclosed herein, the numbering of amino acid residues or positions, are done according to SEQ ID NO: 1.

In an embodiment, the variant has sequence identity of at least at least 85%, e.g., at least 90%, at least 91%, at least 92%, at least 93%, at least 94%, at least 95%, at least 96%, at least 97%, at least 98%, or at least 99%, but less than 100%, to the amino acid sequence of the parent mannanase.

In another embodiment, the variant has at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or to the polypeptide of SEQ ID NO: 2.

In another embodiment, the variant has at least 91%, at least 92%, at least 93%, at least 94%, at least 95%, such as at least 96%, at least 97%, at least 98%, or at least 99%, but less than 100%, sequence identity to the polypeptide of SEQ ID NO: 3 or to the polypeptide of SEQ ID NO: 4, i.e., a truncated mannanase lacking a CBM.

As described above the stability, such as the in-detergent stability or thermostability, may be determined as described in the Examples. In particular, the stability may be determined at a pH of 8-8.5.

Thus, in one embodiment, the variant of the present invention has an improved stability when measured at pH 8-8.5.

Stability may not only be measured at pH 8-8.5 but may also be measured at either more alkaline or acidic pH. The pH that stability is measured at may vary depending on the detergent composition the variant (or enzyme) needs to be stable in. Thus, the present invention also encompass stability at other pH, such as pH 10-11 e.g., pH 10.5. Thus, in one embodiment, the variant of the present invention has an improved stability when measured at pH 10-11.

In one embodiment, is the improved stability of the variant of the present invention at least 1.0 for a measure of stability at pH 8-8.5 and/or pH 10-11.

In one embodiment, the improved stability of the variant of the present invention is measured either at pH 8-8.5 or 10-11, or the improved stability is seen at both pHs, i.e. pH 8 and pH 10.8. Thus in one embodiment, the variant has an improved stability compared to the parent mannanase, when the stability is measured at pH 8-8.5 and/or pH 10-11.

In one embodiment, the variant has an Improvement Factor of at least 1.1, at least 1.2, at least 1.3, at least 1.4, at least 1.5, at least 2.0, at least 2.5, at least 3.0 for a measure of stability at pH 8 and/or pH 10.5.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for mannanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one embodiment, the variant comprises a second modification in one or more of the following positions compared to the parent mannanase: 1, 2, 3, 4, 5, 6, 8, 9, 10, 11, 12, 14, 17, 18, 19, 21, 22, 23, 25, 30, 35, 37, 38, 42, 45, 48, 49, 53, 57, 61, 63, 65, 68, 72, 74, 76, 78, 83, 86, 89, 94, 96, 97, 100, 105, 110, 111, 112, 115, 117, 118, 121, 122, 123, 126, 129, 130, 134, 137, 139, 142, 143, 148, 160, 161, 162, 164, 165, 169, 170, 171, 174, 179, 181, 183, 184, 185, 188, 189, 192, 193, 195, 198, 210, 213, 217, 218, 228, 235, 242, 249, 252, 254, 259, 260, 267, 270, 272, 296, 301, 304, 312, 315, 321, 322, 323, 324, 342, 344, 347, 351, 352, 354, 355, 358, 363, 368, 377, 379, 380, 391, 398, 403, 414, 417, 419, 422, 423, 437, 438, 440, 442, 443, 452, 454, 462, 463, 466, 467, 470, 472, 477, 479, 480, 482, 483, 484, 487, 488, 489, 490 of the polypeptide of SEQ ID NO: 1.

In another embodiment, the second modification is a deletion or a substitution in the position corresponding to position 1 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 1*, 1S, 1T, 1G, 1D, 1I, 1V, 1Y. In an embodiment, the deletion or substitution is A1*, A1S, A1T, A1V, A1G, A1D, A1I, A1Y.

In another embodiment, the second modification is a deletion in the position corresponding to position 2 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 2*. In an embodiment, the deletion or substitution is 12*.

In another embodiment, the second modification is a deletion or a substitution in the position corresponding to position 3 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 3*, 3A, 3E, 3G. In an embodiment, the deletion or substitution is T3*, T3A, T3E, T3G.

In another embodiment, the second modification is a deletion or a substitution in the position corresponding to position 4 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 4*, 4D, 4N, 4G, 4M, 4Y. In an embodiment, the deletion or substitution is V4*, V4D, V4N, V4G, V4M, V4Y.

In another embodiment, the second modification is a deletion in the position corresponding to position 5 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion is 5*. In an embodiment, the deletion is P5*.

In another embodiment, the second modification is a deletion or substitution in the position corresponding to position 6 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 6*, 6P. In an embodiment, the deletion or substitution is G6*, G6P.

In another embodiment, the second modification is a deletion or a substitution in the position corresponding to position 8 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 8*, 8A, 8Q, 8F, 8D, 8W. In an embodiment, the deletion or substitution is V8*, V8A, V8Q, V8F, V8D, V8W.

In another embodiment, the second modification is a deletion or a substitution in the position corresponding to position 9 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 9*, 9A, 9D, 9G, 9M, 9P. In an embodiment, the deletion or substitution is V9*, V9D, V9A, V9G, V9M, V9P.

In another embodiment, the second modification is a deletion or substitution in the position corresponding to position 10 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 10**, 10Y, 10G. In an embodiment, the deletion or substitution is E10*, E10Y, E10G.

In another embodiment, the second modification is a substitution in the position corresponding to position 11 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 11A, 11L, 11E, 11I, 11N. In an embodiment, the substitution is P11A, P11L, P11E, P11I, P11N.

In another embodiment, the second modification is a substitution in the position corresponding to position 12 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 12A, 12D, 12E, 12G, 12L, 12P, 12Q, 12R, 12V. In an embodiment, the substitution is H12A, H12D, H12E, H12G, H12L, H12P, H12Q, H12R, H12V.

In another embodiment, the second modification is a substitution in the position corresponding to position 14 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 14Q, 14R, 14E, 14H, 14N, 14V. In an embodiment, the substitution is S14Q, S14R, S14E, S14H, S14N, S14V.

In another embodiment, the second modification is a substitution in the position corresponding to position 17 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 17K, 17A. In an embodiment, the substitution is Q17K, Q17A.

In another embodiment, the second modification is a substitution in the position corresponding to position 18 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 18S. In an embodiment, the substitution is N18S.

In another embodiment, the second modification is a substitution in the position corresponding to position 19 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 19N. In an embodiment, the substitution is Q19N.

In another embodiment, the second modification is a substitution in the position corresponding to position 21 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 21L. In an embodiment, the substitution is 121 L.

In another embodiment, the second modification is a substitution in the position corresponding to position 22 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 22V, 22Q, 22T. In an embodiment, the substitution is I22V. I22Q, I22T In another embodiment, the second modification is a substitution in the position corresponding to position 23 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 23I, 23T, 23V, 23M, 23S. In an embodiment, the substitution is A23I, A23T, A23V, A23M, A23S.

In another embodiment, the second modification is a substitution in the position corresponding to position 25 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 25W, 25Y. In an embodiment, the substitution is F25W, F25Y.

In another embodiment, the second modification is a substitution in the position corresponding to position 30 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 30L. In an embodiment, the substitution is 130L.

In another embodiment, the second modification is a deletion in the position corresponding to position 35 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion is 35*. In an embodiment, the deletion is 135*.

In another embodiment, the second modification is a substitution in the position corresponding to position 37 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 37V. In an embodiment, the substitution is K37V.

In another embodiment, the second modification is a substitution in the position corresponding to position 38 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 38C, 38F, 38L, 38M, 38T. In an embodiment, the substitution is R38C, R38F, R38L, R38M, R38T.

In another embodiment, the second modification is a substitution in the position corresponding to position 42 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 42E. In an embodiment, the substitution is T42E.

In another embodiment, the second modification is a substitution in the position corresponding to position 45 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 45M, 45L, 45R. In an embodiment, the substitution is A45L, A45M, A45R.

In another embodiment, the second modification is a substitution in the position corresponding to position 48 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 48A, 48P, 48S. In an embodiment, the substitution is D48A, D48P, D48S.

In another embodiment, the second modification is a substitution in the position corresponding to position 49 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 49M. In an embodiment, the substitution is L49M.

In another embodiment, the second modification is a substitution in the position corresponding to position 53 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 53C, 53E, 53H, 53K, 53P, 53Q. In an embodiment, the substitution is T53C, T53E, T53H, T53K, T53P, T53Q.

In another embodiment, the second modification is a substitution in the position corresponding to position 57 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 57P, 57R. In an embodiment, the substitution is S57P, S57R.

In another embodiment, the second modification is a substitution in the position corresponding to position 61 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 61D. In an embodiment, the substitution is E61D.

In another embodiment, the second modification is a substitution in the position corresponding to position 63 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 63C. In an embodiment, the substitution is D63C.

In another embodiment, the second modification is a substitution in the position corresponding to position 65 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 65C, 65F, 65H, 65N, 65Q, 65S, 65T. In an embodiment, the substitution is K65C, K65F, K65H, K65N, K65Q, K65S, K65T.

In another embodiment, the second modification is a substitution in the position corresponding to position 68 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 68M, 68T. In an embodiment, the substitution is V68M, V68T.

In another embodiment, the second modification is a substitution in the position corresponding to position 69 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 69P, 69R, 69S, 69T. In an embodiment, the substitution is Q69P, Q69R, Q69S, Q69T.

In another embodiment, the second modification is a substitution in the position corresponding to position 72 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 72F. In an embodiment, the substitution is S72F.

In another embodiment, the second modification is a substitution in the position corresponding to position 74 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 74A, 74Q, 74E. In an embodiment, the substitution is T74A, T74Q, T74E.

In another embodiment, the second modification is a substitution in the position corresponding to position 76 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 76T, 76E. In an embodiment, the substitution is Q76T, Q76E.

In another embodiment, the second modification is a substitution in the position corresponding to position 83 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 83E, 83S. In an embodiment, the substitution is G83E, G83S.

In another embodiment, the second modification is a substitution in the position corresponding to position 86 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 86D. In an embodiment, the substitution is E86D.

In another embodiment, the second modification is a substitution in the position corresponding to position 89 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 89F. In an embodiment, the substitution is L89F.

In another embodiment, the second modification is a substitution in the position corresponding to position 94 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 94M. In an embodiment, the substitution is P94M.

In another embodiment, the second modification is a substitution in the position corresponding to position 96 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 97E, 97D, 96E, 96D, 96R. In an embodiment, the substitution is G96E, G96D, G96R.

In another embodiment, the second modification is a substitution in the position corresponding to position 97 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 97Y. In an embodiment, the substitution is N97E, N97D, N97Y.

In another embodiment, the second modification is a substitution in the position corresponding to position 100 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 100R. In an embodiment, the substitution is K100R.

In another embodiment, the second modification is a substitution in the position corresponding to position 105 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 105V. In an embodiment, the substitution is S105V.

In another embodiment, the second modification is a substitution in the position corresponding to position 110 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 110R, 110D, 110P, 110C, 110S. In an embodiment, the substitution is G110R, G110D, G110P, G110C, G110S.

In another embodiment, the second modification is a substitution in the position corresponding to position 111 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 111L. In an embodiment, the substitution is A111L.

In another embodiment, the second modification is a substitution in the position corresponding to position 112 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 112V. In an embodiment, the substitution is G112V.

In another embodiment, the second modification is a substitution in the position corresponding to position 115 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 115W, 115Y, 115V, 115I, 115F. In an embodiment, the substitution is T115W, T115Y, T115V, T115I, T115F.

In another embodiment, the second modification is a substitution in the position corresponding to position 117 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 117P. In an embodiment, the substitution is S117P.

In another embodiment, the second modification is a substitution in the position corresponding to position 118 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 118V. In an embodiment, the substitution is A118V.

In another embodiment, the second modification is a substitution in the position corresponding to position 121 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 121A. In an embodiment, the substitution is P121A.

In another embodiment, the second modification is a substitution in the position corresponding to position 122 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 122P. In an embodiment, the substitution is G122P.

In another embodiment, the second modification is a substitution in the position corresponding to position 123 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 123R. In an embodiment, the substitution is T123R.

In another embodiment, the second modification is a substitution in the position corresponding to position 126 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 126D, 126S, 126T. In an embodiment, the substitution is A126D, A126S, A126T.

In another embodiment, the second modification is a substitution in the position corresponding to position 129 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 129R, 129L, 129M. In an embodiment, the substitution is K129R, K129L, K129M.

In another embodiment, the second modification is a substitution in the position corresponding to position 130 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 130I, 130V. In an embodiment, the substitution is M130I, M130V.

In another embodiment, the second modification is a substitution in the position corresponding to position 134 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 134I, 134V, 134P, 134T. In an embodiment, the substitution is L134I, L134V, L134P, L134T.

In another embodiment, the second modification is a substitution in the position corresponding to position 137 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 137A, 137D, 137W. In an embodiment, the substitution is S137A, S137D, S137W.

In another embodiment, the second modification is a substitution in the position corresponding to position 139 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 139I, 139K, 139A. In an embodiment, the substitution is N139I, N139K, N139A.

In another embodiment, the second modification is a substitution in the position corresponding to position 143 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 143T, 143S, 143R. In an embodiment, the substitution is Q143T, Q143S, Q143R.

In another embodiment, the second modification is a substitution in the position corresponding to position 155 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 155H. In an embodiment, the substitution is Y155H.

In another embodiment, the second modification is a substitution in the position corresponding to position 160 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 160I, 160F, 160K, 160L, 160N, 160V. In an embodiment, the substitution is R160I, R160F, R160K, R160L, R160N, R160V.

In another embodiment, the second modification is a substitution in the position corresponding to position 161 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 161S, 161T. In an embodiment, the substitution is V161S, V161T.

In another embodiment, the second modification is a deletion or substitution in the position corresponding to position 164 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the deletion or substitution is 164, R164Q. In an embodiment, the deletion is R164, R164Q.

In another embodiment, the second modification is a substitution in the position corresponding to position 165 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 165E, 165D, 165T, 165L. In an embodiment, the substitution is I165E, I165D, I165T, I165L.

In another embodiment, the second modification is a substitution in the position corresponding to position 169 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 169P, 169Q, 169T, 169V. In an embodiment, the substitution is K169P, K169Q, K169T, K169V.

In another embodiment, the second modification is a substitution in the position corresponding to position 170 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 170E, 170H. In an embodiment, the substitution is T170E, T170H.

In another embodiment, the second modification is a substitution in the position corresponding to position 171 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 171E, 171N, 171I, 171K, 171Q. In an embodiment, the substitution is M171E, M171I, M171K, M171N, M171Q.

In another embodiment, the second modification is a substitution in the position corresponding to position 174 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 174K. In an embodiment, the substitution is P174K.

In another embodiment, the second modification is a substitution in the position corresponding to position 179 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 179S, 179H, 179Q, 179N, 179R. In an embodiment, the substitution is K179S, K179H, K179Q, K179N, K179R.

In another embodiment, the second modification is a substitution in the position corresponding to position 181 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 181T. In an embodiment, the substitution is S181T.

In another embodiment, the second modification is a substitution in the position corresponding to position 183 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 183E. In an embodiment, the substitution is Q183E.

In another embodiment, the second modification is a substitution in the position corresponding to position 184 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 184T. In an embodiment, the substitution is A184T.

In another embodiment, the second modification is a substitution in the position corresponding to position 185 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 184N, 185Q. In an embodiment, the substitution is K185N, K185Q.

In another embodiment, the second modification is a substitution in the position corresponding to position 188 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 188F, 188I, 188Y. In an embodiment, the substitution is M188F, M188I, M188Y.

In another embodiment, the second modification is a substitution in the position corresponding to position 189 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 189S. In an embodiment, the substitution is K189S.

In another embodiment, the second modification is a substitution in the position corresponding to position 192 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 192A, 192V. In an embodiment, the substitution is T192A, T192V.

In another embodiment, the second modification is a substitution in the position corresponding to position 193 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 193W, 193S. In an embodiment, the substitution is N193W, N193S.

In another embodiment, the second modification is a substitution in the position corresponding to position 195 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 195H. In an embodiment, the substitution is S195H.

In another embodiment, the second modification is a substitution in the position corresponding to position 197 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 197A, 197D, 197F, 197M, 197N, 197Y. In an embodiment, the substitution is K197A, K197D, K197F, K197M, K197N, K197Y.

In another embodiment, the second modification is a substitution in the position corresponding to position 210 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 210E, 210F, 210T, 210Q, 210S. In an embodiment, the substitution is A210E, A210Q, A210F, A210T, A210S.

In another embodiment, the second modification is a substitution in the position corresponding to position 213 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 213K, 213Q, 213R. In an embodiment, the substitution is Y213K, Y213Q, Y213R.

In another embodiment, the second modification is a substitution in the position corresponding to position 217 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 217Q. In an embodiment, the substitution is G217Q.

In another embodiment, the second modification is a substitution in the position corresponding to position 218 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 218R. In an embodiment, the substitution is K218R.

In another embodiment, the second modification is a substitution in the position corresponding to position 228 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 228I. In an embodiment, the substitution is M228I.

In another embodiment, the second modification is a substitution in the position corresponding to position 235 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 235L. In an embodiment, the substitution is V235L.

In another embodiment, the second modification is a substitution in the position corresponding to position 242 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 242T. In an embodiment, the substitution is N242T.

In another embodiment, the second modification is a substitution in the position corresponding to position 249 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 249H, 249L, 249Q. In an embodiment, the substitution is E249H, E249L, E249Q.

In another embodiment, the second modification is a substitution in the position corresponding to position 252 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 252G, 252E. In an embodiment, the substitution is K252G, K252E.

In another embodiment, the second modification is a substitution in the position corresponding to position 254 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 254S. In an embodiment, the substitution is G254S.

In another embodiment, the second modification is a substitution in the position corresponding to position 259 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 259V. In an embodiment, the substitution is L259V.

In another embodiment, the second modification is a substitution in the position corresponding to position 260 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 260C. In an embodiment, the substitution is S260C.

In another embodiment, the second modification is a substitution in the position corresponding to position 267 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 267L. In an embodiment, the substitution is K267L.

In another embodiment, the second modification is a substitution in the position corresponding to position 270 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 270C. In an embodiment, the substitution is G270C.

In another embodiment, the second modification is a substitution in the position corresponding to position 272 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 272D. In an embodiment, the substitution is N272D.

In another embodiment, the second modification is a substitution in the position corresponding to position 285 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 285D. In an embodiment, the substitution is E285D.

In another embodiment, the second modification is a substitution in the position corresponding to position 296 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 296A. In an embodiment, the substitution is N296A.

In another embodiment, the second modification is a substitution in the position corresponding to position 301 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 301K. In an embodiment, the substitution is E301K.

In another embodiment, the second modification is a substitution in the position corresponding to position 304 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 304A, 304F, 304Q, 304R, 304S. In an embodiment, the substitution is K304A, K304F, K304Q, K304R, K304S.

In another embodiment, the second modification is a substitution in the position corresponding to position 312 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 312V. In an embodiment, the substitution is A312V.

In another embodiment, the second modification is a substitution in the position corresponding to position 315 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 315A, 315V. In an embodiment, the substitution is T315A, T315V.

In another embodiment, the second modification is a substitution in the position corresponding to position 321 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 321K, 321W. In an embodiment, the substitution is Q321K, Q321W.

In another embodiment, the second modification is a substitution in the position corresponding to position 322 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 322R, 322A, 322D. In an embodiment, the substitution is E322R, E322A, E322D.

In another embodiment, the second modification is a substitution in the position corresponding to position 323 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 323A. In an embodiment, the substitution is H323A.

In another embodiment, the second modification is a substitution in the position corresponding to position 324 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 324K, 324N. In an embodiment, the substitution is H324N.

In another embodiment, the second modification is a substitution in the position corresponding to position 342 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 342G. In an embodiment, the substitution is W342G.

In another embodiment, the second modification is a substitution in the position corresponding to position 344 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 344C. In an embodiment, the substitution is A344C.

In another embodiment, the second modification is a substitution in the position corresponding to position 347 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 347D. In an embodiment, the substitution is P347D.

In another embodiment, the second modification is a substitution in the position corresponding to position 351 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 351V. In an embodiment, the substitution is K351V.

In another embodiment, the second modification is a substitution in the position corresponding to position 352 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 352Q. In an embodiment, the substitution is K352Q.

In another embodiment, the second modification is a substitution in the position corresponding to position 354 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 354W. In an embodiment, the substitution is Y354W.

In another embodiment, the second modification is a substitution in the position corresponding to position 355 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 355Q. In an embodiment, the substitution is R355Q.

In another embodiment, the second modification is a substitution in the position corresponding to position 358 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 358W. In an embodiment, the substitution is Y358W.

In another embodiment, the second modification is a substitution in the position corresponding to position 363 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 363H. In an embodiment, the substitution is E363H.

In another embodiment, the second modification is a substitution in the position corresponding to position 364 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 364D, 364R, 364Y. In an embodiment, the substitution is K364D, K364R, K364Y.

In another embodiment, the second modification is a substitution in the position corresponding to position 368 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 368D. In an embodiment, the substitution is N368D.

In another embodiment, the second modification is a substitution in the position corresponding to position 377 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 377E. In an embodiment, the substitution is V377E.

In another embodiment, the second modification is a substitution in the position corresponding to position 379 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 379K, 379P. In an embodiment, the substitution is E379K, E379P.

In another embodiment, the second modification is a substitution in the position corresponding to position 380 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 380T, 380D. In an embodiment, the substitution is E380T, E380D.

In another embodiment, the second modification is a substitution in the position corresponding to position 391 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 391L. In an embodiment, the substitution is V391L.

In another embodiment, the second modification is a substitution in the position corresponding to position 398 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 398F, 398E. In an embodiment, the substitution is P398F, P398E.

In another embodiment, the second modification is a substitution in the position corresponding to position 403 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 403Q, 403R. In an embodiment, the substitution is S403Q, S403R.

In another embodiment, the second modification is a substitution in the position corresponding to position 414 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 414T, 414S, 414P. In an embodiment, the substitution is F414T, F414S, F414P.

In another embodiment, the second modification is a substitution in the position corresponding to position 417 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 417G, 417E, 417Q. In an embodiment, the substitution is K417G, K417E, K417Q.

In another embodiment, the second modification is a substitution in the position corresponding to position 419 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 419V. In an embodiment, the substitution is K419V.

In another embodiment, the second modification is a substitution in the position corresponding to position 422 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 422R, 422I. In an embodiment, the substitution is V422R, V422I.

In another embodiment, the second modification is a substitution in the position corresponding to position 423 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 423G. In an embodiment, the substitution is A423G.

In another embodiment, the second modification is a substitution in the position corresponding to position 437 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 437I, 437A. In an embodiment, the substitution is Q437I, Q437A.

In another embodiment, the second modification is a substitution in the position corresponding to position 438 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 438A. In an embodiment, the substitution is T438A.

In another embodiment, the second modification is a substitution in the position corresponding to position 440 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 440Q. In an embodiment, the substitution is G440Q.

In another embodiment, the second modification is a substitution in the position corresponding to position 442 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 442N. In an embodiment, the substitution is H442N.

In another embodiment, the second modification is a substitution in the position corresponding to position 443 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 443G. In an embodiment, the substitution is W443G.

In another embodiment, the second modification is a substitution in the position corresponding to position 452 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 452N. In an embodiment, the substitution is D452N.

In another embodiment, the second modification is a substitution in the position corresponding to position 454 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 454I. In an embodiment, the substitution is L454I.

In another embodiment, the second modification is a substitution in the position corresponding to position 462 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 462A, 462R, 462L, 462P. In an embodiment, the substitution is K462A, K462R, K462L, K462P.

In another embodiment, the second modification is a substitution in the position corresponding to position 463 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 463Q. In an embodiment, the substitution is E463Q.

In another embodiment, the second modification is a substitution in the position corresponding to position 466 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 466F, 466H, 466N, 466Q. In an embodiment, the substitution is K466F, K466H, K466N, K466Q.

In another embodiment, the second modification is a substitution in the position corresponding to position 467 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 467H, 467Y. In an embodiment, the substitution is K467H, K467Y.

In another embodiment, the second modification is a substitution in the position corresponding to position 470 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 470Y. In an embodiment, the substitution is N470Y.

In another embodiment, the second modification is a substitution in the position corresponding to position 472 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 472G, 472Y. In an embodiment, the substitution is D472G, D472Y.

In another embodiment, the second modification is a substitution in the position corresponding to position 477 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 477F. In an embodiment, the substitution is L477F.

In another embodiment, the second modification is a substitution in the position corresponding to position 479 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 479R. In an embodiment, the substitution is E479R.

In another embodiment, the second modification is a substitution in the position corresponding to position 480 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 480I. In an embodiment, the substitution is L480I.

In another embodiment, the second modification is a substitution in the position corresponding to position 482 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 482A, 482P, 482D, 482G, 482Q, 482R. In an embodiment, the substitution is K482A, K482P, K482D, K482G, K482Q, K482R.

In another embodiment, the second modification is a substitution in the position corresponding to position 483 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 483A, 483D. In an embodiment, the substitution is G483A, G483D.

In another embodiment, the second modification is a substitution in the position corresponding to position 484 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 484Q. In an embodiment, the substitution is L484Q.

In another embodiment, the second modification is a substitution in the position corresponding to position 487 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 487R, 487G. In an embodiment, the substitution is S487R, S487G.

In another embodiment, the second modification is a substitution in the position corresponding to position 488 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 488I, 488L. In an embodiment, the substitution is P488I, P488L.

In another embodiment, the second modification is a substitution in the position corresponding to position 489 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 489F, 489K, 489N, 489P. In an embodiment, the substitution is R489K, R489F, R489N, R489P.

In another embodiment, the second modification is a substitution in the position corresponding to position 490 of the polypeptide of SEQ ID NO: 1, or of a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide of SEQ ID NO: 1 which has mannanase activity, and further the variant has improved stability compared to the mannanase of SEQ ID NO: 1. In one embodiment, the substitution is 490A. In an embodiment, the substitution is W490A.

In another aspect, a variant comprises a substitution at two or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at three or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at four or more positions corresponding to any of positions:

Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at five or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at six or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at seven or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at eight or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at nine or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at ten or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at eleven or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at twelve or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at thirteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at fourteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at fifteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at sixteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at seventeen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at eighteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at nineteen or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at twenty or more positions corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In another aspect, a variant comprises a substitution at each position corresponding to any of positions: Q168D, Q168F, Q168M, Q168P, F7*, F7A, F7D, F7G, F7I, F7P, T13I, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R and a second modification is a substitution or deletion and is in at least one or more positions corresponding to positions: A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P11I, P11N, H12A, H12D, H12E, H12G, H12L, H12P, H12Q, H12R, H12V, S14Q, S14R, S14E, S14H, S14N, S14V, Q17K, Q17A, N18S, Q19N, I21L, I22V, I22Q, I22T, A23I, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, I165E, I165D, I165T, I165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A.

In one aspect, a variant comprises substitutions at positions corresponding to positions: L413T, K491R, K482D, R489N and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: Q168D+ L454I, Q168D+ L413A, K26E+ Q168D, E64P+ Q168D, K26H+ Q168D, Q17A+ Q168D, A23M+ Q168D, S103V+ Q168D, S103E+ Q168D, Q69P+ Q168D, H12A+ Q168D, K65S+ Q168D, N97Y+ Q168D, Q168D+ K304F, Q168D+ K179V, M130V+ Q168D, D410M+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ N296A, Q168D+ D385P+ L413A, Q168D+ Q183E+ L413A, R38Q+ Q168D+ D385F, K26E+ Q168D+ N283Y, R38Q+ Q168D+ L413T, R38Q+ Q168D+ T192V, R38Q+ Q168D+ S239A, K26E+ Q168D+ K408T, K26E+ Q168D+ K197F, K26E+ Q168D+ L413T, K26E+ Q168D+ D385A, K26E+ Q168D+ R355Q, K26E+ Q168D+ P347D, K26E+ Q168D+ G483D, K26E+ Q168D+ T192V, K26E+ Q168D+ A210E, K26E+ Q168D+ N193S, K26E+ Q168D+ S239A, K26E+ Q69P+ Q168D, K26E+ E61D+ Q168D, K26E+ K36E+ Q168D, K26E+ R38M+ Q168D, K26E+ K36T+ Q168D, K26E+ E64P+ Q168D, H12D+ K26E+ Q168D, K26E+ K70E+ Q168D, K26E+ T42E+ Q168D, K26E+ T53C+ Q168D, K26E+ T53P+ Q168D, K26E+ K70M+ Q168D, K26E+ K70P+ Q168D, K26E+ S72F+ Q168D, K26E+ A101I+ Q168D, K26E+ A101L+ Q168D, K26E+ S103E+ Q168D, K26E+ S103I+ Q168D, K26E+ Q168D+ Y354W, K26E+ Q168D+ L413V, K26E+ Q168D+ E249L, K26E+ R38L+ Q168D, K26E+ Q168D+ R489P, K26E+ Q168D+ L477F, K26E+ Q168D+ K491P, K26E+ Q168D+ N283M, K26E+ Q168D+ Y195H, D410M+ L413T+ K466F, K408M+ D410M+ L413T, D410M+ L413T+ N473Y and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: Q168D+ E249Q+ N283Y+ L413A, K26E+ Q168D+ N283Y+ N296A, K26E+ Q168D+ Q183E+ L413A, K26E+ Q168D+ S271Y+ L454I, K26E+ Q168D+ E249L+ P347D, K26E+ Q168D+ L259F+ S271G, K26E+ Q168D+ L259F+ N283Y, K26E+ T53E+ E61D+ Q168D, K26E+ T53E+ E64P+ Q168D, K26E+ T53E+ K65N+ Q168D, K26E+ R38T+ Q168D+ D385A, K26E+ S103V+ Q168D+ D385A, K26E+ K36T+ Q168D+ D385A, K26E+ R38M+ Q168D+ D385A, K26E+ K36A+ Q168D+ D385A, K26E+ R38L+ Q168D+ D385A, K26E+ S103C+ Q168D+ D385A, K26E+ K70M+ Q168D+ D385A, K26E+ S103I+ Q168D+ D385A, K26E+ K70I+ Q168D+ D385A, K26E+ R38F+ Q168D+ D385A, K26E+ S103Q+ Q168D+ D385A, K26E+ A101C+ Q168D+ D385A, K26E+ K70E+ Q168D+ D385A, K26E+ A101L+ Q168D+ D385A, K26E+ K36C+ Q168D+ D385A, K26E+ S103D+ Q168D+ D385A, K26E+ K70T+ Q168D+ D385A, K26E+ A101Q+ Q168D+ D385A, K26E+ K65N+ Q168D+ D385A, K26E+ K100R+ Q168D+ D385A, K26E+ S103L+ Q168D+ D385A, K26E+ K36M+ Q168D+ D385A, K26E+ T53P+ Q168D+ D385A, K26E+ A101N+ Q168D+ D385A, K26E+ K36D+ Q168D+ D385A, K26E+ T53C+ Q168D+ D385A, K26E+ K65T+ Q168D+ D385A, K26E+ R38L+ K70P+ Q168D, K26E+ T42E+ Q69P+ Q168D, K26E+ Q168D+ N283Y+ K408S, K26E+ K70P+ Q168D+ D385A, K26E+ K70P+ Q168D+ E249L, K26E+ K70P+ Q168D+ Y354W, K26E+ K70P+ Q168D+ L413V, K26E+ S103E+ Q168D+ D385A, K26E+ S103E+ Q168D+ L413V, K26E+ Q168D+ N283Y+ D385A, K26E+ K36E+ Q168D+ D385A, D410M+ L413T+ D472G+ W490A, D385A+ K408M+ D410M+ L413T, D410M+ L413T+ K417Q+ K462P and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: Q168D+ A210E+ N283Y+ L413A+ R489K, K26E+ Q168D+ S181T+ K408C+ K482Q, K26E+ R164A+ Q168D+ S181T+ N296A, K26E+ Q168D+ N283Y+ N296A+ S403Q, K169P+ Q183E+ S260C+ N283Y+ L413A, K26E+ Q168D+ N296A+ D385F+ K482Q, K26E+ Q168D+ A210Q+ S271Y+ V377E, K26E+ Q168D+ A210Q+ S271Y+ L454I, K26E+ Q168D+ F190Y+ N242T+ T315A, K26E+ Q168D+ Y213K+ S260C+ G366H, K26E+ Q168D+ K252E+ R253W+ K378H, K26E+ Q168D+ A210E+ S271G+ N283Y, K26E+ Q168D+ A210E+ L259F+ S271G, K26E+ R38L+ K70P+ A101L+ Q168D, K26E+ R38C+ A126S+ Q168D+ D385A, K26E+ A101V+ S103Y+ Q168D+ D385A, V4D+ K26E+ K65T+ K120P+ Q168D, H12D+ Q17A+ K26E+ E64P+ Q168D, K26E+ A101E+ Q168D+ K197A+ K408S, K26E+ T42E+ Q69P+ Q168D+ D385A, K26E+ Q168D+ N283Y+ D385A+ K408S, K26E+ Q168D+ K197A+ N283Y+ K408S, K26E+ K36E+ E64P+ Q168D+ D385A, K26E+ K36E+ S103V+ Q168D+ D385A, K26E+ K36E+ Q168D+ D385A+ K417Q, K26E+ K70A+ S103V+ Q168D+ D385A, K26E+ K70M+ S103V+ Q168D+ D385A, K26E+ K70I+

S103V+ Q168D+ D385A, K26E+ S103V+ K120P+ Q168D+ D385A, K26E+ K36E+ T53P+ Q168D+ D385A, K26E+ K36T+ S103V+ Q168D+ D385A, K26E+ R38M+ S103V+ Q168D+ D385A, K26E+ T42E+ S103V+ Q168D+ D385A, K26E+ T53P+ S103V+ Q168D+ D385A, K26E+ K36E+ K70A+ Q168D+ D385A, K26E+ K36E+ K70P+ Q168D+ D385A, K26E+ K36E+ S72F+ Q168D+ D385A, K26E+ K36E+ A101L+ Q168D+ D385A, K26E+ K70P+ Q168D+ K197F+ N283Y, K26E+ K70P+ S103V+ Q168D+ D385A, N283Y+ D385A+ K408M+ D410M+ L413T, T315V+ D385A+ K408M+ D410M+ L413T, D385A+ K408M+ D410M+ L413T+ P488I, D385A+ K408M+ D410M+ L413T+ P488L, K378Q+ D385A+ K408M+ D410M+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ A210E+ S271G+ N283Y+ N296A, K26E+ Q168D+ A210Q+ E249Q+ S271Y+ N296A, K26E+ Q168D+ K252E+ N296A+ A344C+ D385P, K26E+ R164H+ Q168D+ F190Y+ S271G+ N296A, K26E+ Q168D+ F190Y+ S239A+ S271G+ N296A, K26E+ Q168D+ N283Y+ N296A+ S403Q+ L413T, K26E+ K36N+ Q168D+ K198N+ L413A+ N473F, Q168D+ Q183E+ K252E+ R253W+ K408T+ L413A, K26E+ Q168D+ A210Q+ S239A+ E249Q+ K364Y, K26E+ Q168D+ A184T+ F190Y+ N242T+ T315A, K26E+ Q168D+ K197N+ K252E+ R253W+ K408T, K26E+ Q168D+ K197N+ K252E+ R253W+ K378H, V4D+ K26E+ T53P+ K120P+ Q168D+ D385A, K26E+ K36E+ S72F+ Q168D+ D385A+ W443G, K26E+ K36E+ K70P+ K120P+ Q168D+ D385A, K26E+ T42E+ Q69P+ S103V+ Q168D+ D385A, K26E+ K36E+ S103V+ Q168D+ F190Y+ D385A, K26E+ K36E+ S103V+ Q168D+ S271G+ D385A, K26E+ K36E+ S103V+ Q168D+ D385A+ L413V, K26E+ K36E+ S103V+ Q168D+ D385A+ K417Q, K26E+ K36E+ S103V+ Q168D+ D385A+ K462L, K26E+ K36E+ S103V+ Q168D+ D385A+ K408T, K26E+ K36E+ S103V+ K120P+ Q168D+ D385A, K26E+ R38L+ K70P+ A101L+ Q168D+ N283Y, K26E+ R38L+ K70P+ A101L+ Q168D+ K408D, K26E+ R38L+ K70P+ A101L+ Q168D+ L413A, K26E+ R38L+ K70P+ A101L+ Q168D+ L413T, K26E+ R38L+ K70P+ A101L+ S109D+ Q168D, K26E+ R38L+ K70P+ A101L+ Q168D+ D385A, K26E+ K70P+ Q168D+ N283Y+ K408S+ L413T, K26E+ K70P+ Q168D+ N283Y+ D385A+ S403Q, K26E+ K70A+ S103V+ Q168D+ K197A+ D385A, K26E+ K70A+ S103V+ Q168D+ D385A+ K462P, K26E+ E64P+ K70A+ S103V+ Q168D+ D385A, K26E+ K36T+ K70A+ S103V+ Q168D+ D385A, K26E+ K70A+ S103V+ Q168D+ K304R+ D385A, N283Y+ D385A+ K408M+ D410M+ L413T+ R489N, N283Y+ D385A+ K408M+ D410M+ L413T+ K482D, N283Y+ D385A+ K408M+ D410M+ L413T+ S487G, N283Y+ K378D+ D385A+ K408M+ D410M+ L413T, N283Y+ K378Q+ D385A+ K408M+ D410M+ L413T, N283Y+ D385A+ K408M+ D410M+ L413T+ N473Y, S271G+ N283Y+ D385A+ K408M+ D410M+ L413T, K378Q+ D385A+ K408M+ D410M+ L413T+ N473Y, K378Q+ D385A+ K408M+ D410M+ L413T+ R489N and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ A210E+ S260C+ N283Y+ N296A+ K482Q, K26E+ Q168D+ A210E+ S260C+ S271G+ N283Y+ N296A, K26E+ Q168D+ A210Q+ S239A+ E249Q+ S271Y+ N296A, K26E+ Q168D+ A184T+ N242T+ N296A+ E380D+ T438A, K26E+ R164A+ Q168D+ S181T+ N296A+ K408S+ L413V, K26E+ R164A+ Q168D+ S181T+ N296A+ Q321W+ K408S, K26E+ Q168D+ Y213K+ K252E+ E285D+ N296A+ D385P, K26E+ Q168D+ T192A+ Y213K+ N296A+ A344C+ D385P, K26E+ Q168D+ S271G+ N296A+ Y354W+ V377E+ K408A, K26E+ Q168D+ N283Y+ N296A+ D385S+ S403Q+ K408C, K26E+ Q168D+ N283Y+ N296A+ S403Q+ K408C+ L413T, K26E+ Q168D+ S181T+ E249Q+ N283Y+ D385A+ L413A, K26E+ Q168D+ A184T+ F190Y+ N242T+ E322D+ H323A, K26E+ Q168D+ A184T+ F190Y+ N242T+ T315A+ E380D, K26E+ Q168D+ F190Y+ N242T+ N283Y+ E322D+ H323A, K26E+ Q168D+ A210E+ N283Y+ D385A+ L413A+ R489K, K26E+ Q168D+ S181T+ A210E+ N283Y+ L413A+ R489K, K26E+ Q168D+ A210E+ L259F+ S271G+ N283Y+ R489K, K26E+ Q168D+ N283Y+ D385A+ K408S+ D452N+ K466Q, V4D+ K26E+ T53P+ K65Q+ K120P+ Q168D+ D385A, H12D+ Q17A+ K26E+ E64P+ A111L+ Q168D+ D385A, H12D+ Q17A+ K26E+ E64P+ V68T+ Q168D+ D385A, K26E+ K36E+ K70P+ S103V+ K120P+ Q168D+ D385A, F25Y+ K36E+ T53P+ S103V+ Q168D+ T192V+ D385A, K26E+ R38L+ K70P+ A101L+ A126T+ Q168D+ E379P, K26E+ K70P+ Q168D+ K197A+ K408S+ K462L+ K466Q, K26E+ K70P+ Q168D+ K197F+ N283Y+ K408S+ L413T, H12D+ K26E+ R38L+ T42E+ K70P+ A101L+ Q168D, K26E+ K36E+ S103V+ Q168D+ D385A+ L413V+ K462L, K26E+ K36E+ S103V+ Q168D+ K197D+ D385A+ K462L, N283Y+ K378D+ D385A+ K408M+ D410M+ L413T+ K482D, S258G+ S271G+ N283Y+ D385A+ K408M+ D410M+ L413T, N283Y+ K378Q+ D385A+ K408M+ D410M+ L413T+ P488L, S271G+ N283Y+ K378Q+ D385A+ K408M+ D410M+ L413T, K378Q+ D385A+ K408M+ D410M+ L413T+

H442N+ N473Y, E299W+ K378Q+ D385A+ K408M+ D410M+ L413T+ N473Y, N283Y+ K378Q+ D385A+ K408M+ D410M+ L413T+ N473Y, N283Y+ E380D+ D385A+ K408M+ D410M+ L413T+ G440Q, N283Y+ K378Q+ D385A+ K408M+ D410M+ L413T+ H442N, G366H+ K378Q+ D385A+ K408M+ D410M+ L413T+ N473Y and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ A184T+ N296A+ E322D+ H323A+ E380D+ T438A, K26E+ R164A+ Q168D+ S181T+ N296A+ Q321W+ K408S+ L413V, K26E+ Q168D+ K252E+ E285D+ N296A+ A344C+ G366H+ D385P, K26E+ Q168D+ N283Y+ N296A+ D385S+ S403Q+ K408C+ L413T, K26E+ Q168D+ S181T+ K197F+ V235L+ E249Q+ N283Y+ L413A H12D+ Q17A+ K26E+ E64P+ V68T+ A111L+ Q168D+ D385A, H12D+ K26E+ T42E+ E64P+ K70P+ S103V+ Q168D+ D385A, K26E+ K36E+ E64P+ K70P+ S103V+ Q168D+ N283Y+ D385A, K26E+ K36E+ T53P+ K65Q+ Q168D+ F190Y+ K197A+ D385A, N283Y+ K378D+ D385A+ S403Q+ K408M+ D410M+ L413T+ K482D, K378Q+ D385A+ K408M+ D410M+ L413T+ N473Y+ K482R+ K491E, S258G+ S271G+ N283Y+ K378Q+ D385A+ K408M+ D410M+ L413A, S271G+ N283Y+ K378Q+ D385A+ K408M+ D410M+ L413T+ H442N, S258G+ S271G+ N283Y+ K378Q+ D385A+ K408M+ D410M+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ A184T+ N242T+ N296A+ E322D+ H323A+ E380D+ T438A, H12D+ K26E+ K36E+ T42E+ E64P+ K70P+ A101L+ Q168D+ D385A, K26E+ K36E+ E64P+ K70P+ S103V+ Q168D+ T192V+ N283Y+ D385A, K26E+ K36E+ E64P+ K70P+ S103V+ E162D+ Q168D+ N283Y+ D385A, K26E+ K36E+ E64P+ K70P+ S103V+ S109D+ Q168D+ N283Y+ D385A, K26E+ K36E+ E64P+ K70P+ S103V+ Q168D+ K197Y+ N283Y+ D385A, K26E+ K36E+ E64P+ K70P+ S103V+ Q168D+ N283Y+ D385A+ L477F, K26E+ K36E+ E64P+ K70P+ S103V+ Q168D+ N283Y+ D385A+ L413T, F25Y+ K26E+ K36E+ T53P+ S103V+ Q168D+ T192V+ D385A+ K462L, K26E+ K36E+ E64P+ S103V+ K120P+ Q168D+ N283Y+ D385A+ K462L, K26E+ K36E+ E64P+ K70P+ S103V+ K169T+ N283Y+ D385A+ L477F, K26E+ K36E+ E64P+ Q69P+ S103V+ Q168D+ N283Y+ D385A+ L477F, S271G+ N283Y+ E299W+ K378Q+ D385A+ K408M+ D410M+ L413T+ N473Y, S271G+ N283Y+ K378Q+ D385A+ K408M+ D410M+ L413T+ H442D+ S487R, S271G+ N283Y+ E299W+ K378D+ D385A+ K408M+ D410M+ L413T+ N473Y, S258G+ 269+ S271G+ N283Y+ K378Q+ D385A+ K408M+ D410M+ L413T, S258G+ S271G+ N283Y+ K378Q+ D385A+ K408M+ D410M+ L413T+ + G440Q, M248I+ S258G+ S271G+ N283Y+ K378Q+ D385A+ K408M+ D410M+ L413T, S258G+ S271G+ N283Y+ K378Q+ D385A+ K408M+ D410M+ L413T+ G440Q T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ Q168D+ A184T+ N242T+ N296A+ E322D+ H323A+ K364Y+ E380D+ T438A, K26E+ K36E+ E64P+ K70P+ S103V+ Q168D+ F190Y+ N283Y+ D385A+ W443G, K26E+ K36E+ E64P+ K70P+ S103V+ Q168D+ F190Y+ N283Y+ D385A+ L413T, K26E+ K36E+ E64P+ K70P+ S103V+ Q168D+ S271G+ N283Y+ D385A+ L413T, K26E+ K36E+ E64P+ K70P+ S103V+ Q168D+ N283Y+ D385A+ K408T+ L413T, K26E+ K36E+ E64P+ K70P+ S103V+ Q168D+ T192V+ N283Y+ D385A+ L413T, K26E+ K36E+ E64P+ K70P+ S103V+ Q168D+ N283Y+ D385A+ L413T+ K462P, K26E+ K36E+ E64P+ K70P+ S103V+ E162D+ Q168D+ N283Y+ D385A+ L413T, K26E+ K36E+ E64P+ K70P+ S103V+ S109D+ Q168D+ N283Y+ D385A+ L413T, K26E+ K36E+ E64P+ K70P+ S103V+ Q168D+ N283Y+ D385A+ L413T+ K466Q, V4Y+ K26E+ K36E+ E64P+ K70P+ S103V+ Q168D+ N283Y+ D385A+ L413T, K26E+ K36E+ D48A+ E64P+ K70P+ S103V+ Q168D+ N283Y+ D385A+ L413T, K26E+ K36E+ E64P+ K70P+ S103V+ P163E+ Q168D+ N283Y+ D385A+ L413T, K26E+ K36E+ E64P+ K70P+ S103V+ Q168D+ K197D+ N283Y+ D385A+ L413T, K26E+ K36E+ E64P+ K70P+ S103V+

Q168D+ N283Y+ D385A+ L413T+ K417E, K26E+ K36E+ E64P+ K70P+ S103V+ Q168D+ N283Y+ D385A+ L413T+ L477F, F25Y+ K36E+ T53P+ E64P+ K70P+ S103V+ Q168D+ T192V+ N283Y+ D385A, K26E+ K36E+ T53P+ E64P+ K70P+ S103V+ Q168D+ T192V+ N283Y+ D385A, K26E+ K36E+ E64P+ K70P+ S103V+ Q168D+ K197D+ N283Y+ D385P+ L413T, K26E+ K36E+ E64P+ K70P+ S103V+ Q168F+ K197D+ N283Y+ D385A+ L413T, K26E+ K36E+ E64P+ K70P+ S103V+ Q168M+ K197D+ N283Y+ D385A+ L413T, K26E+ K36E+ E64P+ K70P+ S103V+ K169V+ K197D+ N283Y+ D385A+ L413T, K26E+ K36E+ E64P+ K70P+ S103V+ E162D+ Q168D+ N283Y+ D385A+ L477F, K26E+ K36E+ E64P+ K70P+ S103V+ E162Q+ Q168D+ N283Y+ D385A+ L477F, K26E+ K36E+ E64P+ K70P+ S103V+ I165A+ Q168D+ N283Y+ D385A+ L477F, K26E+ K36E+ E64P+ K70P+ S103V+ T166P+ Q168D+ N283Y+ D385A+ L477F, K26E+ K36E+ E64P+ K70P+ S103V+ K169T+ N283Y+ D385A+ L413T+ L477F, K26E+ K36E+ E64P+ Q69T+ S103V+ Q168D+ N283Y+ D385A+ L413T+ L477F, K26E+ K36E+ E64P+ Q69R+ S103V+ Q168D+ N283Y+ D385A+ L413T+ L477F, K26E+ K36E+ E64P+ K70P+ S103V+ Q168P+ N283Y+ D385A+ L413T+ L477F, M172I+ K197D+ M248I+ S258G+ S271G+ N283Y+ D385A+ K408M+ D410M+ L413T, S271G+ N283Y+ K378Q+ D385A+ K408M+ D410M+ L413T+ H442D+ K482D+ S487R, S239A+ M248I+ S258G+ S271G+ N283Y+ K378Q+ D385A+ K408M+ D410M+ L413T, S271G+ N283Y+ E299W+ K378D+ D385A+ K408M+ D410M+ L413T+ N473Y+ K482Q, S258G+ S271G+ R280K+ N283Y+ K378Q+ D385A+ K408M+ D410M+ L413T+ G440Q, M248I+ S258G+ S271G+ N283Y+ K378Q+ D385A+ K408M+ D410M+ L413T+ G440Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: K26E+ K36E+ T53P+ E64P+ K70P+ A101I+ Q168D+ N283Y+ D385A+ K408S+ L413T, F25Y+ K36E+ T53P+ E64P+ K70P+ S103V+ Q168D+ T192V+ K197N+ N283Y+ D385A, F25Y+ K36E+ T53P+ E64P+ K70P+ S103V+ E162D+ Q168D+ T192V+ N283Y+ D385A, S14N+ K26E+ K36E+ E64P+ K70P+ S103V+ Q168D+ K197D+ N283Y+ D385A+ L413T, K26E+ K36E+ E64P+ K70P+ S103V+ Q168D+ M172I+ K197D+ N283Y+ D385A+ L413T, K26E+ K36E+ E64P+ K70P+ S103V+ T167K+ Q168D+ K197D+ N283Y+ D385A+ L413T, K26E+ K36E+ E64P+ K70P+ S103V+ I165L+ Q168D+ K197D+ N283Y+ D385A+ L413T, K26E+ K36E+ E64P+ K70P+ S103V+ T166P+ Q168D+ K197D+ N283Y+ D385A+ L413T, K26E+ K36E+ E64P+ K70P+ S103V+ P163N+ Q168D+ K197D+ N283Y+ D385A+ L413T, K26E+ K36E+ E64P+ K70P+ S103V+ R164H+ Q168D+ K197D+ N283Y+ D385A+ L413T, S14N+ K26E+ K36E+ E64P+ Q69S+ S103V+ Q168D+ K197D+ N283Y+ D385A+ L413T, S14N+ K26E+ K36E+ E64P+ K70P+ S103V+ K169P+ K197D+ N283Y+ D385A+ L413T, K26E+ K36E+ E64P+ K70P+ S103V+ Q168D+ K169Q+ N283Y+ D385A+ L413T+ L477F, H12P+ K26E+ K36E+ E64P+ K70P+ S103V+ Q168D+ N283Y+ D385A+ L413T+ L477F, K26E+ K36E+ E64P+ K70P+ S103V+ T166L+ Q168D+ N283Y+ D385A+ L413T+ L477F, K26E+ K36E+ E64P+ K70P+ S103V+ T166Q+ Q168D+ N283Y+ D385A+ L413T+ L477F, K26E+ K36E+ E64P+ K70P+ S103V+ T166V+ Q168D+ N283Y+ D385A+ L413T+ L477F, K26E+ K36E+ E64P+ K70P+ S103V+ T166G+ Q168D+ N283Y+ D385A+ L413T+ L477F, K26E+ K36E+ E64P+ K70P+ S103V+ T166N+ Q168D+ N283Y+ D385A+ L413T+ L477F, K26E+ K36E+ E64P+ K70P+ S103V+ T166I+ Q168D+ N283Y+ D385A+ L413T+ L477F, K26E+ K36E+ E64P+ K70P+ S103V+ T166W+ Q168D+ N283Y+ D385A+ L413T+ L477F, K26E+ K36E+ E64P+ K70P+ S103V+ T166R+ Q168D+ N283Y+ D385A+ L413T+ L477F, K26E+ K36E+ E64P+ K70P+ S103V+ T166E+ Q168D+ N283Y+ D385A+ L413T+ L477F, K26E+ K36E+ S57R+ E64P+ K70P+ S103V+ Q168D+ N283Y+ D385A+ L413T+ L477F, K26E+ K36E+ S57P+ E64P+ K70P+ S103V+ Q168D+ N283Y+ D385A+ L413T+ L477F, K26E+ K36E+ E64P+ K70P+ S103V+ T166P+ Q168D+ K197Y+ N283Y+ D385A+ L413T, K26E+ K36E+ E64P+ K70P+ S103V+ T166P+ Q168D+ N283Y+ D385A+ L413T+ L477F, K26E+ K36E+ E64P+ K70P+ S103V+ I165D+ Q168D+ K197D+ N283Y+ D385A+ L413T, K26E+ K36E+ E64P+ K70P+ S103V+ T166P+ Q168D+ F190Y+ N283Y+ D385A+ L477F, K26E+ K36E+ E64P+ K70P+ S103V+ T166P+ Q168D+ T192V+ N283Y+ D385A+ L477F, V4D+ K26E+ K36E+ E64P+ K70P+ S103V+ T166P+ Q168D+ N283Y+ D385A+ L477F, S258G+ S271G+ N283Y+ K378Q+ D385A+ K408M+ D410M+ L413T+ H442N+ K466N+ K482G, S258G+ S271G+ N283Y+ E299W+ K378Q+ D385A+ K408M+ D410M+ L413T+ N473Y+ K491R, K26E+ K36E+ E64P+ K70P+ S103V+ T166P+ Q168D+ K197Y+ N283Y+ D385A+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: S14N+ K26E+ K36E+ E64P+ K70P+ S103V+ Q168D+ K197D+ N283Y+ D385A+ D410M+ L413T, S14N+ K26E+ K36E+ E64P+ K70P+ S103V+ Q168D+ K169Q+ K197D+ N283Y+ D385A+ L413T, K26E+ K36E+ E64P+ Q69P+ N97Y+

S103V+ T123R+ Q168D+ K197D+ N283Y+ D385A+ L413T, K26E+ K36E+ E64P+ K70P+ S103V+ T166P+ Q168D+ K197D+ N283Y+ D385A+ D410L+ L413T, K26E+ K36E+ E64P+ K70P+ S103V+ T166P+ Q168D+ K197D+ N283Y+ D385A+ D410M+ L413T, K26E+ K36E+ E64P+ K70P+ S103V+ E162D+ T166P+ Q168D+ K197D+ N283Y+ D385A+ L413T, K26E+ K36E+ E64P+ K70P+ S103V+ T166P+ Q168D+ K197D+ N283Y+ D385A+ K408M+ L413T, H12V+ K26E+ K36E+ E64P+ K70P+ S103V+ T166P+ Q168D+ K197D+ N283Y+ D385A+ L413T, S14N+ K26E+ K36E+ E64P+ K70P+ S103V+ T166P+ Q168D+ K197D+ N283Y+ D385A+ L413T, V4Y+ K26E+ K36E+ E64P+ K70P+ S103V+ I165L+ Q168D+ N283Y+ D385A+ L413T+ L477F, K26E+ K36E+ E64P+ K70P+ S103V+ T166P+ Q168D+ M171N+ K197D+ N283Y+ D385A+ L413T, K26E+ K36E+ E64P+ K70P+ S103V+ T166P+ Q168D+ M171Q+ K197D+ N283Y+ D385A+ L413T, K26E+ K36E+ E64P+ K70P+ S103V+ T166P+ Q168D+ M171E+ K197D+ N283Y+ D385A+ L413T, K26E+ K36E+ E64P+ K70P+ S103V+ E162D+ T166P+ Q168D+ K197D+ N283Y+ D385H+ L413T, K26E+ K36E+ E64P+ K70P+ S103V+ T166P+ Q168D+ S178D+ K197D+ N283Y+ D385A+ L413T, K26E+ K36E+ E64P+ K70P+ S103V+ T166P+ Q168D+ K179N+ K197D+ N283Y+ D385A+ L413T, K26E+ K36E+ E64P+ K70P+ S103V+ R164*+ I165*+ Q168D+ K197D+ N283Y+ D385H+ L413T, S178P+ K197D+ S239A+ M248I+ S258G+ S271G+ N283Y+ K378Q+ D385A+ K408M+ D410M+ L413T, S239A+ M248I+ S258G+ S271G+ R280K+ N283Y+ K378Q+ D385A+ K408M+ D410M+ L413T+ G440Q, G217Q+ S239A+ M248I+ S258G+ S271G+ N283Y+ K378Q+ D385A+ K408M+ D410M+ L413T+ G440Q, S239A+ M248I+ S258G+ S271G+ R280K+ N283Y+ K378Q+ D385A+ K408M+ D410M+ L413T+ T438A and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: S14N+ K26E+ K36E+ E64P+ K70P+ S103V+ I165A+ Q168D+ K197D+ N283Y+ D385A+ D410M+ L413T, S14N+ K26E+ K36E+ E64P+ K70P+ S103V+ I165L+ Q168D+ K197D+ N283Y+ D385A+ D410M+ L413T, S14N+ K26E+ K36E+ E64P+ K70P+ S103V+ T166P+ Q168D+ K197D+ N283Y+ D385A+ D410M+ L413T, V4D+ S14N+ K26E+ K36E+ E64P+ K70P+ S103V+ Q168D+ K197D+ N283Y+ D385A+ D410M+ L413T, S14N+ K26E+ K36E+ E64P+ K70P+ S103V+ P163N+ Q168D+ K197D+ N283Y+ D385A+ D410M+ L413T, S15Q+ K26E+ K36E+ E64P+ K70P+ S103V+ G112V+ T166P+ Q168D+ K197D+ N283Y+ D385A+ L413T, F25Y+ K26E+ K36E+ E64P+ K70P+ S103V+ T166P+ Q168D+ K197D+ N283Y+ D385A+ L413T+ L477F, K26E+ K36E+ E64P+ K70P+ S103V+ T166P+ Q168D+ T170H+ K197D+ N283Y+ D385A+ D410M+ L413T, S15Q+ K26E+ K36E+ E64P+ K70P+ S103V+ T166P+ Q168D+ K197D+ N283Y+ D385A+ D410M+ L413T, K26E+ K36E+ E64P+ K70P+ S103V+ E162D+ T166P+ Q168D+ K197D+ N283Y+ T315V+ D385A+ L413T, K26E+ K36E+ E64P+ K70P+ S103V+ E162D+ T166P+ Q168D+ K197D+ N283Y+ D385A+ K408A+ L413T, K26E+ K36E+ E64P+ K70P+ S103V+ E162D+ T166P+ Q168D+ K197D+ N283Y+ D385A+ K408Q+ L413T, H12E+ K26E+ K36E+ E64P+ K70P+ S103V+ E162D+ T166P+ Q168D+ K197D+ N283Y+ D385A+ L413T, H12R+ K26E+ K36E+ E64P+ K70P+ S103V+ E162D+ T166P+ Q168D+ K197D+ N283Y+ D385A+ L413T, H12V+ K26E+ K36E+ E64P+ K70P+ S103V+ E162D+ T166P+ Q168D+ K197D+ N283Y+ D385A+ L413T, S14N+ K26E+ K36E+ E64P+ K70P+ S103V+ E162D+ T166P+ Q168D+ K197D+ N283Y+ D385A+ L413T, K26E+ K36E+ E64P+ Q69P+ K70P+ S103V+ E162D+ T166P+ Q168D+ K197D+ N283Y+ D385A+ L413T, K26E+ K36E+ E64P+ K70P+ S103V+ T166P+ Q168D+ S178P+ K197D+ N283Y+ D385A+ D410M+ L413T, K26E+ K36E+ E64P+ K70P+ S103V+ E162D+ T166P+ Q168D+ K197D+ S271G+ N283Y+ D385A+ L413T, S15Q+ K26E+ K36E+ E64P+ K70P+ S103V+ E162D+ T166P+ Q168D+ K197D+ N283Y+ D385A+ L413T, K26E+ K36E+ E64P+ K70P+ S103V+ T166P+ Q168D+ M171Q+ K197D+ N283Y+ D385A+ K408Q+ L413T, H12R+ K26E+ K36E+ E64P+ K70P+ S103V+ T166P+ Q168D+ M171Q+ K197D+ N283Y+ D385A+ L413T, K26E+ K36E+ E64P+ K70P+ S103V+ E162D+ T166P+ Q168D+ K197D+ S271G+ N283Y+ D385H+ L413T, K26E+ K36E+ E64P+ K70P+ S103V+ E162D+ T166P+ Q168D+ M172I+ K197D+ N283Y+ D385H+ L413T, K26E+ K36E+ E64P+ K70P+ S103V+ E162D+ T166P+ Q168D+ K197D+ M248I+ N283Y+ D385H+ L413T, F25Y+ K26E+ K36E+ E64P+ K70P+ S103V+ E162D+ T166P+ Q168D+ K197D+ N283Y+ D385H+ L413T, V4N+ K26E+ K36E+ E64P+ K70P+ S103V+ E162D+ T166P+ Q168D+ K197D+ N283Y+ D385H+ L413T, S15Q+ K26E+ K36E+ E64P+ K70P+ S103V+ E162D+ T166P+ Q168D+ K197D+ N283Y+ D385H+ L413T, S239A+ M248I+ S258G+ S271G+ R280K+ N283Y+ W342G+ K378Q+ D385A+ K408M+ D410M+ L413T+ G440Q, S239A+ M248I+ S258G+ S271G+ N283Y+ E299W+ K378Q+ D385A+ K408M+ D410M+ L413T+ N473Y+ K491R, K197D+ S239A+ M248I+ S258G+ S271G+ R280K+ N283Y+ K378Q+ D385A+ K408M+ D410M+ L413T+ T438A, Q214R+ S239A+ M248I+ S258G+ S271G+ N283Y+ E299W+ K378Q+ D385A+ K408M+ D4100M+ L413T+ N473Y and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: S14N+ K26E+ K36E+ T53P+ E64P+ K70P+ S103V+ R160N+ T166P+ Q168D+ K197D+ N283Y+ D385A+ L413T, S15Q+ K26E+ K36E+ E64P+ K70P+ S103V+ T166P+ Q168D+ K197D+ S271G+ N283Y+ D385A+ D410M+ L413T, S15Q+ K26E+ K36E+ E64P+ K70P+ S103V+ T166P+ Q168D+ K197D+ M248I+ N283Y+ D385A+ D410M+ L413T, S15Q+ K26E+ K36E+ T53P+ E64P+ K70P+ S103V+ T166P+ Q168D+ K197D+ N283Y+ D385A+ D410M+ L413T, S15Q+ K26E+ K36E+ E64P+ K70P+ S103V+ P163N+ T166P+ Q168D+ K197D+ N283Y+ D385A+ D4100M+ L413T, H12R+ K26E+ K36E+ E64P+ K70P+ S103V+ T166P+ Q168D+ M171Q+ F190Y+ K197D+ N283Y+ D385A+ L413T, H12R+ K26E+ K36E+ E64P+ K70P+ S103V+ T166P+ Q168D+ M171Q+ K197D+ S271G+ N283Y+ D385A+ L413T, H12R+ K26E+ K36E+ E64P+ K70P+ S103V+ E162D+ T166P+ Q168D+ M171Q+ K197D+ N283Y+ D385A+ L413T, H12R+ K26E+ K36E+ E64P+ K70P+ S103V+ T166P+ Q168D+ M171Q+ K197D+ N283Y+ D385A+ K408M+ L413T, K26E+ K36E+ E64P+ K70P+ S103V+ T166P+ Q168D+ T170H+ S178P+ K197D+ N283Y+ D385A+ D410M+ L413T, H12R+ K26E+ K36E+ K65H+ K70P+ S103V+ T166P+ Q168D+ M171Q+ K197D+ S271G+ N283Y+ D385A+ L413T, H12R+ K26E+ K36E+ K65H+ K70P+ S103V+ T166P+ Q168D+ T170H+ K197D+ S271G+ N283Y+ D385A+ L413T, M248I+ S258G+ S271G+ N283Y+ E299W+ G366H+ K378Q+ D385A+ K408M+ D410M+ L413T+ H442N+ N473Y+ K491R, Q214R+ S239A+ M248I+ S258G+ S271G+ N283Y+ E299W+ K378Q+ D385A+ K408M+ D4100M+ L413T+ N473Y+ K491R, Q214R+ S239A+ M248I+ S258G+ S271G+ R280K+ N283Y+ K304Q+ K378Q+ D385A+ K408M+ D410M+ L413T+ G440Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: S15Q+ K26E+ K36E+ E64P+ K70P+ S103V+ T166P+ Q168D+ K197D+ M248I+ S271G+ N283Y+ D385A+ D410M+ L413T, H12R+ K26E+ K36E+ E64P+ K70P+ S103V+ T166P+ Q168D+ M171Q+ K197D+ A210E+ N283Y+ E322D+ D385A+ L413T, S15Q+ K26E+ K36E+ E64P+ K70P+ S103V+ T166P+ Q168D+ K197D+ M248I+ S271G+ N283Y+ D385A+ D410M+ L413T, S14N+ K26E+ K36E+ L49M+ E64P+ K70P+ S103V+ E162D+ T166P+ Q168D+ K197D+ N283Y+ D385A+ K408A+ L413T, H12R+ K26E+ K36E+ E64P+ K70P+ S103V+ T166P+ Q168D+ M171Q+ F190Y+ K197D+ S271G+ N283Y+ D385A+ L413T, H12R+ K26E+ K36E+ E64P+ K70P+ S103V+ T166P+ Q168D+ M171Q+ K197D+ M248I+ S271G+ N283Y+ D385A+ L413T, H12R+ K26E+ K36E+ E64P+ K70P+ S103V+ T166P+ Q168D+ M171Q+ K197D+ S271G+ N283Y+ D385A+ K408M+ L413T, H12R+ K26E+ K36E+ E46Y+ E64P+ K70P+ S103V+ T166P+ Q168D+ M171Q+ K197D+ S271G+ N283Y+ D385A+ L413T, S15Q+ K26E+ K36E+ E64P+ K70P+ S103V+ I165D+ Q168D+ K197D+ M248I+ S271G+ N283Y+ D385A+ D410M+ L413T, S14N+ K26E+ K36E+ L49M+ E64P+ K70P+ S103V+ E162D+ T166P+ Q168D+ K197D+ N283Y+ D385A+ K408E+ L413T, S14N+ K26E+ K36E+ L49M+ E64P+ K70P+ S103V+ E162D+ T166P+ Q168D+ K197D+ N283Y+ D385A+ K408M+ L413T, H12R+ K26E+ K36E+ K65H+ K70P+ S103V+ E162D+ T166P+ Q168D+ M171Q+ K197D+ S271G+ N283Y+ D385A+ L413T, H12R+ K26E+ K36E+ E46Y+ E64P+ K70P+ S103E+ T166P+ Q168D+ M171Q+ K197D+ S271G+ N283Y+ D385A+ L413T, H12R+ K26E+ K36E+ E46Y+ E64P+ K70P+ S103D+ T166P+ Q168D+ M171Q+ K197D+ S271G+ N283Y+ D385A+ L413T, S15Q+ K26E+ K36E+ E64P+ K70P+ S103V+ P163N+ T166P+ Q168D+ K197D+ S271G+ N283Y+ D385A+ D410M+ L413T, S15Q+ K26E+ K36E+ E64P+ K70P+ S103V+ T166P+ Q168D+ K197D+ S271G+ N283Y+ D385A+ S403R+ D410M+ L413T, F190Y+ K197D+ Q214R+ S239A+ M248I+ S258G+ S271G+ N283Y+ E299W+ K378Q+ D385A+ K408M+ D410M+ L413T+ N473Y, Q214R+ S239A+ M248I+ S258G+ S271G+ N283Y+ E299W+ K378Q+ D385A+ K408M+ D410M+ L413T+ V422I+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: H12R+ K26E+ K36E+ E64P+ K70P+ S103V+ K129M+ E162D+ T166P+ Q168D+ M171Q+ K197D+ S271G+ N283Y+ D385A+ L413T, S15Q+ K26E+ K36E+ E64P+ K70P+ S103V+ E162D+ T166P+ Q168D+ K197D+ M248I+ S271G+ N283Y+ D385A+ D410M+ L413T, S15Q+ K26E+ K36E+ E64P+ K70P+ S103V+ T166P+ Q168D+ S178P+ K197D+ M248I+ S271G+ N283Y+ D385A+ D410M+ L413T, S15Q+ K26E+ K36E+ E64P+ K70P+ S103V+ T166P+ Q168D+ K197D+ M248I+ S271G+ N283Y+ D385A+ K408M+ D410M+ L413T, S15Q+ K26E+ K36E+ D48S+ E64P+ K70P+ S103V+ T166P+ Q168D+ K197D+ M248I+ S271G+ N283Y+ D385A+ D410M+ L413T, S15Q+ K26E+ K36E+ E64P+ K70P+ S103V+ P163E+ T166P+ Q168D+ K197D+ M248I+ S271G+ N283Y+ D385A+ D410M+ L413T, S14N+ K26E+ K36E+ L49M+ E64P+ K70P+ S103V+ E162D+ T166P+ Q168D+ K197D+ S258G+ N283Y+ D385A+ K408A+ L413T, V4G+ S14N+ K26E+ K36E+ L49M+ E64P+ K70P+ S103V+ E162D+ T166P+ Q168D+ K197D+ N283Y+ D385A+ K408A+ L413T, H12R+ K26E+ K36E+ E46Y+ E64P+ K70P+ S103V+ T166P+ Q168D+ M171Q+ K197D+ S271G+ N283Y+ D385A+ L413T+ G483D, H12R+ K26E+ K36E+ E46Y+ E64P+ K70P+ S103V+ T166P+ Q168D+ M171Q+ K197D+ S271G+ N283Y+ K378Q+ D385A+ L413T, H12R+ K26E+ K36E+ E46Y+ E64P+ K70P+ S103V+ T166P+ Q168D+ M171Q+ K197D+ S271G+ N283Y+ D385A+ K408A+ L413T, H12R+ K26E+ K36E+ E46Y+ E64P+ K70P+ S103V+ E162D+ T166P+ Q168D+ M171Q+ K197D+ S271G+ N283Y+ D385A+ L413T, H12R+ K26E+ K36E+ E46Y+ E64P+ K70P+ S103V+ T166P+ Q168D+ M171Q+ K197D+ S271G+ N283Y+ K304R+ D385A+ L413T, H12R+ K26E+ K36E+ E46Y+ E64P+ K70P+ S103V+ T166P+ Q168D+ M171Q+ K197D+ S271G+ N283Y+ K304S+ D385A+ L413T, F7P+ H12R+ K26E+ K36E+ E46Y+ E64P+ K70P+ S103V+ T166P+ Q168D+ M171Q+ K197D+ S271G+ N283Y+ D385A+ L413T, H12R+ K26E+ K36E+ E64P+ K70P+ S103V+ G110S+ T166P+ Q168D+ M171Q+ K197D+ S271G+ N283Y+ D385A+ K408M+ L413T, H12R+ K26E+ K36E+ E64P+ K70P+ S103V+ G110C+ T166P+ Q168D+ M171Q+ K197D+ S271G+ N283Y+ D385A+ K408M+ L413T, H12R+ K26E+ K36E+ E46Y+ E64P+ K70P+ S103V+ T166P+ Q168D+ M171Q+ K197D+ S258G+ S271G+ N283Y+ D385A+ L413T, H12R+ K26E+ K36E+ E46Y+ E64P+ K70P+ S103V+ T166P+ Q168D+ M171Q+ K197D+ A210S+ S271G+ N283Y+ D385A+ L413T, H12R+ K26E+ K36E+ E46Y+ E64P+ K70P+ S103V+ T166P+ Q168D+ M171Q+ K197D+ S271G+ N283Y+ D385A+ K408E+ L413T, H12R+ K26E+ K36E+ E46Y+ E64P+ K70P+ S103V+ T166P+ Q168D+ M171Q+ K197D+ S271G+ N283Y+ D385A+ K408V+ L413T, H12R+ K26E+ K36E+ E46Y+ E64P+ K70P+ S103E+ T166P+ Q168D+ M171Q+ K197D+ S271G+ N283Y+ K378Q+ D385A+ L413T, H12R+ K26E+ K36E+ E46Y+ E64P+ K70P+ S103V+ T166P+ Q168D+ M171Q+ K197D+ S271G+ N283Y+ D385A+ L413T+ Q437A, H12R+ K26E+ K36E+ E46Y+ E64P+ K70P+ S103V+ T166P+ Q168D+ M171Q+ K197D+ E249H+ S271G+ N283Y+ D385A+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: S15Q+ K26E+ K36E+ E46Y+ E64P+ K70P+ S103V+ T166P+ Q168D+ K197D+ M248I+ S271G+ N283Y+ D385A+ K408M+ D410M+ L413T, S14N+ K26E+ K36E+ L49M+ E64P+ K70P+ S103V+ E162D+ T166P+ Q168D+ K197D+ S239A+ S258G+ N283Y+ D385A+ K408A+ L413T, H12R+ A23S+ F25W+ K26E+ K36E+ E46Y+ E64P+ K70P+ S103V+ T166P+ Q168D+ M171Q+ K197D+ S271G+ N283Y+ D385A+ L413T, H12R+ K26E+ K36E+ E46Y+ E64P+ K70P+ S103V+ T166P+ Q168D+ M171Q+ K197D+ Q214R+ S271G+ N283Y+ K378Q+ D385A+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: F7I+ H12R+ K26E+ K36E+ E46Y+ E64P+ K70P+ S103V+ T166P+ Q168D+ M171Q+ K197D+ S271G+ N283Y+ D385A+ V391L+ D410M+ L413T, H12R+ S15Q+ A23S+ F25W+ K26E+ K36E+ E46Y+ E64P+ K70P+ S103V+ T166P+ Q168D+ M171Q+ K197D+ S271G+ N283Y+ D385A+ L413T, S15Q+ K26E+ K36E+ E46Y+ E64P+ K70P+ S103V+ P163A+ T166P+ Q168D+ K197D+ M248I+ S271G+ N283Y+ D385A+ K408M+ D410M+ L413T, S15Q+ K26E+ K36E+ E46Y+ E64P+ K70P+ S103V+ Y155H+ T166P+ Q168D+ K197D+ M248I+ S271G+ N283Y+ D385A+ K408M+ D410M+ L413T, S15Q+ K26E+ K36E+ E46Y+ E64P+ K70P+ S103V+ R160N+ T166P+ Q168D+ K197D+ M248I+ S271G+ N283Y+ D385A+ K408M+ D410M+ L413T, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ D472Y, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ K482G, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ D486V, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ N470Y, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ P488L, H12R+ K26E+ K36E+ E46Y+ E64P+ K70P+ S103V+ E162D+ I165L+ T166P+ Q168D+ M171Q+ K197D+ S271G+ N283Y+ K378Q+ D385A+ L413T, H12R+ K26E+ K36E+ E46Y+ E64P+ K70P+ S103V+ T166P+ Q168D+ M171Q+ K197D+ M248I+ E249L+ S271G+ N283Y+ K378Q+ D385A+ L413T, S15Q+ K26E+ K36E+ E46Y+ E64P+ K70P+ S103V+ T166P+ Q168D+ K197D+ M248I+ S271G+ N283Y+ D385A+ K408M+ D410M+ L413T+ L484Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: V4D+ H12R+ S14N+ A23S+ F25W+ K26E+ K36E+ E46Y+ E64P+ K70P+ S103V+ T166P+ Q168D+ M171Q+ K197D+ S271G+ N283Y+ D385A+ L413T, S15Q+ K26E+ K36E+ E46Y+ E64P+ K70P+ S103V+ P163A+ T166P+ Q168D+ S178P+ K197D+ M248I+ S271G+ N283Y+ D385A+ K408M+ D410M+ L413T, S15Q+ K26E+ K36E+ E46Y+ E64P+ K70P+ S103V+ R160N+ P163A+ T166P+ Q168D+ K197D+ M248I+ S271G+ N283Y+ D385A+ K408M+ D410M+ L413T, S15Q+ K26E+ K36E+ E46Y+ E64P+ K70P+ S103V+ P163A+ T166P+ Q168D+ M171N+ K197D+ M248I+ S271G+ N283Y+ D385A+ K408M+ D410M+ L413T, S15Q+ K26E+ K36E+ E46Y+ E64P+ K70P+ S103V+ P163A+ T166P+ Q168D+ M171Q+ K197D+ M248I+ S271G+ N283Y+ D385A+ K408M+ D410M+ L413T, S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T, S15Q+ K26E+ K36E+ E46Y+ E64P+ K70P+ S103V+ R160L+ T166P+ Q168D+ K197D+ M248I+ S271G+ N283Y+ D385A+ K408M+ D410M+ L413T+ N470Y, S15Q+ K26E+ K36E+ E46Y+ E64P+ K70P+ S103V+ R160N+ T166P+ Q168D+ K197D+ M248I+ S271G+ N283Y+ D385A+ K408M+ D410M+ L413T+ N470Y, S15Q+ K26E+ K36E+ E46Y+ E64P+ K70P+ S103V+ P163A+ T166P+ Q168D+ M172I+ K197D+ M248I+ S258G+ S271G+ N283Y+ D385A+ K408M+ D410M, V4N+ S15Q+ K26E+ K36E+ E46Y+ E64P+ K70P+ S103V+ P163A+ T166P+ Q168D+ S178E+ K197D+ M248I+ S258G+ S271G+ N283Y+ D385A+ K408M, S15Q+ K26E+ K36E+ E46Y+ E64P+ K70P+ S103V+ P163A+ T166P+ Q168D+ M171Q+ K197D+ M248I+ S258G+ S271G+ N283Y+ D385A+ K408M+ D410M, S15M+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T, S15Q+ K26E+ K36E+ E46Y+ E64P+ K70P+ S103V+ P163A+ T166P+ Q168D+ S178P+ K197D+ M248I+ S258G+ S271G+ N283Y+ D385A+ K408M+ D410M, S15Q+ K26E+ K36E+ E46Y+ E64P+ K70P+ S103V+ P163A+ T166P+ Q168D+ K197D+ M248I+ S258G+ S271G+ N283Y+ K304Q+ D385A+ K408M+ D410M, S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T, S15Q+ K26E+ K36E+ E46Y+ E64P+ K70P+ S103V+ P163A+ T166P+ Q168D+ K197D+ M248I+ S258G+ S271G+ N283Y+ K378D+ D385A+ K408M+ D410M, S15Q+ K26E+ K36E+ E46Y+ E64P+ K70P+ S103V+

P163A+ T166P+ Q168D+ M171E+ K197D+ M248I+ S258G+ S271G+ N283Y+ D385A+ K408M+ D410M, A1Y+ S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M, S15Q+ K26E+ K36E+ E46Y+ E64P+ K70P+ S103V+ P163A+ T166P+ Q168D+ S178H+ K197D+ M248I+ S258G+ S271G+ N283Y+ D385A+ K408M+ D410M, S15Q+ K26E+ K36E+ E46Y+ E64P+ K70P+ S103V+ P163A+ T166P+ Q168D+ S178T+ K197D+ M248I+ S258G+ S271G+ N283Y+ D385A+ K408M+ D410M, F7G+ S15Q+ K26E+ K36E+ E46Y+ E64P+ K70P+ S103V+ P163A+ T166P+ Q168D+ S178P+ K197D+ M248I+ S258G+ S271G+ N283Y+ D385A+ K408M, S15Q+ K26E+ K36E+ E46Y+ E64P+ K70P+ S103V+ P163A+ T166P+ Q168D+ S178P+ K197D+ M248I+ S258G+ S271G+ N283Y+ T315V+ D385A+ K408M, S15Q+ K26E+ K36E+ E46Y+ T53P+ E64P+ K70P+ S103V+ P163A+ T166P+ Q168D+ S178P+ K197D+ M248I+ S258G+ S271G+ N283Y+ D385A+ K408M, S15Q+ K26E+ K36E+ E46Y+ T53H+ E64P+ K70P+ S103V+ P163A+ T166P+ Q168D+ K197D+ M248I+ S271G+ N283Y+ D385A+ K408M+ D410M+ L413T, S15Q+ K26E+ K36E+ E46Y+ E64P+ K70P+ S103V+ P163A+ T166P+ Q168D+ M188Y+ K197D+ M248I+ S271G+ N283Y+ D385A+ K408M+ D410M+ L413T, S15Q+ K26E+ K36E+ E46Y+ E64P+ K70P+ S103V+ P163A+ T166P+ Q168D+ K197D+ M248I+ S271G+ N283Y+ Y358W+ D385A+ K408M+ D410M+ L413T, S15Q+ K26E+ K36E+ E46Y+ E64P+ K70P+ S103V+ P163N+ T166P+ Q168D+ M172I+ S178P+ K197D+ M248I+ S258G+ S271G+ N283Y+ D385A+ K408M, S15Q+ K26E+ K36E+ E46Y+ E64P+ K70P+ S103V+ P163E+ T166P+ Q168D+ M172I+ S178P+ K197D+ M248I+ S258G+ S271G+ N283Y+ D385A+ K408M, S15Q+ K26E+ K36E+ E46Y+ E64P+ K70P+ S103V+ P163A+ T166P+ Q168D+ M172I+ K179R+ K197D+ M248I+ S258G+ S271G+ N283Y+ D385A+ K408M, S15Q+ K26E+ K36E+ E46Y+ E64P+ K70P+ S103V+ P163A+ T166P+ Q168D+ M172I+ S178P+ F190Y+ K197D+ Y213R+ M248I+ S258G+ S271G+ N283Y, S15Q+ K26E+ K36E+ E46Y+ E64P+ K70P+ S103V+ Q143R+ P163A+ T166P+ Q168D+ M172I+ S178P+ K197D+ M248I+ S258G+ S271G+ N283Y+ D385A, V8W+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, S15Q+ K26E+ K36E+ E46Y+ E64P+ K70P+ S103V+ P163A+ T166P+ Q168D+ M172I+ S178P+ M188I+ K197D+ M248I+ S258G+ S271G+ N283Y+ K378R, S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y+ D385A, S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G+ S271G, S15Q+ K26E+ K36E+ E46Y+ E64P+ K70P+ S103V+ I165E+ T166P+ Q168D+ M172I+ S178H+ K197D+ M248I+ S258G+ S271G+ N283Y+ D385A+ K408M, S15Q+ K26E+ K36E+ E46Y+ E64P+ K70P+ S103V+ E162D+ T166P+ Q168D+ M172I+ S178P+ F190Y+ K197D+ M248I+ S258G+ S271G+ N283Y+ D385A, S15Q+ K26E+ K36E+ E46Y+ E64P+ K70P+ S103V+ P163A+ T166P+ Q168D+ M172I+ S178P+ A184T+ F190Y+ K197D+ M248I+ S258G+ S271G+ N283Y, T3E+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, V9P+

S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A, T3E+ V9P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y, V9P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, S15Q+ K26E+ K36E+ E46Y+ E64P+ K70P+ S103V+ P163A+ T166P+ Q168D+ M172I+ S178P+ K197D+ M248I+ S258G+ S271G+ N283Y+ K378Q+ D385A, V9P+ S15Q+ K26E+ K36E+ E46Y+ E64P+ K70P+ S103V+ P163A+ T166P+ Q168D+ M172I+ S178P+ K197D+ S239A+ M248I+ S258G+ S271G+ N283Y, V4M+ S15Q+ K26E+ K36E+ E46Y+ E64P+ K70P+ S103V+ P163A+ T166P+ Q168D+ M172I+ S178P+ K197D+ S239A+ M248I+ S258G+ S271G+ N283Y, S15Q+ K26E+ K36E+ E46Y+ T53P+ E64P+ K70P+ S103V+ P163A+ T166P+ Q168D+ M172I+ S178P+ K197D+ S239A+ M248I+ S258G+ S271G+ N283Y, F7P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A+ K408M, A1T+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A+ K408M, S15Q+ K26E+ K36E+ E46Y+ E64P+ K70P+ S103V+ P121A+ Q143R+ P163A+ T166P+ Q168D+ M172I+ S178P+ F190Y+ K197D+ Y213Q+ M248I+ S258G, S15Q+ K26E+ K36E+ E46Y+ E64P+ K70P+ S103V+ P163A+ T166P+ Q168D+ M172I+ S178P+ K197D+ Q214R+ M248I+ S258G+ S271G+ N283Y+ T315V, F7G+ S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y, S15Q+ K26E+ K36E+ E46Y+ E64P+ K70P+ S103V+ P163A+ T166P+ Q168D+ M172I+ S178P+ K197D+ Q214R+ M248I+ S258G+ S271G+ N283Y+ D385A, S15Q+ K26E+ K36E+ E46Y+ E64P+ K70P+ S103V+ I165E+ T166P+ Q168D+ M172I+ S178P+ K197D+ Y213Q+ M248I+ S258G+ S271G+ N283Y+ D385A, V4N+ S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y, S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y+ K378Q, S15Q+ K26E+ K36E+ E46Y+ E64P+ K70P+ S103V+ P163A+ T166P+ Q168D+ M172I+ S178P+ K197D+ Q215E+ M248I+ S258G+ S271G+ N283Y+ D385A, V4M+ S15Q+ K26E+ K36E+ E46Y+ T53Q+ E64P+ K70P+ S103V+ P163A+ T166P+ Q168D+ M172I+ S178P+ K197D+ Y213Q+ M248I+ S258G+ S271G, S15Q+ K26E+ K36E+ E46Y+ E64P+ K70P+ S103V+ P163A+ T166P+ Q168D+ M172I+ S178P+ M188Y+ K197D+ S239A+ M248I+ S258G+ S271G+ N283Y, S15Q+ K26E+ K36E+ E46Y+ E61D+ E64P+ K70P+ S103V+ P163A+ T166P+ Q168D+ M172I+ S178P+ K197D+ S239A+ M248I+ S258G+ S271G+ N283Y, S15Q+ K26E+ K36E+ E46Y+ K65N+ K70P+ S103V+ P163A+ T166P+ Q168D+ M172I+ S178P+ K197D+ S239A+ M248I+ S258G+ S271G+ N283Y+ K378Q, S15Q+ K26E+ K36E+ E46Y+ K65N+ K70P+ S103V+ A126T+ P163A+ T166P+ Q168D+ M172I+ S178P+ K197D+ Y213R+ S239A+ M248I+ S258G+ S271G, S15Q+ K26E+ K36E+ E46Y+ E64P+ K70P+ S103V+ A126T+ P163A+ T166P+ Q168D+ M172I+ S178P+ K197D+ Q214R+ S239A+ M248I+ S258G+ S271G, S15Q+ K26E+ K36E+ E46Y+ E64P+ K70P+ S103V+ A126T+ P163A+ T166P+ Q168D+ M172I+ S178P+ K197D+ Y213R+ S239A+ M248I+ S258G+ S271G, S15T+ K26E+ K36E+ E46Y+ T53Q+ E64P+ K70P+ S103V+ P121A+ P163A+ T166P+ Q168D+ M172I+ S178P+ K197D+ S239A+ M248I+ S258G+ S271G, S15Q+ K26E+ K36E+ E46Y+ E64P+ K70P+ S103V+ P163A+ T166P+ Q168D+ M172I+ S178P+ K197D+ Y213Q+ S239A+ M248I+ S258G+ S271G+ N283Y, S15Q+ K26E+ K36E+ E46Y+ E64P+ K70P+ S103V+ P163A+ T166P+ Q168D+ M172I+ S178P+ F190Y+ K197D+ Y213Q+ S239A+ M248I+ S258G+ S271G, S15Q+ K26E+ K36E+ E46Y+ E64P+ K70P+ S103V+ A126T+ L134T+ E162D+ P163E+ T166P+ Q168D+ M172I+ S178P+ K197D+ Y213R+ S239A+ M248I, S15Q+ K26E+ K36E+ E46Y+ E64P+ K70P+ S103V+ A126T+ E162D+ P163E+ T166P+ Q168D+ M172I+ S178P+ K197D+ Y213R+ S239A+ M248I+ S258G, V9P+ S15Q+ K26E+ K36E+ E46Y+ E64P+ K70P+ S103V+ Q143R+ P163A+ T166P+ Q168D+ M172I+ S178P+ K197D+ S239A+ M248I+ S258G+ S271G, V8W+ S15Q+ K26E+ K36E+ E46Y+ E64P+ K70P+ S103V+ P163E+ T166P+ Q168D+ M172I+ S178P+ F190Y+ K197D+ Y213R+ S239A+ M248I+ S258G, V8W+ S15Q+ K26E+ K36E+ E46Y+ E64P+ K70P+ S103V+ P121A+ P163E+ T166P+ Q168D+ M172I+ S178P+ F190Y+ K197D+ Y213R+ S239A+ M248I, T3E+ S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G, F7G+ S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G, S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G, S15Q+ K26E+ K36E+ E46Y+ T53P+ E64P+ K70P+ S103V+ P121A+ P163A+ T166P+ Q168D+ M172I+ S178P+ K197D+ Y213Q+ S239A+ M248I+ S258G, S15Q+ K26E+ K36E+ E46Y+ E64P+ K70P+ S103V+ P121A+ Q143R+ P163A+ T166P+ Q168D+ M172I+ S178P+ K197D+ Q214R+ S239A+ M248I+ S258G, S15Q+ K26E+ K36E+ E46Y+ E64P+ K70P+ S103V+ P121A+ Q143R+ P163A+ T166P+ Q168D+ M172I+ S178P+ K197D+ Y213Q+ S239A+ M248I+ S258G, S15Q+ K26E+ K36E+ E46Y+ E64P+ K70P+ S103V+ E162D+ T166P+ Q168D+ M172I+ S178P+ K197D+ Q214R+ S239A+ M248I+ S258G+ S271G+ N283Y, S15Q+ K26E+ K36E+ E46Y+ E64P+ K70P+ S103V+ P163A+ T166P+ Q168D+ M172I+ S178P+ K197D+ Q214R+ S239A+ M248I+ S258G+ S271G+ N283Y, S15Q+ K26E+ K36E+ E46Y+ E64P+ K70P+ S103V+ Q143R+ P163A+ T166P+ Q168D+ M172I+ S178P+ K197D+ Y213Q+ S239A+ M248I+ S258G+ S271G, S15Q+ K26E+ K36E+ E46Y+ E64P+ K70P+ S103V+ P163A+ T166P+ Q168D+ M172I+ S178P+ F190Y+ K197D+ S239A+ M248I+ S258G+ S271G+ N283Y, A1Y+ F7D+ S15Q+ K26E+ K36E+ E46Y+ E64P+ K70P+ S103V+ P121A+ Q143R+ I165E+ T166P+ Q168D+ M172I+ S178P+ K197D+ S239A+ M248I, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ M188Y+ K197N, A1Y+ F7G+ S15Q+ K26E+ K36E+ E46Y+ E64P+ K70P+ S103V+ P121A+ Q143R+ V161T+ P163A+ T166P+ Q168D+ M172I+

S178P+ K197D+ S239A, T3E+ F7G+ S15Q+ A20G+ K26D+ K36E+ E46Y+ E64P+ K70P+ S103V+ S141R+ P163A+ T166P+ Q168D+ M172I+ S178P+ F190Y+ K197D+ Q214R, T3E+ F7G+ S15Q+ A20G+ K26E+ K36E+ E46Y+ E64P+ K70P+ S103V+ K120A+ S141R+ P163A+ T166P+ Q168D+ M172I+ S178P+ F190Y+ K197D, T3E+ F7G+ S15Q+ A20G+ K26E+ K36E+ E46Y+ E64P+ K70P+ S103A+ S141R+ P163A+ T166P+ Q168D+ M172I+ S178P+ F190Y+ K197D+ Q214R, T3E+ V9G+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R, T3E+ V9M+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R, T3E+ V9A+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R, T3E+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I, T3E+ F7G+ S15Q+ K26E+ K36E+ E46Y+ E64P+ K70P+ S103V+ P121A+ Q143R+ P163A+ I165E+ T166P+ Q168D+ M172I+ S178P+ K197D+ S239A, A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D, A1Y+ F7G+ S15Q+ I22V+ K26E+ K36E+ E46Y+ T53K+ E64P+ K70P+ S103V+ P121A+ Q143R+ I165E+ T166P+ Q168D+ M171Q+ K179N+ K197D, A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N, A1Y+ F7G+ S15Q+ I22V+ K26E+ K36E+ E46Y+ T53K+ E64P+ K70P+ S103V+ P121A+ Q143R+ E162D+ I165E+ T166P+ Q168D+ M171Q+ K179N, T3G+ F7G+ T13I+ S15Q+ A20V+ K26E+ K36E+ E46Y+ E64P+ K70P+ S103V+ S141R+ P163A+ T166P+ Q168D+ M172I+ S178P+ F190Y+ K197N, T3E+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N, S15Q+ K26E+ K36E+ E46Y+ E64P+ K70P+ S103V+ P163A+ T166P+ Q168D+ M188Y+ K197D+ M248I+ S271G+ N283Y+ D385A+ K408M+ D410M+ L413T; S15Q+ K26E+ K36E+ E46Y+ E64P+ K70P+ S103V+ P163A+ T166P+ Q168D+ K197D+ M248I+ S271G+ N283Y+ Y358W+ D385A+ K408M+ D410M+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1Y+ V4G+ S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M, S15Q+ F25Y+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T, F7A+ S15Q+ K26E+ K36E+ E46Y+ T53Q+ E64P+ K70P+ S103V+ P163A+ T166P+ Q168D+ M172I+ S178P+ K197D+ M248I+ S258G+ S271G+ N283Y+ D385A, V9P+ S15Q+ K26E+ K36E+ E46Y+ T53Q+ E64P+ K70P+ S103V+ P163A+ T166P+ Q168D+ M172I+ K197D+ M248I+ S258G+ S271G+ N283Y+ D385A+ K408M, V9P+ S15Q+ K26E+ K36E+ E46Y+ E64P+ K70P+ S103V+ P163A+ T166P+ Q168D+ M172I+ K197D+ M248I+ S258G+ S271G+ N283Y+ D385A+ K408M+ D410M, T3E+ V8W+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, V8W+ S15Q+ K26E+ K36E+ E46Y+ E64P+ K70P+ S103V+ P121A+ P163A+ T166P+ Q168D+ M172I+ S178P+ K197D+ M248I+ S258G+ S271G+ N283Y+ D385A, A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ D385A, A1T+ V8W+ S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A, A1Y+ F7P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A, A1T+ F7G+ S15Q+ K26E+ K36E+ E46Y+ T53Q+ E64P+ K70P+ S103V+ P163A+ T166P+ Q168D+ M172I+ S178P+ K197D+ M248I+ S258G+ S271G+ N283Y, A1T+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ D385A, A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ K378Q, A1Y+ F7G+ S15Q+ K26E+ K36E+ E46Y+ E64P+ K70P+ S103V+ I165E+ T166P+ Q168D+ M172I+ S178P+ K197N+ M248I+ S258G+ S271G+ N283Y+ D385A, A1Y+ F7G+ S15Q+ K26E+ K36E+ E46Y+ E64P+ K70P+ S103V+ I165E+ T166P+ Q168D+ M172I+ S178P+ K197N+ M248I+ S258G+ S271G+ N283Y+ K364R, A1Y+ F7G+ S15Q+ K26E+ K36E+ E46Y+ E64P+ K70P+ S103V+ I165E+ T166P+ Q168D+ M172I+ S178P+ K197D+ N242T+ M248I+ S258G+ S271G+ N283Y, A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ T315V, A1Y+ F7G+ S15Q+ K26E+ K36E+ E46Y+ E64P+ K70P+ S103V+ Q143R+ I165E+ T166P+ Q168D+ M172I+ S178P+ K197D+ M248I+ S258G+ S271G+ N283Y, A1Y+ F7G+ S15Q+ K26E+ K36E+ E46Y+ E64P+ K70P+ S103V+ I165E+ T166P+ Q168D+ M172I+ S178P+ K197D+ Q214R+ M248I+ S258G+ S271G+ N283Y, A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ K304Q, A1Y+ F7G+ S15Q+ K26E+ K36E+ E46Y+ T53P+ E64P+ K70P+ S103V+ I165E+ T166P+ Q168D+ M172I+ S178P+ K197D+ M248I+ S258G+ S271G+ N283Y, A1Y+ F7G+ S15Q+ K26E+ K36E+ E46Y+ E64P+ K70P+ S103V+ E162D+ I165E+ T166P+ Q168D+ M172I+ S178P+ K197D+ M248I+ S258G+ S271G+ N283Y, A1Y+ F7G+ S15Q+ K26E+ K36E+ E46Y+ E64P+ K70P+ S103V+ P121A+ I165E+ T166P+ Q168D+ M172I+ S178P+

K197D+ M248I+ S258G+ S271G+ N283Y, A1Y+ F7G+ S15Q+ K26E+ K36E+ E46Y+ T53K+ E64P+ K70P+ S103V+ I165E+ T166P+ Q168D+ M172I+ S178P+ K197D+ M248I+ S258G+ S271G+ N283Y, A1Y+ F7G+ S15Q+ K26E+ K36E+ E46Y+ E64P+ K70P+ S103V+ I165E+ T166P+ Q168D+ M172I+ S178P+ K197D+ S239A+ M248I+ S258G+ S271G+ N283Y, A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7G+ S15Q+ K26E+ K36E+ E46Y+ E64P+ K70P+ S103V+ Q143R+ I165E+ T166P+ Q168D+ M172I+ S178P+ K197D+ Q214R+ S239A+ M248I+ S258G, V4D+ V8D+ S15Q+ K26E+ K36E+ E46Y+ E64P+ K70P+ S103V+ P163A+ T166P+ Q168D+ M172I+ S178P+ F190Y+ K197D+ S239A+ M248I+ S258G+ S271G, A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ Q214R+ S239A+ M248I, A1Y+ F7G+ S15Q+ K26E+ K36E+ E46Y+ E64P+ K70P+ S103V+ P121A+ I165E+ T166P+ Q168D+ M172I+ S178P+ K197D+ S239A+ M248I+ S258G+ S271G, A1Y+ F7G+ S15Q+ K26E+ K36E+ E46Y+ E64P+ K70P+ S103V+ P121A+ I165E+ T166P+ Q168D+ M172I+ S178P+ K197D+ S239A+ M248I+ R253A+ S258G, A1Y+ F7G+ S15Q+ K26E+ K36E+ E46Y+ E64P+ K70P+ S103V+ P121A+ R160N+ I165E+ T166P+ Q168D+ M172I+ S178P+ K197D+ Y219W+ S239A+ M248I, A1Y+ F7G+ S15Q+ K26E+ K36E+ E46Y+ E64P+ K70P+ S103V+ P121A+ Q143R+ I165E+ T166P+ Q168D+ M172I+ S176N+ S178P+ K197D+ S239A+ M248I, A1Y+ F7G+ S15Q+ K26E+ K36E+ E46Y+ E64P+ K70P+ S103V+ P121A+ R160K+ P163A+ I165E+ T166P+ Q168D+ M172I+ S178P+ K197D+ S239A+ M248I, A1Y+ F7G+ S15Q+ K26E+ K36E+ E46Y+ E64P+ K70P+ S103V+ P121A+ R160V+ P163A+ I165E+ T166P+ Q168D+ M172I+ S178P+ K197D+ S239A+ M248I, A1Y+ F7G+ S15Q+ K26E+ K36E+ E46Y+ E64P+ K70P+ S103V+ P121A+ E162G+ P163A+ I165E+ T166P+ Q168D+ M172I+ S178P+ K197D+ S239A+ M248I, T3E+ F7G+ S15Q+ K26E+ K36E+ E46Y+ E64P+ K70P+ S103V+ S141R+ P163A+ T166P+ Q168D+ M172I+ S178P+ F190Y+ K197D+ Q214R+ S239A+ M248I, T3E+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G, A1S+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7D+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7D+ S15Q+ K26E+ K36E+ E46Y+ E64P+ K70P+ S103V+ P121A+ L134P+ Q143R+ I165E+ T166P+ Q168D+ M172I+ S178P+ K197D+ S239A+ M248I, A1Y+ F7G+ Q17A+ K26E+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7G+ S15Q+ N18S+ K26E+ K36E+ E46Y+ E64P+ K70P+ S103V+ P121A+ Q143R+ I165E+ T166P+ Q168D+ M172I+ S178P+ K197D+ S239A+ M248I, A1Y+ F7G+ S15Q+ K26E+ K36E+ E46Y+ E64P+ K70P+ S103V+ P121A+ P163A+ I165E+ T166P+ Q168D+ M172I+ S178P+ K197D+ S239A+ M248I+ S258G, A1Y+ F7G+ S15Q+ K26E+ K36E+ E46Y+ E64P+ K70P+ S103V+ P121A+ A126T+ P163A+ I165E+ T166P+ Q168D+ M172I+ S178P+ K197D+ S239A+ M248I, A1Y+ F7G+ S14N+

S15Q+ K26E+ K36E+ E46Y+ E64P+ K70P+ S103V+ P121A+ Q143R+ I165E+ T166P+ Q168D+ M172I+ S178P+ K197D+ S239A+ M248I, A1Y+ F7G+ S15Q+ A23S+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7G+ S15Q+ K26E+ 130L+ K36E+ E46Y+ E64P+ K70P+ S103V+ P121A+ Q143R+ I165E+ T166P+ Q168D+ M172I+ S178P+ K197D+ S239A+ M248I, A1Y+ F7G+ S15D+ K26E+ K36E+ E46Y+ E64P+ K70P+ S103V+ P121A+ Q143R+ I165E+ T166P+ Q168D+ M172I+ S178P+ K197D+ S239A+ M248I+ S258G, A1Y+ F7G+ S15C+ K26E+ K36E+ E46Y+ E64P+ K70P+ S103V+ P121A+ Q143R+ I165E+ T166P+ Q168D+ M172I+ S178P+ K197D+ S239A+ M248I+ S258G, T3E+ F7G+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R+ S239A, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214W+ S239A, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ G217Q, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q215E+ S239A, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ S239A+ A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214W+ G217Q, A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ S239A+ M248I, A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ K179N+ K197D+ S239A and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: A1*+ 12*+ T3*+ V4*+ P5*+ S15Q+ K26E+ K36E+ E46Y+ E64P+ K70P+ S103V+ P121A+ Q143R+ I165E+ T166P+ Q168D+ M172I+ S178P+ K197D+ S239A, A1Y+ G6*+ F7*+ V8*+ V9*+ E10*+ S15Q+ K26E+ K36E+ E46Y+ E64P+ K70P+ S103V+ P121A+ Q143R+ I165E+ T166P+ Q168D+ M172I+ S178P+ K197D, F7G+ T3*+ G6*+ P5*+ V4*+ 12*+ A1*+ S15Q+ K26E+ K36E+ E46Y+ E64P+ K70P+

S103V+ P163A+ T166P+ Q168D+ M172I+ S178P+ F190Y+ K197D and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: T3*+ V9*+ V8*+ G7*+ G6*+ P5*+ V4*+ 12*+ A1*+ F7G+ S15Q+ K26E+ K36E+ E46Y+ E64P+ K70P+ S103V+ P163A+ T166P+ Q168D+ M172I+ S178P and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: E10*+ V9*+ V8*+ F7*+ G6*+ P5*+ V4*+ T3*+ 12*+ A1*+ S15Q+ K26E+ K36E+ E46Y+ E64P+ K70P+ S103V+ P121A+ Q143R+ I165E+ T166P+ Q168D+ M172I and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ N283Y+ K378Q+ D385A+ K408M+ D410M+ L413T and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: T3E+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ N283Y+ K378Q+ D385A+ K408M+ D410M+ L413T+ G440Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: T3E+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y; T3E+ F7G+ S15Q+ K26E+ K36E+ E46Y+ E64P+ K70P+ S103V+ P121A+ Q143R+ P163A+ I165E+ T166P+ Q168D+ M172I+ S178P+ K197D+ S239A+ M248I+ S258G+ S271G+ N283Y+ K378Q+ D385A+ K408M+ D410M+ L413T+ G440Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions: A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ R280K+ N283Y+ K378Q+ D385A+ K408M+ D410M+ L413T+ G440Q and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K378Q+ D385A+ K408M+ D410M+ L413T+ G440Q; A1Y+ F7G+ S15Q+ I22V+ K26E+ K36E+ E46Y+ T53K+ E64P+ K70P+ S103V+ P121A+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ F7G+ S15Q+ I21L+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ S15Q+ I22V+ K26E+ K36E+ E46Y+ T53K+ E64P+ K70P+ S103V+ K120P+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ V8A+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1G+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ S15Q+ I22V+ K26E+ K36E+ E46Y+ T53K+ E64P+ K70P+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3E+ F7G+ S15D+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R; V4N+ F7G+ S15Q+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R; V4W+ F7G+ S15Q+ A20G+

K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ P11A+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ P11L+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ S15Q+ I22V+ K26E+ K36E+ E46Y+ T53K+ E64P+ Q69P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ N368D+ K378Q+ D385A+ K408M+ D410M+ L413T+ T438A; T3G+ F7G+ T13I+ S15Q+ A20G+ K26E+ K36E+ E46Y+ E64P+ K70P+ S103V+ S141R+ P163E+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R; A1V+ F7G+ P11L+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ G217Q+ S239A+ M248I+ S258G+ S271G+ R280K+ N283Y+ W342G+ K378Q+ D385A+ K408M+ D410M+ L413T+ G440Q; A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; T3G+ F7G+ T13I+ S15Q+ A20V+ K26E+ K36E+ E46Y+ E64P+ K70P+ S103V+ S141R+ P163A+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3E+ F7G+ S15Q+ A20G+ K26E+ 130L+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R; T3G+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ I22V+ K26E+ K36E+ E46Y+ T53K+ E64P+ K70P+ T74A+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ T13I+ S15Q+ A20S+ K26E+ K36E+ E46Y+ T53K+ E64P+ K70P+ T74A+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ T13I+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ S15Q+ I22V+ K26E+ K36E+ E46Y+ T53K+ E64P+ K70P+ Q76T+ S103V+ P121A+ M130I+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ P11A+ S15Q+ I22V+ K26E+ K36E+ E46Y+ T53K+ E64P+ K70P+ Q76T+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1Y+ F7G+ P11E+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ P11I+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ T13M+ S15Q+ I22V+ K26E+ K36E+ E46Y+ T53K+ E64P+ K70P+ S103V+ P121A+ Q143R+ I165E+ T166P+

Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ T13N+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ T13W+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ T13Y+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ S14Q+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ S14R+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ S15Q+ I22V+ K26E+ K36E+ A45M+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ G6P+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ V8Q+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q; A1Y+ F7G+ T13I+ S15Q+ I22V+ K26E+ K36E+ E46Y+ T53K+ E64P+ K70P+ Q76T+ S103V+ P121A+ Q143R+ P163N+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; F7G+ T3*+ G6*+ P5*+ V4*+ 12*+ A1*+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y; T3E+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ V422I+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: V4Y+ G6*+ F7G+ V8F+ S15Q+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R; T3G+ F7G+ T13I+ S15Q+ A20G+ K26E+ K36E+ E46Y+ E64P+ K70P+ S103V+ S141R+ P163A+ T166P+ Q168D+ M172I+ S176N+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1Y+ F7G+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ F190Y+ K197D+ Q214R+ S239A+ M248I+ S258G+ S271G+ R280K+ N283Y+ K378Q+ D385A+ K408M+ D4100M+ L413T+ T438A; A1V+ F7G+ P11A+ S15Q+ I22V+ K26E+ K36E+ E46Y+ T53K+ E64P+ K70P+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A; T3G+ F7G+ T13I+ S15Q+ A20G+ K26E+ 130L+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; T3G+ F7G+ T13I+ S15Q+ A20G+ K26E+ K36E+ E46Y+ E64P+ K70P+ S103V+ K120A+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; T3G+ F7G+ S15Q+ A20G+ K26E+ K36E+ E46M+ E64P+ K70P+ S103V+ K120S+ S141R+ P163A+ T166P+ Q168D+ M172I+ S176N+ S178P+ F190Y+ K197D+ Q214R+ S239A+ M248I+ R253A+ S258G+ S271G+ N283Y+ E299W+ K378Q+ D385A+ K408M+ D410M+ L413T+ N473Y+ K491R; T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R; T3G+ F7G+ T13I+ S15Q+ A20G+ K26E+ K36E+ E46Y+ E64P+ K70P+ N82T+ S103V+ S141R+ P163A+ T166P+ Q168D+ M172I+ S178P+ F190Y+ K197N+ Q214R+ Y219W+ S239A+ M248I+ S258G+ S271G+ N283Y+

E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103A+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103V+ S141R+ P163T+ T166P+ Q168D+ M172I+ S178P+ F190Y+ K197D+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ K197D+ S239A+ M248I+ S258G+ S271G+ R280K+ N283Y+ T315V+ K378Q+ D385A+ K408M+ D410M+ L413T+ T438A; T3G+ F7G+ S15Q+ A20G+ K26E+ 130L+ K36E+ E46M+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R; T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378R+ K408M+ D410M+ L413T+ N473Y+ K491R; A1Y+ F7H+ T13I+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ E322A+ K378Q+ D385A+ K408M+ D410M+ L413T+ T438A; A1Y+ F7G+ T13I+ S15Q+ I22V+ K26E+ K36E+ E46Y+ T53K+ E64P+ Q69S+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ T13I+ S15Q+ A20G+ K26E+ 130L+ K36E+ E46Y+ T53P+ E64P+ K70P+ S103V+ S141R+ P163A+ T166P+ Q168D+ M172I+ S176N+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R; T3G+ F7G+ S15Q+ A20G+ K26E+ K36E+ E46M+ E64P+ K70P+ S103V+ M130I+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ D385A+ K408M+ D410M+ L413T+ N473Y+ K491R; A1V+ F7G+ P11A+ S15Q+ I21L+ K26E+ K36E+ E46Y+ T53K+ E64P+ K70P+ Q76T+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A; A1V+ F7G+ P11A+ S15Q+ I21L+ K26E+ K36E+ E46Y+ T53K+ E64P+ K70P+ Q76T+ S103V+ P121A+ M130I+ Q143R+ Y155H+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; A1V+ F7G+ P11A+ S15Q+ I21L+ K26E+ K36E+ E46Y+ T53K+ E64P+ K70P+ Q76T+ S103V+ S109D+ P121A+ M130I+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A; T3G+ F7G+ S15Q+ A20G+ K26E+ K36E+ E46M+ E64P+ K70P+ N82A+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R; T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ K185Q+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R; A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ T192V+ K197D+ S239A+ M248I+ S258G+ S271G+ R280K+ N283Y+ T315V+ K378Q+ D385A+ K408M+ D410M+ L413T+ T438A; A1V+ F7G+ T13I+ S15Q+ A20G+ K26E+ 130L+ 135*+ K36E+ E46Y+ E64P+ K70P+ S103A+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103E+ S109D+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103A+ S109D+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; A1V+ F7G+ T13I+ S15Q+ A20G+ K26E+ 130L+ K36E+ E46Y+ E64P+ K70P+ S103A+ S141R+ W148Q+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; T3G+ F7G+ S15Q+ A20G+ K26E+ K36E+ E46M+ E64P+ K70P+ N82T+ S103E+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ T13I+ S15Q+ A20G+ K26E+ K36E+ E46Y+ E64P+ K70P+ N97E+ S103V+ K120A+ S141R+ P163A+ T166P+ Q168D+ M172I+ S178P+ K185N+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R; T3G+ F7G+ S15Q+ A20G+ K26E+ K36E+ E46M+ E64P+ K70P+ S103V+ K120A+ S141A+ P163A+ T166P+ Q168D+ M172I+ S176N+ S178P+ F190Y+ K197D+ A210E+ Q214R+ S239A+ M248I+ R253A+ S258G+ S271G+ R280K+ N283Y+ K378Q+ D385A+ K408M+ D410M+ L413T+ V422I+ N473Y+ K491R; T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ A210E+ Q214R+ S239A+ M248I+ R253A+ S258G+ S271G+ N283Y+ E299W+ K378Q+ D385A+ K408M+ D410M+ L413T+ V422I+ N473Y+ K491R; A1V+ F7G+ P11A+ S15Q+ I21L+ K26E+ K36E+ E46Y+ T53K+ E64P+ Q69P+ K70P+ Q76T+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A; T3*+ V9*+ V8*+ G7*+ G6*+ P5*+ V4*+ 12*+ A1*+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G, F7G, S15Q, A20G, K26E, 130L, K36E, E46M, E64P, K70P, Q76T, S103V, M130I, S141R, P163A, T166P, Q168D, M172I, S176N, S178P, F190Y, K197D, Q214R, Y219W, S239A, M248I, R253A, S258G, S271G, N283Y, E299W, K378Q, D385A, K408M, D410M, L413T, N473Y, K491R; T3G, F7G, T13I, S15Q, A20G, K26E, 130L, K36E, E46M, E64P, K70P, S103V, K120A, S141R, P163A, T166P, Q168D, M172I, S176N, S178P, F190Y, K197D, Q214R, Y219W, S239A, M248I, R253A, S258G, S271G, N283Y, E299W, K378Q, K408M, D410M, L413T, N473Y, K482A, K491R; T3G, F7G, S15Q, A20G, K26E, K36E, E46M, E64P, K70P, S103V, K120A, S141R, P163A, T166P, Q168D, M172I, S176N, S178P, F190Y, K197D, Q214R, Y219W, S239A, M248I, R253A, S258G, S271G, R280K, N283Y, E299W, K304Q, T315V, K378Q, K408M, D410M, L413T, N473Y, K491R; A1V, F7G, P11A, S15Q, I21L, K26E, K36E, E46Y, T53K, E64P, K70P, Q76T, S103V, P121A, M130I, Q143R, E162D, I165E, T166P, Q168D, M171Q, K179N, K197D, Y219W, S239A, M248I, S258G, S271G, H276Y, R280K, N283Y, E299D, K378Q, D385A, K408M, D410M, L413T, T438A; A1V, F7G, T13I, S15Q, A20G, K26E, 130L, K36E, E46Y, E61D, E64P, Q69P, K70P, Q76T, S141R, E162D, T166P, Q168D, M172I, S178P, F190Y, K197N, Q214R, Y219W, S239A, M248I, S258G, S271G, R280K, N283Y, E299W, K378Q, D385A, K408M, D410M, L413T, N473Y, K491R; T3G, F7G, V9A, S15Q, A20G, K26E, K36E, E46M, E64P, Q69P, K70P, N82T, S103E, K120A, S141R, P163A, T166P, Q168D, M172I, S176N, S178P, F190Y, K197D, Q214R, Y219W, S239A, M248I, R253A, S258G, S271G, N283Y, E299W, K378Q, K408M, D410M, L413T, N473Y, K491R; A1V, F7G, T13I, S15Q, A20G, K26E, 130L, K36E, E46Y, E64P, K70P, S103E, S109D, S141R, E162D, T166P, Q168D, M172I, S178P, F190Y, K197N, Q214R, Q215E, Y219W, S239A, M248I, S258G, S271G, R280K, N283Y, E299W, K378Q, D385A, K408M, D410M, L413T, N473Y, K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V, F7G, T13I, S15Q, A20G, K26E, 130L, K36E, E46Y, E61D, E64P, Q69P, K70P, Q76T, S109D, S141R, E162D, T166P, Q168D, M172I, S178P, F190Y, K197N, Q214R, Y219W, S239A, M248I, S258G, S271G, R280K, N283Y, E299W, K378Q, D385A, K408M, D410M, L413T, N473Y, K491R; T3G, F7G, V9A, S15Q, A20G, K26E, K36E, E46M, E61D, E64P, Q69P, K70P, N82T, S103E, K120A, S141R, P163A, T166P, Q168D, M172I, S176N, S178P, F190Y, K197D, Q214R, Y219W, S239A, M248I, R253A, S258G, S271G, N283Y, E299W, K378Q, K408M, D410M, L413T, N473Y, K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G, F7G, S15Q, A20G, K26E, 130L, K36E, E46M, E64P, K70P, Q76T, A101R, S103V, G110R, M130I, S141R, P163A, T166P, Q168D, M172I, S176N, S178P, F190Y, K197D, Q214R, Y219W, S239A, M248I, R253A, S258G, S271G, N283Y, E299W, K378Q, D385A, K408M, D410M, L413T, N473Y, K491R; T3G, F7G, S15Q, A20G, K26E, 130L, K36E, E46M, K70P, Q76T, A101R, S103V, G110R, M130I, S141Q, P163A, T166P, Q168D, M172I, S176N, S178P, F190Y, K197D, Q214R, Q215E, Y219W, S239A, M248I, R253A, S258G, S271G, N283Y, E299W, K378Q, D385A, K408M, D410M, L413T, N473Y, K491R; A1V, F7G, T13I, S15Q, A20G, K26E, 130L, K36E, E46Y, E61D, E64P, Q69P, K70P, Q76T, S103R, G122P, S141R, E162D, T166P, Q168D, M172I, S178P, F190Y, K197N, Q214R, Y219W, S239A, M248I, S258G, S271G, R280K, N283Y, E299W, K378Q, D385A, K408M, D410M, L413T, N473Y, K491R; T3G, F7G, V9A, S15Q, A20G, K26E, K36E, E46M, E64P, Q69P, K70P, N82T, S103E, K120A, S141R, P163A, T166P, Q168D, M172I, S176N, S178P, F190Y, K197D, Q214R, Q215E, Y219W, S239A, M248I, R253A, S258G, S271G, R280K, N283Y, E299W, K378Q, K408M, D410M, L413T, N473Y, K491R; T3G, F7G, V9A, S15Q, A20G, K26E, K36E, E46M, E61D, E64P, Q69P, K70P, N82T, S103E, K120A, S141R, P163T, T166P, Q168D, M172I, S176N, S178P, F190Y, K197D, Q214R, Y219W, S239A, M248I, R253A, S258G, S271G, R280K, N283Y, E299W, K378Q, K408M, D410M, L413T, N473Y, K491R; T3G, F7G, V9A, S15Q, A20G, K26E, K36E, E46M, E61D, E64P, Q69P, K70P, N82T, S103E, K120A, S141R, P163A, T166P, Q168D, M172I, S176N, S178P, F190Y, K197D, Q214R, Y219W, S239A, M248I, R253A, S258G, S271G, R280K, N283Y, E299W, K378Q, K408M, D410M, L413T, N473Y, K491R; T3G, F7G, V9A, S15Q, I22Q, K26E, K36E, E46M, E64P, Q69P, K70P, N82T, A101V, K120A, S141R, P163A, T166P, Q168D, M172I, S176N, S178P, F190Y, K197D, Q214R, Q215E, Y219W, S239A, M248I, R253A, S258G, S271G, R280K, N283Y, E299W, K378Q, K408M, D410M, L413T, N473Y, K491R; T3G, F7G, V9A, S15Q, A20G, K26E, K36E, E46M, E64P, Q69P, K70P, T74Q, Q76T, N82T, S103E, K120A, S141R, P163A, T166P, Q168D, M172I, S176N, S178P, F190Y, K197D, Q214R, Y219W, S239A, M248I, R253A, S258G, S271G, N283Y, E299W, K378Q, K408M, D410M, L413T, N473Y, K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ S15Q+ A20G+ K26E+ 130L+ K36E+ E46M+ K70P+ Q76T+ A101R+ S103V+ G110R+ M130I+ S141Q+ P163A+ T166P+ Q168D+ M172I+ S176N+ S178P+ F190Y+ K197D+ Q214R+ Q215E+ Y219W+ S239A+ M248I+ R253A+ S258G+ S271G+ N283Y+ E299W+ K378Q+ D385A+ K408M+ D410M+ L413V+ N473Y+ D486K+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M171Q+ M172I+ S176N+ S178R+ F190Y+ K197D+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141A+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ H324N+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197A+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R; T3G+ F7G+ T13N+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46Y+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ T13I+ S15Q+ A20G+ K26E+ K36E+ E46M+ E64P+ Q69P+

K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141I+ P163A+ T166P+ Q168D+ K169P+ M172I+ S176N+ S178P+ F190Y+ K197A+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ F7G+ P11N+ S15Q+ I21L+ K26E+ K36E+ E46Y+ T53K+ E64P+ Q69P+ K70P+ Q76T+ N82T+ S103V+ S109D+ K120A+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ Q76T+ N82T+ S103V+ S109D+ K120A+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ Q76T+ N82T+ S103E+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ T74E+ Q76T+ N82T+ S103E+ S109D+ P121A+ M130I+ Q143R+ P163A+ R164Q+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; T3G+ F7G+ V9A+ S15Q+ A20G+ K26E+ K36E+ E46Y+ T53K+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ I22V+ K26E+ 130L+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ E31Q+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; A1V+ G6P+ F7G+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ G96R+ S103E+ K120A+ S141R+ P163A+ T166E+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ T170E+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ M188F+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ T74E+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A+ K462R; A1V+ F7G+ P11A+ S15Q+ I21L+ K26E+ K36E+ E46Y+ T53K+ E64P+ Q69P+ K70P+ T74E+ Q76T+ N82T+ S103E+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ P11A+ S15Q+ I21L+ K26E+ 130L+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; A1V+ F7G+ T13I+ S15Q+ I21L+ K26E+ 130L+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ T13I+ S14N+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ R280K+ N283Y+ E299W+ H324N+ K378Q+ D385H+ K408M+ D410M+ L413T+ N473Y+ K491R; T3G+ F7G+ V9A+ S15Q+ A20G+ K26E+ 130L+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ S403R+ K408M+ D410M+ L413T+ N473Y+ K491R; T3G+ F7G+ V9A+ S15Q+ A20G+ K26E+ E31Q+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ Q321K+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197A+ Q214R+ Q215E+ Y219W+ S239A+ M248I+ R253W+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82A+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ Q76E+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ F7G+ P11A+ T13I+ S15Q+ Q19N+ A20G+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A; T3G+ F7G+ T13I+ S14N+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ P399A+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103N+ S109E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ S109D+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ Q76T+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ E10Y+ T13I+ S15Q+ A20G+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ K179H+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ T13I+ S14N+ S15Q+ A20G+ K26E+ K36E+ E46Y+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ S487R+ K491R; T3G+ F7G+ V9A+ S15Q+ A20G+ K26E+ K36E+ E46M+ E64P+ Q69P+ K70P+ K78E+ N82A+ S103E+ K120A+ S141R+ R160F+ E162D+ T166P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ K26E+ K36E+ E46M+ E64P+ Q69P+ K70P+ N82T+ S103E+ K120A+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ 130L+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ E86D+ S103E+ K120A+ S141R+ V161S+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ I22T+ K26E+ 130L+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D4100M+ L413T+ N473Y+ K491R; T3G+ F7G+ V9A+ S15Q+ A20G+ K26E+ K36E+ E46M+ E64P+ Q69P+ K70P+ Q76E+ S103E+ K120A+ N139K+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

S17G+ T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280L+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ K304Q+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ K129R+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163E+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ K304Q+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ Q76E+ S103E+ K120A+ S141R+ V161S+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R; T3G+ F7G+ V9A+ S15Q+ K26E+ K36E+ E46Y+ D48A+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V9A+ S15Q+ A20G+ K26E+ K36E+ E46M+ E64P+ Q69P+ K70P+ N82T+ S103E+ S109E+ K120A+ S141R+ P163A+ T166P+ Q168D+ M171Q+ M172I+ S176N+ S178P+ K189S+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ T13I+ S14H+ S15Q+ A20G+ K26E+ K36E+ E46M+ E64P+ Q69P+ K70P+ Q76T+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ T13I+ S14N+ S15Q+ A20G+ K26E+ 130L+ K36E+ E46Y+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ I165T+ T166P+ Q168D+ M171K+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ H12Q+ T13I+ S15Q+ A20G+ K26E+ K36E+ E46M+ E64P+ K65Q+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ T13E+ S15Q+ A20G+ K26E+ K36E+ E46M+ E64P+ Q69P+ K70P+ K78E+ N82A+ S103E+ S109D+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ K78E+ N82A+ S103E+ S109D+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ T13I+ S14H+ S15Q+ A20G+ K26E+ K36E+ E46M+ E64P+ Q69P+ K70P+ Q76T+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ 130L+ K36E+ E46Y+ E64P+ Q69P+ K70P+ N82T+ S103E+

S109E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ E31Q+ K36E+ E46Y+ E64P+ Q69P+ K70P+ N82T+ S103E+ K120A+ S141R+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ E31Q+ K36E+ E46M+ E64P+ Q69P+ K70P+ N82T+ S103E+ S109E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413V+ N473Y+ D486E+ K491R; T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ R489F+ K491R; S17G+ T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R; T3G+ F7G+ V9A+ S15Q+ A20G+ K26E+ K36E+ E46M+ T53K+ E64P+ Q69P+ K70P+ Q76E+ S103E+ K120A+ S141R+ P163A+ T166P+ Q168D+ K169P+ M172I+ S176N+ S178P+ K179Q+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ R489F+ K491R; T3G+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ E10Y+ T13I+ S15Q+ A20G+ K26E+ K36E+ E46M+ E64P+ Q69P+ K70P+ Q76T+ K78R+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ E10Y+ T13I+ S15Q+ A20G+ K26E+ K36E+ E46M+ E64P+ Q69P+ K70P+ N82T+ S103E+ K120A+ S141R+ P163A+ R164Q+ T166P+ Q168D+ M171K+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ K26E+ K36E+ E46Y+ D48A+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ K252G+ R253A+ S258G+ S271G+ H276C+ R280K+ N283Y+ F286C+ E299W+ K378Q+ D385H+ K408M+ D410M+ L413T+ N473Y+ K491R; A1V+ V4M+ F7G+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82A+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82A+ A101R+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ K26E+ K36E+ E46M+ E64P+ Q69P+ K70P+ N82T+ A101R+ K120A+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R; T3G+ F7G+ V9A+ S15Q+ K26E+ K36E+ E46M+ E64P+ Q69P+ K70P+ N82T+ S103E+ K120P+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R; T3G+ F7G+ V9A+ S15Q+ K26E+ K36E+ E46M+ E64P+ Q69P+ K70P+ N82T+ S103E+ S109E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R; T3G+ F7G+ T13I+ S15Q+ A20G+ A23V+ K26E+ K36E+ E46M+ E64P+ Q69P+ K70P+ N82T+ S103E+ K120A+ S141R+ P163A+ T166P+ T167P+ Q168D+

M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23I+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23I+ K26E+ K36E+ E46M+ E64P+ Q69P+ K70P+ N82T+ S103E+ K120P+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V9A+ S15Q+ A20G+ K26E+ 130L+ K36E+ E46M+ E64P+ Q69P+ K70P+ N82T+ S103E+ S109E+ K120A+ S141R+ P163A+ T166P+ Q168D+ M171Q+ M172I+ S176N+ S178P+ K189S+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ E10Y+ T13I+ S15Q+ A20G+ K26E+ K36E+ E46M+ E64P+ Q69P+ K70P+ K78E+ N82A+ S103E+ K120A+ S141R+ R160F+ E162D+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ V9A+ S15Q+ A20G+ K26E+ K36E+ E46M+ E64P+ Q69P+ K70P+ N82T+ S103E+ S109E+ K120A+ S141R+ P163A+ T166P+ Q168D+ M171K+ M172I+ S176N+ S178P+ K189S+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ K26E+ K36E+ A45M+ E46Y+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20G+ I22V+ K26E+ 130L+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; T3G+ F7G+ E10Y+ T13I+ S15Q+ A20G+ I22V+ K26E+ 130L+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R; A1V+ V4M+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ T13I+ S15Q+ A20P+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R; A1V+ T3E+ F7G+ V9A+ S15Q+ A20G+ A23V+ K26E+ K36E+ E46M+ E64P+ Q69P+ K70P+ N82T+ S103E+ K120A+ S141R+

P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103E+ K120A+ S141R+ V161S+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103E+ K120A+ S141I+ R160I+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103E+ K120A+ S141R+ R160I+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103I+ T115I+ K120A+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23I+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ E379K+ D385H+ K408M+ D410M+ L413T+ N473Y+ K491R; T3G+ F7G+ V9A+ S15Q+ A20G+ A23I+ K26E+ K36E+ E46M+ E64P+ Q69P+ K70P+ N82T+ S103E+ K120P+ S141R+ Q143R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ K26E+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ T115Y+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ E10G+ T13I+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ T53K+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ T115W+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ S15Q+ A20P+ K26E+ K36E+ E46M+ E64P+ Q69P+ K70P+ N82A+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23V+ K26E+ K36E+ E46M+ E64P+ Q69P+ K70P+ N82T+ S103E+ T115I+ K120A+ A126T+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R; T3G+ F7G+ V9A+ S15Q+ A20G+ A23V+ K26E+ K36E+ E46M+ E64P+ Q69P+ K70P+ N82T+ S103E+ A118V+ K120A+ L134I+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+

E299W+ K378Q+ D385H+ K408M+ D410M+ L413T+ N473Y+ K491R; T3G+ F7G+ V9A+ S15Q+ A20G+ A23I+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ S103E+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ R160N+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ P163A+ I165D+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S109D+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M4+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ S109D+ T115Y+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ S109E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9A+ S15Q+ A20G+ A23T+ K26E+ K36E+ E46M+ E64P+ Q69P+ K70P+ N82T+ S103E+ T115W+ K120A+ S141R+ V161T+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ R160I+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ A101R+ K120A+ S141R+ E162G+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+

K491R; T3G+ F7G+ V9A+ T13I+ S15Q+ I22V+ K26E+ K36E+ E46M+ E64P+ Q69P+ K70P+ N82T+ S103E+ K120A+ S141R+ R160F+ E162D+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ I165D+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ G6P+ F7G+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R; T3G+ F7G+ V8A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R; T3G+ F7G+ V9A+ S15Q+ A20G+ A23T+ K26E+ K36E+ E46M+ E64P+ Q69P+ K70P+ N82T+ S103E+ T115Y+ K120A+ S141R+ V161T+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ A101R+ K120A+ S141R+ Y155H+ E162G+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20T+ K26E+ K36E+ E46M+ E64P+ Q69P+ K70P+ N82T+ A101R+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8D+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ N193W+ K197D+ Q214R+ Q215E+ Y219W+ S239A+ M248I+ R253A+ S258G+ S271G+ H276C+ R280K+ N283Y+

F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R; A1V+ V4D+ F7G+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1T+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82A+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ I22V+ K26E+ K36E+ E46M+ E64P+ Q69P+ K70P+ N82T+ S103E+ S109D+ K120A+ S141R+ R160L+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R; T3G+ F7G+ V8A+ T13I+ S15Q+ I22V+ K26E+ K36E+ E46M+ E64P+ Q69P+ K70P+ N82T+ S103E+ T115V+ K120A+ S137A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ I22V+ K26E+ K36E+ E46M+ E64P+ Q69P+ K70P+ N82T+ S103E+ K120A+ S141R+ Y155H+ E162D+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S137A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120P+ S137A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ A210F+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53P+ E64P+ Q69P+ K70P+ N82T+ A101R+ K120A+ S141R+ Y155H+

P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ S103V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ N242T+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E322R+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ E31Q+ K36E+ E46Y+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ T115Y+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ S141R+ R160I+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M4+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82A+ A101R+ G110R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1D+ F7G+ V8A+ T13I+ S15Q+ A20P+ K26E+ K36E+ A45M+ E46Y+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ I22V+ K26E+ 130L+ E31Q+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ T115Y+ K120A+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M171K+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D4100M+ L413T+ N473Y+ D486E+ K491R; T3G+ F7A+ T13I+ S15Q+ A20P+ K26E+ K36E+ E46M+ E64P+ Q69P+ K70P+ N82A+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+

R280K+ N283Y+ F286C+ E299W+ G366N+ K378Q+ D385H+ K408M+ D410M+ L413T+ N473Y+ D486E+ K491R; T3G+ F7G+ V8A+ S15K+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4D+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ K304A+ G366N+ K378Q+ D385H+ K408M+ D410M+ L413T+ N473Y+ D486E+ K491R; T3G+ F7G+ V8A+ T13I+ S15Q+ A20P+ K26E+ E31Q+ K36E+ E46Y+ T53K+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ G110R+ T115Y+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109E+ T115Y+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ A210T+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115I+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ N193W+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R; A1D+ T3G+ F7G+ V8A+ T13I+ S15Q+ A20P+ K26E+ K36E+ A45M+ E46Y+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ A20P+ K26E+ K36E+ E46M+ E64P+ Q69P+ K70P+ N82T+ A101R+ T115Y+ K120A+ K129R+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+

E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ G110R+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ H12E+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ G110R+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163*+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115I+ K120A+ K129L+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ K120A+ A126T+ L134V+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ 130L+ K36E+ E46M+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ F7I+ T13I+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ K26E+ K36E+ A45M+ E46Y+ E64P+ V68M+ Q69P+ K70P+ N82A+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109E+ T115Y+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109E+ T115Y+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45M+ E46Y+ E64P+ Q69P+ K70P+ N82T+ A101R+ S109D+ T115Y+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E380T+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R; A1V+ V4N+ F7G+ V9P+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109D+ T115Y+ K120A+ N139I+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45M+ E46Y+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109D+ T115Y+ K120A+ A126T+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82A+ A101R+ G110D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109E+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ G110D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+

K26E+ K36E+ E46M+ E64P+ Q69P+ K70P+ N82A+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ N139A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ K179S+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1D+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20G+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141I+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20G+ K26E+ K36E+ E46M+ E64P+ K65N+ Q69P+ K70P+ N82A+ A101R+ S109E+ K120A+ A126T+ L134I+ S141I+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1I+ F7G+ T13I+ S15Q+ A20P+ K26E+ K36E+ A45R+ E46Y+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ K65N+ Q69P+ K70P+ N82A+ A101R+ S109E+ T115I+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ K65N+ Q69P+ K70P+ N82A+ A101R+ S109E+ T115I+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ V68M+ Q69P+ K70P+ Q76E+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ V68M+ Q69P+ K70P+ N82A+ A101L+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ K26E+ K36E+ E46M+ E64P+ K65N+ Q69P+ K70P+ N82T+ A101I+ S109E+ K120A+ A126T+ L134I+ S141R+ Q143T+ Y155H+ P163A+ T166P+ T167R+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ T13I+ S14N+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ K218R+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9D+ T13I+ S15Q+ A20P+ K26E+ K36E+ E46M+ T53K+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+

T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ K65N+ Q69P+ K70P+ N82T+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ A20P+ K26E+ K36E+ E46M+ E64P+ Q69P+ K70P+ N82T+ L89F+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ M228I+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ L259V+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ P94M+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E301K+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ L480I+ D486E+ K491R; A1V+ V4N+ F7G+ T13I+ S15Q+ A20P+ K26E+ K36E+ E46M+ E64P+ Q69P+ K70P+ N82T+ A101L+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101L+ S109D+ T115Y+ K120A+ K129L+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+

G366N+ K378Q+ D385H+ K408M+ D410M+ L413T+ N473Y+ D486E+ K491R; A1V+ V4N+ F7G+ T13I+ S15Q+ A20P+ K26E+ D27N+ K36E+ E46M+ E64P+ Q69P+ K70P+ N82T+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ Q76T+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ G122P+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ I142L+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Q143S+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S14E+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S14E+ S15Q+ A20G+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V9P+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ F414S+ N473Y+ D486E+ K491R; T3G+ F7G+ H12P+ T13I+ S15Q+ A20P+ K26E+ K36E+ A45L+ E46Y+ E61D+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ 130L+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+

G366N+ K378Q+ D385H+ K408M+ D410M+ L413T+ N473Y+ D486E+ K491R; T3G+ F7G+ V8A+ T13I+ S15Q+ A20P+ K26E+ 130L+ K36E+ A45M+ E46Y+ E64P+ V68M+ Q69P+ K70P+ N82T+ A101L+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ E10Y+ T13I+ S15Q+ K26E+ K36E+ E46M+ E64P+ K65N+ Q69P+ K70P+ N82T+ A101R+ S109D+ G110P+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ P174K+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ G96D+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1-V+ V4N+ F7G+ T13I+ S15Q+ K26E+ 130L+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E301K+ G366N+ K378Q+ D385H+ K408M+ D410M+ L413T+ F414T+ N473Y+ D486E+ K491R; T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K417G+ N473Y+ L480I+ D486E+ K491R; A1V+ V4N+ F7G+ T13I+ S15Q+ A20P+ K26E+ K36E+ E46M+ E64P+ Q69P+ K70P+ N82T+ A101L+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R; A1V+ V4N+ F7G+ T13I+ S15Q+

A20P+ K26E+ K36E+ E46M+ E64P+ Q69P+ K70P+ N82T+ N97E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ N97E+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101L+ S109D+ T115Y+ K120A+ K129L+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ D27N+ K36E+ E46M+ E64P+ Q69P+ K70P+ N82T+ G96E+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ T3E+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ E46M+ T53P+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ E46M+ E61D+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82T+ A101R+ S109D+ G122P+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413Q+ N473Y+ D486E+ K491R; A1V+ V4N+ F7G+ T13I+ S15Q+ A20P+ K26E+ K36E+ A45M+ E46Y+ T53P+ E64P+ K65N+ Q69P+ K70P+ N82A+ A101L+ S109E+ T115Y+ K120A+ S141R+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S14E+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ K482P+ D486E+ K491R; T3G+ F7G+ P11A+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45R+ E46Y+ T53P+ E64P+ K65N+ Q69P+ K70P+ N82A+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+

F286C+ E299W+ G366N+ K378Q+ D385H+ K408M+ D410M+ L413T+ N473Y+ D486E+ K491R; T3G+ F7G+ P11A+ T13I+ S15Q+ K26E+ K36E+ A45M+ E46Y+ T53K+ E64P+ Q69P+ K70P+ N82T+ A101R+ S109D+ K120A+ K129L+ S141R+ Q143T+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ V8A+ T13I+ S15Q+ Q17K+ A20G+ K26E+ K36E+ E46M+ E64P+ K65N+ Q69P+ K70P+ Q76T+ K78S+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ K36E+ E46M+ E64P+ K65N+ Q69P+ K70P+ N82A+ N97D+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ Q17K+ A20G+ K26E+ 130L+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ K198G+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ V422R+ N473Y+ D486E+ K491R; T3G+ F7G+ P11A+ T13I+ S15Q+ A20P+ K26E+ K36E+ E46I+ T53K+ E64P+ Q69P+ K70P+ N82A+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ V8A+ T13I+ S15Q+ K26E+ K36E+ A45M+ E46Y+ T53K+ E64P+ Q69P+ K70P+ N82T+ A101R+ S109D+ K120A+ K129L+ S141R+ Q143T+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ V8A+ T13I+ S15Q+ A20P+ K26E+ K36E+ A45M+ E46Y+ T53K+ E64P+ V68M+ Q69P+ K70P+ N82T+ A101L+ S109D+ T115V+ K120A+ A126D+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ T53P+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ N97E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ W148Q+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ 268/+ G270C+ 271/+ S271G+ N272D+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324N+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120P+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ T438A+

N473Y+ D486E+ K491R; A1V+ V4N+ F7G+ T13E+ S15Q+ A20P+ K26E+ K36E+ E46M+ T53P+ E64P+ Q69P+ K70P+ N82A+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ N97E+ A101R+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ E249H+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ D27N+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ A423G+ N473Y+ E479R+ D486E+ K491R; A1V+ T3E+ F7G+ P11A+ T13I+ S15Q+ A20P+ K26E+ K36E+ E46M+ T53K+ E64P+ Q69P+ K70P+ N82T+ N97E+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ A101L+ S109D+ T115Y+ K120A+ A126T+ K129L+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R; A1V+ V4N+ F7G+ V9M+ T13I+ S15Q+ A20P+ K26E+ K36E+ E46M+ E64P+ Q69P+ K70P+ N82T+ N97E+ A101L+ S109D+ T115Y+ K120A+ K129L+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4D+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45M+ E46Y+ T53P+ E64P+ K65N+ Q69P+ K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82T+ A101R+ S109D+ K120A+ K129L+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ V8A+ T13I+ S15Q+ A20P+ K26E+ K36E+ A45M+ E46Y+ T53P+ E64P+ K65N+ Q69P+ K70P+ N82A+ A101L+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45R+ E46Y+ T53P+ E64P+ K65N+ Q69P+ K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82A+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82T+ A101R+ S109D+ K120A+ K129L+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299K+ G366N+ K378Q+ D385H+ P398F+ K408M+ D410M+ L413Q+ N473Y+ D486E+ K491R; T3G+ F7G+ V8A+ T13I+ S15Q+ Q17K+ A20G+ K26E+ 130L+ K36E+ E46M+ E64P+ K65N+ Q69P+ K70P+ Q76E+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ A45M+ E46Y+ T53P+ E64P+ K65N+ Q69P+

K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; S6P+ A1V+ V4N+ F7G+ T13I+ S15Q+ A20P+ K26E+ K36E+ E46M+ E64P+ Q69P+ K70P+ N82T+ N97E+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In one aspect, a variant comprises substitutions at positions corresponding to positions selected from a group consisting of: A1V+ V4N+ F7G+ T13I+ S15Q+ A20P+ K26E+ 130L+ K36E+ E46M+ T53K+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ V422I+ Q437I+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; A1V+ V4D+ F7G+ P11A+ T13I+ S15Q+ A20P+ K26E+ K36E+ E46M+ T53K+ E61D+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ T53P+ E64P+ K65N+ Q69P+ K70P+ N82A+ A101R+ S109E+ K120A+ A126T+ L134I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R; T3G+ F7G+ V8A+ T13I+ S15Q+ A20P+ K26E+ K36E+ A45M+ E46Y+ T53P+ E64P+ K65N+ Q69P+ K70P+ N82A+ A101L+ S109E+ K120A+ A126T+ L134I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82A+ N97E+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R; T3G+ F7G+ P11A+ T13I+ S15Q+ A20P+ K26E+ K36E+ A45M+ E46Y+ T53K+ E64P+ Q69P+ K70P+ N82A+ A101R+ S109D+ G112E+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

In an embodiment, the variant has improved in-detergent stability compared to the parent enzyme.

In an embodiment, the variant has improved thermostability compared to the parent enzyme.

In an embodiment, the variant has improved protease stability compared to the parent enzyme.

In an embodiment, the variant has improved surfactant stability compared to the parent enzyme.

In an embodiment, the variant has improved pH stability compared to the parent enzyme.

In one aspect, the mannanase variants comprises at least one of the following substitutions:

Q168D+ L454I;
Q168D+ L413A;
K26E+ Q168D+ N296A;
Q168D+ D385P+ L413A;
Q168D+ E249Q+ N283Y+ L413A;
Q168D+ A210E+ N283Y+ L413A+ R489K;
Q168D+ Q183E+ L413A;
K26E+ Q168D;
K26E+ Q168D+ S181T+ K408C+ K482Q;
K26E+ Q168D+ N283Y+ N296A;
K26E+ Q168D+ A210E+ S260C+ N283Y+ N296A+ K482Q;
K26E+ Q168D+ A210E+ S260C+ S271G+ N283Y+ N296A;
K26E+ Q168D+ A210E+ S271G+ N283Y+ N296A;
K26E+ Q168D+ A210Q+ S239A+ E249Q+ S271Y+ N296A;
K26E+ Q168D+ A210Q+ E249Q+ S271Y+ N296A;
K26E+ Q168D+ A184T+ N242T+ N296A+ E380D+ T438A;
K26E+ Q168D+ A184T+ N296A+ E322D+ H323A+ E380D+ T438A;
K26E+ Q168D+ A184T+ N242T+ N296A+ E322D+ H323A+ E380D+ T438A;
K26E+ Q168D+ A184T+ N242T+ N296A+ E322D+ H323A+ K364Y+ E380D+ T438A;
K26E+ R164A+ Q168D+ S181T+ N296A+ Q321W+ K408S+ L413V;
K26E+ R164A+ Q168D+ S181T+ N296A+ K408S+ L413V;
K26E+ R164A+ Q168D+ S181T+ N296A;
K26E+ R164A+ Q168D+ S181T+ N296A+ Q321W+ K408S;
K26E+ Q168D+ Y213K+ K252E+ E285D+ N296A+ D385P;
K26E+ Q168D+ K252E+ E285D+ N296A+ A344C+ G366H+ D385P;
K26E+ Q168D+ T192A+ Y213K+ N296A+ A344C+ D385P;
K26E+ Q168D+ K252E+ N296A+ A344C+ D385P;
K26E+ R164H+ Q168D+ F190Y+ S271G+ N296A;
K26E+ Q168D+ S271G+ N296A+ Y354W+ V377E+ K408A;
K26E+ Q168D+ F190Y+ S239A+ S271G+ N296A;
K26E+ Q168D+ N283Y+ N296A+ S403Q;
K26E+ Q168D+ N283Y+ N296A+ D385S+ S403Q+ K408C;
K26E+ Q168D+ N283Y+ N296A+ S403Q+ L413T;
K26E+ Q168D+ N283Y+ N296A+ D385S+ S403Q+ K408C+ L413T;
K26E+ Q168D+ N283Y+ N296A+ S403Q+ K408C+ L413T;
K26E+ K36N+ Q168D+ K198N+ L413A+ N473F;
R38Q+ Q168D+ D385F;
Q168D+ Q183E+ K252E+ R253W+ K408T+ L413A;
K169P+ Q183E+ S260C+ N283Y+ L413A;
K26E+ Q168D+ Q183E+ L413A;
K26E+ Q168D+ S181T+ E249Q+ N283Y+ D385A+ L413A;
K26E+ Q168D+ S181T+ K197F+ V235L+ E249Q+ N283Y+ L413A;
K26E+ Q168D+ N296A+ D385F+ K482Q;
E64P+ Q168D;
K26E+ Q168D+ A210Q+ S239A+ E249Q+ K364Y;
K26E+ Q168D+ S271Y+ L454I;
K26E+ Q168D+ A210Q+ S271Y+ V377E;
K26E+ Q168D+ A210Q+ S271Y+ L454I;
K26E+ Q168D+ A184T+ F190Y+ N242T+ E322D+ H323A;
K26E+ Q168D+ F190Y+ N242T+ T315A;
K26E+ Q168D+ A184T+ F190Y+ N242T+ T315A+ E380D;
K26E+ Q168D+ A184T+ F190Y+ N242T+ T315A;
K26E+ Q168D+ F190Y+ N242T+ N283Y+ E322D+ H323A;
K26E+ Q168D+ Y213K+ S260C+ G366H;
K26E+ Q168D+ E249L+ P347D;
K26E+ Q168D+ K252E+ R253W+ K378H;
K26E+ Q168D+ K197N+ K252E+ R253W+ K408T;
K26E+ Q168D+ K197N+ K252E+ R253W+ K378H;
K26E+ Q168D+ A210E+ N283Y+ D385A+ L413A+ R489K;
K26E+ Q168D+ S181T+ A210E+ N283Y+ L413A+ R489K;
K26E+ Q168D+ A210E+ S271G+ N283Y;
K26E+ Q168D+ L259F+ S271G;
K26E+ Q168D+ N283Y;
K26E+ Q168D+ A210E+ L259F+ S271G;
K26E+ Q168D+ A210E+ L259F+ S271G+ N283Y+ R489K;
K26E+ Q168D+ L259F+ N283Y;
R38Q+ Q168D+ L413T;
R38Q+ Q168D+ T192V;
R38Q+ Q168D+ S239A;
K26E+ Q168D+ K408T;
K26E+ Q168D+ K197F;
K26E+ Q168D+ L413T;
K26E+ Q168D+ D385A;
K26E+ Q168D+ R355Q;
K26E+ Q168D+ P347D;
K26E+ Q168D+ G483D;
K26E+ Q168D+ T192V;
K26E+ Q168D+ A210E;
K26E+ Q168D+ N193S;
K26E+ Q168D+ S239A;
K26H+ Q168D;
K26E+ Q69P+ Q168D;
K26E+ E61D+ Q168D;
K26E+ T53E+ E61D+ Q168D;
K26E+ T53E+ E64P+ Q168D;
K26E+ T53E+ K65N+ Q168D;
K26E+ K36E+ Q168D;
K26E+ R38M+ Q168D;
K26E+ K36T+ Q168D;
Q17A+ Q168D;
A23M+ Q168D;
S103V+ Q168D;
S103E+ Q168D;
Q69P+ Q168D;
H12A+ Q168D;
K65S+ Q168D;
N97Y+ Q168D;
Q168D+ K304F;
Q168D+ K179V;
K26E+ E64P+ Q168D;
H12D+ K26E+ Q168D;
K26E+ K70E+ Q168D;
K26E+ T42E+ Q168D;

K26E+ T53C+ Q168D;
K26E+ T53P+ Q168D;
K26E+ K70M+ Q168D;
K26E+ K70P+ Q168D;
K26E+ S72F+ Q168D;
K26E+ A101I+ Q168D;
K26E+ A101L+ Q168D;
K26E+ S103E+ Q168D;
K26E+ S103I+ Q168D;
K26E+ Q168D+ Y354W;
K26E+ Q168D+ L413V;
K26E+ Q168D+ E249L;
K26E+ R38L+ Q168D;
K26E+ R38L+ K70P+ A101L+ Q168D;
K26E+ K36E+ Q168D+ D385A;
K26E+ R38T+ Q168D+ D385A;
K26E+ S103V+ Q168D+ D385A;
K26E+ K36T+ Q168D+ D385A;
K26E+ R38M+ Q168D+ D385A;
K26E+ K36A+ Q168D+ D385A;
K26E+ S103E+ Q168D+ D385A;
K26E+ R38C+ A126S+ Q168D+ D385A;
K26E+ R38L+ Q168D+ D385A;
K26E+ S103C+ Q168D+ D385A;
K26E+ K70M+ Q168D+ D385A;
K26E+ S103I+ Q168D+ D385A;
K26E+ K70P+ Q168D+ D385A;
K26E+ A101V+ S103Y+ Q168D+ D385A;
K26E+ K70I+ Q168D+ D385A;
K26E+ R38F+ Q168D+ D385A;
K26E+ S103Q+ Q168D+ D385A;
K26E+ A101C+ Q168D+ D385A;
K26E+ K70E+ Q168D+ D385A;
K26E+ A101L+ Q168D+ D385A;
K26E+ K36C+ Q168D+ D385A;
K26E+ S103D+ Q168D+ D385A;
K26E+ K70T+ Q168D+ D385A;
K26E+ A101Q+ Q168D+ D385A;
K26E+ K65N+ Q168D+ D385A;
K26E+ K100R+ Q168D+ D385A;
K26E+ S103L+ Q168D+ D385A;
K26E+ K36M+ Q168D+ D385A;
K26E+ T53P+ Q168D+ D385A;
K26E+ A101N+ Q168D+ D385A;
K26E+ K36D+ Q168D+ D385A;
K26E+ T53C+ Q168D+ D385A;
K26E+ K65T+ Q168D+ D385A;
K26E+ Q168D+ R489P;
K26E+ Q168D+ L477F;
K26E+ Q168D+ K491P;
K26E+ R38L+ K70P+ Q168D;
K26E+ T42E+ Q69P+ Q168D;
V4D+ K26E+ K65T+ K120P+ Q168D;
H12D+ Q17A+ K26E+ E64P+ Q168D;
K26E+ Q168D+ N283Y+ D385A+ K408S+ D452N+ K466Q;
K26E+ A101E+ Q168D+ K197A+ K408S;
K26E+ Q168D+ N283M;
K26E+ Q168D+ Y195H;
K26E+ T42E+ Q69P+ Q168D+ D385A;
V4D+ K26E+ T53P+ K65Q+ K120P+ Q168D+ D385A;
V4D+ K26E+ T53P+ K120P+ Q168D+ D385A;
H12D+ Q17A+ K26E+ E64P+ A111L+ Q168D+ D385A;
K26E+ Q168D+ N283Y+ D385A+ K408S;
K26E+ Q168D+ N283Y+ K408S;
K26E+ Q168D+ K197A+ N283Y+ K408S;
K26E+ K70P+ Q168D+ E249L;
K26E+ K70P+ Q168D+ Y354W;
K26E+ K70P+ Q168D+ L413V;
K26E+ S103E+ Q168D+ L413V;
H12D+ Q17A+ K26E+ E64P+ V68T+ Q168D+ D385A;
H12D+ Q17A+ K26E+ E64P+ V68T+ A111L+ Q168D+ D385A;
K26E+ Q168D+ N283Y+ D385A;
K26E+ K36E+ E64P+ Q168D+ D385A;
K26E+ K36E+ S72F+ Q168D+ D385A+ W443G;
K26E+ K36E+ S103V+ Q168D+ D385A;
K26E+ K36E+ Q168D+ D385A+ K417Q;
K26E+ K70A+ S103V+ Q168D+ D385A;
K26E+ K70M+ S103V+ Q168D+ D385A;
K26E+ K70I+ S103V+ Q168D+ D385A;
K26E+ S103V+ K120P+ Q168D+ D385A;
M130V+ Q168D;
K26E+ K36E+ T53P+ Q168D+ D385A;
K26E+ K36E+ A101L+ Q168D+ D385A;
K26E+ K36T+ S103V+ Q168D+ D385A;
K26E+ R38M+ S103V+ Q168D+ D385A;
K26E+ T42E+ S103V+ Q168D+ D385A;
K26E+ T53P+ S103V+ Q168D+ D385A;
H12D+ K26E+ K36E+ T42E+ E64P+ K70P+ A101L+ Q168D+ D385A;
K26E+ K36E+ K70P+ K120P+ Q168D+ D385A;
K26E+ T42E+ Q69P+ S103V+ Q168D+ D385A;
K26E+ K36E+ K70P+ S103V+ K120P+ Q168D+ D385A;
H12D+ K26E+ T42E+ E64P+ K70P+ S103V+ Q168D+ D385A;
F25Y+ K36E+ T53P+ S103V+ Q168D+ T192V+ D385A;
K26E+ K36E+ E64P+ K70P+ S103V+ Q168D+ N283Y+ D385A;
K26E+ K36E+ S103V+ Q168D+ F190Y+ D385A;
K26E+ K36E+ S103V+ Q168D+ S271G+ D385A;
K26E+ K36E+ S103V+ Q168D+ D385A+ L413V;
K26E+ K36E+ S103V+ Q168D+ D385A+ K417Q;
K26E+ K36E+ S103V+ Q168D+ D385A+ K462L;
K26E+ K36E+ S103V+ Q168D+ D385A+ K408T;
K26E+ K36E+ S103V+ K120P+ Q168D+ D385A;
K26E+ K36E+ K70A+ Q168D+ D385A;
K26E+ K36E+ K70P+ Q168D+ D385A;
K26E+ K36E+ S72F+ Q168D+ D385A;
K26E+ R38L+ K70P+ A101L+ Q168D+ N283Y;
K26E+ R38L+ K70P+ A101L+ Q168D+ K408D;
K26E+ R38L+ K70P+ A101L+ Q168D+ L413A;
K26E+ R38L+ K70P+ A101L+ Q168D+ L413T;
K26E+ R38L+ K70P+ A101L+ S109D+ Q168D;
K26E+ R38L+ K70P+ A101L+ Q168D+ D385A;
K26E+ R38L+ K70P+ A101L+ A126T+ Q168D+ E379P;
K26E+ K70P+ Q168D+ K197A+ K408S+ K462L+ K466Q;
K26E+ K70P+ Q168D+ K197F+ N283Y+ K408S+ L413T;
K26E+ K70P+ Q168D+ K197F+ N283Y;
K26E+ K70P+ Q168D+ N283Y+ K408S+ L413T;
K26E+ K70P+ Q168D+ N283Y+ D385A+ S403Q;
H12D+ K26E+ R38L+ T42E+ K70P+ A101L+ Q168D;
K26E+ K70A+ S103V+ Q168D+ K197A+ D385A;
K26E+ K70A+ S103V+ Q168D+ D385A+ K462P;
K26E+ E64P+ K70A+ S103V+ Q168D+ D385A;
K26E+ K36T+ K70A+ S103V+ Q168D+ D385A;
K26E+ K70A+ S103V+ Q168D+ K304R+ D385A;
K26E+ K70P+ S103V+ Q168D+ D385A;
K26E+ K36E+ T53P+ K65Q+ Q168D+ F190Y+ K197A+ D385A;

K26E+ K36E+ E64P+ K70P+ S103V+ Q168D+ F190Y+ N283Y+ D385A+ W443G;
K26E+ K36E+ E64P+ K70P+ S103V+ Q168D+ N283Y+ D385A+ L413T;
K26E+ K36E+ E64P+ K70P+ S103V+ Q168D+ T192V+ N283Y+ D385A;
K26E+ K36E+ E64P+ K70P+ S103V+ E162D+ Q168D+ N283Y+ D385A;
K26E+ K36E+ E64P+ K70P+ S103V+ S109D+ Q168D+ N283Y+ D385A;
K26E+ K36E+ E64P+ K70P+ S103V+ Q168D+ K197Y+ N283Y+ D385A;
K26E+ K36E+ E64P+ K70P+ S103V+ Q168D+ N283Y+ D385A+ L477F;
K26E+ K36E+ S103V+ Q168D+ D385A+ L413V+ K462L;
K26E+ K36E+ S103V+ Q168D+ K197D+ D385A+ K462L;
K26E+ K36E+ T53P+ E64P+ K70P+ A101I+ Q168D+ N283Y+ D385A+ K408S+ L413T;
K26E+ K36E+ E64P+ K70P+ S103V+ Q168D+ F190Y+ N283Y+ D385A+ L413T;
K26E+ K36E+ E64P+ K70P+ S103V+ Q168D+ S271G+ N283Y+ D385A+ L413T;
K26E+ K36E+ E64P+ K70P+ S103V+ Q168D+ N283Y+ D385A+ K408T+ L413T;
K26E+ K36E+ E64P+ K70P+ S103V+ Q168D+ T192V+ N283Y+ D385A+ L413T;
K26E+ K36E+ E64P+ K70P+ S103V+ Q168D+ N283Y+ D385A+ L413T+ K462P;
K26E+ K36E+ E64P+ K70P+ S103V+ E162D+ Q168D+ N283Y+ D385A+ L413T;
K26E+ K36E+ E64P+ K70P+ S103V+ S109D+ Q168D+ N283Y+ D385A+ L413T;
K26E+ K36E+ E64P+ K70P+ S103V+ Q168D+ N283Y+ D385A+ L413T+ K466Q;
V4Y+ K26E+ K36E+ E64P+ K70P+ S103V+ Q168D+ N283Y+ D385A+ L413T;
K26E+ K36E+ D48A+ E64P+ K70P+ S103V+ Q168D+ N283Y+ D385A+ L413T;
K26E+ K36E+ E64P+ K70P+ S103V+ P163E+ Q168D+ N283Y+ D385A+ L413T;
K26E+ K36E+ E64P+ K70P+ S103V+ Q168D+ K197D+ N283Y+ D385A+ L413T;
K26E+ K36E+ E64P+ K70P+ S103V+ Q168D+ N283Y+ D385A+ L413T+ K417E;
K26E+ K36E+ E64P+ K70P+ S103V+ Q168D+ N283Y+ D385A+ L413T+ L477F;
F25Y+ K36E+ T53P+ E64P+ K70P+ S103V+ Q168D+ T192V+ N283Y+ D385A;
K26E+ K36E+ T53P+ E64P+ K70P+ S103V+ Q168D+ T192V+ N283Y+ D385A;
F25Y+ K26E+ K36E+ T53P+ S103V+ Q168D+ T192V+ D385A+ K462L;
K26E+ K36E+ E64P+ S103V+ K120P+ Q168D+ N283Y+ D385A+ K462L;
F25Y+ K36E+ T53P+ E64P+ K70P+ S103V+ Q168D+ T192V+ K197N+ N283Y+ D385A;
F25Y+ K36E+ T53P+ E64P+ K70P+ S103V+ E162D+ Q168D+ T192V+ N283Y+ D385A;
S14N+ K26E+ K36E+ E64P+ K70P+ S103V+ Q168D+ K197D+ N283Y+ D385A+ L413T;
K26E+ K36E+ E64P+ K70P+ S103V+ Q168D+ M172I+ K197D+ N283Y+ D385A+ L413T;
K26E+ K36E+ E64P+ K70P+ S103V+ T167K+ Q168D+ K197D+ N283Y+ D385A+ L413T;
K26E+ K36E+ E64P+ K70P+ S103V+ I165L+ Q168D+ K197D+ N283Y+ D385A+ L413T;
K26E+ K36E+ E64P+ K70P+ S103V+ T166P+ Q168D+ K197D+ N283Y+ D385A+ L413T;
K26E+ K36E+ E64P+ K70P+ S103V+ P163N+ Q168D+ K197D+ N283Y+ D385A+ L413T;
K26E+ K36E+ E64P+ K70P+ S103V+ Q168D+ K197D+ N283Y+ D385P+ L413T;
K26E+ K36E+ E64P+ K70P+ S103V+ R164H+ Q168D+ K197D+ N283Y+ D385A+ L413T;
K26E+ K36E+ E64P+ K70P+ S103V+ Q168F+ K197D+ N283Y+ D385A+ L413T;
K26E+ K36E+ E64P+ K70P+ S103V+ Q168M+ K197D+ N283Y+ D385A+ L413T;
K26E+ K36E+ E64P+ K70P+ S103V+ K169V+ K197D+ N283Y+ D385A+ L413T;
K26E+ K36E+ E64P+ K70P+ S103V+ K169T+ N283Y+ D385A+ L477F;
K26E+ K36E+ E64P+ Q69P+ S103V+ Q168D+ N283Y+ D385A+ L477F;
K26E+ K36E+ E64P+ K70P+ S103V+ E162D+ Q168D+ N283Y+ D385A+ L477F;
K26E+ K36E+ E64P+ K70P+ S103V+ E162Q+ Q168D+ N283Y+ D385A+ L477F;
K26E+ K36E+ E64P+ K70P+ S103V+ I165A+ Q168D+ N283Y+ D385A+ L477F;
K26E+ K36E+ E64P+ K70P+ S103V+ T166P+ Q168D+ N283Y+ D385A+ L477F;
S14N+ K26E+ K36E+ E64P+ K70P+ S103V+ Q168D+ K197D+ N283Y+ D385A+ D410M+ L413T;
S14N+ K26E+ K36E+ E64P+ Q69S+ S103V+ Q168D+ K197D+ N283Y+ D385A+ L413T;
S14N+ K26E+ K36E+ E64P+ K70P+ S103V+ Q168D+ K169Q+ K197D+ N283Y+ D385A+ L413T;
S14N+ K26E+ K36E+ E64P+ K70P+ S103V+ K169P+ K197D+ N283Y+ D385A+ L413T;
K26E+ K36E+ E64P+ Q69P+ N97Y+ S103V+ T123R+ Q168D+ K197D+ N283Y+ D385A+ L413T;
K26E+ K36E+ E64P+ K70P+ S103V+ K169T+ N283Y+ D385A+ L413T+ L477F;
K26E+ K36E+ E64P+ K70P+ S103V+ Q168D+ K169Q+ N283Y+ D385A+ L413T+ L477F;
H12P+ K26E+ K36E+ E64P+ K70P+ S103V+ Q168D+ N283Y+ D385A+ L413T+ L477F;
K26E+ K36E+ E64P+ Q69T+ S103V+ Q168D+ N283Y+ D385A+ L413T+ L477F;
K26E+ K36E+ E64P+ Q69R+ S103V+ Q168D+ N283Y+ D385A+ L413T+ L477F;
K26E+ K36E+ E64P+ K70P+ S103V+ T166L+ Q168D+ N283Y+ D385A+ L413T+ L477F;
K26E+ K36E+ E64P+ K70P+ S103V+ T166Q+ Q168D+ N283Y+ D385A+ L413T+ L477F;
K26E+ K36E+ E64P+ K70P+ S103V+ T166V+ Q168D+ N283Y+ D385A+ L413T+ L477F;
K26E+ K36E+ E64P+ K70P+ S103V+ T166G+ Q168D+ N283Y+ D385A+ L413T+ L477F;
K26E+ K36E+ E64P+ K70P+ S103V+ T166N+ Q168D+ N283Y+ D385A+ L413T+ L477F;
K26E+ K36E+ E64P+ K70P+ S103V+ T166I+ Q168D+ N283Y+ D385A+ L413T+ L477F;
K26E+ K36E+ E64P+ K70P+ S103V+ T166W+ Q168D+ N283Y+ D385A+ L413T+ L477F;
K26E+ K36E+ E64P+ K70P+ S103V+ T166R+ Q168D+ N283Y+ D385A+ L413T+ L477F;
K26E+ K36E+ E64P+ K70P+ S103V+ T166E+ Q168D+ N283Y+ D385A+ L413T+ L477F;

K26E+ K36E+ E64P+ K70P+ S103V+ Q168P+ N283Y+ D385A+ L413T+ L477F;
K26E+ K36E+ S57R+ E64P+ K70P+ S103V+ Q168D+ N283Y+ D385A+ L413T+ L477F;
K26E+ K36E+ S57P+ E64P+ K70P+ S103V+ Q168D+ N283Y+ D385A+ L413T+ L477F;
S14N+ K26E+ K36E+ E64P+ K70P+ S103V+ I165A+ Q168D+ K197D+ N283Y+ D385A+ D410M+ L413T;
S14N+ K26E+ K36E+ E64P+ K70P+ S103V+ I165L+ Q168D+ K197D+ N283Y+ D385A+ D410M+ L413T;
S14N+ K26E+ K36E+ E64P+ K70P+ S103V+ T166P+ Q168D+ K197D+ N283Y+ D385A+ D410M+ L413T;
V4D+ S14N+ K26E+ K36E+ E64P+ K70P+ S103V+ Q168D+ K197D+ N283Y+ D385A+ D410M+ L413T;
S14N+ K26E+ K36E+ E64P+ K70P+ S103V+ P163N+ Q168D+ K197D+ N283Y+ D385A+ D410M+ L413T;
K26E+ K36E+ E64P+ K70P+ S103V+ T166P+ Q168D+ K197D+ N283Y+ D385A+ D410L+ L413T;
K26E+ K36E+ E64P+ K70P+ S103V+ T166P+ Q168D+ K197D+ N283Y+ D385A+ D410M+ L413T;
K26E+ K36E+ E64P+ K70P+ S103V+ E162D+ T166P+ Q168D+ K197D+ N283Y+ D385A+ L413T;
K26E+ K36E+ E64P+ K70P+ S103V+ T166P+ Q168D+ K197D+ N283Y+ D385A+ K408M+ L413T;
S15Q+ K26E+ K36E+ E64P+ K70P+ S103V+ G112V+ T166P+ Q168D+ K197D+ N283Y+ D385A+ L413T;
H12V+ K26E+ K36E+ E64P+ K70P+ S103V+ T166P+ Q168D+ K197D+ N283Y+ D385A+ L413T;
S14N+ K26E+ K36E+ E64P+ K70P+ S103V+ T166P+ Q168D+ K197D+ N283Y+ D385A+ L413T;
K26E+ K36E+ E64P+ K70P+ S103V+ T166P+ Q168D+ K197Y+ N283Y+ D385A+ L413T;
F25Y+ K26E+ K36E+ E64P+ K70P+ S103V+ T166P+ Q168D+ K197D+ N283Y+ D385A+ L413T+ L477F;
K26E+ K36E+ E64P+ K70P+ S103V+ T166P+ Q168D+ N283Y+ D385A+ L413T+ L477F;
V4Y+ K26E+ K36E+ E64P+ K70P+ S103V+ I165L+ Q168D+ N283Y+ D385A+ L413T+ L477F;
S14N+ K26E+ K36E+ T53P+ E64P+ K70P+ S103V+ R160N+ T166P+ Q168D+ K197D+ N283Y+ D385A+ L413T;
K26E+ K36E+ E64P+ K70P+ S103V+ I165D+ Q168D+ K197D+ N283Y+ D385A+ L413T;
K26E+ K36E+ E64P+ K70P+ S103V+ T166P+ Q168D+ M171N+ K197D+ N283Y+ D385A+ L413T;
K26E+ K36E+ E64P+ K70P+ S103V+ T166P+ Q168D+ M171Q+ K197D+ N283Y+ D385A+ L413T;
K26E+ K36E+ E64P+ K70P+ S103V+ T166P+ Q168D+ M171E+ K197D+ N283Y+ D385A+ L413T;
K26E+ K36E+ E64P+ K70P+ S103V+ T166P+ Q168D+ T170H+ K197D+ N283Y+ D385A+ D410M+ L413T;
S15Q+ K26E+ K36E+ E64P+ K70P+ S103V+ T166P+ Q168D+ K197D+ N283Y+ D385A+ D410M+ L413T;
K26E+ K36E+ E64P+ K70P+ S103V+ E162D+ T166P+ Q168D+ K197D+ N283Y+ T315V+ D385A+ L413T;
K26E+ K36E+ E64P+ K70P+ S103V+ E162D+ T166P+ Q168D+ K197D+ N283Y+ D385H+ L413T;
K26E+ K36E+ E64P+ K70P+ S103V+ E162D+ T166P+ Q168D+ K197D+ N283Y+ D385A+ K408A+ L413T;
K26E+ K36E+ E64P+ K70P+ S103V+ E162D+ T166P+ Q168D+ K197D+ N283Y+ D385A+ K408Q+ L413T;
H12E+ K26E+ K36E+ E64P+ K70P+ S103V+ E162D+ T166P+ Q168D+ K197D+ N283Y+ D385A+ L413T;
H12R+ K26E+ K36E+ E64P+ K70P+ S103V+ E162D+ T166P+ Q168D+ K197D+ N283Y+ D385A+ L413T;
H12V+ K26E+ K36E+ E64P+ K70P+ S103V+ E162D+ T166P+ Q168D+ K197D+ N283Y+ D385A+ L413T;
S14N+ K26E+ K36E+ E64P+ K70P+ S103V+ E162D+ T166P+ Q168D+ K197D+ N283Y+ D385A+ L413T;
K26E+ K36E+ E64P+ Q69P+ K70P+ S103V+ E162D+ T166P+ Q168D+ K197D+ N283Y+ D385A+ L413T;
K26E+ K36E+ E64P+ K70P+ S103V+ T166P+ Q168D+ S178D+ K197D+ N283Y+ D385A+ L413T;
K26E+ K36E+ E64P+ K70P+ S103V+ T166P+ Q168D+ S178P+ K197D+ N283Y+ D385A+ D410M+ L413T;
K26E+ K36E+ E64P+ K70P+ S103V+ T166P+ Q168D+ K179N+ K197D+ N283Y+ D385A+ L413T;
K26E+ K36E+ E64P+ K70P+ S103V+ E162D+ T166P+ Q168D+ K197D+ S271G+ N283Y+ D385A+ L413T;
S15Q+ K26E+ K36E+ E64P+ K70P+ S103V+ E162D+ T166P+ Q168D+ K197D+ N283Y+ D385A+ L413T;
K26E+ K36E+ E64P+ K70P+ S103V+ T166P+ Q168D+ M171Q+ K197D+ N283Y+ D385A+ K408Q+ L413T;
H12R+ K26E+ K36E+ E64P+ K70P+ S103V+ T166P+ Q168D+ M171Q+ K197D+ N283Y+ D385A+ L413T;
K26E+ K36E+ E64P+ K70P+ S103V+ T166P+ Q168D+ F190Y+ N283Y+ D385A+ L477F;
K26E+ K36E+ E64P+ K70P+ S103V+ T166P+ Q168D+ T192V+ N283Y+ D385A+ L477F;
V4D+ K26E+ K36E+ E64P+ K70P+ S103V+ T166P+ Q168D+ N283Y+ D385A+ L477F;
S15Q+ K26E+ K36E+ E64P+ K70P+ S103V+ T166P+ Q168D+ K197D+ S271G+ N283Y+ D385A+ D4100M+ L413T;
S15Q+ K26E+ K36E+ E64P+ K70P+ S103V+ T166P+ Q168D+ K197D+ M248I+ N283Y+ D385A+ D410M+ L413T;
S15Q+ K26E+ K36E+ T53P+ E64P+ K70P+ S103V+ T166P+ Q168D+ K197D+ N283Y+ D385A+ D4100M+ L413T;
S15Q+ K26E+ K36E+ E64P+ K70P+ S103V+ P163N+ T166P+ Q168D+ K197D+ N283Y+ D385A+ D410M+ L413T;
K26E+ K36E+ E64P+ K70P+ S103V+ E162D+ T166P+ Q168D+ K197D+ S271G+ N283Y+ D385H+ L413T;
K26E+ K36E+ E64P+ K70P+ S103V+ E162D+ T166P+ Q168D+ M172I+ K197D+ N283Y+ D385H+ L413T;
K26E+ K36E+ E64P+ K70P+ S103V+ E162D+ T166P+ Q168D+ K197D+ M248I+ N283Y+ D385H+ L413T;
F25Y+ K26E+ K36E+ E64P+ K70P+ S103V+ E162D+ T166P+ Q168D+ K197D+ N283Y+ D385H+ L413T;
V4N+ K26E+ K36E+ E64P+ K70P+ S103V+ E162D+ T166P+ Q168D+ K197D+ N283Y+ D385H+ L413T;
S15Q+ K26E+ K36E+ E64P+ K70P+ S103V+ E162D+ T166P+ Q168D+ K197D+ N283Y+ D385H+ L413T;
K26E+ K36E+ E64P+ K70P+ S103V+ R164*+ I165*+ Q168D+ K197D+ N283Y+ D385H+ L413T;
H12R+ K26E+ K36E+ E64P+ K70P+ S103V+ T166P+ Q168D+ M171Q+ F190Y+ K197D+ N283Y+ D385A+ L413T;
H12R+ K26E+ K36E+ E64P+ K70P+ S103V+ T166P+ Q168D+ M171Q+ K197D+ A210E+ N283Y+ E322D+ D385A+ L413T;
H12R+ K26E+ K36E+ E64P+ K70P+ S103V+ T166P+ Q168D+ M171Q+ K197D+ S271G+ N283Y+ D385A+ L413T;
H12R+ K26E+ K36E+ E64P+ K70P+ S103V+ E162D+ T166P+ Q168D+ M171Q+ K197D+ N283Y+ D385A+ L413T;
H12R+ K26E+ K36E+ E64P+ K70P+ S103V+ T166P+ Q168D+ M171Q+ K197D+ N283Y+ D385A+ K408M+ L413T;

S15Q+ K26E+ K36E+ E64P+ K70P+ S103V+ T166P+ Q168D+ K197D+ M248I+ S271G+ N283Y+ D385A+ D410M+ L413T;

S14N+ K26E+ K36E+ L49M+ E64P+ K70P+ S103V+ E162D+ T166P+ Q168D+ K197D+ N283Y+ D385A+ K408A+ L413T;

K26E+ K36E+ E64P+ K70P+ S103V+ T166P+ Q168D+ T170H+ S178P+ K197D+ N283Y+ D385A+ D410M+ L413T;

H12R+ K26E+ K36E+ E64P+ K70P+ S103V+ T166P+ Q168D+ M171Q+ F190Y+ K197D+ S271G+ N283Y+ D385A+ L413T;

H12R+ K26E+ K36E+ E64P+ K70P+ S103V+ K129M+ E162D+ T166P+ Q168D+ M171Q+ K197D+ S271G+ N283Y+ D385A+ L413T;

H12R+ K26E+ K36E+ E64P+ K70P+ S103V+ T166P+ Q168D+ M171Q+ K197D+ M248I+ S271G+ N283Y+ D385A+ L413T;

H12R+ K26E+ K36E+ E64P+ K70P+ S103V+ T166P+ Q168D+ M171Q+ K197D+ S271G+ N283Y+ D385A+ K408M+ L413T;

H12R+ K26E+ K36E+ K65H+ K70P+ S103V+ T166P+ Q168D+ M171Q+ K197D+ S271G+ N283Y+ D385A+ L413T;

H12R+ K26E+ K36E+ E46Y+ E64P+ K70P+ S103V+ T166P+ Q168D+ M171Q+ K197D+ S271G+ N283Y+ D385A+ L413T;

S15Q+ K26E+ K36E+ E64P+ K70P+ S103V+ E162D+ T166P+ Q168D+ K197D+ M248I+ S271G+ N283Y+ D385A+ D410M+ L413T;

S15Q+ K26E+ K36E+ E64P+ K70P+ S103V+ T166P+ Q168D+ S178P+ K197D+ M248I+ S271G+ N283Y+ D385A+ D410M+ L413T;

S15Q+ K26E+ K36E+ E64P+ K70P+ S103V+ T166P+ Q168D+ K197D+ M248I+ S271G+ N283Y+ D385A+ K408M+ D410M+ L413T;

S15Q+ K26E+ K36E+ D48S+ E64P+ K70P+ S103V+ T166P+ Q168D+ K197D+ M248I+ S271G+ N283Y+ D385A+ D410M+ L413T;

S15Q+ K26E+ K36E+ E64P+ K70P+ S103V+ P163E+ T166P+ Q168D+ K197D+ M248I+ S271G+ N283Y+ D385A+ D410M+ L413T;

S15Q+ K26E+ K36E+ E64P+ K70P+ S103V+ I165D+ Q168D+ K197D+ M248I+ S271G+ N283Y+ D385A+ D41G0M+ L413T;

S14N+ K26E+ K36E+ L49M+ E64P+ K70P+ S103V+ E162D+ T166P+ Q168D+ K197D+ S258G+ N283Y+ D385A+ K408A+ L413T;

S14N+ K26E+ K36E+ L49M+ E64P+ K70P+ S103V+ E162D+ T166P+ Q168D+ K197D+ N283Y+ D385A+ K408E+ L413T;

S14N+ K26E+ K36E+ L49M+ E64P+ K70P+ S103V+ E162D+ T166P+ Q168D+ K197D+ N283Y+ D385A+ K408M+ L413T;

V4G+ S14N+ K26E+ K36E+ L49M+ E64P+ K70P+ S103V+ E162D+ T166P+ Q168D+ K197D+ N283Y+ D385A+ K408A+ L413T;

H12R+ K26E+ K36E+ K65H+ K70P+ S103V+ E162D+ T166P+ Q168D+ M171Q+ K197D+ S271G+ N283Y+ D385A+ L413T;

H12R+ K26E+ K36E+ K65H+ K70P+ S103V+ T166P+ Q168D+ T170H+ K197D+ S271G+ N283Y+ D385A+ L413T;

S15Q+ K26E+ K36E+ E46Y+ E64P+ K70P+ S103V+ T166P+ Q168D+ K197D+ M248I+ S271G+ N283Y+ D385A+ K408M+ D410M+ L413T;

H12R+ K26E+ K36E+ E46Y+ E64P+ K70P+ S103V+ T166P+ Q168D+ M171Q+ K197D+ S271G+ N283Y+ D385A+ L413T+ G483D;

H12R+ K26E+ K36E+ E46Y+ E64P+ K70P+ S103V+ T166P+ Q168D+ M171Q+ K197D+ S271G+ N283Y+ K378Q+ D385A+ L413T;

H12R+ K26E+ K36E+ E46Y+ E64P+ K70P+ S103V+ T166P+ Q168D+ M171Q+ K197D+ S271G+ N283Y+ D385A+ K408A+ L413T;

H12R+ K26E+ K36E+ E46Y+ E64P+ K70P+ S103V+ E162D+ T166P+ Q168D+ M171Q+ K197D+ S271G+ N283Y+ D385A+ L413T;

H12R+ K26E+ K36E+ E46Y+ E64P+ K70P+ S103E+ T166P+ Q168D+ M171Q+ K197D+ S271G+ N283Y+ D385A+ L413T;

S14N+ K26E+ K36E+ L49M+ E64P+ K70P+ S103V+ E162D+ T166P+ Q168D+ K197D+ S239A+ S258G+ N283Y+ D385A+ K408A+ L413T;

H12R+ K26E+ K36E+ E46Y+ E64P+ K70P+ S103D+ T166P+ Q168D+ M171Q+ K197D+ S271G+ N283Y+ D385A+ L413T;

H12R+ K26E+ K36E+ E46Y+ E64P+ K70P+ S103V+ T166P+ Q168D+ M171Q+ K197D+ S271G+ N283Y+ K304R+ D385A+ L413T;

H12R+ K26E+ K36E+ E46Y+ E64P+ K70P+ S103V+ T166P+ Q168D+ M171Q+ K197D+ S271G+ N283Y+ K304S+ D385A+ L413T;

F7P+ H12R+ K26E+ K36E+ E46Y+ E64P+ K70P+ S103V+ T166P+ Q168D+ M171Q+ K197D+ S271G+ N283Y+ D385A+ L413T;

F7I+ H12R+ K26E+ K36E+ E46Y+ E64P+ K70P+ S103V+ T166P+ Q168D+ M171Q+ K197D+ S271G+ N283Y+ D385A+ V391L+ D410M+ L413T;

S15Q+ K26E+ K36E+ E64P+ K70P+ S103V+ P163N+ T166P+ Q168D+ K197D+ S271G+ N283Y+ D385A+ D410M+ L413T;

S15Q+ K26E+ K36E+ E64P+ K70P+ S103V+ T166P+ Q168D+ K197D+ S271G+ N283Y+ D385A+ S403R+ D410M+ L413T;

H12R+ K26E+ K36E+ E64P+ K70P+ S103V+ G110S+ T166P+ Q168D+ M171Q+ K197D+ S271G+ N283Y+ D385A+ K408M+ L413T;

H12R+ K26E+ K36E+ E64P+ K70P+ S103V+ G110C+ T166P+ Q168D+ M171Q+ K197D+ S271G+ N283Y+ D385A+ K408M+ L413T;

V4D+ H12R+ S14N+ A23S+ F25W+ K26E+ K36E+ E46Y+ E64P+ K70P+ S103V+ T166P+ Q168D+ M171Q+ K197D+ S271G+ N283Y+ D385A+ L413T;

H12R+ S15Q+ A23S+ F25W+ K26E+ K36E+ E46Y+ E64P+ K70P+ S103V+ T166P+ Q168D+ M171Q+ K197D+ S271G+ N283Y+ D385A+ L413T;

H12R+ K26E+ K36E+ E46Y+ E64P+ K70P+ S103V+ T166P+ Q168D+ M171Q+ K197D+ S258G+ S271G+ N283Y+ D385A+ L413T;

H12R+ A23S+ F25W+ K26E+ K36E+ E46Y+ E64P+ K70P+ S103V+ T166P+ Q168D+ M171Q+ K197D+ S271G+ N283Y+ D385A+ L413T;

S15Q+ K26E+ K36E+ E46Y+ E64P+ K70P+ S103V+ P163A+ T166P+ Q168D+ K197D+ M248I+ S271G+ N283Y+ D385A+ K408M+ D410M+ L413T;

S15Q+ K26E+ K36E+ E46Y+ E64P+ K70P+ S103V+ Y155H+ T166P+ Q168D+ K197D+ M248I+ S271G+ N283Y+ D385A+ K408M+ D410M+ L413T;

S15Q+ K26E+ K36E+ E46Y+ E64P+ K70P+ S103V+ R160N+ T166P+ Q168D+ K197D+ M248I+ S271G+ N283Y+ D385A+ K408M+ D410M+ L413T;

H12R+ K26E+ K36E+ E46Y+ E64P+ K70P+ S103V+ T166P+ Q168D+ M171Q+ K197D+ A210S+ S271G+ N283Y+ D385A+ L413T;
H12R+ K26E+ K36E+ E46Y+ E64P+ K70P+ S103V+ T166P+ Q168D+ M171Q+ K197D+ S271G+ N283Y+ D385A+ K408E+ L413T;
H12R+ K26E+ K36E+ E46Y+ E64P+ K70P+ S103V+ T166P+ Q168D+ M171Q+ K197D+ S271G+ N283Y+ D385A+ K408V+ L413T;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ D472Y;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ K482G;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ D486V;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ N470Y;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ P488L;
H12R+ K26E+ K36E+ E46Y+ E64P+ K70P+ S103E+ T166P+ Q168D+ M171Q+ K197D+ S271G+ N283Y+ K378Q+ D385A+ L413T;
H12R+ K26E+ K36E+ E46Y+ E64P+ K70P+ S103V+ E162D+ I165L+ T166P+ Q168D+ M171Q+ K197D+ S271G+ N283Y+ K378Q+ D385A+ L413T;
H12R+ K26E+ K36E+ E46Y+ E64P+ K70P+ S103V+ T166P+ Q168D+ M171Q+ K197D+ M248I+ E249L+ S271G+ N283Y+ K378Q+ D385A+ L413T;
H12R+ K26E+ K36E+ E46Y+ E64P+ K70P+ S103V+ T166P+ Q168D+ M171Q+ K197D+ Q214R+ S271G+ N283Y+ K378Q+ D385A+ L413T;
S15Q+ K26E+ K36E+ E46Y+ E64P+ K70P+ S103V+ T166P+ Q168D+ K197D+ M248I+ S271G+ N283Y+ D385A+ K408M+ D410M+ L413T+ L484Q;
S15Q+ K26E+ K36E+ E46Y+ E64P+ K70P+ S103V+ P163A+ T166P+ Q168D+ S178P+ K197D+ M248I+ S271G+ N283Y+ D385A+ K408M+ D410M+ L413T;
S15Q+ K26E+ K36E+ E46Y+ E64P+ K70P+ S103V+ R160N+ P163A+ T166P+ Q168D+ K197D+ M248I+ S271G+ N283Y+ D385A+ K408M+ D410M+ L413T;
S15Q+ K26E+ K36E+ E46Y+ E64P+ K70P+ S103V+ P163A+ T166P+ Q168D+ M171N+ K197D+ M248I+ S271G+ N283Y+ D385A+ K408M+ D4100M+ L413T;
S15Q+ K26E+ K36E+ E46Y+ E64P+ K70P+ S103V+ P163A+ T166P+ Q168D+ M171Q+ K197D+ M248I+ S271G+ N283Y+ D385A+ K408M+ D410M+ L413T;
S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T;
H12R+ K26E+ K36E+ E46Y+ E64P+ K70P+ S103V+ T166P+ Q168D+ M171Q+ K197D+ S271G+ N283Y+ D385A+ L413T+ Q437A;
H12R+ K26E+ K36E+ E46Y+ E64P+ K70P+ S103V+ T166P+ Q168D+ M171Q+ K197D+ E249H+ S271G+ N283Y+ D385A+ L413T;
S15Q+ K26E+ K36E+ E46Y+ E64P+ K70P+ S103V+ R160L+ T166P+ Q168D+ K197D+ M248I+ S271G+ N283Y+ D385A+ K408M+ D410M+ L413T+ N470Y;
S15Q+ K26E+ K36E+ E46Y+ E64P+ K70P+ S103V+ R160N+ T166P+ Q168D+ K197D+ M248I+ S271G+ N283Y+ D385A+ K408M+ D410M+ L413T+ N470Y;
S15Q+ K26E+ K36E+ E46Y+ E64P+ K70P+ S103V+ P163A+ T166P+ Q168D+ M172I+ K197D+ M248I+ S258G+ S271G+ N283Y+ D385A+ K408M+ D410M+ L413T;
V4N+ S15Q+ K26E+ K36E+ E46Y+ E64P+ K70P+ S103V+ P163A+ T166P+ Q168D+ S178E+ K197D+ M248I+ S258G+ S271G+ N283Y+ D385A+ K408M+ D410M+ L413T;
S15Q+ K26E+ K36E+ E46Y+ E64P+ K70P+ S103V+ P163A+ T166P+ Q168D+ M171Q+ K197D+ M248I+ S258G+ S271G+ N283Y+ D385A+ K408M+ D410M;
A1Y+ V4G+ S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M;
S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T+ K491R;
K482R;
S15M+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T;
K482D;
S15Q+ K26E+ K36E+ E46Y+ E64P+ K70P+ S103V+ P163A+ T166P+ Q168D+ S178P+ K197D+ M248I+ S258G+ S271G+ N283Y+ D385A+ K408M+ D410M;
S15Q+ F25Y+ K26E+ K36E+ E46Y+ E64P+ K70P+ S103V+ P163A+ T166P+ Q168D+ K197D+ M248I+ S258G+ S271G+ N283Y+ D385A+ K408M+ D410M+ L413T;
S15Q+ K26E+ K36E+ E46Y+ E64P+ K70P+ S103V+ P163A+ T166P+ Q168D+ K197D+ M248I+ S258G+ S271G+ N283Y+ K304Q+ D385A+ K408M+ D410M;
R489N;
S15Q+ K26E+ K36E+ E46Y+ E64P+ K70P+ S103V+ P163A+ T166P+ Q168D+ K197D+ M248I+ S258G+ S271G+ N283Y+ K378D+ D385A+ K408M+ D410M;
S15Q+ K26E+ K36E+ E46Y+ E64P+ K70P+ S103V+ P163A+ T166P+ Q168D+ M171E+ K197D+ M248I+ S258G+ S271G+ N283Y+ D385A+ K408M+ D410M;
A1Y+ S15Q+ K26E+ K36E+ E46Y+ E64P+ K70P+ S103V+ P163A+ T166P+ Q168D+ K197D+ M248I+ S258G+ S271G+ N283Y+ D385A+ K408M+ D410M;
S15Q+ K26E+ K36E+ E46Y+ E64P+ K70P+ S103V+ P163A+ T166P+ Q168D+ S178H+ K197D+ M248I+ S258G+ S271G+ N283Y+ D385A+ K408M+ D410M;
S15Q+ K26E+ K36E+ E46Y+ E64P+ K70P+ S103V+ P163A+ T166P+ Q168D+ S178T+ K197D+ M248I+ S258G+ S271G+ N283Y+ D385A+ K408M+ D410M;
F7G+ S15Q+ K26E+ K36E+ E46Y+ E64P+ K70P+ S103V+ P163A+ T166P+ Q168D+ S178P+ K197D+ M248I+ S258G+ S271G+ N283Y+ D385A+ K408M;
S15Q+ K26E+ K36E+ E46Y+ E64P+ K70P+ S103V+ P163A+ T166P+ Q168D+ S178P+ K197D+ M248I+ S258G+ S271G+ N283Y+ T315V+ D385A+ K408M;
S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A+ K408M;
S15Q+ K26E+ K36E+ E46Y+ T53P+ E64P+ K70P+ S103V+ P163A+ T166P+ Q168D+ S178P+ K197D+ M248I+ S258G+ S271G+ N283Y+ D385A+ K408M;
S15Q+ K26E+ K36E+ E46Y+ T53H+ E64P+ K70P+ S103V+ P163A+ T166P+ Q168D+ K197D+ M248I+ S271G+ N283Y+ D385A+ K408M+ D410M+ L413T;

S15Q+ K26E+ K36E+ E46Y+ E64P+ K70P+ S103V+ P163A+ T166P+ Q168D+ M188Y+ K197D+ M248I+ S271G+ N283Y+ D385A+ K408M+ D410M+ L413T;
S15Q+ K26E+ K36E+ E46Y+ E64P+ K70P+ S103V+ P163A+ T166P+ Q168D+ K197D+ M248I+ S271G+ N283Y+ Y358W+ D385A+ K408M+ D410M+ L413T;
S15Q+ K26E+ K36E+ E46Y+ E64P+ K70P+ S103V+ P163N+ T166P+ Q168D+ M172I+ S178P+ K197D+ M248I+ S258G+ S271G+ N283Y+ D385A+ K408M;
S15Q+ K26E+ K36E+ E46Y+ E64P+ K70P+ S103V+ P163E+ T166P+ Q168D+ M172I+ S178P+ K197D+ M248I+ S258G+ S271G+ N283Y+ D385A+ K408M+ D410M+ L413T+ K466F;
F7A+ S15Q+ K26E+ K36E+ E46Y+ T53Q+ E64P+ K70P+ S103V+ P163A+ T166P+ Q168D+ M172I+ S178P+ K197D+ M248I+ S258G+ S271G+ N283Y+ D385A+ K408M+ D410M+ L413T;
D410M+ L413T+ D472G+ W490A;
V9P+ S15Q+ K26E+ K36E+ E46Y+ T53Q+ E64P+ K70P+ S103V+ P163A+ T166P+ Q168D+ M172I+ K197D+ M248I+ S258G+ S271G+ N283Y+ D385A+ K408M;
V9P+ S15Q+ K26E+ K36E+ E46Y+ E64P+ K70P+ S103V+ P163A+ T166P+ Q168D+ M172I+ K197D+ M248I+ S258G+ S271G+ N283Y+ D385A+ K408M+ D410M;
S15Q+ K26E+ K36E+ E46Y+ E64P+ K70P+ S103V+ P163A+ T166P+ Q168D+ M172I+ K179R+ K197D+ M248I+ S258G+ S271G+ N283Y+ D385A+ K408M;
S15Q+ K26E+ K36E+ E46Y+ E64P+ K70P+ S103V+ P163A+ T166P+ Q168D+ M172I+ S178P+ F190Y+ K197D+ Y213R+ M248I+ S258G+ S271G+ N283Y+ D385A+ K408M+ D410M+ L413T;
S15Q+ K26E+ K36E+ E46Y+ E64P+ K70P+ S103V+ Q143R+ P163A+ T166P+ Q168D+ M172I+ S178P+ K197D+ M248I+ S258G+ S271G+ N283Y+ D385A;
T3E+ V8W+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
V8W+ S15Q+ K26E+ K36E+ E46Y+ E64P+ K70P+ S103V+ P121A+ P163A+ T166P+ Q168D+ M172I+ S178P+ K197D+ M248I+ S258G+ S271G+ N283Y+ D385A;
V8W+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
S15Q+ K26E+ K36E+ E46Y+ E64P+ K70P+ S103V+ P163A+ T166P+ Q168D+ M172I+ S178P+ M188I+ K197D+ M248I+ S258G+ S271G+ N283Y+ K378R;
S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y+ D385A;
S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G+ S271G;
N283Y+ D385A+ K408M+ D410M+ L413T;
A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ D385A;
S15Q+ K26E+ K36E+ E46Y+ E64P+ K70P+ S103V+ I165E+ T166P+ Q168D+ M172I+ S178H+ K197D+ M248I+ S258G+ S271G+ N283Y+ D385A+ K408M;
S15Q+ K26E+ K36E+ E46Y+ E64P+ K70P+ S103V+ E162D+ T166P+ Q168D+ M172I+ S178P+ F190Y+ K197D+ M248I+ S258G+ S271G+ N283Y+ D385A;
S15Q+ K26E+ K36E+ E46Y+ E64P+ K70P+ S103V+ P163A+ T166P+ Q168D+ M172I+ S178P+ A184T+ F190Y+ K197D+ M248I+ S258G+ S271G+ N283Y;
T3E+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
V9P+ S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A;
T3E+ V9P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y;
V9P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
S15Q+ K26E+ K36E+ E46Y+ E64P+ K70P+ S103V+ P163A+ T166P+ Q168D+ M172I+ S178P+ K197D+ M248I+ S258G+ S271G+ N283Y+ K378Q+ D385A;
A1T+ V8W+ S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A+ D410M+ L413T+ N473Y;
V9P+ S15Q+ K26E+ K36E+ E46Y+ E64P+ K70P+ S103V+ P163A+ T166P+ Q168D+ M172I+ S178P+ K197D+ S239A+ M248I+ S258G+ S271G+ N283Y;
V4M+ S15Q+ K26E+ K36E+ E46Y+ E64P+ K70P+ S103V+ P163A+ T166P+ Q168D+ M172I+ S178P+ K197D+ S239A+ M248I+ S258G+ S271G+ N283Y;
S15Q+ K26E+ K36E+ E46Y+ T53P+ E64P+ K70P+ S103V+ P163A+ T166P+ Q168D+ M172I+ S178P+ K197D+ S239A+ M248I+ S258G+ S271G+ N283Y;
S15Q+ K26E+ K36E+ E46Y+ E64P+ K70P+ S103V+ P163A+ T166P+ Q168D+ M172I+ S178P+ K197D+ S239A+ M248I+ S258G+ S271G+ N283Y+ K378Q;
S15Q+ K26E+ K36E+ E46Y+ E64P+ K70P+ S103V+ A126T+ P163A+ T166P+ Q168D+ M172I+ S178P+ K197D+ Y213R+ S239A+ M248I+ S258G+ S271G;
A1Y+ F7P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
F7P+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A+ D410M+ L413T+ K417Q+ K462P;
A1T+ F7G+ S15Q+ K26E+ K36E+ E46Y+ T53Q+ E64P+ K70P+ S103V+ P163A+ T166P+ Q168D+ M172I+ S178P+ K197D+ M248I+ S258G+ S271G+ N283Y;
A1T+ S15Q+ K26E+ K36E+ E46Y+ E64P+ K70P+ S103V+ P163A+ T166P+ Q168D+ M172I+ S178P+ K197D+ M248I+ S258G+ S271G+ N283Y+ D385A;
S15Q+ K26E+ K36E+ E46Y+ E64P+ K70P+ S103V+ E162D+ T166P+ Q168D+ M172I+ S178P+ K197D+ M248I+ S258G+ S271G+ N283Y+ D385A+ K408M;
A1T+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ D385A;
A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ K378Q+ D385A+ K408M+ D410M+ L413T+ P488L;
A1Y+ F7G+ S15Q+ K26E+ K36E+ E46Y+ E64P+ K70P+ S103V+ I165E+ T166P+ Q168D+ M172I+ S178P+ K197N+ M248I+ S258G+ S271G+ N283Y+ D385A;

A1Y+ F7G+ S15Q+ K26E+ K36E+ E46Y+ E64P+ K70P+ S103V+ I165E+ T166P+ Q168D+ M172I+ S178P+ K197N+ M248I+ S258G+ S271G+ N283Y+ K364R;

A1Y+ F7G+ S15Q+ K26E+ K36E+ E46Y+ E64P+ K70P+ S103V+ I165E+ T166P+ Q168D+ M172I+ S178P+ K197D+ N242T+ M248I+ S258G+ S271G+ N283Y+ S15Q+ K26E+ K36E+ E46Y+ E64P+ K70P+ S103V+ P121A+ Q143R+ P163A+ T166P+ Q168D+ M172I+ S178P+ F190Y+ K197D+ Y213Q+ M248I+ S258G+ S271G+ N283Y+ D385A+ K408M+ D410M+ L413T;

S15Q+ K26E+ K36E+ E46Y+ E64P+ K70P+ S103V+ P163A+ T166P+ Q168D+ M172I+ S178P+ K197D+ Q214R+ M248I+ S258G+ S271G+ N283Y+ T315V;

F7G+ S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y;

S15Q+ K26E+ K36E+ E46Y+ E64P+ K70P+ S103V+ P163A+ T166P+ Q168D+ M172I+ S178P+ K197D+ Q214R+ M248I+ S258G+ S271G+ N283Y+ D385A;

S15Q+ K26E+ K36E+ E46Y+ E64P+ K70P+ S103V+ I165E+ T166P+ Q168D+ M172I+ S178P+ K197D+ Y213Q+ M248I+ S258G+ S271G+ N283Y+ D385A;

V4N+ S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y;

S15Q+ K26E+ K36E+ E46Y+ E64P+ K70P+ S103V+ P163A+ T166P+ Q168D+ M172I+ S178P+ K197D+ Y213Q+ M248I+ S258G+ S271G+ N283Y+ K378Q;

S15Q+ K26E+ K36E+ E46Y+ E64P+ K70P+ S103V+ P163A+ T166P+ Q168D+ M172I+ S178P+ K197D+ Q215E+ M248I+ S258G+ S271G+ N283Y+ D385A;

M172I+ K197D+ M248I+ S258G+ S271G+ N283Y+ D385A+ K408M+ D410M+ L413T V4M+ S15Q+ K26E+ K36E+ E46Y+ T53Q+ E64P+ K70P+ S103V+ P163A+ T166P+ Q168D+ M172I+ S178P+ K197D+ Y213Q+ M248I+ S258G+ S271G;

A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ T315V+ K378Q+ D385A+ K408M+ D410M+ L413T;

A1Y+ F7G+ S15Q+ K26E+ K36E+ E46Y+ E64P+ K70P+ S103V+ Q143R+ I165E+ T166P+ Q168D+ M172I+ S178P+ K197D+ M248I+ S258G+ S271G+ N283Y;

A1Y+ F7G+ S15Q+ K26E+ K36E+ E46Y+ E64P+ K70P+ S103V+ I165E+ T166P+ Q168D+ M172I+ S178P+ K197D+ Q214R+ M248I+ S258G+ S271G+ N283Y;

T315V+ D385A+ K408M+ D410M+ L413T;

A1Y+ F7G+ S15Q+ K26E+ K36E+ E46Y+ E64P+ K70P+ S103V+ I165E+ T166P+ Q168D+ M172I+ S178P+ K197D+ M248I+ S258G+ S271G+ N283Y+ K304Q;

A1Y+ F7G+ S15Q+ K26E+ K36E+ E46Y+ T53P+ E64P+ K70P+ S103V+ I165E+ T166P+ Q168D+ M172I+ S178P+ K197D+ M248I+ S258G+ S271G+ N283Y;

A1Y+ F7G+ S15Q+ K26E+ K36E+ E46Y+ E64P+ K70P+ S103V+ E162D+ I165E+ T166P+ Q168D+ M172I+ S178P+ K197D+ M248I+ S258G+ S271G+ N283Y;

A1Y+ F7G+ S15Q+ K26E+ K36E+ E46Y+ E64P+ K70P+ S103V+ P121A+ I165E+ T166P+ Q168D+ M172I+ S178P+ K197D+ M248I+ S258G+ S271G+ N283Y;

A1Y+ F7G+ S15Q+ K26E+ K36E+ E46Y+ T53K+ E64P+ K70P+ S103V+ I165E+ T166P+ Q168D+ M172I+ S178P+ K197D+ M248I+ S258G+ S271G+ N283Y+ D385A+ K408M+ D410M+ L413T+ P488I;

S15Q+ K26E+ K36E+ E46Y+ E64P+ K70P+ S103V+ P163A+ T166P+ Q168D+ M172I+ S178P+ M188Y+ K197D+ S239A+ M248I+ S258G+ S271G+ N283;

S15Q+ K26E+ K36E+ E46Y+ E64P+ K70P+ S103V+ P163A+ T166P+ Q168D+ M172I+ S178P+ F190Y+ K197D+ S239A+ M248I+ S258G+ S271G+ N283Y;

S15Q+ K26E+ K36E+ E46Y+ E61D+ E64P+ K70P+ S103V+ P163A+ T166P+ Q168D+ M172I+ S178P+ K197D+ S239A+ M248I+ S258G+ S271G+ N283Y;

S15Q+ K26E+ K36E+ E46Y+ K65N+ K70P+ S103V+ P163A+ T166P+ Q168D+ M172I+ S178P+ K197D+ S239A+ M248I+ S258G+ S271G+ N283Y+ K378Q+ N283Y+ D385A+ K408M+ D410M+ L413T+ R489N;

S15Q+ K26E+ K36E+ E46Y+ K65N+ K70P+ S103V+ A126T+ P163A+ T166P+ Q168D+ M172I+ S178P+ K197D+ Y213R+ S239A+ M248I+ S258G+ S271G+ N283Y+ D385A+ K408M+ D410M+ L413T+ K482D;

N283Y+ D385A+ K408M+ D410M+ L413T+ S487G;

N283Y+ K378D+ D385A+ K408M+ D410M+ L413T;

S15Q+ K26E+ K36E+ E46Y+ E64P+ K70P+ S103V+ A126T+ P163A+ T166P+ Q168D+ M172I+ S178P+ K197D+ Q214R+ S239A+ M248I+ S258G+ S271G+ N283Y+ K378D+ D385A+ S403Q+ K408M+ D410M+ L413T+ K482D;

N283Y+ K378D+ D385A+ K408M+ D410M+ L413T+ K482D;

S15T+ K26E+ K36E+ E46Y+ T53Q+ E64P+ K70P+ S103V+ P121A+ P163A+ T166P+ Q168D+ M172I+ S178P+ K197D+ S239A+ M248I+ S258G+ S271G;

N283Y+ K378Q+ D385A+ K408M+ D410M+ L413T;

S15Q+ K26E+ K36E+ E46Y+ E64P+ K70P+ S103V+ P163A+ T166P+ Q168D+ M172I+ S178P+ K197D+ Y213Q+ S239A+ M248I+ S258G+ S271G+ N283Y;

S15Q+ K26E+ K36E+ E46Y+ E64P+ K70P+ S103V+ P163A+ T166P+ Q168D+ M172I+ S178P+ F190Y+ K197D+ Y213Q+ S239A+ M248I+ S258G+ S271G;

S15Q+ K26E+ K36E+ E46Y+ E64P+ K70P+ S103V+ A126T+ L134T+ E162D+ P163E+ T166P+ Q168D+ M172I+ S178P+ K197D+ Y213R+ S239A+ M248I;

S258G+ S271G+ N283Y+ D385A+ K408M+ D410M+ L413T;

S15Q+ K26E+ K36E+ E46Y+ E64P+ K70P+ S103V+ A126T+ E162D+ P163E+ T166P+ Q168D+ M172I+ S178P+ K197D+ Y213R+ S239A+ M248I+ S258G;

N283Y+ D385A+ K408M+ D410M+ L413T+ N473Y;

V9P+ S15Q+ K26E+ K36E+ E46Y+ E64P+ K70P+ S103V+ Q143R+ P163A+ T166P+ Q168D+ M172I+ S178P+ K197D+ S239A+ M248I+ S258G+ S271G;

V8W+ S15Q+ K26E+ K36E+ E46Y+ E64P+ K70P+ S103V+ P163E+ T166P+ Q168D+ M172I+ S178P+ F190Y+ K197D+ Y213R+ S239A+ M248I+ S258G;

V8W+ S15Q+ K26E+ K36E+ E46Y+ E64P+ K70P+ S103V+ P121A+ P163E+ T166P+ Q168D+ M172I+ S178P+ F190Y+ K197D+ Y213R+ S239A+ M248I;

T3E+ S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G;

F7G+ S15Q+ K26E+ K36E+ E46Y+ E64P+ K70P+ S103V+ P163A+ T166P+ Q168D+ M172I+ S178P+ F190Y+ K197D+ Y213R+ S239A+ M248I+ S258G;

A1Y+ F7G+ S15Q+ K26E+ K36E+ E46Y+ E64P+ K70P+ S103V+ I165E+ T166P+ Q168D+ M172I+ S178P+ K197D+ S239A+ M248I+ S258G+ S271G+ N283Y;

S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ K378Q+ D385A+ K408M+ D410M+ L413T+ P488L;

K378Q+ D385A+ K408M+ D410M+ L413T+ N473Y;

S15Q+ K26E+ K36E+ E46Y+ T53P+ E64P+ K70P+ S103V+ P121A+ P163A+ T166P+ Q168D+ M172I+ S178P+ K197D+ Y213Q+ S239A+ M248I+ S258G+ S271G+ N283Y+ K378Q+ D385A+ K408M+ D410M+ L413T;

S15Q+ K26E+ K36E+ E46Y+ E64P+ K70P+ S103V+ P121A+ Q143R+ P163A+ T166P+ Q168D+ M172I+ S178P+ K197D+ Q214R+ S239A+ M248I+ S258G;

S15Q+ K26E+ K36E+ E46Y+ E64P+ K70P+ S103V+ P121A+ Q143R+ P163A+ T166P+ Q168D+ M172I+ S178P+ K197D+ Y213Q+ S239A+ M248I+ S258G+;

S15Q+ K26E+ K36E+ E46Y+ E64P+ K70P+ S103V+ E162D+ T166P+ Q168D+ M172I+ S178P+ K197D+ Q214R+ S239A+ M248I+ S258G+ S271G+ N283Y+ K378Q+ D385A+ K408M+ D410M+ L413T+ R489N;

S15Q+ K26E+ K36E+ E46Y+ E64P+ K70P+ S103V+ P163A+ T166P+ Q168D+ M172I+ S178P+ K197D+ Q214R+ S239A+ M248I+ S258G+ S271G+ N283Y;

A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7G+ S15Q+ K26E+ K36E+ E46Y+ E64P+ K70P+ S103V+ P121A+ I165E+ T166P+ Q168D+ M172I+ S178P+ K197D+ S239A+ M248I+ S258G+ S271G;

A1Y+ F7G+ S15Q+ K26E+ K36E+ E46Y+ E64P+ K70P+ S103V+ Q143R+ I165E+ T166P+ Q168D+ M172I+ S178P+ K197D+ Q214R+ S239A+ M248I+ S258G;

S15Q+ K26E+ K36E+ E46Y+ E64P+ K70P+ S103V+ Q143R+ P163A+ T166P+ Q168D+ M172I+ S178P+ K197D+ Y213Q+ S239A+ M248I+ S258G+ S271G+ K378Q+ D385A+ K408M+ D410M+ L413T+ H442N+ N473Y;

E299W+ K378Q+ D385A+ K408M+ D410M+ L413T+ N473Y;

K378Q+ D385A+ K408M+ D410M+ L413T+ N473Y+ K482R+ K491E V4D+ V8D+ S15Q+ K26E+ K36E+ E46Y+ E64P+ K70P+ S103V+ P163A+ T166P+ Q168D+ M172I+ S178P+ F190Y+ K197D+ S239A+ M248I+ S258G+ S271G+ N283Y+ K378Q+ D385A+ K408M+ D410M+ L413T+ N473Y;

A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ Q214R+ S239A+ M248I+ S258G+ S271G+ N283Y+ K378Q+ D385A+ K408M+ D410M+ L413T+ H442N+ K466N+ K482G;

S258G+ S271G+ N283Y+ K378Q+ D385A+ K408M+ D410M+ L413A;

N283Y+ E380D+ D385A+ K408M+ D410M+ L413T+ G440Q;

N283Y+ K378Q+ D385A+ K408M+ D410M+ L413T+ H442N;

A1Y+ F7G+ S15Q+ K26E+ K36E+ E46Y+ E64P+ K70P+ S103V+ P121A+ I165E+ T166P+ Q168D+ M172I+ S178P+ K197D+ S239A+ M248I+ R253A+ S258G;

S271G+ N283Y+ K378Q+ D385A+ K408M+ D410M+ L413T+ H442N;

T3E+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G;

S271G+ N283Y+ E299W+ K378Q+ D385A+ K408M+ D410M+ L413T+ N473Y;

G366H+ K378Q+ D385A+ K408M+ D410M+ L413T+ N473Y;

A1Y+ F7G+ S15Q+ K26E+ K36E+ E46Y+ E64P+ K70P+ S103V+ P121A+ R160N+ I165E+ T166P+ Q168D+ M172I+ S178P+ K197D+ Y219W+ S239A+ M248I;

S258G+ S271G+ N283Y+ K378Q+ D385A+ K408M+ D410M+ L413T;

A1Y+ F7G+ S15Q+ K26E+ K36E+ E46Y+ E64P+ K70P+ S103V+ P121A+ Q143R+ I165E+ T166P+ Q168D+ M172I+ S176N+ S178P+ K197D+ S239A+ M248I;

S271G+ N283Y+ K378Q+ D385A+ K408M+ D4100M+ L413T+ H442D+ S487R;

S271G+ N283Y+ K378Q+ D385A+ K408M+ D410M+ L413T+ H442D+ K482D+ S487R;

S271G+ N283Y+ K378Q+ D385A+ K408M+ D410M+ L413T+ G440Q;

A1Y+ F7G+ S15Q+ K26E+ K36E+ E46Y+ E64P+ K70P+ S103V+ P121A+ R160K+ P163A+ I165E+ T166P+ Q168D+ M172I+ S178P+ K197D+ S239A+ M248I;

A1Y+ F7G+ S15Q+ K26E+ K36E+ E46Y+ E64P+ K70P+ S103V+ P121A+ R160V+ P163A+ I165E+ T166P+ Q168D+ M172I+ S178P+ K197D+ S239A+ M248I;

A1Y+ F7G+ S15Q+ K26E+ K36E+ E46Y+ E64P+ K70P+ S103V+ P121A+ E162G+ P163A+ I165E+ T166P+ Q168D+ M172I+ S178P+ K197D+ S239A+ M248I;

A1*+ 12*+ T3*+ V4*+ P5*+ S15Q+ K26E+ K36E+ E46Y+ E64P+ K70P+ S103V+ P121A+ Q143R+ I165E+ T166P+ Q168D+ M172I+ S178P+ K197D+ S239A;

M248I+ S258G+ S271G+ N283Y+ K378Q+ D385A+ K408M+ D410M+ L413T;

A1Y+ G6*+ F7*+ V8*+ V9*+ E10*+ S15Q+ K26E+ K36E+ E46Y+ E64P+ K70P+ S103V+ P121A+ Q143R+ I165E+ T166P+ Q168D+ M172I+ S178P+ K197D;

S239A+ M248I+ S258G+ S271G+ N283Y+ K378Q+ D385A+ K408M+ D410M+ L413T;

E10*+ V9*+ V8*+ F7*+ G6*+ P5*+ V4*+ T3*+ 12*+ A1*+ S15Q+ K26E+ K36E+ E46Y+ E64P+ K70P+ S103V+ P121A+ Q143R+ I165E+ T166P+ Q168D+ M172I;

S178P+ K197D+ S239A+ M248I+ S258G+ S271G+ N283Y+ K378Q+ D385A+ K408M+ D410M+ L413T;

T3E+ F7G+ S15Q+ K26E+ K36E+ E46Y+ E64P+ K70P+ S103V+ S141R+ P163A+ T166P+ Q168D+ M172I+ S178P+ F190Y+ K197D+ Q214R+ S239A+ M248I;

S258G+ S271G+ N283Y+ E299W+ K378Q+ D385A+ K408M+ D410M+ L413T+ N473Y+ K491R;

S271G+ N283Y+ E299W+ K378D+ D385A+ K408M+ D410M+ L413T+ N473Y+ K482Q S271G+ N283Y+ E299W+ K378D+ D385A+ K408M+ D410M+ L413T+ N473Y;

A1S+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7D+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7D+ S15Q+ K26E+ K36E+ E46Y+ E64P+ K70P+ S103V+ P121A+ L134P+ Q143R+ I165E+ T166P+ Q168D+ M172I+ S178P+ K197D+ S239A+ M248I;

A1Y+ F7D+ S15Q+ K26E+ K36E+ E46Y+ E64P+ K70P+ S103V+ P121A+ Q143R+ I165E+ T166P+ Q168D+ M172I+ S178P+ K197D+ S239A+ M248I;

S258G+ 269+ S271G+ N283Y+ K378Q+ D385A+ K408M+ D410M+ L413T;

A1Y+ F7G+ Q17A+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7G+ S15Q+ N18S+ K26E+ K36E+ E46Y+ E64P+ K70P+ S103V+ P121A+ Q143R+ I165E+ T166P+ Q168D+ M172I+ S178P+ K197D+ S239A+ M248I;

S258G+ S271G+ N283Y+ K378Q+ D385A+ K408M+ D410M+ L413T+ G440Q;

A1Y+ F7G+ S15Q+ K26E+ K36E+ E46Y+ E64P+ K70P+ S103V+ P121A+ P163A+ I165E+ T166P+ Q168D+ M172I+ S178P+ K197D+ S239A+ M248I+ S258G;

A1Y+ F7G+ S15Q+ K26E+ K36E+ E46Y+ E64P+ K70P+ S103V+ P121A+ A126T+ P163A+ I165E+ T166P+ Q168D+ M172I+ S178P+ K197D+ S239A+ M248I;

A1Y+ F7G+ S14N+ S15Q+ K26E+ K36E+ E46Y+ E64P+ K70P+ S103V+ P121A+ Q143R+ I165E+ T166P+ Q168D+ M172I+ S178P+ K197D+ S239A+ M248I;

A1Y+ F7G+ S15Q+ A23S+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ S239A+ M248I;

S258G+ S271G+ N283Y+ K378Q+ D385A+ K408M+ D410M+ L413T+ G440Q;

A1Y+ F7G+ S15Q+ K26E+ 130L+ K36E+ E46Y+ E64P+ K70P+ S103V+ P121A+ Q143R+ I165E+ T166P+ Q168D+ M172I+ S178P+ K197D+ S239A+ M248I;

A1Y+ F7G+ S15D+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

A1Y+ F7G+ S15C+ K26E+ K36E+ E46Y+ E64P+ K70P+ S103V+ P121A+ Q143R+ I165E+ T166P+ Q168D+ M172I+ S178P+ K197D+ S239A+ M248I+ S258G;

T3E+ F7G+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R+ S239A;

M248I+ S258G+ S271G+ N283Y+ E299W+ G366H+ K378Q+ D385A+ K408M+ D410M+ L413T+ H442N+ N473Y+ K491R;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ G217Q;

S239A+ M248I+ S258G+ S271G+ R280K+ N283Y+ K378Q+ D385A+ K408M+ D410M+ L413T+ G440Q;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214W+ S239A;

M248I+ S258G+ S271G+ R280K+ N283Y+ K378Q+ D385A+ K408M+ D410M+ L413T+ G440Q;

S239A+ M248I+ S258G+ S271G+ R280K+ N283Y+ W342G+ K378Q+ D385A+ K408M+ D410M+ L413T+ G440Q;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q215E+ S239A;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ S239A;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214W+ G217Q;

S258G+ S271G+ R280K+ N283Y+ K378Q+ D385A+ K408M+ D410M+ L413T+ G440Q A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ K179N+ K197D+ S239A;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ M188Y+ K197N;

G217Q+ S239A+ M248I+ S258G+ S271G+ N283Y+ K378Q+ D385A+ K408M+ D410M+ L413T+ G440Q;

A1Y+ F7G+ S15Q+ K26E+ K36E+ E46Y+ E64P+ K70P+ S103V+ P121A+ Q143R+ V161T+ P163A+ T166P+ Q168D+ M172I+ S178P+ K197D+ S239A;

T3E+ F7G+ S15Q+ A20G+ K26D+ K36E+ E46Y+ E64P+ K70P+ S103V+ S141R+ P163A+ T166P+ Q168D+ M172I+ S178P+ F190Y+ K197D+ Q214R;

S239A+ M248I+ S258G+ S271G+ N283Y+ E299W+ K378Q+ D385A+ K408M+ D410M+ L413T+ N473Y+ K491R;

T3E+ F7G+ S15Q+ A20G+ K26E+ K36E+ E46Y+ E64P+ K70P+ S103V+ K120A+ S141R+ P163A+ T166P+ Q168D+ M172I+ S178P+ F190Y+ K197D;

Q214R+ S239A+ M248I+ S258G+ S271G+ N283Y+ E299W+ K378Q+ D385A+ K408M+ D410M+ L413T+ N473Y+ K491R;

T3E+ F7G+ S15Q+ A20G+ K26E+ K36E+ E46Y+ E64P+ K70P+ S103A+ S141R+ P163A+ T166P+ Q168D+ M172I+ S178P+ F190Y+ K197D+ Q214R;

T3E+ V9G+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R;

T3E+ V9M+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R;
T3E+ V9A+ S15Q+ A20G+ K26E+ K36E+ E46Y+ E64P+ K70P+ S103V+ S141R+ P163A+ T166P+ Q168D+ M172I+ S178P+ F190Y+ K197D+ Q214R;
T3E+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I;
T3E+ F7G+ S15Q+ K26E+ K36E+ E46Y+ E64P+ K70P+ S103V+ P121A+ Q143R+ P163A+ I165E+ T166P+ Q168D+ M172I+ S178P+ K197D+ S239A;
M248I+ S258G+ S271G+ N283Y+ K378Q+ D385A+ K408M+ D410M+ L413T+ G440Q A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D;
Q214R+ S239A+ M248I+ S258G+ S271G+ R280K+ N283Y+ K304Q+ K378Q+ D385A+ K408M+ D410M+ L413T+ G440Q;
A1Y+ F7G+ S15Q+ I22V+ K26E+ K36E+ E46Y+ T53K+ E64P+ K70P+ S103V+ P121A+ Q143R+ I165E+ T166P+ Q168D+ M171Q+ K179N+ K197D;
S239A+ M248I+ S258G+ S271G+ R280K+ N283Y+ K378Q+ D385A+ K408M+ D410M+ L413T+ T438A;
A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N;
K197D+ S239A+ M248I+ S258G+ S271G+ R280K+ N283Y+ K378Q+ D385A+ K408M+ D410M+ L413T+ T438A;
A1Y+ F7G+ S15Q+ I22V+ K26E+ K36E+ E46Y+ T53K+ E64P+ K70P+ S103V+ P121A+ Q143R+ E162D+ I165E+ T166P+ Q168D+ M171Q+ K179N;
F7G+ T3*+ G6*+ P5*+ V4*+ 12*+ A1*+ S15Q+ K26E+ K36E+ E46Y+ E64P+ K70P+ S103V+ P163A+ T166P+ Q168D+ M172I+ S178P+ F190Y+ K197D;
Q214R+ S239A+ M248I+ S258G+ S271G+ N283Y+ E299W+ K378Q+ D385A+ K408M+ D410M+ L413T+ N473Y;
T3*+ V9*+ V8*+ G7*+ G6*+ P5*+ V4*+ 12*+ A1*+ F7G+ S15Q+ K26E+ K36E+ E46Y+ E64P+ K70P+ S103V+ P163A+ T166P+ Q168D+ M172I+ S178P;
F190Y+ K197D+ Q214R+ S239A+ M248I+ S258G+ S271G+ N283Y+ E299W+ K378Q+ D385A+ K408M+ D410M+ L413T+ N473Y;
T3G+ F7G+ T13I+ S15Q+ A20V+ K26E+ K36E+ E46Y+ E64P+ K70P+ S103V+ S141R+ P163A+ T166P+ Q168D+ M172I+ S178P+ F190Y+ K197N;
T3E+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N;
Q214R+ S239A+ M248I+ S258G+ S271G+ N283Y+ E299W+ K378Q+ D385A+ K408M+ D410M+ L413T+ V422I+ N473Y+ K491R;
K26E+ K36E+ E64P+ K70P+ S103V+ T166P+ Q168D+ K197Y+ N283Y+ D385A+ L413T;
S15Q+ K26E+ K36E+ E64P+ K70P+ S103V+ T166P+ Q168D+ K197D+ M248I+ S271G+ N283Y+ D385A+ D410M+ L413T;
S15Q+ K26E+ K36E+ E46Y+ E64P+ K70P+ S103V+ P163A+ T166P+ Q168D+ M188Y+ K197D+ M248I+ S271G+ N283Y+ D385A+ K408M+ D410M+ L413T;
S15Q+ K26E+ K36E+ E46Y+ E64P+ K70P+ S103V+ P163A+ T166P+ Q168D+ K197D+ M248I+ S271G+ N283Y+ Y358W+ D385A+ K408M+ D410M+ L413T;
A1Y+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ N283Y+ K378Q+ D385A+ K408M+ D410M+ L413T;
T3E+ F7G+ S15Q+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ N283Y+ K378Q+ D385A+ K408M+ D410M+ L413T+ G440Q;
T3E+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y;
T3E+ F7G+ S15Q+ K26E+ K36E+ E46Y+ E64P+ K70P+ S103V+ P121A+ Q143R+ P163A+ I165E+ T166P+ Q168D+ M172I+ S178P+ K197D+ S239A+ M248I+ S258G+ S271G+ N283Y+ K378Q+ D385A+ K408M+ D410M+ L413T+ G440Q;
A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ S239A+ M248I+ S258G+ S271G+ R280K+ N283Y+ K378Q+ D385A+ K408M+ D410M+ L413T+ G440Q;
A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K378Q+ D385A+ K408M+ D410M+ L413T+ G440Q;
A1Y+ F7G+ S15Q+ I22V+ K26E+ K36E+ E46Y+ T53K+ E64P+ K70P+ S103V+ P121A+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;
A1V+ F7G+ S15Q+ I21L+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;
A1V+ F7G+ S15Q+ I22V+ K26E+ K36E+ E46Y+ T53K+ E64P+ K70P+ S103V+ K120P+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;
A1V+ V8A+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;
A1G+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;
A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D4100M+ L413T+ T438A;
A1Y+ F7G+ S15Q+ I22V+ K26E+ K36E+ E46Y+ T53K+ E64P+ K70P+ S103V+ P121A+ Q143R+

E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

T3E+ F7G+ S15D+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R;

V4N+ F7G+ S15Q+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R;

V4W+ F7G+ S15Q+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ P11A+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ P11L+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1Y+ F7G+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1Y+ F7G+ S15Q+ I22V+ K26E+ K36E+ E46Y+ T53K+ E64P+ Q69P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ N368D+ K378Q+ D385A+ K408M+ D410M+ L413T+ T438A;

T3G+ F7G+ T13I+ S15Q+ A20G+ K26E+ K36E+ E46Y+ E64P+ K70P+ S103V+ S141R+ P163E+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R;

A1V+ F7G+ P11L+ S15Q+ I22V+ K26E+ K36E+ E46Y+ T53K+ E64P+ K70P+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1Y+ F7G+ S15Q+ I22V+ K26E+ K36E+ E46Y+ E64P+ K70P+ S103V+ P121A+ Q143R+ I165E+ T166P+ Q168D+ M172I+ S178P+ K197D+ Q214R+ G217Q+ S239A+ M248I+ S258G+ S271G+ R280K+ N283Y+ W342G+ K378Q+ D385A+ K408M+ D410M+ L413T+ G440Q;

A1Y+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

T3G+ F7G+ T13I+ S15Q+ A20V+ K26E+ K36E+ E46Y+ E64P+ K70P+ S103V+ S141R+ P163A+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R;

T3E+ F7G+ S15Q+ A20G+ K26E+ 130L+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R;

T3G+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ I22V+ K26E+ K36E+ E46Y+ T53K+ E64P+ K70P+ T74A+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ T13I+ S15Q+ A20S+ K26E+ K36E+ E46Y+ T53K+ E64P+ K70P+ T74A+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1Y+ F7G+ T13I+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1Y+ F7G+ S15Q+ I22V+ K26E+ K36E+ E46Y+ T53K+ E64P+ K70P+ Q76T+ S103V+ P121A+ M130I+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ P11A+ S15Q+ I22V+ K26E+ K36E+ E46Y+ T53K+ E64P+ K70P+ Q76T+ S103V+ P121A+ M130I+ Q143R+ I165E+ T166P+ Q168D+

M171Q+ K179N+ K197D+ S239A+ M248I+ S258G+ S271G+ R280K+ N283Y+ K378Q+ D385A+ K408M+ D410M+ L413T+ T438A;

A1Y+ F7G+ P11E+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ P11I+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ T13M+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ T13N+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ T13W+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ T13Y+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ S14Q+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ S14R+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ S15Q+ I22V+ K26E+ K36E+ A45M+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ G6P+ F7G+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ V8Q+ S15Q+ I22V+ K26E+ K36E+ E46Y+ T53K+ E64P+ K70P+ S103V+ P121A+ Q143R+ I165E+ T166P+ Q168D+ M172I+ S178P+ K197D+ Q214R+ S239A+ M248I+ S258G+ S271G+ R280K+ N283Y+ K304Q+ K378Q+ D385A+ K408M+ D410M+ L413T+ G440Q;

A1Y+ F7G+ T13I+ S15Q+ I22V+ K26E+ K36E+ E46Y+ T53K+ E64P+ K70P+ Q76T+ S103V+ P121A+ Q143R+ P163N+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

F7G+ T3*+ G6*+ P5*+ V4*+ 12*+ A1*+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y;

T3E+ F7G+ T13I+ S15Q+ A20G+ K26E+ K36E+ E46Y+ E64P+ K70P+ S103V+ S141R+ P163A+ T166P+ Q168D+ M172I+ S178P+ F190Y+ K197N+ Q214R+ S239A+ M248I+ S258G+ S271G+ N283Y+ E299W+ K378Q+ D385A+ K408M+ D410M+ L413T+ V422I+ N473Y+ K491R;

V4Y+ G6*+ F7G+ V8F+ S15Q+ A20G+ K26E+ K36E+ E46M+ E64P+ K70P+ S103V+ K120A+ S141R+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y+ K491R;

T3G+ F7G+ T13I+ S15Q+ A20G+ K26E+ K36E+ E46Y+ E64P+ K70P+ S103V+ S141R+ P163A+ T166P+ Q168D+ M172I+ S176N+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1Y+ F7G+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ F190Y+ K197D+ Q214R+ S239A+ M248I+ S258G+ S271G+ R280K+ N283Y+ K378Q+ D385A+ K408M+ D410M+ L413T+ T438A;

A1V+ F7G+ P11A+ S15Q+ I22V+ K26E+ K36E+ E46Y+ T53K+ E64P+ K70P+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A;

T3G+ F7G+ T13I+ S15Q+ A20G+ K26E+ 130L+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

T3G+ F7G+ T13I+ S15Q+ A20G+ K26E+ K36E+ E46Y+ E64P+ K70P+ S103V+ K120A+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

T3G+ F7G+ S15Q+ A20G+ K26E+ K36E+ E46M+ E64P+ K70P+ S103V+ K120S+ S141R+ P163A+ T166P+ Q168D+ M172I+ S176N+ S178P+ F190Y+ K197D+ Q214R+ S239A+ M248I+ R253A+ S258G+

S271G+ N283Y+ E299W+ K378Q+ D385A+ K408M+ D410M+ L413T+ N473Y+ K491R;

T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

T3G+ F7G+ T13I+ S15Q+ A20G+ K26E+ K36E+ E46Y+ E64P+ K70P+ N82T+ S103V+ S141R+ P163A+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103A+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103V+ S141R+ P163T+ T166P+ Q168D+ M172I+ S178P+ F190Y+ K197D+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ K197D+ S239A+ M248I+ S258G+ S271G+ R280K+ N283Y+ T315V+ K378Q+ D385A+ K408M+ D410M+ L413T+ T438A;

T3G+ F7G+ S15Q+ A20G+ K26E+ 130L+ K36E+ E46M+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378R+ K408M+ D410M+ L413T+ N473Y+ K491R;

A1Y+ F7H+ T13I+ S15Q+ I22V+ K26E+ K36E+ E46Y+ T53K+ E64P+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ E322A+ K378Q+ D385A+ K408M+ D410M+ L413T+ T438A;

A1Y+ F7G+ T13I+ S15Q+ I22V+ K26E+ K36E+ E46Y+ T53K+ E64P+ Q69S+ K70P+ Q76T+ S103V+ P121A+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

T3G+ F7G+ T13I+ S15Q+ A20G+ K26E+ 130L+ K36E+ E46Y+ T53P+ E64P+ K70P+ S103V+ S141R+ P163A+ T166P+ Q168D+ M172I+ S176N+ S178P+ F190Y+ K197N+ Q214R+ S239A+ M248I+ S258G+ S271G+ N283Y+ E299W+ K378Q+ D385A+ K408M+ D410M+ L413T+ N473Y+ K491R;

T3G+ F7G+ S15Q+ A20G+ K26E+ K36E+ E46M+ E64P+ K70P+ S103V+ M130I+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ D385A+ K408M+ D410M+ L413T+ N473Y+ K491R;

A1V+ F7G+ P11A+ S15Q+ I21L+ K26E+ K36E+ E46Y+ T53K+ E64P+ K70P+ Q76T+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A;

A1V+ F7G+ P11A+ S15Q+ I21L+ K26E+ K36E+ E46Y+ T53K+ E64P+ K70P+ Q76T+ S103V+ P121A+ M130I+ Q143R+ Y155H+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

A1V+ F7G+ P11A+ S15Q+ I21L+ K26E+ K36E+ E46Y+ T53K+ E64P+ K70P+ Q76T+ S103V+ S109D+ P121A+ M130I+ Q143R+ E162D+ I165E+ T166P+ Q168D+ M171Q+ K179N+ K197D+ S239A+ M248I+ S258G+ S271G+ R280K+ N283Y+ K378Q+ D385A+ K408M+ D410M+ L413T+ T438A;

T3G+ F7G+ S15Q+ A20G+ K26E+ K36E+ E46M+ E64P+ K70P+ N82A+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ K185Q+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

A1V+ F7G+ P11A+ S15Q+ I21L+ K26E+ K36E+ E46Y+ T53K+ E64P+ K70P+ Q76T+ S103V+ P121A+ M130I+ Q143R+ I165E+ T166P+ Q168D+ M171Q+ K179N+ T192V+ K197D+ S239A+ M248I+ S258G+ S271G+ R280K+ N283Y+ T315V+ K378Q+ D385A+ K408M+ D410M+ L413T+ T438A;

A1V+ F7G+ T13I+ S15Q+ A20G+ K26E+ 130L+ 135*+ K36E+ E46Y+ E64P+ K70P+ S103A+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103E+ S109D+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103A+ S109D+ S141R+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E64P+ K70P+ S103A+ S141R+ W148Q+ E162D+ T166P+ Q168D+ M172I+ S178P+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

T3G+ F7G+ S15Q+ A20G+ K26E+ K36E+ E46M+ E64P+ K70P+ N82T+ S103E+ K120A+ S141R+ P163A+ T166P+ Q168D+ M172I+ S176N+ S178P+ F190Y+ K197D+ Q214R+ Y219W+ S239A+ M248I+

R253A+ S258G+ S271G+ N283Y+ E299W+ K378Q+ K408M+ D410M+ L413T+ N473Y+ K491R;

T3G+ F7G+ T13I+ S15Q+ A20G+ K26E+ K36E+ E46Y+ E64P+ K70P+ N97E+ S103V+ K120A+ S141R+ P163A+ T166P+ Q168D+ M172I+ S178P+ K185N+ F190Y+ K197N+ Q214R+ Y219W+ S239A+ M248I+ S258G+ S271G+ N283Y+ E299W+ K378Q+ D385A+ K408M+ D410M+ L413T+ N473Y+ K491R;

T3G+ F7G+ S15Q+ A20G+ K26E+ K36E+ E46M+ E64P+ K70P+ S103V+ K120A+ S141A+ P163A+ T166P+ Q168D+ M172I+ S176N+ S178P+ F190Y+ K197D+ A210E+ Q214R+ S239A+ M248I+ R253A+ S258G+ S271G+ R280K+ N283Y+ K378Q+ D385A+ K408M+ D410M+ L413T+ V422I+ N473Y+ K491R;

T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ A210E+ Q214R+ S239A+ M248I+ R253A+ S258G+ S271G+ N283Y+ E299W+ K378Q+ D385A+ K408M+ D410M+ L413T+ V422I+ N473Y+ K491R;

A1V+ F7G+ P11A+ S15Q+ I21L+ K26E+ K36E+ E46Y+ T53K+ E64P+ Q69P+ K70P+ Q76T+ S103V+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K378Q+ D385A+ K408M+ D410M+ L413T+ T438A;

T3*+ V9*+ V8*+ G7*+ G6*+ P5*+ V4*+ 12*+ A1*+ F7G+ S15Q+ K26E+ K36E+ E46Y+ E64P+ K70P+ S103V+ P163A+ T166P+ Q168D+ M172I+ S178P+ F190Y+ K197D+ Q214R+ S239A+ M248I+ S258G+ S271G+ N283Y+ E299W+ K378Q+ D385A+ K408M+ D410M+ L413T+ N473Y;

T3G+ F7G+ S15Q+ A20G+ K26E+ 130L+ K36E+ E46M+ E64P+ K70P+ Q76T+ S103V+ M130I+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ D385A+ K408M+ D410M+ L413T+ N473Y+ K491R;

T3G+ F7G+ T13I+ S15Q+ A20G+ K26E+ 130L+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K482A+ K491R;

T3G+ F7G+ S15Q+ A20G+ K26E+ K36E+ E46M+ E64P+ K70P+ S103V+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ R280K+ N283Y+ E299W+ K304Q+ T315V+ K378Q+ K408M+ D410M+ L413T+ N473Y+ K491R;

A1V+ F7G+ P11A+ S15Q+ I21L+ K26E+ K36E+ E46Y+ T53K+ E64P+ K70P+ Q76T+ S103V+ P121A+ M130I+ Q143R+ E162D+ I165E+ T166P+ Q168D+ M171Q+ K179N+ K197D+ Y219W+ S239A+ M248I+ S258G+ S271G+ H276Y+ R280K+ N283Y+ E299D+ K378Q+ D385A+ K408M+ D410M+ L413T+ T438A;

A1V+ F7G+ T13I+ S15Q+ A20G+ K26E+ 130L+ K36E+ E46Y+ E61D+ E64P+ Q69P+ K70P+ Q76T+ S141R+ E162D+ T166P+ Q168D+ M172I+ S178P+ F190Y+ K197N+ Q214R+ Y219W+ S239A+ M248I+ S258G+ S271G+ R280K+ N283Y+ E299W+ K378Q+ D385A+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

A1V+ F7G+ T13I+ S15Q+ A20G+ K26E+ 130L+ K36E+ E46Y+ E64P+ K70P+ S103E+ S109D+ S141R+ E162D+ T166P+ Q168D+ M172I+ S178P+ F190Y+ K197N+ Q214R+ Q215E+ Y219W+ S239A+ M248I+ S258G+ S271G+ R280K+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E61D+ E64P+ Q69P+ K70P+ Q76T+ S109D+ S141R+ E162D+ T166P+ Q168D+ M172I+ S178P+ F190Y+ K197N+ Q214R+ Y219W+ S239A+ M248I+ S258G+ S271G+ R280K+ N283Y+ E299W+ K378Q+ D385A+ K408M+ D410M+ L413T+ N473Y+ K491R;

T3G+ F7G+ V9A+ S15Q+ A20G+ K26E+ K36E+ E46M+ E61D+ E64P+ Q69P+ K70P+ N82T+ S103E+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

T3G+ F7G+ S15Q+ A20G+ K26E+ 130L+ K36E+ E46M+ E64P+ K70P+ Q76T+ A101R+ S103V+ G110R+ M130I+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ D385A+ K408M+ D410M+ L413T+ N473Y+ K491R;

T3G+ F7G+ S15Q+ A20G+ K26E+ 130L+ K36E+ E46M+ K70P+ Q76T+ A101R+ S103V+ G110R+ M130I+ S141Q+ P163A+ T166P+ Q168D+ M172I+ S176N+ S178P+ F190Y+ K197D+ Q214R+ Q215E+ Y219W+ S239A+ M248I+ R253A+ S258G+ S271G+ N283Y+ E299W+ K378Q+ D385A+ K408M+ D410M+ L413T+ N473Y+ K491R;

A1V+ F7G+ T13I+ S15Q+ A20G+ K26E+ 130L+ K36E+ E46Y+ E61D+ E64P+ Q69P+ K70P+ Q76T+ S103R+ G122P+ S141R+ E162D+ T166P+ Q168D+ M172I+ S178P+ F190Y+ K197N+ Q214R+ Y219W+ S239A+ M248I+ S258G+ S271G+ R280K+ N283Y+ E299W+ K378Q+ D385A+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ V9A+ S15Q+ A20G+ K26E+ K36E+ E46M+ E61D+ E64P+ Q69P+ K70P+ N82T+ S103E+ K120A+ S141R+ P163T+ T166P+ Q168D+ M172I+ S176N+ S178P+ F190Y+ K197D+ Q214R+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ V9A+ S15Q+ A20G+ K26E+ K36E+ E46M+ E61D+ E64P+ Q69P+ K70P+ N82T+ S103E+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ V9A+ S15Q+ I22Q+ K26E+ K36E+ E46M+ E64P+ Q69P+ K70P+ N82T+ A101V+ K120A+

S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ T74Q+ Q76T+ N82T+ S103E+ K120A+ S141R+ P163A+ T166P+ Q168D+ M172I+ S176N+ S178P+ F190Y+ K197D+ Q214R+ Y219W+ S239A+ M248I+ R253A+ S258G+ S271G+ N283Y+ E299W+ K378Q+ K408M+ D410M+ L413T+ N473Y+ K491R;

T3G+ F7G+ S15Q+ A20G+ K26E+ 130L+ K36E+ E46M+ K70P+ Q76T+ A101R+ S103V+ G110R+ M130I+ S141Q+ P163A+ T166P+ Q168D+ M172I+ S176N+ S178P+ F190Y+ K197D+ Q214R+ Q215E+ Y219W+ S239A+ M248I+ R253A+ S258G+ S271G+ N283Y+ E299W+ K378Q+ D385A+ K408M+ D410M+ L413V+ N473Y+ D486K+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M171Q+ M172I+ S176N+ S178R+ F190Y+ K197D+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141A+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ H324N+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197A+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R;

T3G+ F7G+ T13N+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46Y+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141I+ P163A+ T166P+ Q168D+ K169P+ M172I+ S176N+ S178P+ F190Y+ K197A+ Q214R+ Q215E+ Y219W+ S239A+ M248I+ R253A+ S258G+ S271G+ R280K+ N283Y+ E299W+ K378Q+ K408M+ D410M+ L413T+ N473Y+ K491R;

A1V+ F7G+ P11N+ S15Q+ I21L+ K26E+ K36E+ E46Y+ T53K+ E64P+ Q69P+ K70P+ Q76T+ N82T+ S103V+ S109D+ K120A+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ Q76T+ N82T+ S103V+ S109D+ K120A+ P121A+ M130I+ Q143R+ E162D+ I165E+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ Q76T+ N82T+ S103E+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ T74E+ Q76T+ N82T+ S103E+ S109D+ P121A+ M130I+ Q143R+ P163A+ R164Q+ T166P+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

T3G+ F7G+ V9A+ S15Q+ A20G+ K26E+ K36E+ E46Y+ T53K+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ I22V+ K26E+ 130L+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ E31Q+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+

K120A+ S141R+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

A1V+ G6P+ F7G+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ G96R+ S103E+ K120A+ S141R+ P163A+ T166E+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ T170E+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ M188F+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ T74E+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A+ K462R;

A1V+ F7G+ P11A+ S15Q+ I21L+ K26E+ K36E+ E46Y+ T53K+ E64P+ Q69P+ K70P+ T74E+ Q76T+ N82T+ S103E+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ P11A+ S15Q+ I21L+ K26E+ 130L+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

A1V+ F7G+ T13I+ S15Q+ I21L+ K26E+ 130L+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ T13I+ S14N+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ R280K+ N283Y+ E299W+ H324N+ K378Q+ D385H+ K408M+ D410M+ L413T+ N473Y+ K491R;

T3G+ F7G+ V9A+ S15Q+ A20G+ K26E+ 130L+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ S403R+ K408M+ D410M+ L413T+ N473Y+ K491R;

T3G+ F7G+ V9A+ S15Q+ A20G+ K26E+ E31Q+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ Q321K+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197A+ Q214R+ Q215E+ Y219W+ S239A+ M248I+ R253W+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+

K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82A+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ Q76E+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

A1V+ F7G+ P11A+ T13I+ S15Q+ Q19N+ A20G+ K26E+ K36E+ E46Y+ T53K+ E64P+ Q69P+ K70P+ Q76T+ N82T+ S103V+ S109D+ P121A+ M130I+ Q143R+ E162D+ I165E+ T166P+ T167A+ Q168D+ M171Q+ K179N+ K197D+ Y219W+ S239A+ M248I+ S258G+ S271G+ R280K+ N283Y+ K304Q+ E363H+ K378Q+ D385A+ K408M+ D410M+ L413T+ T438A;

T3G+ F7G+ T13I+ S14N+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ P399A+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103N+ S109E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ S109D+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ Q76T+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ E10Y+ T13I+ S15Q+ A20G+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ K179H+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ T13I+ S14N+ S15Q+ A20G+ K26E+ K36E+ E46Y+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ S487R+ K491R;

T3G+ F7G+ V9A+ S15Q+ A20G+ K26E+ K36E+ E46M+ E64P+ Q69P+ K70P+ K78E+ N82A+ S103E+ K120A+ S141R+ R160F+ E162D+ T166P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ I165D+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ K120A+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ 130L+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ E86D+ S103E+ K120A+ S141R+ V161S+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ I22T+ K26E+ 130L+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ Q76E+ S103E+ K120A+ N139K+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

S-17G+ T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280L+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ K304Q+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ K129R+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163E+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ K304Q+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ Q76E+ S103E+ K120A+ S141R+ V161S+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R;

T3G+ F7G+ V9A+ S15Q+ K26E+ K36E+ E46Y+ D48A+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ S109E+ K120A+ S141R+ P163A+ T166P+ Q168D+ M171Q+ M172I+ S176N+ S178P+ K189S+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ T13I+ S14H+ S15Q+ A20G+ K26E+ K36E+ E46M+ E64P+ Q69P+ K70P+ Q76T+ N82T+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ T13I+ S14N+ S15Q+ A20G+ K26E+ 130L+ K36E+ E46Y+ E64P+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ I165T+ T166P+ Q168D+ M171K+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ H12Q+ T13I+ S15Q+ A20G+ K26E+ K36E+ E46M+ E64P+ K65Q+ Q69P+ K70P+ K78E+ N82T+ S103E+ K120A+ N139K+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ T13E+ S15Q+ A20G+ K26E+ K36E+ E46M+ E64P+ Q69P+ K70P+ K78E+ N82A+ S103E+ S109D+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ K78E+ N82A+ S103E+ S109D+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+

S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ T13I+ S14H+ S15Q+ A20G+ K26E+ K36E+ E46M+ E64P+ Q69P+ K70P+ Q76T+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ 130L+ K36E+ E46Y+ E64P+ Q69P+ K70P+ N82T+ S103E+ S109E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ E31Q+ K36E+ E46Y+ E64P+ Q69P+ K70P+ N82T+ S103E+ K120A+ S141R+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ E31Q+ K36E+ E46M+ E64P+ Q69P+ K70P+ N82T+ S103E+ S109E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413V+ N473Y+ D486E+ K491R;

T3G+ F7G+ V9A+ S15Q+ A20G+ K26E+ K36E+ E46M+ E64P+ Q69P+ K70P+ K78E+ N82A+ S103E+ K120A+ S141R+ P163A+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ R489F+ K491R;

S-17G+ T3G+ F7G+ V9A+ S15Q+ A20G+ K26E+ K36E+ E46M+ E64P+ Q69P+ K70P+ K78E+ N82T+ S103E+ K120A+ N139K+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ R280K+ N283Y+ E299W+ K378Q+ D385H+ K408M+ D410M+ L413T+ N473Y+ K491R;

T3G+ F7G+ V9A+ S15Q+ A20G+ K26E+ K36E+ E46M+ T53K+ E64P+ Q69P+ K70P+ Q76E+ S103E+ K120A+ S141R+ P163A+ T166P+ Q168D+ K169P+ M172I+ S176N+ S178P+ K179Q+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ R489F+ K491R;

T3G+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ E10Y+ T13I+ S15Q+ A20G+ K26E+ K36E+ E46M+ E64P+ Q69P+ K70P+ Q76T+ K78R+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ E10Y+ T13I+ S15Q+ A20G+ K26E+ K36E+ E46M+ E64P+ Q69P+ K70P+ N82T+ S103E+ K120A+ S141R+ P163A+ R164Q+ T166P+ Q168D+ M171K+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ K26E+ K36E+ E46Y+ D48A+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ K252G+ R253A+ S258G+ S271G+ H276C+ R280K+ N283Y+ F286C+ E299W+ K378Q+ D385H+ K408M+ D410M+ L413T+ N473Y+ K491R;

A1V+ V4M+ F7G+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82A+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82A+ A101R+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+

Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ K26E+ K36E+ E46M+ E64P+ Q69P+ K70P+ N82T+ A101R+ K120A+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ K120P+ S141R+ R160F+ E162D+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R;

T3G+ F7G+ V9A+ S15Q+ K26E+ K36E+ E46M+ E64P+ Q69P+ K70P+ N82T+ S103E+ S109E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R;

T3G+ F7G+ T13I+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23I+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23I+ K26E+ K36E+ E46M+ E64P+ Q69P+ K70P+ N82T+ S103E+ K120P+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ 130L+ K36E+ E46M+ E64P+ Q69P+ K70P+ N82T+ S103E+ S109E+ K120A+ S141R+ P163A+ T166P+ Q168D+ M171Q+ M172I+ S176N+ S178P+ K189S+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ E10Y+ T13I+ S15Q+ A20G+ K26E+ K36E+ E46M+ E64P+ Q69P+ K70P+ K78E+ N82A+ S103E+ K120A+ S141R+ R160F+ E162D+ T166P+ Q168D+ M171Q+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ V9A+ S15Q+ A20G+ K26E+ K36E+ E46M+ E64P+ Q69P+ K70P+ N82T+ S103E+ S109E+ K120A+ S141R+ P163A+ T166P+ Q168D+ M171K+ M172I+ S176N+ S178P+ K189S+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ K26E+ K36E+ A45M+ E46Y+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20G+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20G+ I22V+ K26E+ 130L+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

T3G+ F7G+ E10Y+ T13I+ S15Q+ A20G+ I22V+ K26E+ 130L+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276N+ R280K+ N283Y+ E299W+ A312V+ K378Q+ K408M+ D410M+ L413T+ N473Y+ K491R;

A1V+ V4M+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ T13I+ S15Q+ A20P+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K364D+ K378Q+ D385H+ K408M+ D410M+ L413T+ N473Y+ K491R;

A1V+ T3E+ F7G+ V9A+ S15Q+ A20G+ A23V+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103E+ K120A+ S141R+ V161S+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103E+ K120A+ S141I+ R160I+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103E+ K120A+ S141R+ R160I+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103I+ T115I+ K120A+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23I+ K26E+ K36E+ E46M+ E64P+ Q69P+ K70P+ N82T+ S103E+ K120A+ S141R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ E379K+ D385H+ K408M+ D410M+ L413T+ N473Y+ K491R;

T3G+ F7G+ V9A+ S15Q+ A20G+ A23I+ K26E+ K36E+ E46M+ E64P+ Q69P+ K70P+ N82T+ S103E+ K120P+ S141R+ Q143R+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V8A+ T13I+ S15Q+ K26E+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ T115Y+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ E10G+ T13I+ S15Q+ A20G+ A23T+ K26E+ K36E+ E46M+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ T53K+ E64P+ Q69P+ K70P+ N82T+ S103E+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ T115W+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ S15Q+ A20P+ K26E+ K36E+ E46M+ E64P+ Q69P+ K70P+ N82A+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+

E299W+ G366N+ K378Q+ D385H+ K408M+ D410M+ L413T+ N473Y+ D486E+ K491R;

T3G+ F7G+ V9A+ S15Q+ A20G+ A23V+ K26E+ K36E+ E46M+ E64P+ Q69P+ K70P+ N82T+ S103E+ T115I+ K120A+ A126T+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23V+ K26E+ K36E+ E46M+ E64P+ Q69P+ K70P+ N82T+ S103E+ A118V+ K120A+ L134I+ S141R+ P163A+ T166P+ T167P+ Q168D+ M172I+ S176N+ S178P+ F190Y+ K197D+ Q214R+ Q215E+ Y219W+ S239A+ M248I+ R253W+ S258G+ S271G+ H276C+ R280K+ N283Y+ F286C+ E299W+ K378Q+ D385H+ K408M+ D410M+ L413T+ N473Y+ K491R;

T3G+ F7G+ V9A+ S15Q+ A20G+ A23I+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ K378Q+ D385H+ K408M+ D410M+ L413T+ N473Y+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ S103E+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ R160N+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ P163A+ I165D+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S109D+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ S109D+ T115Y+ K120A+ S141R+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ S109E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ T115W+ K120A+ S141R+ V161T+ P163A+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ R160I+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ A101R+ K120A+ S141R+ E162G+ P163A+ T166P+ Q168D+

K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9A+ T13I+ S15Q+ I22V+ K26E+ K36E+ E46M+ E64P+ Q69P+ K70P+ N82T+ S103E+ K120A+ S141R+ R160F+ E162D+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Y155H+ P163A+ I165D+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ G6P+ F7G+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R;

T3G+ F7G+ V8A+ T13I+ S15Q+ I22V+ K26E+ K36E+ E46M+ E64P+ Q69P+ K70P+ N82T+ A101R+ K120A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R;

T3G+ F7G+ V9A+ S15Q+ A20G+ A23T+ K26E+ K36E+ E46M+ E64P+ Q69P+ K70P+ N82T+ S103E+ T115Y+ K120A+ S141R+ V161T+ P163A+ T166P+ Q168D+ M171K+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ A101R+ K120A+ S141R+ Y155H+ E162G+ P163A+ T166P+ Q168D+ K169P+ M172I+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20G+ A23T+ K26E+ K36E+ E46M+ E64P+ Q69P+ K70P+ N82T+ S103E+ K120A+ S141R+ P163A+ I165E+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20T+ K26E+ K36E+ E46M+ E64P+ Q69P+ K70P+ N82T+ A101R+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8D+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ N193W+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R;

A1V+ V4D+ F7G+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1T+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82A+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ S109D+ K120A+ S141R+ R160L+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K462A+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ T115V+ K120A+ S137A+ S141R+ Y155H+ P163A+ T166P+ Q168D+ K169P+ M172I+ S176N+ S178P+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Q143R+ V161T+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ I22V+ K26E+ K36E+ E46M+ E64P+ Q69P+ K70P+ N82T+ S103E+ K120A+ S141R+ Y155H+ E162D+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S137A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120P+ S137A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ A210F+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53P+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ S103V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ N242T+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E322R+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+

R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ E31Q+ K36E+ E46Y+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ T115Y+ K120P+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ S141R+ R160I+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82A+ A101R+ G110R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1D+ F7G+ V8A+ T13I+ S15Q+ A20P+ K26E+ K36E+ A45M+ E46Y+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R;

T3G+ F7G+ V8A+ T13I+ S15Q+ I22V+ K26E+ 130L+ E31Q+ K36E+ E46M+ E64P+ Q69P+ K70P+ N82T+ S103E+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ T115Y+ K120A+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M171K+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7A+ T13I+ S15Q+ A20P+ K26E+ K36E+ E46M+ E64P+ Q69P+ K70P+ N82A+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ S15K+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4D+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ K304A+ G366N+ K378Q+ D385H+ K408M+ D410M+ L413T+ N473Y+ D486E+ K491R;

T3G+ F7G+ V8A+ T13I+ S15Q+ A20P+ K26E+ E31Q+ K36E+ E46Y+ T53K+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ G110R+ T115Y+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109E+ T115Y+ K120A+ S141R+ Y155H+ P163A+

T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ S141R+ Y155H+ P163A+ T166P+ T167P+ Q168D+ M172I+ S176N+ S178P+ P182R+ F190Y+ K197D+ A210T+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115I+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ K120A+ S141R+ Y155H+ P163A+ T166P+ T167P+ Q168D+ M172I+ S176N+ S178P+ P182R+ F190Y+ N193W+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R;

A1D+ T3G+ F7G+ V8A+ T13I+ S15Q+ A20P+ K26E+ K36E+ A45M+ E46Y+ E64P+ Q69P+ K70P+ A101R+ K120A+ S141R+ Y155H+ P163A+ T166P+ T167P+ Q168D+ M172I+ S176N+ S178P+ P182R+ F190Y+ K197F+ Q214R+ Q215E+ Y219W+ S239A+ M248I+ R253A+ S258G+ S271G+ H276C+ R280K+ N283Y+ F286C+ E299W+ G366N+ K378Q+ D385H+ P398E+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ T115Y+ K120A+ K129R+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ G110R+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ H12E+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ G110R+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163*+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115I+ K120A+ K129L+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ K120A+ A126T+ L134V+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ 130L+ K36E+ E46M+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ F7I+ T13I+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ K26E+ K36E+ A45M+ E46Y+ E64P+ V68M+ Q69P+ K70P+ N82A+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109E+ T115Y+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109E+ T115Y+ K120P+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ A45M+ E46Y+ E64P+ Q69P+ K70P+ N82T+ A101R+ S109D+ T115Y+ K120A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E380T+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ V9P+ T13I+ S15Q+ A20P+ K26E+ K36E+ E46M+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109D+ T115Y+ K120A+ N139I+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+

G366N+ K378Q+ D385H+ K408M+ D410M+ L413T+ N473Y+ D486E+ K491R;

A1V+ V4N+ F7G+ T13I+ S15Q+ A20P+ K26E+ K36E+ A45M+ E46Y+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109D+ T115Y+ K120A+ A126T+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ A101R+ S109D+ T115V+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82A+ A101R+ G110D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109E+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ G110D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82A+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ N139A+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ K179S+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1D+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20G+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+

H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141I+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20G+ K26E+ K36E+ E46M+ E64P+ K65N+ Q69P+ K70P+ N82A+ A101R+ S109E+ K120A+ A126T+ L134I+ S141I+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1I+ F7G+ T13I+ S15Q+ A20P+ K26E+ K36E+ A45R+ E46Y+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ K65N+ Q69P+ K70P+ N82A+ A101R+ S109E+ T115I+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ K65N+ Q69P+ K70P+ N82A+ A101R+ S109E+ T115I+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ V68M+ Q69P+ K70P+ Q76E+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ V68M+ Q69P+ K70P+ N82A+ A101L+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ K26E+ K36E+ E46M+ E64P+ K65N+ Q69P+ K70P+ N82T+ A101I+ S109E+ K120A+ A126T+ L134I+ S141R+ Q143T+ Y155H+ P163A+ T166P+ T167R+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ T13I+ S14N+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ K218R+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9D+ T13I+ S15Q+ A20P+ K26E+ K36E+ E46M+ T53K+ E64P+ Q69P+ K70P+ N82T+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ K65N+ Q69P+ K70P+ N82T+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ Q69P+ K70P+ N82T+ L89F+ A101R+ S109D+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ M228I+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101R+ S109D+ T115Y+ K120A+ S141R+ Q143T+ Y155H+ P163A+ T166P+ T167P+ Q168D+ M171I+ M172I+

S176N+ S178P+ P182R+ F190Y+ K197D+ Q214R+ Q215E+ Y219W+ S239A+ M248I+ R253A+ S258G+ L259V+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ P94M+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E301K+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ L480I+ D486E+ K491R;

A1V+ V4N+ F7G+ T13I+ S15Q+ A20P+ K26E+ K36E+ E46M+ E64P+ Q69P+ K70P+ N82T+ A101L+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ A101L+ S109D+ T115Y+ K120A+ K129L+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ D27N+ K36E+ E46M+ E64P+ Q69P+ K70P+ N82T+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ Q17K+ A20G+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ Q76T+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53K+ E64P+ Q69P+ K70P+ N82T+ A101R+

S109D+ G122P+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ I142L+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ E46M+ E64P+ K65N+ Q69P+ K70P+ N82A+ A101R+ S109E+ K120A+ A126T+ L134I+ S141R+ Q143S+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S14E+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S14E+ S15Q+ A20G+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V9P+ T13I+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ Q17K+ A20G+ K26E+ K36E+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ F414S+ N473Y+ D486E+ K491R;

T3G+ F7G+ H12P+ T13I+ S15Q+ A20P+ K26E+ K36E+ A45L+ E46Y+ E61D+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ 130L+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ 130L+ K36E+ A45M+ E46Y+ E64P+ V68M+ Q69P+ K70P+ N82T+ A101L+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ E10Y+ T13I+ S15Q+ K26E+ K36E+ E46M+ E64P+ K65N+ Q69P+ K70P+ N82T+ A101R+ S109D+ G110P+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ V68M+ Q69P+ K70P+ N82T+ A101R+ S109D+ T115V+ K120A+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R;

T3G+ F7G+ V8A+ T13I+ S15Q+ A20P+ K26E+ K36E+ A45M+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T13I+ S15Q+ Q17K+ A20G+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ P174K+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ G96D+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ K26E+ 130L+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E301K+ G366N+ K378Q+ D385H+ K408M+ D410M+ L413T+ F414T+ N473Y+ D486E+ K491R;

T3G+ F7G+ P11A+ T13I+ S15Q+ A20P+ K26E+ K36E+ E46M+ E64P+ Q69P+ K70P+ N82T+ A101R+ S109D+ K120A+ A126T+ L134I+ S141R+ Q143R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ K417G+ N473Y+ L480I+ D486E+ K491R;

A1V+ V4N+ F7G+ T13I+ S15Q+ A20P+ K26E+ K36E+ E46M+ E64P+ Q69P+ K70P+ N82T+ A101L+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324K+ G366N+ K378Q+ D385H+ K408M+ D410M+ L413T+ N473Y+ D486E+ K491R;

A1V+ V4N+ F7G+ T13I+ S15Q+ A20P+ K26E+ K36E+ E46M+ E64P+ Q69P+ K70P+ N82T+ N97E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ N97E+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ A101L+ S109D+ T115Y+ K120A+ K129L+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ D27N+ K36E+ E46M+ E64P+ Q69P+ K70P+ N82T+ G96E+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+

E299W+ G366N+ K378Q+ D385H+ K408M+ D410M+ L413T+ N473Y+ D486E+ K491R;

A1V+ T3E+ F7G+ P11A+ T131+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ A20P+ K26E+ K36E+ A45M+ E46Y+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R;

T3G+ F7G+ V8A+ T131+ S15Q+ Q17K+ A20G+ K26E+ K36E+ E46M+ T53P+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ Q17K+ A20G+ K26E+ K36E+ E46M+ E61D+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82T+ A101R+ S109D+ G122P+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413Q+ N473Y+ D486E+ K491R;

A1V+ V4N+ F7G+ T131+ S15Q+ A20P+ K26E+ K36E+ A45M+ E46Y+ T53P+ E64P+ K65N+ Q69P+ K70P+ N82A+ A101L+ S109E+ T115Y+ K120A+ S141R+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S14E+ S15Q+ A20P+ K26E+ K36E+ E46M+ E64P+ K65N+ Q69P+ K70P+ N82A+ A101R+ S109E+ T115Y+ K120A+ S141R+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ K482P+ D486E+ K491R;

T3G+ F7G+ P11A+ T131+ S15Q+ A20P+ K26E+ K36E+ E46M+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ E379K+ D385H+ K408M+ D410M+ L413T+ N473Y+ D486E+ K491R;

T3G+ F7G+ P11A+ T131+ S15Q+ A20P+ K26E+ K36E+ E46M+ T53K+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ E46M+ T53K+ E64P+ K65N+ Q69P+ K70P+ N82T+ A101R+ S109E+ K120A+ A126T+ L134I+ S141R+ Q143T+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253W+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ A45R+ E46Y+ T53P+ E64P+ K65N+ Q69P+ K70P+ N82A+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ K26E+ K36E+ A45M+ E46Y+ T53K+ E64P+ Q69P+ K70P+ N82T+ A101R+ S109D+ K120A+ K129L+ S141R+ Q143T+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ V8A+ T131+ S15Q+ Q17K+ A20G+ K26E+ K36E+ E46M+ E64P+ K65N+ Q69P+ K70P+ Q76T+ K78S+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ Q17K+ A20G+ K26E+ K36E+ E46M+ E64P+ K65N+ Q69P+ K70P+ N82A+ N97D+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ Q17K+ A20G+ K26E+ 130L+ K36E+ E46M+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+

S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ A20P+ K26E+ K36E+ A45L+ E46Y+ E64P+ Q69P+ K70P+ N82T+ A101R+ S109D+ K120A+ A126T+ L134I+ S141R+ Y155H+ P163A+ T166P+ T167P+ Q168D+ M172I+ S176N+ S178P+ P182R+ F190Y+ K197D+ K198G+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ V422R+ N473Y+ D486E+ K491R;

T3G+ F7G+ P11A+ T131+ S15Q+ A20P+ K26E+ K36E+ E46I+ T53K+ E64P+ Q69P+ K70P+ N82A+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ V8A+ T131+ S15Q+ K26E+ K36E+ A45M+ E46Y+ T53K+ E64P+ Q69P+ K70P+ N82T+ A101R+ S109D+ K120A+ K129L+ S141R+ Q143T+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ V8A+ T131+ S15Q+ A20P+ K26E+ K36E+ A45M+ E46Y+ T53K+ E64P+ V68M+ Q69P+ K70P+ N82T+ A101L+ S109D+ T115V+ K120A+ A126D+ S141R+ Y155H+ P163A+ T166P+ T167P+ Q168D+ M172I+ S176N+ S178P+ P182E+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ A20P+ K26E+ K36E+ A45M+ E46Y+ T53P+ E64P+ K65N+ Q69P+ K70P+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ N97E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ A20P+ K26E+ K36E+ E46M+ E64P+ Q69P+ K70P+ N82T+ A101R+ S109D+ T115Y+ K120A+ S141R+ W148Q+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ 268/+ G270C+ 271/+ S271G+ N272D+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ H324N+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ G96E+ A101R+ S109D+ T115Y+ K120P+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ T438A+ N473Y+ D486E+ K491R;

A1V+ V4N+ F7G+ T13E+ S15Q+ A20P+ K26E+ K36E+ E46M+ T53P+ E64P+ Q69P+ K70P+ N82A+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ N97E+ A101R+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ E249H+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ D27N+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ A423G+ N473Y+ E479R+ D486E+ K491R;

A1V+ T3E+ F7G+ P11A+ T131+ S15Q+ A20P+ K26E+ K36E+ E46M+ T53K+ E64P+ Q69P+ K70P+ N82T+ N97E+ A101R+ S109D+ K120A+ A126T+ L134I+ N139I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ A101L+ S109D+ T115Y+ K120A+ A126T+ K129L+ S141R+ Q143T+ Y155H+ P163A+ T166P+ T167P+ Q168D+

M171I+ M172I+ S176N+ S178P+ P182R+ F190Y+ K197D+ Q214R+ Q215E+ Y219W+ S239A+ M248I+ R253A+ S258G+ S271G+ N272D+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ V9M+ T131+ S15Q+ A20P+ K26E+ K36E+ E46M+ E64P+ Q69P+ K70P+ N82T+ N97E+ A101L+ S109D+ T115Y+ K120A+ K129L+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4D+ F7G+ P11A+ T131+ S15Q+ A20P+ K26E+ K36E+ E46M+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ A45M+ E46Y+ T53P+ E64P+ K65N+ Q69P+ K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82T+ A101R+ S109D+ K120A+ K129L+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ V8A+ T131+ S15Q+ A20P+ K26E+ K36E+ A45M+ E46Y+ T53P+ E64P+ K65N+ Q69P+ K70P+ N82A+ A101L+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R;

A1V+ V4N+ F7G+ T131+ S15Q+ A20P+ K26E+ K36E+ A45R+ E46Y+ T53P+ E64P+ K65N+ Q69P+ K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82A+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82T+ A101R+ S109D+ K120A+ K129L+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299K+ G366N+ K378Q+ D385H+ P398F+ K408M+ D410M+ L413Q+ N473Y+ D486E+ K491R;

T3G+ F7G+ V8A+ T131+ S15Q+ Q17K+ A20G+ K26E+ 130L+ K36E+ E46M+ E64P+ K65N+ Q69P+ K70P+ Q76E+ N82A+ A101R+ S109E+ K120A+ A126T+ L134I+ S141R+ Y155H+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ A45M+ E46Y+ T53P+ E64P+ K65N+ Q69P+ K70P+ N82A+ A101L+ S109E+ T115Y+ K120A+ S141R+ Y155H+ E162G+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

S-6P+ A1V+ V4N+ F7G+ T131+ S15Q+ A20P+ K26E+ K36E+ E46M+ E64P+ Q69P+ K70P+ N82T+ N97E+ S109D+ T115Y+ K120A+ A126D+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ 130L+ K36E+ E46M+ T53K+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

A1V+ V4N+ F7G+ T131+ S15Q+ A20P+ K26E+ K36E+ E46M+ E64P+ Q69P+ K70P+ N82T+ G96E+ A101R+ S109D+ T115Y+ K120A+ L134V+ S141R+ Q143T+ Y155H+ P163A+ T166P+ T167P+ Q168D+ M171I+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ V422I+ Q437I+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

A1V+ V4D+ F7G+ P11A+ T131+ S15Q+ A20P+ K26E+ K36E+ E46M+ T53K+ E61D+ E64P+ Q69P+ K70P+ N82T+ A101R+ S109D+ K120A+ A126T+ L134I+ N139I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ K408M+ D410M+ L413T+ N473Y+ D486E+ K491R;

T3G+ F7G+ V8A+ T131+ S15Q+ A20P+ K26E+ K36E+ A45M+ E46Y+ T53P+ E64P+ K65N+ Q69P+ K70P+ N82A+ A101R+ S109E+ K120A+ A126T+ L134I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R;

T3G+ F7G+ V8A+ T131+ S15Q+ A20P+ K26E+ K36E+ A45M+ E46Y+ T53P+ E64P+ K65N+ Q69P+ K70P+ N82A+ A101L+ S109E+ K120A+ A126T+ L134I+ S141R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ E363H+ G366N+ K378Q+ D385H+ K408M+ D410M+ L413T+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82A+ N97E+ A101R+ S109D+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

T3G+ F7G+ P11A+ T131+ S15Q+ A20P+ K26E+ K36E+ A45M+ E46Y+ T53K+ E64P+ Q69P+ K70P+ N82A+ A101R+ S109D+ G112E+ K120A+ K129L+ S141R+ Q143R+ Y155H+ E162G+ P163A+ T166P+ T167P+ Q168D+ M172I+ S176N+ S178P+ P182R+ F190Y+ K197D+ Q214R+ Q215E+ Y219W+ S239A+ M248I+ R253A+ S258G+ S271G+ H276C+ R280K+ N283Y+ F286C+ E299W+ G366N+ K378Q+ D385H+ P398F+ K408M+ D410M+ L413Q+ N473Y+ D486E+ K491R;

and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1.

Parent Mannanase

In an aspect, the parent mannanase is a polypeptide having a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have mannanase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19, or 20 from the polypeptide of SEQ ID NO: 1. In another aspect, the parent comprises or consists of the amino acid sequence of SEQ ID NO: 1. In one aspect, the parent is a fragment of the polypeptide of SEQ ID NO: 1 containing at least 441 amino acids of SEQ ID NO: 1, such as at least 451 amino acids of SEQ ID NO: 1, at least 461 amino acids of SEQ ID NO: 1, at least 471 amino acids of SEQ ID NO: 1, at least 481 amino acids of SEQ ID NO: 1, or at least 486 amino acids of SEQ ID NO: 1.

In an aspect, the parent mannanase is a polypeptide having a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have mannanase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19, or 20, from the polypeptide of SEQ ID NO: 2. In another aspect, the parent comprises or consists of the amino acid sequence of SEQ ID NO: 2. In another aspect, the parent is a fragment of the polypeptide of SEQ ID NO: 2 containing at least 441 amino acids of SEQ ID NO: 2, such as at least 451 amino acids of SEQ ID NO: 2, at least 481 amino acids of SEQ ID NO: 2, at least 486 amino acids of SEQ ID NO: 2.

In an aspect, the parent mannanase is a polypeptide having a sequence identity to the polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have mannanase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19, or 20 from the polypeptide of SEQ ID NO: 3. In another aspect, the parent comprises or consists of the amino acid sequence of SEQ ID NO: 3. In another aspect, the parent is a fragment of the polypeptide of SEQ ID NO: 3 containing at least 280 amino acids of SEQ ID NO: 3, at least 287 amino acids of SEQ ID NO: 3, at least 293 amino acids of SEQ ID NO: 3, at least 299 amino acids of SEQ ID NO: 3, at least 305 amino acids of SEQ ID NO: 3, at least 308 amino acids of SEQ ID NO: 3.

In an aspect, the parent mannanase is a polypeptide having a sequence identity to the polypeptide of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have mannanase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19, or 20, from the polypeptide of SEQ ID NO: 4. In another aspect, the parent comprises or consists of the amino acid sequence of SEQ ID NO: 4. In another aspect, the parent is a fragment of the polypeptide of SEQ ID NO: 4 containing at least 307 amino acids of SEQ ID NO: 4, at least 314 amino acids of SEQ ID NO: 4 or at least 328 amino acids of SEQ ID NO: 4, at least 335 amino acids of SEQ ID NO: 4, at least 338 amino acids of SEQ ID NO: 4.

The parent polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

In one aspect, the polypeptide is a mannanase from a bacterium of the class Bacilli, such as from the order Bacillales, from the family Paenibacillaceae, from the genus *Paenibacillus* or from the species *Paenibacillus illinoisensis* or *Paenibacillus* sp.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having mannanase activity, comprising: (a) introducing into a parent mannanase at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241:

53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention. Thus, in one aspect, the invention relates to a polynucleotide encoding a variant comprising at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in one aspect, the invention relates to a polynucleotide encoding a variant comprising at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. Thus, in one aspect, the invention relates to recombinant host cells, comprising a polynucleotide encoding a variant comprising at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to one or more control sequences that direct the production of a variant comprising at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2.

A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In,

*Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising (a) cultivating a recombinant host cell of the present invention under conditions conducive for production of the variant; and optionally (b) recovering the variant. Thus, in one aspect, the invention relates to methods of producing a variant, comprising (a) cultivating a host cell comprising a polynucleotide encoding a variant comprising at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, operably linked to a one or more control sequences that direct the production under conditions suitable for expression of the variant, and (b) recovering the variant.

The recombinant host cells are cultivated in a nutrient medium suitable for production of the variant using methods known in the art. For example, the cells may be cultivated by shake flask cultivation, or small-scale or large-scale fermentation (including continuous, batch, fed-batch, orsolid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variants may be detected using methods known in the art that are specific for the mannanase variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions, such as detergent compositions, comprising a mannanase variant of the present invention. Preferably, the compositions are enriched in such a variant. The term "enriched" indicates that the mannanase activity of the composition has been increased, e.g., with an enrichment factor of at least 1.1.

The enzyme composition such as a detergent composition may further comprise one or more components selected from the group consisting of hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers. Examples and preferred amounts of the same are discussed below.

The compositions may comprise a mannanase variant of the present invention as the major enzymatic component, e.g., a mono-component composition. Alternatively, the compositions may comprise multiple enzymatic activities, such as one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, laminarinases, and DNAses.

Granules Comprising Mannanase Variants

In an embodiment, the invention relates to a granule comprising a core particle and one or more coatings, wherein the granule comprises a mannanase variant of the invention.

The granule of these embodiments may further comprise one or more formulating agents, as discussed below in the formulation section. Preferred formulating agents are glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

In an embodiment, the granule may further comprise one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, licheninases, laminarinases, and DNAses.

Liquid Formulations Comprising Mannanase Variants

In an embodiment, the invention relates to a liquid composition comprising a polyol and a mannase variant of the present invention.

In one embodiment, the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment, the liquid formulation comprises 5%-80% polyol (i.e. total amount of polyol), preferably 15%-75% polyol, more preferably 25%-70% polyol, more preferably 35%-65% polyol or most preferably 40%-60% polyol. In one embodiment to any part of the seventh or eighth aspect, the liquid formulation comprises 5%-80% polyol, preferably 15%-75% polyol, more preferably 25%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. In one embodiment to any part of the seventh or eighth aspect, the liquid formulation comprises 5%-80% polyol, preferably 15%-75% polyol, more preferably 25%-70% polyol, more preferably 35%-65% polyol or most preferably 40%-60% polyol wherein the polyol is selected from the group consisting of glycerol, sorbitol and propylene glycol (MPG).

In one embodiment, the formulation further comprises 0.001% to 2.0% w/w preservative. In one embodiment, the preservative is selected from the group consisting of phenoxy ethanol, 1,2-benzisothiazolin-3(2H)-one, sodium sorbate, potassium sorbate, sodium benzoate, potassium benzoate, methylisothiazolinone, chloro methylisothiazolinone, methyl parabene, ethyl parabene, propyl parabene, butyl parabene, quarterary ammonium salts (such as BAC/ADBAC; alkylbenzyl quarternary ammonium chloride, dioctyldimethylammonium chloride, didecyldimethylammonium chloride, cetrimonium chloride), essential oils and organic acids or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of phenoxy ethanol, 1,2-benzisothiazolin-3(2H)-one, sodium sorbate, potassium sorbate, sodium benzoate and potassium benzoate or any combination thereof.

In one embodiment, the mannanase variant is dosed between 0.0001% to 10% w/w of liquid formulation, such as 0.001% to 0.1% w/w polypeptide, 0.01% to 1.0% w/w polypeptide or 0.1% to 10% w/w polypeptide.

In one embodiment, the liquid formulation comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1,2-propylene glycol, 1,3-propylene glycol, sodium sulfate, dextrin, cellulose, sodium thiosulfate, kaolin and calcium carbonate.

In one embodiment, the liquid formulation may further comprise one or more additional enzyme selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, licheninases, laminarinases, and DNAses.

Cleaning Compositions and/or Detergent Compositions

The present invention also relates to compositions comprising a mannanase variant having at least two modifications, wherein (a) said first modification is a substitution or a deletion in a position selected from positions 168, 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein numbering is according to SEQ ID NO: 1, wherein the variant has mannanase activity and has at least 60%, e.g., at least 62%, at least 63%, at least 65%, at least 70%, at least 75%, at least 80%, at least 85%, at least 90%, at least 95%, at least 96%, at least 97%, at least 98%, or at least 99%, but less than 100% sequence identity to the mature polypeptide of SEQ ID NO: 1 or the polypeptide of SEQ ID NO: 2, such as cleaning compositions and/or detergent compositions.

In one embodiment, the present invention relates to cleaning compositions and/or detergent compositions comprising a mannanase variant of the invention and a suitable surfactant. In one embodiment, the detergent composition may be adapted for specific uses such as laundry, in particular household laundry, dish washing or hard surface cleaning.

Thus in one embodiment, mannanase variant, detergent composition, granule or liquid formulation may be used for laundering, washing or cleaning a textile and/or a hard surface (such as dish wash). In an embodiment, the mannase variant has an enzyme detergency benefit (i.e. the mannanase variant of the invention improves the cleaning result compared to the same composition without the enzyme present).

The detergent compositions of the invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent compositions of the invention may find use in hard surface cleaning, automatic dishwashing applications, as well as cosmetic applications such as dentures, teeth, hair and skin.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

Unless otherwise noted, all component or composition levels provided herein are made in reference to the active level of that component or composition, and are exclusive of impurities, for example, residual solvents or by-products, which may be present in commercially available sources.

The mannanase of the invention is normally incorporated in the detergent composition (pods/caps, liquid detergent or powder detergent) at a level of from 0.001% to 10% of enzyme protein by weight of the composition, such as 0.001% to 0.1%, 0.01% to 1.0% or 0.1% to 10% of enzyme protein by weight of the composition.

The mannanase of the invention is normally incorporated in the washing composition in such amounts that their concentration in the wash water is at a level of from 0.0001 to 1 ppm enzyme protein, such as 0.0001 to 0.01 ppm, such as 0.001 to 0.1 ppm or such as 0.01 to 1 ppm enzyme protein in wash water.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 10, from about 7 to about 9, or from about 7 to about 8. In some preferred embodiments, granular or liquid laundry products are formulated such that the wash water has a pH from about 5.5 to about 8. Techniques for controlling pH at recommended usage levels include the use of buffers, alkalis, acids, etc., and are well known to those skilled in the art.

Enzyme components weights are based on total protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present invention also find use in detergent additive products. A detergent additive product comprising a mannanase of the invention is ideally suited for inclusion in a wash process when, e.g., temperature is low, such as at temperatures about 40° C. or below, the pH is between 6 and 8 and the washing time short, e.g., below 30 min.

The detergent additive product may be a mannanase of the invention and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment the mannanase according to the invention is employed in a granular composition or liquid, the mannanase may be in form of an encapsulated particle. In one embodiment, the encapsulating material is selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions according to the invention typically comprise one or more detergent ingredients. The term detergent compositions include articles and cleaning and treatment compositions. The term cleaning composition includes, unless otherwise indicated, tablet, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use. The composition can also be in unit dose packages, including those known in the art and those that are water soluble, water insoluble and/or water permeable.

In embodiments in which cleaning and/or detergent components may not be compatible with the mannanase of the present invention, suitable methods may be used for keeping the cleaning and/or detergent components and the mannanase separated (i.e., not in contact with each other) until combination of the two components is appropriate. Such separation methods include any suitable method known in the art (e.g., gelcaps, encapsulation, tablets, and physical separation e.g., by use of a water dissolvable pouch having one or more compartments).

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the invention may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the invention may also be stabilized by adding reversible enzyme inhibitors, e.g., of the protein type (as described in EP 544 777) or the boronic acid type. Other enzyme stabilizers are well known in the art, such as peptide aldehydes and protein hydrolysate, e.g. the mannanases according to the invention may be stabilized using peptide aldehydes or ketones such as described in WO2005/105826 and WO2009/118375.

Protected enzymes for inclusion in a detergent composition of the invention may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

The compositions of the invention may be applied in dosing elements to be used in an auto-dosing device. The dosing elements comprising the composition of the present invention can be placed into a delivery cartridge as that described in WO 2007/052004 and WO 2007/0833141. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964, Formulation of the Mannanase in Granules Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The mannanase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the www.ip.com disclosure IPCOM000200739D.

Another example of formulation of enzymes by the use of co-granulates is disclosed in WO 2013/188331, which relates to a detergent composition comprising (a) a multi-enzyme co-granule; (b) less than 10% w/w zeolite (anhydrous basis); and (c) less than 10% w/w phosphate salt (anhydrous basis), wherein said enzyme co-granule comprises from 10 to 98% w/w moisture sink component and the composition additionally comprises from 20 to 80% w/w detergent moisture sink component.

An embodiment of the invention relates to an enzyme granule/particle comprising the mannanase of the invention. The granule is composed of a core, and optionally one or more coatings (outer layers) surrounding the core.

Typically the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (see also Michael S. Showell (editor); *Powdered detergents*; Surfactant Science Series; 1998; vol. 71; page 140-142; Marcel Dekker).

e) Prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In a particular embodiment the thickness of the coating is below 100 μm. In a more particular embodiment the thickness of the coating is below 60 μm. In an even more particular embodiment the total thickness of the coating is below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 μm, such as less than 10 μm or less than 5 μm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20° C.}$=76%), $Na_2CO_3$ ($CH_{20° C.}$=92%), $NaNO_3$ ($CH_{20° C.}$=73%), $Na_2HPO_4$ ($CH_{20° C.}$=95%), $Na_3PO_4$ ($CH_{25° C.}$=92%), $NH_4Cl$ ($CH_{20° C.}$=79.5%), $(NH_4)_2HPO_4$ ($CH_{20° C.}$=93.0%), $NH_4H_2PO_4$ ($CH_{20° C.}$=93.1%), $(NH_4)_2SO_4$($CH_{20° C.}$=81.1%), KCl ($CH_{20° C.}$=85%), $K_2HPO_4$($CH_{20° C.}$=92%), $KH_2PO_4$ ($CH_{20° C.}$=96.5%), $KNO_3$ ($CH_{20° C.}$=93.5%), $Na_2SO_4$($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{25° C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, the present invention provides a granule, which comprises:

(a) a core comprising a mannanase according to the invention, and (b) optionally a coating consisting of one or more layer(s) surrounding the core.

Other Enzymes

In one embodiment, a mannanase of the invention is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity.

The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase and/or peroxidase, a licheninase, laminarinase, a DNase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of animal, vegetable or microbial origin. Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellulomonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens.*

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases: Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993*, Biochemica et Biophysica Acta,* 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases: Suitable amylases which can be used together with mannanase of the invention may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+ I201F+ A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+ G475K;

S125A+N128C+K178L+T182G+Y305R+G475K; or

S125A+N128C+T131I+T165I+K178L+T182G+Y305R+ G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/

098531, WO2013/001078 and WO2013/001087. Commercially available amylases are Duramyl™, Termamyl™ Fungamyl™, Stainzyme™ Stainzyme PIus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases: Suitable peroxidases/oxidases include those of plant, bacterial or fungal origin. Chemically modified or protein engineered variants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Lichenases/Beta-glucanases: Suitable lichenases (licheninases) include those of bacterial or fungal origin. They may be chemically modified or protein engineered. Examples of useful beta-glucanases include those described in WO 2015/144824 (Novozymes A/S) and WO 99/06516 (Henkel KGAA).

Nucleases: Suitable nucleases include deoxyribonucleases (DNases) and ribonucleases (RNases) which are any enzyme that catalyzes the hydrolytic cleavage of phosphodiester linkages in the DNA or RNA backbone respectively, thus degrading DNA and RNA. There are two primary classifications based on the locus of activity. Exonucleases digest nucleic acids from the ends. Endonucleases act on regions in the middle of target molecules. The nuclease is preferably a DNase, which is preferable is obtainable from a microorganism, preferably a fungi or bacterium. In particular, a DNase which is obtainable from a species of *Bacillus* is preferred; in particular a DNase which is obtainable from *Bacillus cibi, Bacillus subtilis* or *Bacillus licheniformis* is preferred. Examples of such DNases are described in WO 2011/098579, WO2014/087011 and WO2017/060475. Particularly preferred is also a DNase obtainable from a species of *Aspergillus*; in particular a DNase which is obtainable from *Aspergillus oryzae*, such as a DNase described in WO 2015/155350.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Surfactants

Typically, the detergent composition comprises (by weight of the composition) one or more surfactants in the range of 0% to 50%, preferably from 2% to 40%, more preferably from 5% to 35%, more preferably from 7% to 30%, most preferably from 10% to 25%, even most preferably from 15% to 20%. In a preferred embodiment the detergent is a liquid or powder detergent comprising less than 40%, preferably less than 30%, more preferably less than 25%, even more preferably less than 20% by weight of surfactant. The composition may comprise from 1% to 15%, preferably from 2% to 12%, 3% to 10%, most preferably from 4% to 8%, even most preferably from 4% to 6% of one or more surfactants. Preferred surfactants are anionic surfactants, non-ionic surfactants, cationic surfactants, zwitterionic surfactants, amphoteric surfactants, and mixtures thereof. Preferably, the major part of the surfactant is anionic. Suitable anionic surfactants are well known in the art and may comprise fatty acid carboxylates (soap), branched-chain, linear-chain and random chain alkyl sulfates or fatty alcohol sulfates or primary alcohol sulfates or alkyl benzenesulfonates such as LAS and LAB or phenylalknesulfonates or alkenyl sulfonates or alkenyl benzenesulfonates or alkyl ethoxysulfates or fatty alcohol ether sulfates or alpha-olefin sulfonate or dodecenyl/tetradecnylsuccinic acid. The anionic surfactants may be alkoxylated. The detergent composition may also comprise from 1 wt % to 10 wt % of non-ionic surfactant, preferably from 2 wt % to 8 wt %, more preferably from 3 wt % to 7 wt %, even more preferably less than 5 wt % of non-ionic surfactant. Suitable non-ionic surfactants are well known in the art and may comprise alcohol ethoxylates, and/or alkyl ethoxylates, and/or alkylphenol ethoxylates, and/or glucamides such as fatty acid N-glucosyl N-methyl amides, and/or alkyl polyglucosides and/or mono- or diethanolamides or fatty acid amides. The detergent composition may also comprise from 0 wt % to 10 wt % of cationic surfactant, preferably from 0.1 wt % to 8 wt %, more preferably from 0.5 wt % to 7 wt %, even more preferably less than 5 wt % of cationic surfactant. Suitable cationic surfactants are well known in the art and may comprise alkyl quaternary ammonium compounds, and/or alkyl pyridinium compounds and/or alkyl quaternary phosphonium compounds and/or alkyl ternary sulphonium compounds. The composition preferably comprises surfactant in an amount to provide from 100 ppm to 5,000 ppm surfactant in the wash liquor during the laundering process. The composition upon contact with water typically forms a wash liquor comprising from 0.5 g/I to 10 g/I detergent composition. Many suitable surface active compounds are available and fully described in the literature, for example, in "Surface-Active Agents and Detergents", Volumes I and 11, by Schwartz, Perry and Berch.

Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and buffer the pH of the wash water to a level of 9.5 to 11. The buffering capacity is also termed reserve alkalinity, and should preferably be greater than 4.

The detergent compositions of the present invention may comprise one or more detergent builders or builder systems. Many suitable builder systems are described in the literature, for example in Powdered Detergents, Surfactant science series volume 71, Marcel Dekker, Inc. Builder may comprise from 0% to 60%, preferably from 5% to 45%, more preferably from 10% to 40%, most preferably from 15% to 35%, even more preferably from 20% to 30% builder by weight of the subject composition. The composition may comprise from 0% to 15%, preferably from 1% to 12%, 2% to 10%, most preferably from 3% to 8%, even most preferably from 4% to 6% of builder by weight of the subject composition.

Builders include, but are not limited to, the alkali metal, ammonium and alkanolammonium salts of polyphosphates (e.g., tripolyphosphate STPP), alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Bleaches

The detergent compositions of the present invention may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetrahydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;

(4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof; and (5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from 0.0005% to 0.2%, from 0.001% to 0.1%, or even from 0.005% to 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Adjunct Materials

Dispersants—The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives.

Preferred fluorescent whitening agents are Tinopal DMS and Tinopal CBS available from Ciba-Geigy AG, Basel, Switzerland. Tinopal DMS is the disodium salt of 4,4'-bis- (2-morpholino-4 anilino-s-triazin-6-ylamino) stilbene disulphonate. Tinopal CBS is the disodium salt of 2,2'-bis-(phenyl-styryl) disulphonate.

Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Fabric hueing agents—The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1 876 226. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

Soil release polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series, volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose deriviatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof; wherein the compact fluid laundry detergent composition comprises at least one of:

(i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In a preferred aspect of the present invention the mannanase of the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a mannanase of the invention with another stain removing enzyme, e.g., a mannanase of the invention and a protease, a mannanase of the invention and a serine protease, a mannanase of the invention and an amylase, a mannanase of the invention and a cellulase, mannanase of the invention and a lipase, a mannanase of the invention and a cutinase, a mannanase of the invention and a pectinase or a mannanase of the invention and an anti-redeposition enzyme. More particularly preferred is a mannanase variant of the invention and another enzyme having carbolytic activity, e.g., a cellulase such as an endoglucanase and especially a beta-glucanase.

More preferably, the mannanase of the invention is combined with at least two other stain removing enzymes, e.g., a mannanase of the invention, a lipase and an amylase; or a mannanase of the invention, a protease and an amylase; or a mannanase of the invention, a protease and a lipase; or a mannanase of the invention, a protease and a pectinase; or a mannanase of the invention, a protease and a cellulase, such as an endoglucanase or a beta-glucanase; or a mannanase of the invention, a protease and a hemicellulase; or a mannanase of the invention, a protease and a cutinase; or a mannanase of the invention, an amylase and a pectinase; or a mannanase of the invention, an amylase and a cutinase; or a mannanase of the invention, an amylase and a cellulase such as an endoglucanase or a beta-glucanase; or a mannanase of the invention, an amylase and a hemicellulase; or a mannanase of the invention, a lipase and a pectinase; or a mannanase of the invention, a lipase and a cutinase; or a mannanase of the invention, a lipase and a cellulase such as an endoglucanase or a beta-glucanase; or a mannanase of the invention, a lipase and a hemicellulase. Even more preferably, a mannanase of the invention may be combined with at least three other stain removing enzymes, e.g., a mannanase of the invention, a protease, a lipase and an amylase; or a mannanase of the invention, a protease, an amylase and a pectinase; or a mannanase of the invention, a protease, an amylase and a cutinase; or a mannanase of the invention, a protease, an amylase and a cellulase; or a mannanase of the invention, a protease, an amylase and a hemicellulase; or a mannanase of the invention, an amylase, a lipase and a pectinase; or a mannanase of the invention, an amylase, a lipase and a cutinase; or a mannanase of the invention, an amylase, a lipase and a cellulase; or a mannanase of the invention, an amylase, a lipase and a hemicellulase; or a mannanase of the invention, a protease, a lipase and a pectinase; or a mannanase of the invention, a protease, a lipase and a cutinase; or a mannanase of the invention, a protease, a lipase and a cellulase; or a mannanase of the invention, a protease, a lipase and a hemicellulase. A mannanase according to the present invention may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a mannanase of the invention is combined with a serine protease, e.g., an S8 family protease such as Savinase®.

In another embodiment of the present invention, a mannanase of the invention may be combined with one or more metalloproteases, such as an M4 metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one mannanase of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions include various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising a mannanase of the invention, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without the added mannanase of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of mannanase of the invention, such as a conventional amount of such component. In one aspect, the mannanase of the invention is used in detergent compositions wherein said composition is free of at least one component which is a surfactant, a builder, a chelator or chelating agent, bleach system or bleach component and/or polymer.

In an embodiment is provided a detergent composition comprising a mannanase variant as described herein and an amylase, and wherein the amylase is selected from the group consisting of;

a) an amylase having at least 60%, at least 65%, at least 70%, at least 75%, at least 80%, at least 85%, at least 90%, at least 95%, at least 98% or 100% sequence identity to SEQ ID NO 2 or SEQ ID NO 35, or an amylase having at least 60%, at least 65%, at least 70%, at least 75%, at least 80%, at least 85%, at least 90%, at least 95%, at least 98% but less than 100% sequence identity to SEQ ID NO: 5 or SEQ ID NO: 6 comprising a two amino acid deletion in the sequence region R180, S181, T182, G183, compared to SEQ ID NO: 5, wherein each position corresponds to the position in SEQ ID NO: 5;

b) an amylase having at least 60%, at least 65%, at least 70%, at least 75%, at least 80%, at least 85%, at least 90%, at least 95%, at least 98% or 100% sequence identity to SEQ ID NO: 5 or SEQ ID NO: 6, or an amylase having at least 60%, at least 65%, at least 70%, at least 75%, at least 80%, at least 85%, at least 90%, at least 95%, at least 98% but less than 100% sequence identity to SEQ ID NO: 5 or SEQ ID NO: 6 comprising one of the alterations set selected from the group consisting of:

a. R180*, S181*, S243Q, G475K;

b. R180*, T182*, S243Q, G475K;

c. R180*, T182*, G183S, S243Q, G475K; and d. R180*, S181*, Y242F, S243Q, F266Y, G475K compared to SEQ ID NO: 5, wherein each position corresponds to the position in SEQ ID NO: 6;

c) an amylase having at least 60%, at least 65%, at least 70%, at least 75%, at least 80%, at least 85%, at least 90%, at least 95%, at least 98% or 100% sequence identity to SEQ ID NO: 7, or an amylase having at least 60%, at least 65%, at least 70%, at least 75%, at least 80%, at least 85%, at least 90%, at least 95%, at least 98% but less than 100% sequence identity to SEQ ID NO 3, comprising a two amino acid deletion in the sequence region R178, G179, T180, G181 compared to SEQ ID NO: 7, wherein each position corresponds to the position in SEQ ID NO: 7;

d) an amylase having at least 60%, at least 65%, at least 70%, at least 75%, at least 80%, at least 85%, at least 90%, at least 95%, at least 98% or 100% sequence identity to SEQ ID NO: 7, or an amylase having at least 60%, at least 65%, at least 70%, at least 75%, at least 80%, at least 85%, at least 90%, at least 95%, at least 98% but less than 100% sequence identity to SEQ ID NO: 7, comprising one of the alterations set selected from the group consisting of:

i. R178*, G179*, E187P, I203Y, G476K;

ii. R178*, G179*, E187P, M199L, I203Y, G476K;

iii. R178*, G179*, E187P, I203Y R458N, T459S, D460T, G476K;

iv. N126Y, F153W, R178*, G179*, T180H, I203Y, S241Q;

v. N126Y, F153W, R178*, G179*, T180H, I203Y, S241Q, S362A, R377Y;

vi. T38N, N126Y, T129I, F153W, R178*, G179*, T180D, E187P, I203Y, G476K, G477E; and vii. N126Y, F153W, R178*, G179*, T180H, E187P, I203Y, S241Q, G476K, G477E, compared to SEQ ID NO: 7, wherein each position corresponds to the position in SEQ ID NO: 7;

e) an amylase having at least 60%, at least 65%, at least 70%, at least 75%, at least 80%, at least 85%, at least 90%, at least 95%, at least 98% or 100% sequence identity to SEQ ID NO: 8, or an amylase having at least 60%, at least 65%, at least 70%, at least 75%, at least 80%, at least 85%, at least 90%, at least 95%, at least 98% but less than 100% sequence identity to SEQ ID NO: 8, comprising a two amino acid deletion in the sequence region R181, G182, D183, G184 compared to SEQ ID NO: 8, wherein each position corresponds to the position in SEQ ID NO: 8;

f) an amylase having at least 60%, at least 65%, at least 70%, at least 75%, at least 80%, at least 85%, at least 90%, at least 95%, at least 98% or 100% sequence identity to SEQ ID NO: 8, or an amylase having at least 60%, at least 65%, at least 70%, at least 75%, at least 80%, at least 85%, at least 90%, at least 95%, at least 98% but less than 100% sequence identity to SEQ ID NO: 8 comprising an alteration at one or more, preferably at all of the position(s) selected from 3, 4, 5, 74, 118, 167, 170, 177, 195, 202, 204, 271, 320, 330, 377, 385, 445, 458, 475, 476, 314, 315 or 316, compared to SEQ ID NO: 8, wherein each position corresponds to the position in SEQ ID NO: 8;

g) an amylase having at least 60%, at least 65%, at least 70%, at least 75%, at least 80%, at least 85%, at least 90%, at least 95%, at least 98% or 100% sequence identity to SEQ ID NO: 9, or an amylase having at least 60%, at least 65%, at least 70%, at least 75%, at least 80%, at least 85%, at least 90%, at least 95%, at least 98% but less than 100% sequence identity to SEQ ID NO: 9 preferably comprising a two amino acid deletion in the sequence region R181, G182, D183, G184, compared to SEQ ID NO: 9, wherein each position corresponds to the position in SEQ ID NO 5;

h) an amylase having at least 60%, at least 65%, at least 70%, at least 75%, at least 80%, at least 85%, at least 90%, at least 95%, at least 98% or 100% sequence identity to SEQ ID NO: 9, or an amylase having at least 60%, at least 65%, at least 70%, at least 75%, at least 80%, at least 85%, at least 90%, at least 95%, at least 98% but less than 100% sequence identity to SEQ ID NO: 9 comprising one of the alterations set selected from the group consisting of
  a. D183*, G184*, N195F, Y243F;
  b. D183*, G184*, N195F, V206Y, Y243F;
  c. W140Y, D183*, G184*, N195F, V206Y, Y243F, E260G, G304R, G476K;
  d. W140Y, D183*, G184*, N195F, V206Y, Y243F, E260G, G477E;
  e. W140Y, D183*, G184*, N195F, V206Y, Y243F, W284D;
  f. W140Y, N195F, V206Y, Y243F, E260G, G477E;
  g. G109A, W140Y, N195F, V206Y, Y243F, E260G;
  h. T511, S52Q, N54K, G109A, W140Y, N195F, V206Y, Y243F, E260G, G476E;
  i. W140Y, N195F, V206Y, Y243F, E260G, W284R, G477K;
  j. W140Y, N195F, V206Y, Y243F, E260G, W284F, G477R; and
  k. H1*, G7A, G109A, W140Y, D183*, G184*, N195F, V206Y, Y243F, E260G, N280S, G304R, E391A, G476K, compared to SEQ ID NO: 9, wherein each position corresponds to the position in SEQ ID NO: 9;

i) an amylase having at least 60%, at least 65%, at least 70%, at least 75%, at least 80%, at least 85%, at least 90%, at least 95%, at least 98% or 100% sequence identity to SEQ ID NO: 10, or an amylase having at least 60%, at least 65%, at least 70%, at least 75%, at least 80%, at least 85%, at least 90%, at least 95%, at least 98% but less than 100% sequence identity to SEQ ID NO: 10, comprising a two amino acid deletion in the sequence region R181, G182, D183, G184, compared to SEQ ID NO: 10, wherein each position corresponds to the position in SEQ ID NO: 10;

j) an amylase having at least 60%, at least 65%, at least 70%, at least 75%, at least 80%, at least 85%, at least 90%, at least 95%, at least 98% or 100% sequence identity to SEQ ID NO: 10, or an amylase having at least 60%, at least 65%, at least 70%, at least 75%, at least 80%, at least 85%, at least 90%, at least 95%, at least 98% but less than 100% sequence identity to SEQ ID NO: 10, comprising one of the alterations set selected from the group consisting of
  i. R118K, D183*, G184*, N195F, R320K, R458K;
  ii. M91, D183*, G184*, R118K, N195F, M202L, R320K, M323T, R458K;
  iii. M9L, G149A, R118K, G182T, D183*, G184*, G186A, N195F, M202L, T257I, Y295F, N299Y, M323T, A339S, E345R, R458K;
  iv. M9L, G149A, R118K, G182T, D183*, G184*, G186A, N195F, T246V, T257I, Y295F, N299Y, M323T, A339S, E345R, R458K; and
  v. M9L, G149A, G182T, D183*, G184*, G186A, M202L, T257I, Y295F, N299Y, M323T, A339S, E345R, N471E, compared to SEQ ID NO: 10, wherein each position corresponds to the position in SEQ ID NO: 10;

k) an amylase having at least 60%, at least 65%, at least 70%, at least 75%, at least 80%, at least 85%, at least 90%, at least 95%, at least 98% or 100% sequence identity to SEQ ID NO: 11, or an amylase having at least 60%, at least 65%, at least 70%, at least 75%, at least 80%, at least 85%, at least 90%, at least 95%, at least 98% but less than 100% sequence identity to SEQ ID NO: 11, comprising a two amino acid deletion in the sequence region R181, G182, D183, G184, compared to SEQ ID NO: 11, wherein each position corresponds to the position in SEQ ID NO: 11;

l) an amylase having at least 60%, at least 65%, at least 70%, at least 75%, at least 80%, at least 85%, at least 90%, at least 95%, at least 98% or 100% sequence identity to SEQ ID NO: 11, or an amylase having at least 60%, at least 65%, at least 70%, at least 75%, at least 80%, at least 85%, at least 90%, at least 95%, at least 98% but less than 100% sequence identity to SEQ ID NO: 11, comprising one of the alterations set selected from the group consisting of
  a. D183*, G184*, N195F, V206Y, R320K, R458K;
  b. D183*, G184*, N195F, M202L, V206L, R320K, R458K;
  c. G149A, G182T, D183*, G184*, N195F, M202L, V206L, T257I, Y295F, Q299Y, A339S, Q345R, R458K;
  d. G149A, G182T, D183*, G184*, N195F, V206L, M246V, T257I, Y295F, Q299Y, A339S, Q345R, R458K;
  e. G149A, G182T, D183*, G184*, M202L, V206L, T257I, Y295F, Q299Y, A339S, Q345R, H471E; and
  f. H1A, N54S, V56T, K72R, G109A, F113Q, R116Q, W167F, Q172G, A174S, G182*, D183*, G184T, N195F, V206L, K391A, F473R, G476K, compared to SEQ ID NO: 11, wherein each position corresponds to the position in SEQ ID NO: 11;

m) an amylase having at least 60%, at least 65%, at least 70%, at least 75%, at least 80%, at least 85%, at least 90%, at least 95%, at least 98% or 100% sequence identity to SEQ ID NO: 12, or an amylase having at least 60%, at least 65%, at least 70%, at least 75%, at least 80%, at least 85%, at least 90%, at least 95%, at least 98% but less than 100% sequence identity to SEQ ID NO: 12, comprising a two amino acid deletion in the sequence region R181, G182, H183, G184, compared to SEQ ID NO 8, wherein each position corresponds to the position in SEQ ID NO: 12;

n) an amylase having at least 60%, at least 65%, at least 70%, at least 75%, at least 80%, at least 85%, at least 90%, at least 95%, at least 98% or 100% sequence identity to SEQ ID NO: 12, or an amylase having at least 60%, at least 65%, at least 70%, at least 75%, at least 80%, at least 85%, at least 90%, at least 95%, at least 98% but less than 100% sequence identity to SEQ ID NO: 12, comprising one of the alterations set selected from the group consisting of
  a. H183*, G184*, 1405L, A421H, A422P, A428T;
  b. R118K, H183*, G184*, N195F, R320K, R458K;
  c. M91, H183*, G184*, R118K, N195F, M202L, R320K, S323T, R458K;
  d. M9L, G149A, R118K, G182T, H183*, G184*, N195F, M202L, T257I, Y295F, N299Y, A339S, E345R, R458K;

e. M9L, G149A, R118K, G182T, H183*, G184*, N195F, T246V, T257I, Y295F, N299Y, A339S, E345R, R458K; and f. M9L, G149A, G182T, H183*, G184*, M202L, T257I, Y295F, N299Y, S323T, A339S, E345R, compared to SEQ ID NO: 12, wherein each position corresponds to the position in SEQ ID NO: 12;

o) an amylase having at least 60%, at least 65%, at least 70%, at least 75%, at least 80%, at least 85%, at least 90%, at least 95%, at least 98% or 100% sequence identity to SEQ ID NO: 13, or an amylase having at least 60%, at least 65%, at least 70%, at least 75%, at least 80%, at least 85%, at least 90%, at least 95%, at least 98% but less than 100% sequence identity to SEQ ID NO: 13, comprising a two amino acid deletion in the sequence region R181, G182, G182, D183, compared to SEQ ID NO: 13, wherein each position corresponds to the position in SEQ ID NO: 13;

p) an amylase having at least 60%, at least 65%, at least 70%, at least 75%, at least 80%, at least 85%, at least 90%, at least 95%, at least 98% or 100% sequence identity to SEQ ID NO: 13, or an amylase having at least 60%, at least 65%, at least 70%, at least 75%, at least 80%, at least 85%, at least 90%, at least 95%, at least 98% but less than 100% sequence identity to SEQ ID NO: 13, comprising one of the alterations set selected from the group consisting of a. H1*, D183*, G184*, N195F, V206Y;

b. H1*, D183*, G184*, N195F, M202L, V206L, R320K, R458K;

c. G149A, G182T, D183*, G184*, N195F, M202L, V206L, T257I, Y295F, Q299Y, A339S, Q345R, R458K;

d. G149A, G182T, D183*, G184*, N195F, V206L, M246V, T257I, Y295F, Q299Y, A339S, Q345R, R458K;

e. G149A, G182T, D183*, G184*, M202L, V206L, T257I, Y295F, Q299Y, A339S, Q345R, f. H1*, N54S, V56T, G109A, Q169E, Q172K, A174*, G182*, D183*, N195F, V206L, K391A, G476K;

g. G182*, D183*, N195F, W140Y, N260G, S304R, R320A, G476K, V410I, V429I, F451W, C474V;

h. H1*, N54S, V56T, K72R, G109A, F113Q, R116Q, W167F, Q172G, A174S, G182*, D183*, G184T, N195F, V206L, K391A, P473R, G476K;

i. H1*, N54S, V56T, G109A, Q169E, Q172K, A174*, G182*, D183*, N195F, V206L, K391A, G476K;

j. H1*, N54S, V56T, G109A, R116H, A174S, G182*, D183*, N195F, V206L, K391A, G476K;

k. H1*, N54S, V56T, K72R, G109A, F113Q, R116Q, W167F, Q172G, A174S, G182*, D183*, G184T, N195F, V206L, K391A, P473R, G476K;

l. H1*, N54S, V56T, G109A, F113Q, R116Q, Q172N, A174S, G182*, D183*, N195F, V206L, A265G, K391A, P473R, G476K;

m. H1*, N54S, V56T, K72R, G109A, F113Q, W167F, Q172R, A174S, G182*, D183*, N195F, V206L, K391A, G476K;

n. H1*, N54S, V56T, K72R, G109A, R116H, T134E, W167F, Q172G, L173V, A174S, G182*, D183*, N195F, V206L, G255A, K391A, G476K;

o. H1*, N54S, V56T, K72R, G109A, R116H, T134E, W167F, Q172G, L173V, A174S, G182*, D183*, N195F, V206L, G255A, K391A, Q395P, T444Q, P473R, G476K;

p. H1*, N54S, V56T, G109A, T134E, A174S, G182*, D183*, N195F, V206L, K391A, G476K;

q. H1*, N54S, V56T, K72R, G109A, A174S, G182*, D183*, N195F, V206L, G255A, K391A, G476K;

r. H1*, N54S, V56T, G109A, W167F, Q172E, L173P, A174K, G182*, D183*, N195F, V206L, K391A, G476K;

s. H1*, N54S, V56T, G109A, R116Q, V120L, Q172G, L173V, A174S, G182*, D183*, G184T, N195F, V206L, A422P; and t. H1*, N54S, V56T, G109A, F113Q, R116Q, W167F, Q172G, 1173V, A174S, G182*, D183*, G184T, N195F, V206L, A422P compared to SEQ ID NO: 13, wherein each position corresponds to the position in SEQ ID NO: 13.

In an embodiment is provided a detergent composition comprising a mannanase variant as described herein and a protease, and wherein the protease is selected from the group consisting of;

a) a protease having at least 60%, at least 65%, at least 70%, at least 75%, at least 80%, at least 85%, at least 90%, at least 95%, at least 98%, at least 99% or 100% sequence identity to SEQ ID NO: 14, preferably obtained from *Bacillus lentus;* b) a protease having at least 60%, at least 65%, at least 70%, at least 75%, at least 80%, at least 85%, at least 90%, at least 95%, at least 98%, at least 99% or 100% sequence identity to SEQ ID NO: 15; preferably obtained from *Bacillus amyloliquefaciens;* c) a protease having at least 60%, at least 65%, at least 70%, at least 75%, at least 80%, at least 85%, at least 90%, at least 95%, at least 98%, at least 99% or 100% sequence identity to SEQ ID NO: 16, preferably obtained from *Bacillus* sp.;

d) a protease having at least 60%, at least 65%, at least 70%, at least 75%, at least 80%, at least 85%, at least 90%, at least 95%, at least 98%, at least 99% or 100% sequence identity to SEQ ID NO: 17, preferably obtained from *Bacillus gibsonii;* e) a protease having at least 60%, at least 65%, at least 70%, at least 75%, at least 80%, at least 85%, at least 90%, at least 95%, at least 98%, at least 99% or 100% sequence identity to SEQ ID NO: 18, preferably obtained from *Bacillus lentus;* f) a protease having at least 60%, at least 65%, at least 70%, at least 75%, at least 80%, at least 85%, at least 90%, at least 95%, at least 98%, at least 99% or 100% sequence identity to SEQ ID NO: 19, preferably obtained from *Bacillus licheniformis;* g) or a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the substitution T22R or T22A compared to SEQ ID NO: 14, wherein the position corresponds to the position of SEQ ID NO: 14;

h) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S3T, V41, A188P and V199I, compared to SEQ ID NO: 14, wherein the positions correspond to the positions of SEQ ID NO: 14;

i) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of N114L, T207A, A226V, and E265F, compared to SEQ ID NO: 14, wherein the positions correspond to the positions of SEQ ID NO: 14;

j) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all substitutions selected from the group consisting of: S97D, S101A, V102I and G157S compared to SEQ ID NO: 14, wherein the positions correspond to the positions of SEQ ID NO: 14;

k) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S85N, G116V, S126L, P127Q and S128A compared to SEQ ID NO: 14, wherein the positions correspond to the positions of SEQ ID NO: 14;

l) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: Y161A, R164S and A188P, compared to SEQ ID NO: 14, wherein the positions correspond to the positions of SEQ ID NO: 14;

m) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S3T, R19L, and A188P, wherein the positions correspond to the positions of SEQ ID NO: 14;

n) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S9R, R19L, and N60D, wherein the positions correspond to the positions of SEQ ID NO: 14;

o) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid Arginine (R), at a position corresponding to a position selected from the group consisting of: 9, 42 and 239 of SEQ ID NO: 14;

p) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid Glutamic acid (E) or Aspartic acid (D), at a position corresponding to a position selected from the group consisting of: 9, 42, 60, 61, 74, 157, 176, 179, 182, 212, 250, 253 and 256 of SEQ ID NO: 14;

q) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises an insertion of the amino acid Aspartic acid (D) or Glutamic acid (E) at a position corresponding to position 97 of SEQ ID NO: 14;

r) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid selected from the group consisting of: Glutamic acid (E), Aspartic acid (D), Glycine (G), Arginine (R) and Methionine (M) at a position corresponding to position 99 of SEQ ID NO:14;

s) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid selected from the group consisting of: Glutamic acid (E), Aspartic acid (D) and Glutamine (Q), at a position corresponding to position 211 of SEQ ID NO: 14;

t) a protease having at least 60%, at least 65%, at least 70%, at least 75%, at least 80%, at least 85%, at least 90%, at least 95%, at least 98% but less than 100% sequence identity to SEQ ID NO: 15, wherein the protease comprises the amino acid selected from the group consisting of: Glutamic acid (E), Aspartic acid (D) and Glutamine (Q), at a position corresponding to position 217 of SEQ ID NO: 15;

u) a protease having at least 60%, at least 65%, at least 70%, at least 75%, at least 80%, at least 85%, at least 90%, at least 95%, at least 98% but less than 100% sequence identity to SEQ ID NO: 15, wherein the protease comprises one or more of the substitutions selected from the group consisting of: S24G/R, S53G, S78N, S101N, G128A/S and Y217Q/L, compared to SEQ ID NO: 15, wherein the positions correspond to the positions of SEQ ID NO: 15.

In an embodiment is provided a detergent composition comprising a mannanase variant as described herein and a cellulase, and wherein the cellulase is selected from the group consisting of;

a) a cellulase having at least 60%, at least 65%, at least 70%, at least 75%, at least 80%, at least 85%, at least 90%, at least 95%, at least 98% or 100% sequence identity to SEQ ID NO: 20;

b) a cellulase having at least 60%, at least 65%, at least 70%, at least 75%, at least 80%, at least 85%, at least 90%, at least 95%, at least 98% or 100% sequence identity to SEQ ID NO: 21;

c) a cellulase having at least 60%, at least 65%, at least 70%, at least 75%, at least 80%, at least 85%, at least 90%, at least 95%, at least 98% or 100% sequence identity to SEQ ID NO: 22;

d) a cellulase having at least 60%, at least 65%, at least 70%, at least 75%, at least 80%, at least 85%, at least 90%, at least 95%, at least 98% or 100% sequence identity to SEQ ID NO: 23, e) a cellulase having at least 60%, at least 65%, at least 70%, at least 75%, at least 80%, at least 85%, at least 90%, at least 95%, at least 98% or 100% sequence identity to SEQ ID NO: 24, and f) a cellulase having at least 60%, at least 65%, at least 70%, at least 75%, at least 80%, at least 85%, at least 90%, at least 95%, at least 98% or 100% sequence identity to SEQ ID NO: 25.

In an embodiment is provided a detergent composition comprising a mannanase variant as described herein and a lipase, and wherein the lipase is a lipase having at least 60%, at least 65%, at least 70%, at least 75%, at least 80%, at least 85%, at least 90%, at least 95%, at least 98% or 100% sequence identity to SEQ ID NO: 26, or a lipase having at least 60%, at least 65%, at least 70%, at least 75%, at least 80%, at least 85%, at least 90%, at least 95%, at least 98% but less than 100% sequence identity to SEQ ID NO: 26 comprising one or more of the substitutions selected from the group consisting of D27R, G38A, G91A/Q, D96E, G163K, T231R, N233R, D254S and P256T, compared to SEQ ID NO: 26, wherein each position corresponds to the position in SEQ ID NO: 26.

In an embodiment is provided a detergent composition comprising a mannanase variant as described herein and a beta-glucanase, and wherein the beta-glucanase is selected from the group consisting of;

a) a beta-glucanase, wherein the beta-glucanase preferably comprises a beta-glucanase having licheninase activity;
  i. a beta-glucanase having at least 60%, at least 65%, at least 70%, at least 75%, at least 80%, at least 85%, at least 90%, at least 95%, at least 98% or 100% sequence identity to SEQ ID NO: 27;
  ii. a beta-glucanase having at least 60%, at least 65%, at least 70%, at least 75%, at least 80%, at least 85%, at least 90%, at least 95%, at least 98% or 100% sequence identity to SEQ ID NO: 28; and
  iii. a beta-glucanase having at least 60%, at least 65%, at least 70%, at least 75%, at least 80%, at least 85%, at least 90%, at least 95%, at least 98% or 100% sequence identity to SEQ ID NO: 29;
  iv. a beta-glucanase having at least 60%, at least 65%, at least 70%, at least 75%, at least 80%, at least 85%, at least 90%, at least 95%, at least 98% or 100% sequence identity to SEQ ID NO: 30; and
  v. a beta-glucanase having at least 60%, at least 65%, at least 70%, at least 75%, at least 80%, at least 85%, at least 90%, at least 95%, at least 98% or 100% sequence identity to SEQ ID NO: 31;
b) a beta-glucanase, wherein the beta-glucanase preferably comprises a beta-glucanase having laminarinase activity;
  i. a beta-glucanase having at least 60%, at least 65%, at least 70%, at least 75%, at least 80%, at least 85%, at least 90%, at least 95%, at least 98% or 100% sequence identity to SEQ ID NO: 32;
  ii. a beta-glucanase having at least 60%, at least 65%, at least 70%, at least 75%, at least 80%, at least 85%, at least 90%, at least 95%, at least 98% or 100% sequence identity to SEQ ID NO: 33;
  iii. a beta-glucanase having at least 60%, at least 65%, at least 70%, at least 75%, at least 80%, at least 85%, at least 90%, at least 95%, at least 98% or 100% sequence identity to SEQ ID NO: 34;
  iv. a beta-glucanase having at least 60%, at least 65%, at least 70%, at least 75%, at least 80%, at least 85%, at least 90%, at least 95%, at least 98% or 100% sequence identity to SEQ ID NO: 35;
  v. a beta-glucanase having at least 60%, at least 65%, at least 70%, at least 75%, at least 80%, at least 85%, at least 90%, at least 95%, at least 98% or 100% sequence identity to SEQ ID NO: 36; and
  vi. a beta-glucanase having at least 60%, at least 65%, at least 70%, at least 75%, at least 80%, at least 85%, at least 90%, at least 95%, at least 98% or 100% sequence identity to SEQ ID NO: 37.

In an embodiment is provided a detergent composition comprising a mannanase variant as described herein and an additional mannanase, and wherein the additional mannanase is selected from the group consisting of;

a) a mannanase having at least 60%, at least 65%, at least 70%, at least 75%, at least 80%, at least 85%, at least 90%, at least 95%, at least 98% or 100% sequence identity to SEQ ID NO: 38, or a mannanase having at least 60%, at least 65%, at least 70%, at least 75%, at least 80%, at least 85%, at least 90%, at least 95%, at least 98% but less than 100% sequence identity to SEQ ID NO: 38 comprising one or more of the substitutions selected from the group consisting of A30T, Y93Q, S95D, D118K, A136P, D139R, N200T, S202R, R210G, W260F, N283H, L288I, L294P, and S295V, compared to SEQ ID NO: 38, wherein each position corresponds to the position in SEQ ID NO: 38;
b) a mannanase having at least 60%, at least 65%, at least 70%, at least 75%, at least 80%, at least 85%, at least 90%, at least 95%, at least 98% or 100% sequence identity to SEQ ID NO: 39; and
c) a mannanase having at least 60%, at least 65%, at least 70%, at least 75%, at least 80%, at least 85%, at least 90%, at least 95%, at least 98% or 100% sequence identity to SEQ ID NO: 40.

In an embodiment is provided a detergent composition comprising a mannanase variant as described herein and a pectinase, and wherein the pectinase has at least 60%, at least 65%, at least 70%, at least 75%, at least 80%, at least 85%, at least 90%, at least 95%, at least 98% or 100% sequence identity to SEQ ID NO: 41.

In an embodiment is provided a detergent composition comprising a mannanase variant as described herein and a DNase, and wherein the DNase is selected from the group consisting of;

a) a DNAse having at least 60%, at least 65%, at least 70%, at least 75%, at least 80%, at least 85%, at least 90%, at least 95%, at least 98% or 100% sequence identity to SEQ ID NO: 42; and
b) a DNase having at least 60%, at least 65%, at least 70%, at least 75%, at least 80%, at least 85%, at least 90%, at least 95%, at least 98% or 100% sequence identity to SEQ ID NO: 43.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a mannanase of the invention.

A preferred embodiment concerns a method of cleaning, said method comprising the steps of: contacting an object with a cleaning composition comprising a mannanase of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a mannanase of the invention under conditions suitable for cleaning said object.

Low Temperature Uses

One embodiment of the invention concerns a method of doing laundry, dish wash or industrial cleaning comprising contacting a surface to be cleaned with a mannanase of the invention, and wherein said laundry, dish wash, industrial or institutional cleaning is performed at a temperature of about 40° C. or below. One embodiment of the invention relates to the use of a mannanase in laundry, dish wash or a cleaning process wherein the temperature in laundry, dish wash, industrial cleaning is about 40° C. or below In another embodiment, the invention concerns the use of a mannanase according to the invention in a protein removing process, wherein the temperature in the protein removing process is about 400C or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

Uses

The mannanases of the invention may be used in applications where mannan needs to be degraded. Examples of where mannanases could be used are in the production of bioethanol from softwood and palm kernel press cake, for the improvement of animal feed and in the hydrolysis of coffee. Furthermore, guar gum is used in many food products and in the oil and gas industry, so the mannanases of the invention could be used in detergents to remove mannan containing stains, for hydraulic fracturing to create subterranean fractures that extend from the borehole into rock formation in order to increase the rate at which fluids can be produced by the formation or for cleaning borehole filtercake. The mannan may thus be used in fracturing of a subterranean formation perpetrated by a well bore or the mannan may be used as a component in borehole filtercake.

In one aspect, the polypeptide of aspect one or two, detergent composition of aspect three or four, granule of aspect five or six or liquid formulation of aspect seven or eight may be used for degrading mannan, such as linear mannan, galactomannan, glucomannan and galactoglucomannan. In one aspect, the polypeptide of aspect one or two, detergent composition of aspect three or four, granule of aspect five or six or liquid formulation of aspect seven or eight may be used in a process for degrading mannan, such as linear mannan, galactomannan, glucomannan and galactoglucomannan.

In one aspect, the polypeptide of aspect one or two, detergent composition of aspect three or four, granule of aspect five or six or liquid formulation of aspect seven or eight may be used for controlling the viscosity of drilling fluids. In one aspect, the polypeptide of aspect one or two, detergent composition of aspect three or four, granule of aspect five or six or liquid formulation of aspect seven or eight may be used in fracturing of a subterranean formation perpetrated by a well bore.

The mannanases of the invention may be used for preventing, reducing or removing malodor from an item. Thus in one embodiment, the polypeptide of aspect one or two, detergent composition of aspect three or four, granule of aspect five or six or liquid formulation of aspect seven or eight may be used for preventing, reducing or removing malodor from an item.

Use of Mannanases of the Invention in Preventing, Reducing or Removing a Biofilm Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms or biofilm.

The present invention concerns the use of the polypeptide of aspect one or two, detergent composition of aspect three or four, granule of aspect five or six or liquid formulation of aspect seven or eight for preventing, reducing or removing a biofilm from an item, wherein the polypeptide is obtained from a fungal source and wherein the item is a textile. In one embodiment, the polypeptide of aspect one or two, detergent composition of aspect three or four, granule of aspect five or six or liquid formulation of aspect seven or eight is used for preventing, reducing or removing the stickiness of an item.

Use of Mannanases of the Invention in Food Processing and Animal Feed

Several anti-nutritional factors can limit the use of specific plant material in the preparation of animal feed and food for humans. For example, plant material containing oligomannans such as mannan, galactomannan, glucomannan and galactoglucomannan can reduce the digestibility and absorption of nutritional compounds such as minerals, vitamins, sugars and fats by the animals. The negative effects are in particular due to the high viscosity of the mannan-containing polymers and to the ability of the mannan-containing polymers to adsorb nutritional compounds. These effects are reduced using mannan-containing polymers degrading enzymes, namely endo-beta-mannanase enzymes such as the mannanases described herein, which permit a higher proportion of mannan-containing polymers containing cheap plant material to be included in the feed resulting in a reduction of feed costs. Additionally, through the activity of the mannanases of the invention, mannan-containing polymers are broken down to simpler sugars, which can be more readily assimilated to provide additional energy. Accordingly, the invention further relates to using the mannanases of the invention for processing and/or manufacturing of food or animal feed.

Accordingly, the present invention relates to an animal feed composition and/or animal feed additive composition and/or pet food comprising a mannanase of the invention.

The present invention further relates to a method for preparing such animal feed composition and/or animal feed additive composition and/or pet food comprising mixing the mannanase of the invention with one or more animal feed ingredients and/or animal feed additive ingredients and/or pet food ingredients.

Furthermore, the present invention relates to the use of the mannanase of the invention in the preparation of an animal feed composition and/or animal feed additive composition and/or pet food.

Use of Mannanases of the Invention for Fermented Beverages

In one aspect, the invention relates to a method of preparing a fermented beverage, such as beer or wine, comprising mixing the polypeptide of aspect one or two, granule of aspect five or six or liquid formulation of aspect seven or eight with malt and/or adjunct.

Another aspect concerns a method of providing a fermented beverage comprising the step of contacting a mash and/or a wort with the polypeptide of aspect one or two, the granule of aspect five or six or the liquid formulation of aspect seven or eight.

In the context of the present invention, the term "fermented beverage" is meant to comprise any beverage such as wine or beer produced by a method comprising a fermentation process, such as a microbial, bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like may be used as a source of starch As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

Use of Mannanases of the Invention for Treating Coffee Extracts

The mannanase of the invention may also be used for hydrolyzing galactomannans present in liquid coffee extracts. In certain preferred embodiments, the mannanase of the invention is used to inhibit gel formation during freeze drying of liquid coffee extracts. The decreased viscosity of the extract reduces the energy consumption during drying. In certain other preferred embodiments, the mannanase of the invention is applied in an immobilized form in order to reduce enzyme consumption and avoid contamination of the coffee extract. This use is further disclosed in EP 676 145.

In general terms the coffee extract is incubated in the presence of an isolated mannanase of the invention or fragment or variant thereof under conditions suitable for hydrolyzing galactomannans present in liquid coffee extract.

Thus in one embodiment, then invention relates to a process for producing a coffee extract, comprising the steps:

(a) providing roast and ground coffee beans;
(b) adding to said coffee beans water and the polypeptide of aspect one or two, granule of aspect five or six or liquid formulation of aspect seven or eight;
(c) incubating to make an aqueous coffee extract; and
(d) separating the coffee extract from the extracted coffee beans.

Use of Mannanase of the Invention in Bakery Food Products

In another aspect, the invention relates to a method of preparing baked products comprising adding the polypeptide of aspect one or two, granule of aspect five or six or liquid formulation of aspect seven or eight to a dough, followed by baking the dough.

Examples of baked products are well known to those skilled in the art and include breads, rolls, puff pastries, sweet fermented doughs, buns, cakes, crackers, cookies, biscuits, waffles, wafers, tortillas, breakfast cereals, extruded products, and the like.

The mannanase of the invention may be added to dough as part of a bread improver composition. Bread improvers are compositions containing a variety of ingredients, which improve dough properties and the quality of bakery products, e.g. bread and cakes. Bread improvers are often added in industrial bakery processes because of their beneficial effects e.g. the dough stability and the bread texture and volume. Bread improvers usually contain fats and oils as well as additives like emulsifiers, enzymes, antioxidants, oxidants, stabilizers and reducing agents. In addition to the mannanase of the invention, other enzymes which may also be present in the bread improver including amylases, hemicellulases, amylolytic complexes, lipases, proteases, xylanases, pectinases, pullulanases, non-starch polysaccharide degrading enzymes and redox enzymes like glucose oxidase, lipoxygenase or ascorbic acid oxidase.

In one aspect, the mannanase of the invention may be added to dough as part of a bread improver composition which also comprises a glucomannan and/or galactomannan source such as konjac gum, guar gum, locust bean gum (*Ceratonia siliqua*), copra meal, ivory nut mannan (*Phyteleohas macrocarpa*), seaweed mannan extract, coconut meal, and the cell wall of brewers yeast (may be dried, or used in the form of brewers yeast extract).

A further aspect of the invention relates to the use of the mannanase of the invention in dough to improve dough tolerance, flexibility and stickiness. Preferably the dough to which the mannanase of the invention may be added is not a pure wheat flour dough, but comprises bran or oat, rice, millet, maize, or legume flour in addition to or instead of pure wheat flour.

A yet further aspect of the invention relates to the use of any of the mannanase of the invention in dough to improve the crumb structure and retard staling in the final baked product, such as bread.

Use of Mannanase of the Invention for Use in Dairy Food Products

In one aspect of the current invention, the mannanase of the invention may be added to milk or any other dairy product to which has also been added a glucomannan and/or galactomannan. Typical glucomannan and/or galactomannan sources are listed above in the bakery aspects, and include guar or konjac gum. The combination of the mannanase of the invention with a glucomannan and/or galactomannan releases mannanase hydrolysates (mannooligosaccharides) which act as soluble prebiotics by promoting the selective growth and proliferation of probiotic bacteria (especially Bifidobacteria and *Lactobacillus* lactic acid bacteria) commonly associated with good health when found at favourable population densities in the large intestine or colon.

In one aspect, the invention relates to a method of preparing milk or dairy products comprising adding to the milk or dairy product (a) glucomannan, galactomannan and/or galactoglucomannan and (b) the polypeptide of aspect one or two, granule of aspect five or six or liquid formulation of aspect seven or eight.

In one aspect of the invention the mannanase of the invention is used in combination with any glucomannan or galactomannan prior to or following addition to a dairy based foodstuff to produce a dairy based foodstuff comprising prebiotic mannan hydrolysates. In a further aspect of the invention the thus produced mannooligosacharide-containing dairy product is capable of increasing the population of beneficial human intestinal microflora, and in a yet further aspect of the current invention the dairy based foodstuff may comprise the mannanase of the invention together with any source of glucomannan and/or galactomannan and/or galactoglucomannan, and a dose sufficient for inoculation of at least one strain of bacteria (such as Bifidobacteria or *Lactobacillus*) known to be of benefit in the human large intestine. Preferably said dairy-based foodstuff is a yoghurt or milk drink.

Use of Mannanase of the Invention for Paper Pulp Bleaching

The mannanase of the invention may further be used in the enzyme aided bleaching of paper pulps such as chemical pulps, semi-chemical pulps, kraft pulps, mechanical pulps or pulps prepared by the sulfite method. Thus, the invention relates to a method of bleaching paper pulps comprising incubating the paper pulp with the polypeptide of aspect one or two, detergent composition of aspect three or four, granule of aspect five or six or liquid formulation of aspect seven or eight.

In some embodiments, the pulps are chlorine free pulps bleached with oxygen, ozone, peroxide or peroxyacids. In some embodiments, the mannanase of the invention is used in enzyme aided bleaching of pulps produced by modified or continuous pulping methods that exhibit low lignin contents. In some other embodiments, the mannanase of the invention is applied alone or preferably in combination with xylanase and/or endoglucanase and/or alpha-galactosidase and/or cellobiohydrolase enzymes.

The invention described above is further defined in the following paragraphs:

Paragraph 1. A variant of a parent mannanase, wherein said variant comprises at least two modifications, wherein (a) said first modification is a substitution or a deletion in a position selected from positions 168, 168, 7, 13, 15, 20, 26, 36, 46, 64, 69, 70, 82, 101, 103, 109, 120, 141, 155, 162, 163, 166, 167, 168, 172, 176, 178, 182, 190, 197, 214, 215, 219, 239, 248, 253, 258, 271, 276, 280, 283, 286, 299, 366, 378, 385, 408, 410, 413, 473, 486, 491 and (b) said at least second modification is in any other position of said variant, wherein the variant has mannanase activity and wherein the variant has at least 85%, e.g., at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, but less than 100% sequence identity, or has from 85%-96%, e.g., 86-96%, 87-96%, 88-96%, 89-96%, 90-96%, 91-96%, 92-96%, 93-96%, 94-96% such as 95-96%, or has from 85%-95%, e.g., 86-95%, 87-95%, 88-95%, 89-95%, 90-95%, 91-95%, 92-95%, 93-95%, such as 94-95%, or has from 85%-94%, e.g., 86-94%, 87-94%, 88-94%, 89-94%, 90-94%, 91-94%, 92-94%, such as 93-94% sequence identity or has from 85%-93%, e.g., 86-93%, 87-93%, 88-93%, 89-93%, 90-93%, 91-93%, such as 92-93%, or has from 85%-92%, e.g., 86-92%, 87-92%, 88-92%, 89-92%, 90-92%, such as 91-92%, or has from 85%-91%, e.g., 86-91%, 87-91%, 88-91%, 89-91%, such as 90-91%, or has from 85%-90%, e.g., 86-90%, 87-90%, 88-90%, such as 89-90% sequence identity to the polypeptide of SEQ ID NO: 1, SEQ ID NO: 2, or a fragment thereof having mannanase activity.

Paragraph 2. The variant of paragraph 1, wherein the variant has mannanase activity and wherein the variant has at least 91%, e.g., at least 92%, at least 93%, at least 94%, at least 95%, at least 96%, at least 97%, at least 98%, or at least 99% sequence identity, but less than 100% sequence identity, or has from 91-95%, e.g., 92-95%, 93-95%, such as 94-95%, or has from 91-94%, 92-94%, such as 93-94% sequence identity to the polypeptide of SEQ ID NO: 3, SEQ ID NO: 4 or a fragment thereof having mannanase activity.

Paragraph 3. The variant of any one of the preceding paragraphs, wherein the at least second modification is a substitution or deletion and is in at least one or more positions corresponding to positions: 1, 2, 3, 4, 5, 6, 8, 9, 10, 11, 12, 14, 17, 18, 19, 21, 22, 23, 25, 30, 35, 37, 38, 42, 45, 48, 49, 53, 57, 61, 63, 65, 68, 72, 74, 76, 78, 83, 86, 89, 94, 96, 97, 100, 105, 110, 111, 112, 115, 117, 118, 121, 122, 123, 126, 129, 130, 134, 137, 139, 142, 143, 148, 160, 161, 164, 165, 169, 170, 171, 174, 179, 181, 183, 184, 185, 188, 189, 192, 193, 195, 198, 210, 213, 217, 218, 228, 235, 242, 249, 252, 254, 259, 260, 267, 270, 272, 296, 301, 304, 312, 315, 321, 322, 323, 324, 342, 344, 347, 351, 352, 354, 355, 358, 363, 368, 377, 379, 380, 391, 398, 403, 414, 417, 419, 422, 423, 437, 438, 440, 442, 443, 452, 454, 462, 463, 466, 467, 470, 472, 477, 479, 480, 482, 483, 484, 487, 488, 489, 490 of the polypeptide of SEQ ID NO: 1.

Paragraph 4. The variant of any one of the preceding paragraphs, which has an improved property relative to the parent.

Paragraph 5. The variant of any one of the preceding paragraphs, wherein the said variant has an Improvement Factor of ≥1.0 relative to the parent for a measure of stability.

Paragraph 6. The variant according to any one of the preceding paragraphs, wherein said variant has improved stability is in-detergent stability or thermostability.

Paragraph 7. The variant according to any one of the preceding paragraphs, wherein said variant has an Improvement Factor ≥1.0 for a measure of stability at pH 8-8.5.

Paragraph 8. The variant of any one of the preceding paragraphs, where the first modification comprises a substitution or a deletion selected from the group consisting of: Q168D, Q168F, Q168M, Q168P, F7*, F7A, F7D, F7G, F7I, F7P, T131, T13M, T13N, T13W, T13Y, T13E, S15K, S15C, S15D, S15M, S15Q, S15T, A20S, A20P, A20T, A20G, A20V, K26D, K26E, K26H, K36A, K36C, K36D, K36E, K36M, K36T, E46I, E46F, E46M, E46Y, E64P, Q69P, Q69R, Q69S, Q69T, K70A, K70E, K70I, K70M, K70P, K70T, N82T, N82A, A101R, A101C, A101E, A101I, A101L, A101N, A101Q, A101V, S103R, S103A, S103C, S103D, S103E, S103I, S103L, S103N, S103Q, S103V, S103Y, S109E, S109D, K120S, K120A, K120G, K120I, K120P, S141R, S141I, S141Q, S141A, Y155H, E162D, E162G, E162Q, P163*, P163T, P163A, P163E, P163N, T166E, T166G, T166I, T166L, T166N, T166P, T166Q, T166R, T166V, T166W, T167P, T167A, T167R, T167K, M172I, S176N, S178R, S178E, S178H, S178P, S178T, P182R, P182E, F190Y, K197A, K197D, K197F, K197M, K197N, K197Y, Q214R, Q214W, Q215E, Y219W, S239A, M248I, R253A, R253W, S258G, S271G, S271Y, H276C, H276N, H276Y, R280L, R280K, N283M, N283Y, F286C, E299K, E299D, E299W, G366N, K378D, K378H, K378Q, K378R, D385A, D385F, D385H, D385P, D385S, K408A, K408C, K408D, K408E, K408M, K408Q, K408S, K408T, K408V, D410L, D410M, L413Q, L413A, L413T, L413V, N473Y, D486E, D486K, K491E, K491P, K491R, and combinations thereof.

Paragraph 9. The variant of any one of the preceding paragraphs, where the second modification comprises a substitution or a deletion selected from the group consisting of A1*, A1S, A1T, A1V, A1G, A1D, A1I, A1Y, I2*, T3*, T3A, T3E, T3G, V4*, V4N, V4D, V4G, V4M, V4Y, P5*, G6*, G6P, V8*, V8A, V8Q, V8F, V8D, V8W, V9*, V9D, V9A, V9G, V9M, V9P, E10*, E10Y, E10G, P11A, P11L, P11E, P111, P11N, H12A, H12D, H12E, H12G, H12L, H12P, H12Q, H12R, H12V, S14Q, S14R, S14E, S14H, S14N, S14V, Q17K, Q17A, N18S, Q19N, 121L, 122V, 122Q, 122T, A231, A23T, A23V A23M, A23S, F25W, F25Y, 130L, 135*, K37V, R38C, R38F, R38L, R38M, R38T, T42E, A45L, A45M, A45R, D48A, D48P, D48S, L49M, T53C, T53E, T53H, T53K, T53P, T53Q, S57P, S57R, E61D, D63C, K65C, K65F, K65H, K65N, K65Q, K65S, K65T, V68M, V68T, S72F, T74A, T74Q, T74E, Q76T, Q76E, G83E, G83S, E86D, L89F, P94M, G96E, G96D, G96R, N97E, N97D, N97Y, K100R, A101R, A101C, A101E, A101I, A101L, A101N, A101Q, A101V, Q105V, G110R, G110D, G110P, G110C, G110S, A111L, G112E, G112V, T115W, T115Y, T115V, T115I, S117P, A118V, P121A, G122P, T123R, A126D, A126S, A126T, K129R, K129L, K129M, M130I, M130V, L134I, L134V, L134P, L134T, S137A, S137D, S137W, N139I, N139K, N139A, Q143T, Q143S, Q143R, R160I, R160F, R160K, R160L, R160N, R160V, V161S, V161T, R164*, R164Q, 1165E, 1165D, 1165T, 1165L, K169P, K169Q, K169T, K169V, T170E, T170H, M171E, M171N, M171I, M171K, M171Q, P174K, K179S, K179H, K179Q, K179N, K179R, S181T, Q183E, A184T, K185N, K185Q, M188F, M188I, M188Y, K189S, T192A, T192V, N193W, N193S, Y195H, A210E, A210Q, A210F, A210T, A210S, Y213K, Y213Q, Y213R, G217Q, K218R, M228I, V235L, N242T, E249H, E249L, E249Q, K252G, K252E, G254S, L259V, S260C, K267L, G270C, N272D, E285D, N296A, K304A, E301K, K304F, K304Q, K304R, K304S, A312V, T315A, T315V, Q321K, Q321W, E322R, E322A, E322D, H323A, H324N, W342G, A344C, P347D, K351V, K352Q, Y354W, R355Q, Y358W, E363H, K364D, K364R, K364Y, N368D, V377E, E379K, E379P, E380T, E380D, V391L, P398F, P398E, S403Q, S403R, F414T, F414S, F414P, K417G, K417E, K417Q, K419V, V422R, V422I, A423G, Q437I, Q437A, T438A, G440Q, H442N, W443G, D452N, L454I, K462A, K462R, K462L, K462P, E463Q, K466F, K466H, K466N, K466Q, K467H, K467Y, N470Y, D472G, D472Y, L477F, E479R, L480I, K482A, K482P, K482D, K482G, K482Q, K482R, G483A, G483D, L484Q, S487R, P488I, P488L, R489F, R489K, R489N, R489P, W490A, and combinations thereof.

Paragraph 10. The variant of any one of the preceding paragraphs, which has an improved property relative to the parent, wherein the improved property is selected from the group consisting of in-detergent stability, thermostability, protease stability, surfactant stability, pH stability and combinations thereof.

Paragraph 11. An isolated polynucleotide encoding the variant of any one of paragraphs 1-10.

Paragraph 12. A nucleic acid construct or expression vector comprising the polynucleotide of paragraph 11.

Paragraph 13. A recombinant host cell transformed with the polynucleotide of paragraph 11.

Paragraph 14. A method of producing a mannanase variant, comprising: cultivating the recombinant host cell of paragraph 13 under conditions suitable for expression of the variant; and recovering the variant.

Paragraph 15. A detergent composition comprising the variant of any of paragraphs 1-10, and at least one detergent component.

Paragraph 16. The detergent composition of paragraph 15, wherein the detergent component is selected from surfactants, preferably anionic and/or nonionic, builders and bleach components.

Paragraph 17. The detergent composition of any of paragraphs 15-16 further comprising one or more components selected from the group consisting of hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants and solubilizers.

Paragraph 18. The detergent composition of any of paragraphs 15-17, further comprising one or more additional enzymes.

Paragraph 19. The detergent composition of paragraph 18, wherein the additional enzyme is selected from the group consisting of amylases, proteases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, licheninases laminarinases, DNAses, or any combinations thereof.

Paragraph 20. The detergent composition of any of paragraphs 18-19, wherein the additional enzyme is an amylase, and wherein the amylase is selected from the group consisting of;

a) an amylase having at least 60%, at least 65%, at least 70%, at least 75%, at least 80%, at least 85%, at least 90%, at least 95%, at least 98% or 100% sequence identity to SEQ ID NO 2 or SEQ ID NO 35, or an amylase having at least 60%, at least 65%, at least 70%, at least 75%, at least 80%, at least 85%, at least 90%, at least 95%, at least 98% but less than 100% sequence identity to SEQ ID NO: 5 or SEQ ID NO: 6 comprising a two amino acid deletion in the sequence region R180, S181, T182, G183, compared to SEQ ID NO: 5, wherein each position corresponds to the position in SEQ ID NO: 5;

b) an amylase having at least 60%, at least 65%, at least 70%, at least 75%, at least 80%, at least 85%, at least 90%, at least 95%, at least 98% or 100% sequence identity to SEQ ID NO: 5 or SEQ ID NO: 6, or an amylase having at least 60%, at least 65%, at least 70%, at least 75%, at least 80%, at least 85%, at least 90%, at least 95%, at least 98% but less than 100% sequence identity to SEQ ID NO: 5 or SEQ ID NO: 6 comprising one of the alterations set selected from the group consisting of:
   i. R180*, S181*, S243Q, G475K;
   ii. R180*, T182*, S243Q, G475K;
   iii. R180*, T182*, G183S, S243Q, G475K; and
   iv. R180*, S181*, Y242F, S243Q, F266Y, G475K compared to SEQ ID NO: 5, wherein each position corresponds to the position in SEQ ID NO: 6;

c) an amylase having at least 60%, at least 65%, at least 70%, at least 75%, at least 80%, at least 85%, at least 90%, at least 95%, at least 98% or 100% sequence identity to SEQ ID NO: 7, or an amylase having at least 60%, at least 65%, at least 70%, at least 75%, at least 80%, at least 85%, at least 90%, at least 95%, at least 98% but less than 100% sequence identity to SEQ ID NO 3, comprising a two amino acid deletion in the sequence region R178, G179, T180, G181 compared to SEQ ID NO: 7, wherein each position corresponds to the position in SEQ ID NO: 7;

d) an amylase having at least 60%, at least 65%, at least 70%, at least 75%, at least 80%, at least 85%, at least 90%, at least 95%, at least 98% or 100% sequence identity to SEQ ID NO: 7, or an amylase having at least 60%, at least 65%, at least 70%, at least 75%, at least 80%, at least 85%, at least 90%, at least 95%, at least 98% but less than 100% sequence identity to SEQ ID NO: 7, comprising one of the alterations set selected from the group consisting of:
   i. R178*, G179*, E187P, I203Y, G476K;
   ii. R178*, G179*, E187P, M199L, I203Y, G476K;
   iii. R178*, G179*, E187P, I203Y R458N, T459S, D460T, G476K;
   iv. N126Y, F153W, R178*, G179*, T180H, I203Y, S241Q;
   v. N126Y, F153W, R178*, G179*, T180H, I203Y, S241Q, S362A, R377Y;
   vi. T38N, N126Y, T129I, F153W, R178*, G179*, T180D, E187P, I203Y, G476K, G477E; and
   vii. N126Y, F153W, R178*, G179*, T180H, E187P, I203Y, S241Q, G476K, G477E, compared to SEQ ID NO: 7, wherein each position corresponds to the position in SEQ ID NO: 7;

e) an amylase having at least 60%, at least 65%, at least 70%, at least 75%, at least 80%, at least 85%, at least 90%, at least 95%, at least 98% or 100% sequence identity to SEQ ID NO: 8, or an amylase having at least 60%, at least 65%, at least 70%, at least 75%, at least 80%, at least 85%, at least 90%, at least 95%, at least 98% but less than 100% sequence identity to SEQ ID NO: 8, comprising a two amino acid deletion in the sequence region R181, G182, D183, G184 compared to SEQ ID NO: 8, wherein each position corresponds to the position in SEQ ID NO: 8;

f) an amylase having at least 60%, at least 65%, at least 70%, at least 75%, at least 80%, at least 85%, at least 90%, at least 95%, at least 98% or 100% sequence identity to SEQ ID NO: 8, or an amylase having at least 60%, at least 65%, at least 70%, at least 75%, at least 80%, at least 85%, at least 90%, at least 95%, at least 98% but less than 100% sequence identity to SEQ ID NO: 8 comprising an alteration at one or more, preferably at all of the position(s) selected from 3, 4, 5, 74, 118, 167, 170, 177, 195, 202, 204, 271, 320, 330, 377, 385, 445, 458, 475, 476, 314, 315 or 316, compared to SEQ ID NO: 8, wherein each position corresponds to the position in SEQ ID NO: 8;

g) an amylase having at least 60%, at least 65%, at least 70%, at least 75%, at least 80%, at least 85%, at least 90%, at least 95%, at least 98% or 100% sequence identity to SEQ ID NO: 9, or an amylase having at least 60%, at least 65%, at least 70%, at least 75%, at least 80%, at least 85%, at least 90%, at least 95%, at least 98% but less than 100% sequence identity to SEQ ID NO: 9 preferably comprising a two amino acid deletion in the sequence region R181, G182, D183, G184, compared to SEQ ID NO: 9, wherein each position corresponds to the position in SEQ ID NO 5;

h) an amylase having at least 60%, at least 65%, at least 70%, at least 75%, at least 80%, at least 85%, at least 90%, at least 95%, at least 98% or 100% sequence identity to SEQ ID NO: 9, or an amylase having at least 60%, at least 65%, at least 70%, at least 75%, at least 80%, at least 85%, at least 90%, at least 95%, at least 98% but less than 100% sequence identity to SEQ ID NO: 9 comprising one of the alterations set selected from the group consisting of
   i. D183*, G184*, N195F, Y243F;
   ii. D183*, G184*, N195F, V206Y, Y243F;
   iii. W140Y, D183*, G184*, N195F, V206Y, Y243F, E260G, G304R, G476K;
   iv. W140Y, D183*, G184*, N195F, V206Y, Y243F, E260G, G477E;
   v. W140Y, D183*, G184*, N195F, V206Y, Y243F, W284D;

vi. W140Y, N195F, V206Y, Y243F, E260G, G477E;

vii. G109A, W140Y, N195F, V206Y, Y243F, E260G;

viii. T511, S52Q, N54K, G109A, W140Y, N195F, V206Y, Y243F, E260G, G476E;

ix. W140Y, N195F, V206Y, Y243F, E260G, W284R, G477K;

x. W140Y, N195F, V206Y, Y243F, E260G, W284F, G477R; and xi. H1*, G7A, G109A, W140Y, D183*, G184*, N195F, V206Y, Y243F, E260G, N280S, G304R, E391A, G476K, compared to SEQ ID NO: 9, wherein each position corresponds to the position in SEQ ID NO: 9;

i) an amylase having at least 60%, at least 65%, at least 70%, at least 75%, at least 80%, at least 85%, at least 90%, at least 95%, at least 98% or 100% sequence identity to SEQ ID NO: 10, or an amylase having at least 60%, at least 65%, at least 70%, at least 75%, at least 80%, at least 85%, at least 90%, at least 95%, at least 98% but less than 100% sequence identity to SEQ ID NO: 10, comprising a two amino acid deletion in the sequence region R181, G182, D183, G184, compared to SEQ ID NO: 10, wherein each position corresponds to the position in SEQ ID NO: 10;

j) an amylase having at least 60%, at least 65%, at least 70%, at least 75%, at least 80%, at least 85%, at least 90%, at least 95%, at least 98% or 100% sequence identity to SEQ ID NO: 10, or an amylase having at least 60%, at least 65%, at least 70%, at least 75%, at least 80%, at least 85%, at least 90%, at least 95%, at least 98% but less than 100% sequence identity to SEQ ID NO: 10, comprising one of the alterations set selected from the group consisting of i. R118K, D183*, G184*, N195F, R320K, R458K;

ii. M91, D183*, G184*, R118K, N195F, M202L, R320K, M323T, R458K;

iii. M9L, G149A, R118K, G182T, D183*, G184*, G186A, N195F, M202L, T257I, Y295F, N299Y, M323T, A339S, E345R, R458K;

iv. M9L, G149A, R118K, G182T, D183*, G184*, G186A, N195F, T246V, T257I, Y295F, N299Y, M323T, A339S, E345R, R458K; and v. M9L, G149A, G182T, D183*, G184*, G186A, M202L, T257I, Y295F, N299Y, M323T, A339S, E345R, N471E, compared to SEQ ID NO: 10, wherein each position corresponds to the position in SEQ ID NO: 10;

k) an amylase having at least 60%, at least 65%, at least 70%, at least 75%, at least 80%, at least 85%, at least 90%, at least 95%, at least 98% or 100% sequence identity to SEQ ID NO: 11, or an amylase having at least 60%, at least 65%, at least 70%, at least 75%, at least 80%, at least 85%, at least 90%, at least 95%, at least 98% but less than 100% sequence identity to SEQ ID NO: 11, comprising a two amino acid deletion in the sequence region R181, G182, D183, G184, compared to SEQ ID NO: 11, wherein each position corresponds to the position in SEQ ID NO: 11;

l) an amylase having at least 60%, at least 65%, at least 70%, at least 75%, at least 80%, at least 85%, at least 90%, at least 95%, at least 98% or 100% sequence identity to SEQ ID NO: 11, or an amylase having at least 60%, at least 65%, at least 70%, at least 75%, at least 80%, at least 85%, at least 90%, at least 95%, at least 98% but less than 100% sequence identity to SEQ ID NO: 11, comprising one of the alterations set selected from the group consisting of i. D183*, G184*, N195F, V206Y, R320K, R458K;

ii. D183*, G184*, N195F, M202L, V206L, R320K, R458K;

iii. G149A, G182T, D183*, G184*, N195F, M202L, V206L, T257I, Y295F, Q299Y, A339S, Q345R, R458K;

iv. G149A, G182T, D183*, G184*, N195F, V206L, M246V, T257I, Y295F, Q299Y, A339S, Q345R, R458K;

v. G149A, G182T, D183*, G184*, M202L, V206L, T257I, Y295F, Q299Y, A339S, Q345R, H471E; and vi. H1A, N54S, V56T, K72R, G109A, F113Q, R116Q, W167F, Q172G, A174S, G182*, D183*, G184T, N195F, V206L, K391A, F473R, G476K, compared to SEQ ID NO: 11, wherein each position corresponds to the position in SEQ ID NO: 11;

m) an amylase having at least 60%, at least 65%, at least 70%, at least 75%, at least 80%, at least 85%, at least 90%, at least 95%, at least 98% or 100% sequence identity to SEQ ID NO: 12, or an amylase having at least 60%, at least 65%, at least 70%, at least 75%, at least 80%, at least 85%, at least 90%, at least 95%, at least 98% but less than 100% sequence identity to SEQ ID NO: 12, comprising a two amino acid deletion in the sequence region R181, G182, H183, G184, compared to SEQ ID NO 8, wherein each position corresponds to the position in SEQ ID NO: 12;

n) an amylase having at least 60%, at least 65%, at least 70%, at least 75%, at least 80%, at least 85%, at least 90%, at least 95%, at least 98% or 100% sequence identity to SEQ ID NO: 12, or an amylase having at least 60%, at least 65%, at least 70%, at least 75%, at least 80%, at least 85%, at least 90%, at least 95%, at least 98% but less than 100% sequence identity to SEQ ID NO: 12, comprising one of the alterations set selected from the group consisting of i. H183*, G184*, 1405L, A421H, A422P, A428T;

ii. R118K, H183*, G184*, N195F, R320K, R458K;

iii. M91, H183*, G184*, R118K, N195F, M202L, R320K, S323T, R458K;

iv. M9L, G149A, R118K, G182T, H183*, G184*, N195F, M202L, T257I, Y295F, N299Y, A339S, E345R, R458K;

v. M9L, G149A, R118K, G182T, H183*, G184*, N195F, T246V, T257I, Y295F, N299Y, A339S, E345R, R458K; and vi. M9L, G149A, G182T, H183*, G184*, M202L, T257I, Y295F, N299Y, S323T, A339S, E345R, compared to SEQ ID NO: 12, wherein each position corresponds to the position in SEQ ID NO: 12;

o) an amylase having at least 60%, at least 65%, at least 70%, at least 75%, at least 80%, at least 85%, at least 90%, at least 95%, at least 98% or 100% sequence identity to SEQ ID NO: 13, or an amylase having at least 60%, at least 65%, at least 70%, at least 75%, at least 80%, at least 85%, at least 90%, at least 95%, at least 98% but less than 100% sequence identity to SEQ ID NO: 13, comprising a two amino acid deletion in the sequence region R181, G182, G182, D183, compared to SEQ ID NO: 13, wherein each position corresponds to the position in SEQ ID NO: 13;

p) an amylase having at least 60%, at least 65%, at least 70%, at least 75%, at least 80%, at least 85%, at least 90%, at least 95%, at least 98% or 100% sequence identity to SEQ ID NO: 13, or an amylase having at least 60%, at least 65%, at least 70%, at least 75%, at least 80%, at least 85%, at least 90%, at least 95%, at least 98% but less than 100% sequence identity to SEQ ID NO: 13, comprising one of the alterations set selected from the group consisting of i. H1*, D183*, G184*, N195F, V206Y;

ii. H1*, D183*, G184*, N195F, M202L, V206L, R320K, R458K;

iii. G149A, G182T, D183*, G184*, N195F, M202L, V206L, T257I, Y295F, Q299Y, A339S, Q345R, R458K;

iv. G149A, G182T, D183*, G184*, N195F, V206L, M246V, T257I, Y295F, Q299Y, A339S, Q345R, R458K;

v. G149A, G182T, D183*, G184*, M202L, V206L, T257I, Y295F, Q299Y, A339S, Q345R, vi. H1*, N54S, V56T, G109A, Q169E, Q172K, A174*, G182*, D183*, N195F, V206L, K391A, G476K;

vii. G182*, D183*, N195F, W140Y, N260G, S304R, R320A, G476K, V410I, V429I, F451W, C474V;

viii. H1*, N54S, V56T, K72R, G109A, F113Q, R116Q, W167F, Q172G, A174S, G182*, D183*, G184T, N195F, V206L, K391A, P473R, G476K;

ix. H1*, N54S, V56T, G109A, Q169E, Q172K, A174*, G182*, D183*, N195F, V206L, K391A, G476K;

x. H1*, N54S, V56T, G109A, R116H, A174S, G182*, D183*, N195F, V206L, K391A, G476K;

xi. H1*, N54S, V56T, K72R, G109A, F113Q, R116Q, W167F, Q172G, A174S, G182*, D183*, G184T, N195F, V206L, K391A, P473R, G476K;

xii. H1*, N54S, V56T, G109A, F113Q, R116Q, Q172N, A174S, G182*, D183*, N195F, V206L, A265G, K391A, P473R, G476K;

xiii. H1*, N54S, V56T, K72R, G109A, F113Q, W167F, Q172R, A174S, G182*, D183*, N195F, V206L, K391A, G476K;

xiv. H1*, N54S, V56T, K72R, G109A, R116H, T134E, W167F, Q172G, L173V, A174S, G182*, D183*, N195F, V206L, G255A, K391A, G476K;

xv. H1*, N54S, V56T, K72R, G109A, R116H, T134E, W167F, Q172G, L173V, A174S, G182*, D183*, N195F, V206L, G255A, K391A, Q395P, T444Q, P473R, G476K;

xvi. H1*, N54S, V56T, G109A, T134E, A174S, G182*, D183*, N195F, V206L, K391A, G476K;

xvii. H1*, N54S, V56T, K72R, G109A, A174S, G182*, D183*, N195F, V206L, G255A, K391A, G476K;

xviii. H1*, N54S, V56T, G109A, W167F, Q172E, L173P, A174K, G182*, D183*, N195F, V206L, K391A, G476K;

xix. H1*, N54S, V56T, G109A, R116Q, V120L, Q172G, L173V, A174S, G182*, D183*, G184T, N195F, V206L, A422P; and xx. H1*, N54S, V56T, G109A, F113Q, R116Q, W167F, Q172G, 1173V, A174S, G182*, D183*, G184T, N195F, V206L, A422P compared to SEQ ID NO: 13, wherein each position corresponds to the position in SEQ ID NO: 13.

Paragraph 21. The detergent composition of any of paragraphs 18-20, wherein the additional enzyme is a protease, and wherein the protease is selected from the group consisting of;

a) a protease having at least 60%, at least 65%, at least 70%, at least 75%, at least 80%, at least 85%, at least 90%, at least 95%, at least 98%, at least 99% or 100% sequence identity to SEQ ID NO: 14, preferably obtained from *Bacillus lentus;* b) a protease having at least 60%, at least 65%, at least 70%, at least 75%, at least 80%, at least 85%, at least 90%, at least 95%, at least 98%, at least 99% or 100% sequence identity to SEQ ID NO: 15; preferably obtained from *Bacillus amyloliquefaciens;* c) a protease having at least 60%, at least 65%, at least 70%, at least 75%, at least 80%, at least 85%, at least 90%, at least 95%, at least 98%, at least 99% or 100% sequence identity to SEQ ID NO: 16, preferably obtained from *Bacillus* sp.;

d) a protease having at least 60%, at least 65%, at least 70%, at least 75%, at least 80%, at least 85%, at least 90%, at least 95%, at least 98%, at least 99% or 100% sequence identity to SEQ ID NO: 17, preferably obtained from *Bacillus gibsonii;* e) a protease having at least 60%, at least 65%, at least 70%, at least 75%, at least 80%, at least 85%, at least 90%, at least 95%, at least 98%, at least 99% or 100% sequence identity to SEQ ID NO: 18, preferably obtained from *Bacillus lentus;* f) a protease having at least 60%, at least 65%, at least 70%, at least 75%, at least 80%, at least 85%, at least 90%, at least 95%, at least 98%, at least 99% or 100% sequence identity to SEQ ID NO: 19, preferably obtained from *Bacillus licheniformis;* g) or a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the substitution T22R or T22A compared to SEQ ID NO: 14, wherein the position corresponds to the position of SEQ ID NO: 14;

h) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S3T, V41, A188P and V199I, compared to SEQ ID NO: 14, wherein the positions correspond to the positions of SEQ ID NO: 14;

i) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of N114L, T207A, A226V, and E265F, compared to SEQ ID NO: 14, wherein the positions correspond to the positions of SEQ ID NO: 14;

j) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all substitutions selected from the group consisting of: S97D, S101A, V102I and G157S compared to SEQ ID NO: 14, wherein the positions correspond to the positions of SEQ ID NO: 14;

k) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S85N, G116V, S126L, P127Q and S128A compared to SEQ ID NO: 14, wherein the positions correspond to the positions of SEQ ID NO: 14;

l) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: Y161A, R164S and A188P, compared to SEQ ID NO: 14, wherein the positions correspond to the positions of SEQ ID NO: 14;

m) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S3T, R19L, and A188P, wherein the positions correspond to the positions of SEQ ID NO: 14;

n) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises one or more, preferably all the substitutions selected from the group consisting of: S9R, R19L, and N60D, wherein the positions correspond to the positions of SEQ ID NO: 14;

o) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid Arginine (R), at a position corresponding to a position selected from the group consisting of: 9, 42 and 239 of SEQ ID NO: 14;

p) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid Glutamic acid (E) or Aspartic acid (D), at a position corresponding to a position selected from the group consisting of: 9, 42, 60, 61, 74, 157, 176, 179, 182, 212, 250, 253 and 256 of SEQ ID NO: 14;

q) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises an insertion of the amino acid Aspartic acid (D) or Glutamic acid (E) at a position corresponding to position 97 of SEQ ID NO: 14;

r) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid selected from the group consisting of: Glutamic acid (E), Aspartic acid (D), Glycine (G), Arginine (R) and Methionine (M) at a position corresponding to position 99 of SEQ ID NO: 14;

s) a protease having at least 60%, at least 65%, at least 70%, at least 75%, at least 80%, at least 85%, at least 90%, at least 95%, at least 98% but less than 100% sequence identity to SEQ ID NO: 14, wherein the protease comprises the amino acid selected from the group consisting of: Glutamic acid (E), Aspartic acid (D) and Glutamine (Q), at a position corresponding to position 211 of SEQ ID NO: 14;

t) a protease having at least 60%, at least 65%, at least 70%, at least 75%, at least 80%, at least 85%, at least 90%, at least 95%, at least 98% but less than 100% sequence identity to SEQ ID NO: 15, wherein the protease comprises the amino acid selected from the group consisting of: Glutamic acid (E), Aspartic acid (D) and Glutamine (Q), at a position corresponding to position 217 of SEQ ID NO: 15;

u) a protease having at least 60%, at least 65%, at least 70%, at least 75%, at least 80%, at least 85%, at least 90%, at least 95%, at least 98% but less than 100% sequence identity to SEQ ID NO: 15, wherein the protease comprises one or more of the substitutions selected from the group consisting of: S24G/R, S53G, S78N, S101N, G128A/S and Y217Q/L, compared to SEQ ID NO: 15, wherein the positions correspond to the positions of SEQ ID NO: 15.

Paragraph 22. The detergent composition of any of paragraphs 18-21, wherein the additional enzyme is a cellulase, and wherein the cellulase is selected from the group consisting of;

c) a cellulase having at least 60%, at least 65%, at least 70%, at least 75%, at least 80%, at least 85%, at least 90%, at least 95%, at least 98% or 100% sequence identity to SEQ ID NO: 20;

d) a cellulase having at least 60%, at least 65%, at least 70%, at least 75%, at least 80%, at least 85%, at least 90%, at least 95%, at least 98% or 100% sequence identity to SEQ ID NO: 21;

e) a cellulase having at least 60%, at least 65%, at least 70%, at least 75%, at least 80%, at least 85%, at least 90%, at least 95%, at least 98% or 100% sequence identity to SEQ ID NO: 22;

f) a cellulase having at least 60%, at least 65%, at least 70%, at least 75%, at least 80%, at least 85%, at least 90%, at least 95%, at least 98% or 100% sequence identity to SEQ ID NO: 23, g) a cellulase having at least 60%, at least 65%, at least 70%, at least 75%, at least 80%, at least 85%, at least 90%, at least 95%, at least 98% or 100% sequence identity to SEQ ID NO: 24, and h) a cellulase having at least 60%, at least 65%, at least 70%, at least 75%, at least 80%, at least 85%, at least 90%, at least 95%, at least 98% or 100% sequence identity to SEQ ID NO: 25.

Paragraph 23. The detergent composition of any of paragraphs 18-22, wherein the additional enzyme is a lipase, and wherein the lipase is a lipase having at least 60%, at least 65%, at least 70%, at least 75%, at least 80%, at least 85%, at least 90%, at least 95%, at least 98% or 100% sequence identity to SEQ ID NO: 26, or a lipase having at least 60%, at least 65%, at least 70%, at least 75%, at least 80%, at least 85%, at least 90%, at least 95%, at least 98% but less than 100% sequence identity to SEQ ID NO: 26 comprising one or more of the substitutions selected from the group consisting of D27R, G38A, G91A/Q, D96E, G163K, T231R, N233R, D254S and P256T, compared to SEQ ID NO: 26, wherein each position corresponds to the position in SEQ ID NO: 26.

Paragraph 24. The detergent composition of any of paragraphs 18-23, wherein the additional enzyme is a beta-glucanase, and wherein the beta-glucanase is selected from the group consisting of;

a) a beta-glucanase, wherein the beta-glucanase preferably comprises a beta-glucanase having licheninase activity;

i. a beta-glucanase having at least 60%, at least 65%, at least 70%, at least 75%, at least 80%, at least 85%, at least 90%, at least 95%, at least 98% or 100% sequence identity to SEQ ID NO: 27;

ii. a beta-glucanase having at least 60%, at least 65%, at least 70%, at least 75%, at least 80%, at least 85%, at least 90%, at least 95%, at least 98% or 100% sequence identity to SEQ ID NO: 28; and iii. a beta-glucanase having at least 60%, at least 65%, at least 70%, at least 75%, at least 80%, at least 85%, at least 90%, at least 95%, at least 98% or 100% sequence identity to SEQ ID NO: 29;

iv. a beta-glucanase having at least 60%, at least 65%, at least 70%, at least 75%, at least 80%, at least 85%, at least 90%, at least 95%, at least 98% or 100% sequence identity to SEQ ID NO: 30; and v. a beta-glucanase having at least 60%, at least 65%, at least 70%, at least 75%, at least 80%, at least 85%, at least 90%, at least 95%, at least 98% or 100% sequence identity to SEQ ID NO: 31;

b) a beta-glucanase, wherein the beta-glucanase preferably comprises a beta-glucanase having laminarinase activity;

i. a beta-glucanase having at least 60%, at least 65%, at least 70%, at least 75%, at least 80%, at least 85%, at least 90%, at least 95%, at least 98% or 100% sequence identity to SEQ ID NO: 32;

ii. a beta-glucanase having at least 60%, at least 65%, at least 70%, at least 75%, at least 80%, at least 85%, at least 90%, at least 95%, at least 98% or 100% sequence identity to SEQ ID NO: 33;

iii. a beta-glucanase having at least 60%, at least 65%, at least 70%, at least 75%, at least 80%, at least 85%, at least 90%, at least 95%, at least 98% or 100% sequence identity to SEQ ID NO: 34;

iv. a beta-glucanase having at least 60%, at least 65%, at least 70%, at least 75%, at least 80%, at least 85%, at least 90%, at least 95%, at least 98% or 100% sequence identity to SEQ ID NO: 35;

v. a beta-glucanase having at least 60%, at least 65%, at least 70%, at least 75%, at least 80%, at least 85%, at least 90%, at least 95%, at least 98% or 100% sequence identity to SEQ ID NO: 36; and vi. a beta-glucanase having at least 60%, at least 65%, at least 70%, at least 75%, at least 80%, at least 85%, at least 90%, at least 95%, at least 98% or 100% sequence identity to SEQ ID NO: 37.

Paragraph 25. The detergent composition of any of paragraphs 18-24, wherein the additional enzyme is an additional mannanase, and wherein the additional mannanase is selected from the group consisting of;

a) a mannanase having at least 60%, at least 65%, at least 70%, at least 75%, at least 80%, at least 85%, at least 90%, at least 95%, at least 98% or 100% sequence identity to SEQ ID NO: 38, or a mannanase having at least 60%, at least 65%, at least 70%, at least 75%, at least 80%, at least 85%, at least 90%, at least 95%, at least 98% but less than 100% sequence identity to SEQ ID NO: 38 comprising one or more of the substitutions selected from the group consisting of A30T, Y93Q, S95D, D118K, A136P, D139R, N200T, S202R, R210G, W260F, N283H, L288I, L294P, and S295V, compared to SEQ ID NO: 38, wherein each position corresponds to the position in SEQ ID NO: 38;

b) a mannanase having at least 60%, at least 65%, at least 70%, at least 75%, at least 80%, at least 85%, at least 90%, at least 95%, at least 98% or 100% sequence identity to SEQ ID NO: 39; and c) a mannanase having at least 60%, at least 65%, at least 70%, at least 75%, at least 80%, at least 85%, at least 90%, at least 95%, at least 98% or 100% sequence identity to SEQ ID NO: 40.

Paragraph 26. The detergent composition of any of paragraphs 18-25, wherein the additional enzyme is a pectinase, and wherein the pectinase has at least 60%, at least 65%, at least 70%, at least 75%, at least 80%, at least 85%, at least 90%, at least 95%, at least 98% or 100% sequence identity to SEQ ID NO: 41.

Paragraph 27. The detergent composition of any of paragraphs 18-26, wherein the additional enzyme is a DNase, and wherein the DNase is selected from the group consisting of;

a) a DNAse having at least 60%, at least 65%, at least 70%, at least 75%, at least 80%, at least 85%, at least 90%, at least 95%, at least 98% or 100% sequence identity to SEQ ID NO: 42; and b) a DNase having at least 60%, at least 65%, at least 70%, at least 75%, at least 80%, at least 85%, at least 90%, at least 95%, at least 98% or 100% sequence identity to SEQ ID NO: 43.

Paragraph 28. A detergent composition according to paragraphs 18-27, wherein the composition is a liquid detergent or a solid detergent such as a powder.

Paragraph 29. A detergent composition according to any of paragraphs 18-28, which is a laundry or dish washing composition, optionally in unit dose form.

Paragraph 30. Use of the variant of any of paragraphs 1-10 or the detergent composition of any of paragraphs 18-29 for degrading mannan, such as linear mannan, branched or unbranched mannan, galactomannan, glucomannan galactoglucomannan, locust bean gum, guar gum, tara gum, cassia gum, fenugreek gum, konjac gum, and/or modified guar gum.

Paragraph 31. Use of the variant of any of paragraphs 1-10 or the detergent composition of any of paragraphs 18-29 for laundering, washing, cleaning and/or deep cleaning of a textile and/or a hard surface (such as dish wash).

Paragraph 32. The use of any of paragraphs 30-31, wherein the variant has an enzyme detergency benefit.

Paragraph 33. A process for degrading mannan, such as linear mannan, galactomannan, glucomannan and galactoglucomannan, such as linear mannan, branched or unbranched mannan, galactomannan, glucomannan galactoglucomannan, locust bean gum, guar gum, tara gum, cassia gum, fenugreek gum, konjac gum, and/or modified guar gum, comprising applying the variant of any of paragraphs 1-10 or the detergent composition of any of paragraphs 18-29 to the mannan.

Paragraph 34. The process of paragraph 33, wherein the mannan is on the surface of a textile or hard surface, such as dish wash.

Paragraph 35. A process for preparing a food or feed composition and/or food or feed additive, comprising mixing the variant of any of paragraphs 1-10 with one or more food or feed and/or food or feed additive ingredients.

Paragraph 36. A process for producing a coffee extract, comprising the steps:

(a) providing roast and ground coffee beans;

(b) adding to said coffee beans water and the variant of any of paragraphs 1-10;

(c) incubating to make an aqueous coffee extract; and (d) separating the coffee extract from the extracted coffee beans.

Paragraph 37. A process for degrading a cellulosic material, comprising: treating the cellulosic material with an enzyme composition in the presence of the variant of any of paragraphs 1-10.

Paragraph 38. A process for producing a fermentation product, comprising:

(a) saccharifying a cellulosic material with an enzyme composition in the presence of the variant of any of paragraphs 1-10;

(b) fermenting the saccharified cellulosic material with one or more fermenting microorganisms to produce the fermentation product; and (c) recovering the fermentation product from the fermentation.

The present invention is further described by the following examples that should not be construed as limiting the scope of the invention.

EXAMPLES

Strains

The DNA encoding the GH26 mannanase genes was isolated from *Paenibacillus illinoisensis* isolated from soil samples collected in Virginia, United States in 2014 and from *Paenibacillus* sp. isolated from a sand sample collected in The United States in 1991, and sequenced as described in WO 2019/068715.

Materials

Chemicals used as buffers and substrates were commercial products of at least reagent grade.

Model Detergent Systems

Model a Detergent Composition

| Ingredient (abbreviation) | Explanation | Wt % |
|---|---|---|
| LAS | (C10-C13)alkylbenzene-sulfonic acid | 12.0 |
| SLES | sodium lauryl ether sulfate | 4.9 |
| Soy soap | | 2.5 |
| Coco soap | | 2.7 |
| AEO | alcohol ethoxylate | 11.0 |
| NaOH | Sodium hydroxide | 1.7 |
| Ethanol | | 2.7 |
| Isopropanol | | 0.3 |
| MPG | monopropylene glycol | 5.9 |
| Glycerol | | 1.7 |
| TEA | Triethanolamine | 3.3 |
| Sodium formate | | 1.0 |
| Sodium citrate | | 2.0 |
| DTMPA | diethylenetriaminepentakis(methylene)pentakis (phosphonic acid), heptasodium salt | 0.2 |
| PCA | polycarboxylic acid type polymer, sodium salt | 0.2 |
| Phenoxyethanol | | 0.5 |
| Ion exchanged water | | to 100 |

Model A2 Detergent Composition

| Ingredient (abbreviation) | Explanation | Wt % |
|---|---|---|
| LAS | (C10-C13)alkylbenzene-sulfonic acid | 12.0 |
| SLES | sodium lauryl ether sulfate | 4.1 |
| | Topped Palm Kernel Fatty Acid | 3.0 |
| AEO | alcohol ethoxylate | 12.0 |
| NaOH | Sodium hydroxide | 0.5 |
| Ethanol | | 6.0 |
| MPG | monopropylene glycol | 2.0 |
| TEA | Triethanolamine | 2.0 |
| Sodium citrate | Sodium citrate dihydrate | 3.9 |
| DTMPA | diethylenetriaminepentakis(methylene)pentakis (phosphonic acid), heptasodium salt | 1.6 |
| Phenoxyethanol | | 0.5 |
| Ion exchanged water | | to 100 |

Model B Detergent Composition

| Ingredient (abbreviation) | Explanation | Weight % |
|---|---|---|
| LAS | (C10-C13)alkylbenzene-sulfonic acid | 7.2 |
| SLES | sodium lauryl ether sulfate | 10.6 |
| Soy soap | | 2.7 |
| Coco soap | | 2.7 |
| AEO | alcohol ethoxylate | 6.6 |
| NaOH | Sodium hydroxide | 1.0 |
| Ethanol | | 2.7 |

-continued

| Ingredient (abbreviation) | Explanation | Weight % |
|---|---|---|
| Isopropanol | | 0.3 |
| MPG | monopropylene glycol | 6.0 |
| Glycerol | | 1.7 |
| TEA | triethanolamine | 3.3 |
| Sodium formate | | 1.0 |
| Sodium citrate | | 2.0 |
| DTMPA | diethylenetriaminepentakis(methylene)pentakis (phosphonic acid), heptasodium salt | 0.5 |
| PCA | polycarboxylic acid type polymer, sodium salt | 0.5 |
| Phenoxyethanol | | 0.5 |
| Ion exchanged water | | to 100 |

Model J Detergent Composition

| Ingredient (abbreviation) | Explanation | Wt % |
|---|---|---|
| LAS | (C10-C13)alkylbenzene-sulfonic acid | 5.0 |
| AS | sodium alkyl sulfate | 4.5 |
| AEOS | Sodium alkylether sulfate | 10.0 |
| Coco fatty acid | | 1.0 |
| AEO | alcohol ethoxylate | 5.0 |
| MEA | monoethanolamine | 0.3 |
| ethanol | | 1.35 |
| MPG | monopropylene glycol | 3.0 |

-continued

| Ingredient (abbreviation) | Explanation | Wt % |
|---|---|---|
| DTPA | Diethylenetriaminepentaacetic acid, pentasodium salt | 0.1 |
| Sodium formate | | 1.0 |
| Sodium citrate | | 4.0 |
| Sodium hydroxide | | 0.7 |
| Ion exchanged water | | to 100 |

Model O Detergent Composition

| Ingredient (abbreviation) | Explanation | Weight % |
|---|---|---|
| LAS | sodium (C10-C13)alkylbenzene-sulfonic acid | 4.0 |
| SLES | sodium lauryl ether sulfate | 8.0 |
| Soy soap | | 1.0 |
| AEO | alcohol ethoxylate | 4.0 |
| TEA | triethanolamine | 0.4 |
| Sodium citrate | trisodium citrate dihydrate | 2.0 |
| Calcium chloride | calcium chloride dihydrate | 0.02 |
| Ion exchanged water | | to 100 |

Model T Detergent Composition (without Bleach)

| Ingredient (abbreviation) | Explanation | Weight % |
|---|---|---|
| LAS | alkylbenzene-sulfonic acid. sodium salt | 11.7 |
| AS | sodium alkyl sulfafe, sodium salt | 1.97 |
| Soap | | 2.15 |
| AEO | alcohol ethoxylate | 3.3 |
| Sodium carbonate | | 15.0 |
| Sodium (di)silicate | | 3.1 |
| Zeolite 4A + PCA | zeolite 4A + copoly(acrylic acid/maleic acid), sodium salt | 20.38 |
| HEDP | 1-hydroxyethane-1,1-diylbis(phosphonic acid), tetrasodium salt; tetrasodium etidronate | 0.15 |
| Sodium citrate | | 2.0 |
| CPP | copolymer polyether/polyester | 0.5 |
| Sodium sulfate | | 38.7 |
| Silicone | | 1.0 |

Model T Detergent Composition (with Bleach)

| Ingredient (abbreviation) | Explanation | Weight % |
|---|---|---|
| LAS | alkylbenzene-sulfonic acid. sodium salt | 11.7 |
| AS | sodium alkyl sulfafe, sodium salt | 1.97 |
| Soap | | 2.15 |
| AEO | alcohol ethoxylate | 3.3 |
| Sodium carbonate | | 15.0 |
| Sodium (di)silicate | | 3.1 |
| Zeolite 4A + PCA | zeolite 4A + copoly(acrylic acid/maleic acid), sodium salt | 20.38 |
| HEDP | 1-hydroxyethane-1,1-diylbis(phosphonic acid), tetrasodium salt; tetrasodium etidronate | 0.15 |
| Sodium citrate | | 2.0 |
| CPP | copolymer polyether/polyester | 0.5 |
| Sodium sulfate | | 13.3 |
| Sodium percarbonate | | 22.2 |
| TAED | tetraacetylethyelenediamine | 3.2 |
| Silicone | | 1.0 |

Wash Performance

Automatic Mechanical Stress Assay (AMSA)

The wash performance in laundry washing is assessed using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Colour measurements are made with a professional flatbed scanner (Kodak iQsmart, Kodak, Midtager 29, DK-2605 Brondby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$\text{Int} = \sqrt{r^2 + g^2 + b^2}$$

The experiments are conducted as described in the Automatic Mechanical Stress Assay (AMSA) for laundry method using a 1 cycle wash procedure and the experimental conditions specified in Table 2.

TABLE 2

| Conditions for AMSA Washing Trial | |
|---|---|
| Test Solution | Model B detergent 1 g/L |
| | Model T detergent 1.6 g/L or as otherwise noted |
| Test solution volume | 160 µL |
| pH | Model B, pH unadjusted (measured to be 7.8). |
| | Model T, pH unadjusted (measured to be 9.7) |
| Wash time | 20 minutes |
| Temperature | 20° C. or 40° C. |
| Water hardness | 15° dH |
| $Ca^{2+}$:$Mg^{2+}$:$CO_3^{2-}$ ratio | 4:1:7.5 |

The composition of Model T detergent and Model B detergent are as above.

Water hardness is adjusted by addition of $CaCl_2$, $MgCl_2$, and $NaHCO_3$ to the test system. After washing the textiles are flushed in tap water and air-dried.

Terg-O-Tometer (TOM) Washing Trial

The terg-o-tometer is an industry standard. 1 L of wash solution is incubated in a water bath temperature controlled environment. The solution is mixed for 5 min before adding 1 L to each of the beakers. The temperature in the beakers is measured to be 20.0° C. The washed and rinsed swatches are left to dry overnight in a drying cabinet, and measured as indicated in table 3 below.

TABLE 3

Conditions for Terg-O-tometer Washing Trial

| | |
|---|---|
| Detergent dosage | 3.33 g/L or as noted |
| Test solution volume | 1 L |
| pH | unadjusted |
| Wash time | 30 minutes or as noted |
| Temperature | 20° C. or as noted |
| Water hardness | 15° dH |
| $Ca^{2+}$:$Mg^{2+}$:$CO_3^{2-}$ ratio | 4:1:7.5 |
| Mechanical action | 120 rpm |
| Enzyme dose | 0.001-0.05 ppm or as noted |

Wash performance is expressed as a delta remission value (ΔRem). After washing and rinsing the swatches were spread out flat and allowed to air dry at room temperature overnight. Light reflectance evaluations of the swatches are done using a Macbeth Color Eye 7000 reflectance spectrophotometer with large aperture. The measurements are made without UV in the incident light and remission at 460 nm was extracted. The dry swatches are measured with Color-Eye 2. Measurement with small aperture through 3 layers (3 of the same type of swatch from the same beaker), 2 measurements on each swatch on the front side marked with beaker and swatch number. Remission values for individual swatches are calculated by subtracting the remission value of the control swatch from the remission value of the washed swatch. Calculating the enzyme effect is done by taking the measurements from washed swatches with enzymes and subtract with the measurements from washed without enzyme for each stain. The total enzyme performance is calculated as the average of individual $\Delta Rem_{enzyme}$.

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM or is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Full Scale Wash

This test method evaluates wash performance in full scale wash under EU conditions (washing in a front loader washing machine).

The real items (T-shirts) and ballast are added to each wash together with detergent and enzyme. After wash, the real items (T-shirts) are dried. After drying, round swatches are cut out and washed with detergent added soil (dirty detergent) in miniLOM. Color difference is measured on a MacBeth Color Eye spectrophotometer.

The enzymes are added on basis of weight percent of the detergent dosage in each wash, Equipment Used:

Washing machine: Miele Softtronic W2445

Water meters and automatically data collection system

Macbeth Color Eye spectrophotometer

For the Preparation and Adjustment of Water Hardness the Following Ingredients are Needed:

Calcium chloride ($CaCl_2 \cdot 2H_2O$)

Magnesium chloride ($MgCL_2 \cdot 6H_2O$)

Sodium Hydrogen Carbonate ($NaHCO_3$)

Ballast

The ballast consists of clean white cloth without optical whitener made of cotton, polyester or cotton/polyester. The composition of the ballast is a mix of different items at a cotton/polyester ratio of 65/35 based on weight. The ballast weight, dryness and item composition must be the same in each wash.

After each wash the ballast is inactivated in an industrial washer at 85° C./15 min or in a 95° C. wash (EU machine) without detergent Ballast Example: (Standard EU ballast composition, total 3 kg)

3 T-shirts (100% cotton)

10 shirts, short sleeves (55% cotton 45% polyester)

4 pillow cases (35% cotton, 65% polyester), 110×75 cm 1 small bed sheets, size 100×75 cm (100% cotton)

3 Tea towels (100% cotton)

Socks (80% cotton 20% polyester) as balance

Wash Conditions

Temperature: 30° C.

Washing programme: Normal cotton wash without pre-wash: "Cottons".

Water level 13-14L with "water plus"

Water hardness: Standard EU conditions: 15° dH, Ca2+:Mg2+:HCO3=4:1:7.5

GH26 mannanase variant dosage: 0.001-0.05 ppm.

Detailed steps to carry out full scale wash trial

1. Select wash program as in study plan.
2. The detergent and GH26 mannanase variant are placed in the wash drum in a "washing ball" (both liquid and powder detergents). Place it at the bottom.
3. Place the real items (T-shirts) and ballast in the wash drum.
4. Start digital water meter
5. Start the washer by pressing the knob START
6. After wash, take out real items (T-shirts) and ballast, put real items into drying room.

Drying Procedure

Put stains on tray or hang in line and dry at room temperature. The room has a de-humidifier working for 24h per day to keep the room dry Measurement Round swatches from T-shirts (armpits, front, back and edge) are cut out and washed in miniLOM with dirty detergent added soil. Swatches are evaluated by measurement of Color difference (L values) is measured using a Color Eye (Macbeth Color Eye 7000 reflectance spectrophotometer). The measurements are made without UV in the incident light, and the L value from the CIE Lab color space was extracted.

Swatches

The swatches include a combination of food and technical stains.

| Material | Source |
|---|---|
| KC-H033 Chocolate Ice Cream with Guar Gum | CFT |
| C-S-43 Guar Gum | CFT |
| C-S-73 Locust Bean Gum | CFT |

The above commercial test materials are available from Center for Testmaterials BV, Stoomloggerweg 11, 3133 KT Vlaardingen, the Netherlands.

Example 1

Assay I: Reducing End Assay for Determination of Mannanase Activity

For estimating the mannose yield after substrate hydrolysis, a reducing end assay developed by Lever (1972), Anal. Biochem. 47: 273-279, is used. The assay is based on 4-hydroxybenzoic acid hydrazide, which under alkaline conditions reacts with the reducing ends of saccharides. The product is a strong yellow anion, which absorbs at 410 nm.

Method

4-Hydroxybenzhydrazide (PAHBAH) (Sigma,H9882) is diluted in PAHBAH buffer to a concentration of 15 mg/ml. PAHBAH buffer contained: 50 g/L K—Na-tartrate (Merck, 1.08087) and 20 g/L sodium hydroxide (Sigma, S8045). This PAHBAH mix was made just before usage.

70 µl PAHBAH mix and MiliQ water are mixed in a 96 well PCR plate (Thermo Scientific). Samples from hydrolysis experiment were added. Samples and MiliQ always reached the total volume of 150 µl, but the dilution of the sample differed. The plate is sealed with Adhesive PCR Sealing Foil Sheets (Thermo Scientific). Plates are incubated at 95° C. for 10 min, cooled down and kept at 10° C. for 1 min in PTC-200 Thermal Cycler (MJ Research). 100 µl sample is transferred to a 96 well microtiter plate, flat bottomed (Nunc™) and color development measured at 405 nm on a SpectraMax 190 Absorbance Microplate Reader (Molecular Devices). Results are compared to mannose standards, that had undergone the same treatment and dilution as the samples to which they were compared.

Assay II: Determination of Alpha-Amylase Activity

The alpha-amylase activity may be determined by a method employing the G7-pNP substrate. G7-pNP which is an abbreviation for 4,6-ethylidene ($G_7$)-p-nitrophenyl ($G_1$)-α,D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473). The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0). The alpha-Glucosidase reagent contains 52.4 mM HEPES, 87 mM NaCl, 12.6 mM MgCl2, 0.075 mM $CaCl_2$), ≥4 kU/L alpha-glucosidase). The substrate working solution is made by mixing 1 mL of the alpha-Glucosidase reagent with 0.2 mL of the G7-pNP substrate. This substrate working solution is made immediately before use. Dilution buffer: 50 mM MOPS, 0.05% (w/v) TRITON™ X100 (polyethylene glycol p-(1,1,3,3-tetramethylbutyl)-phenyl ether ($C_{14}H_{22}O(C_2H_4O)_n$ (n=9-10))), 1 mM CaCl2, pH8.0. The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm. The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Assay III: Determination of Cellulase Activity

An AZCL-He-cellulose (azurine dye covalently cross-linked cellulose) assay is used for detection of cellulase (endo-glucanase) activity. AZCL-He-cellulose (75 mg) is suspended in 15 mL detergent (e.g. Model detergent A). To 1 mL of this solution in Eppendorf tubes is added 100 µL enzyme (0.09 mg enzyme protein/mL), incubated for 15 min at 40° C. while shaking at 1250 rpm in a pre-heated thermo mixer and spun down for 2 min at 13200 rpm. 250 µL of the solution is transferred to a micro-titer plate and the sample absorbance is measured at 590 nm.

Assay IV: Determination of DNase Activity

DNase activity is determined on DNase Test Agar with Methyl Green (BD, Franklin Lakes, NJ, USA), which is prepared according to the manual from supplier. Briefly, 21 g of agar is dissolved in 500 ml water and then autoclaved for 15 min at 121° C. Autoclaved agar is temperated to 48° C. in water bath, and 20 ml of agar is poured into petri dishes with and allowed to solidify by incubation o/n at room temperature. On solidified agar plates, 5 µl of enzyme solutions are added and DNase activity is observed as colorless zones around the spotted enzyme solutions.

Assay V: Determination of DNase Activity

DNase activity is determined by using the DNaseAlert™ Kit (11-02-01-04, IDT Intergrated DNA Technologies) according to the supplier's manual. Briefly, 95 µl DNase sample is mixed with 5 μl substrate in a microtiter plate, and fluorescence is immediately measured using a Clariostar microtiter reader from BMG Labtech (536 nm excitation, 556 nm emission).

Assay VI: Determination of Beta-Glucanase (Laminarinase) Activity

AZCL-curdlan and AZCL-pachyman (azurine dye covalently cross-linked beta-glucans from Megazyme) assay are used for detection of endo-glucanase activity (laminarinase activity).

AZCL-curdlan or AZCL-pachyman (75 mg) was suspended in 15 mL detergent (Model detergents A, X, or ADW Model A). To 1 mL of this solution in Eppendorf tubes was added 100 μL enzyme (0.033 mg enzyme protein per milliLiter), incubated for 15 min at 40° C. while shaking at 1250 rpm in a pre-heated thermos-mixer and spun down for 2 min at 13200 rpm, diluted 5 or 10 times with a 5% TRITON™ X-100 including 10 μM $CaCl_2$) and 250 μL of the solution was transferred to a micro-titer plate and the sample absorbance was measured at 590 nm.

Assay VII: Determination of Beta-Glucanase (Licheninase or Lichenase) Activity:

An AZCL-Barley beta-glucan (azurine dye covalently cross-linked beta-glucan) assay was used for detection of endo-glucanase activity (Licheninase or Lichenase activity).

AZCL-Barley beta-glucan (75 mg) was suspended in 15 mL detergent (Model detergents A, X, Z with and without bleach and pH adjusted, ADW Model A). To 1 mL of this solution in Eppendorf tubes was added 10 μL enzyme (0.33 mg enzyme protein/Liter), incubated for 15 min at 40° C. while shaking at 1250 rpm in a pre-heated thermo mixer and spun down for 2 min at 13200 rpm, diluted 5 times with a 5% TRITON™ X-100 including 10 μM $CaCl_2$) and 250 μL of the solution was transferred to a micro-titer plate and the sample absorbance was measured at 590 nm.

Assay VIII: Determination of Lipase Activity

Lipase is diluted with a buffer (10 mM Succinic acid+2 mM CaCl2+0.02% Brij 35 adjusted to pH6.5) to the specified concentration. 10 μL of the 100 ppm lipase solution is added to a 90 μL of detergent composition, stirred for 5 minutes and sealed. Samples are stored at 4° C. in detergent D002 (unstressed) and in detergent D002 at 47° C. (stressed). Storage time is 335.5 hours. After storage possible condensation liquid is collected by centrifugation. To the 100 uL stressed or unstressed sample 235 μL of buffer (0.1M Tris-HCl, 9 mM CaCl2, 0.0225% Brij-30, pH8.0+0.85% 4-FBPA (31.5 g/l)) are added corresponding to a 3.35-fold dilution. After 10 minutes stirring 5 uL sample aliquots are further diluted with the same buffer 60-fold. Then one part of this lipase dilution is mixed with four parts of 0.5 mM pNP-palmitate, 1 mM calcium chloride, 100 mM Tris (pH8.0), 6.5 mM Deoxycholate, 1.4 g/L AOS and for 30 minutes release of the pNP chromophore is measured spectrophotometrically. This is used to determine activity via the initial linear slope of the reaction. Residual activity is calculated as the ratio of the measured velocities of stressed versus unstressed sample. The median value of the residual activity is calculated based on four replicates and normalized by a lipase variant reference run with each experimental set.

Assay IX: Determination of Pectinase Activity

Microtiter Assay for Quantification of Pectate Lyase Activity

Pectate lyase cleaves polygalacturonic acid through a trans elimination mechanism. This means that it leaves a double C—C bond for each substrate split. This bond absorbs at 235 nm allowing direct detection of pectate lyase action on soluble polygalacturonic acid by measuring absorbance at that wavelength.

An enzyme sample is diluted in assay buffer (100 mM Tris-HCl, 0.68 mM $CaCl_2$, pH 8.0) to a concentration between 5 and 100 ng/ml. If the enzyme sample contains detergent it should be diluted at least a 1000-fold with respect to detergent. 100 μl of the enzyme buffer dilution is mixed with 100 μl substrate (1% (w/v) polygalacturonic acid, e.g., P-3850 from Sigma, stirred in assay buffer for at least 15 min and centrifuged for 5 min at 2300 g, supernatant is used) in a heating plate and heated to 40° C. for 10 min in a heating block, preferably a PCR machine or equipment of equivalent accuracy and heating speeds.

100 μl enzyme/substrate solution is mixed with 100 μl stop reagent (50 mM $H_3PO_4$) in a UV-transparent microtiter plate. The UV plate is shaken briefly and gently, and the absorbance at 235 nm is measured in a microtiter spectrometer (e.g., Molecular Devices, SpectraMAX 190). The absorbance readings are corrected for background absorbance by subtracting the absorbance of a control sample, run without enzyme added, to all measured values.

Alternatively, catalytic activity of pectate lyase can be determined by the viscosity assay, APSU.

Viscosity Assay, APSU

APSU units: The APSU assay measures the change in viscosity of a solution of polygalacturonic acid in the absence of added calcium ions. A 5% w/v solution of sodium polygalacturonate (e.g., Sigma P-1879) is solubilised in 0.1 M glycine buffer, pH 10. 4 ml of this solution are preincubated for 5 min at 40° C. Then, 250 microlitre of the enzyme (or enzyme dilution) are added, after which the reaction is mixed for 10 sec on a mixer at the highest speed and incubated for 20 min at 40° C. or at another temperature.

Assay X: Determination of Protease Activity

Proteolytic activity can be determined by a method employing Suc-AAPF-PNA as the substrate. Suc-AAPF-PNA is an abbreviation for N-Succinyl-Alanine-Alanine-Proline-Phenylalanine-p-Nitroanilide and is a blocked peptide which can be cleaved by endo-proteases. Following cleavage, a free PNA molecule is liberated, which has a yellow color and thus can be measured by visible spectrophotometry at wavelength 405 nm. The Suc-AAPF-PNA substrate is manufactured by Bachem (cat. no. L1400, dissolved in DMSO). The protease sample to be analyzed is diluted in residual activity buffer (100 mM Tris pH 8.6). The assay is performed by transferring 30 μl of diluted enzyme samples to 96 well microtiter plate and adding 70 μl substrate working solution (0.72 mg/ml in 100 mM Tris pH8.6). The solution is mixed at room temperature and absorption is measured every 20 seconds over 5 minutes at OD 405 nm. The slope (absorbance per minute) of the time dependent absorption-curve is directly proportional to the activity of the protease in question under the given set of conditions. The protease sample is diluted to a level where the slope is linear.

Example 2: Preparation of Fenugreek Gum

Fenugreek gum is extracted according to a modified procedure (Brummer, Y. et al. *Food Hydrocolloids* 2003, 17, 229-236). 124 g Ground fenugreek seeds, purchased in the local supermarket, but also available online, are extracted with 70° C. warm heptane (880 mL) for 60 min. to remove non-polar lipids. After suction filtration the residue is extracted at 60° C. with 96% ethanol (760 mL) for 150 min. to remove polar lipids. After suction filtration the residue is suspended in 1,200 g 60:40 (w/w: 720:480 g) ethanol:water mixture and stirred for 60 min. at ambient temperature to remove sugars and salts. After suction filtration, the residue is left to dry overnight at ambient temperature.

Example 3: Substrate Specificity of Mannanase Variants

Fenugreek gum and guar gum are galactomannans. Fenugreek gum is the most substituted galactomannan and is prepared as described in Example 2. Guar gum is less substituted and is purchased from Megazyme, USA.

2.5 mg/mL solutions of galactomannans are prepared in a phosphate buffer, pH 7.5 and incubated for 30 min at 30° C. with 0.25 mg/L mannanase or without enzyme (blank). Mannaway is a commercially available mannanase available from Novozymes A/S (Bagsvord, Denmark). The reducing ends are then measured as described in Example 1.

The difference in optical density at 405 nm (ΔOD) is calculated by subtracting the blank sample (no added enzyme, i.e. pure galactomannan solution incubated for 30 min at 30° C.).

The mannanase variants herein are superior at hydrolyzing fenugreek and guar gum compared to the commercial product Mannaway (data not shown).

Example 4: Site-Saturation Library Generation

The gene encoding the GH26 mannanase from *Paenibacillus illinoisensis* (SEQ ID NO: 1) was cloned, expressed, and purified as described elsewhere (WO 2019/068715).

Briefly, the mannanase gene (SEQ ID NO: 44) was cloned into the *Bacillus subtilis* expression cassette and transformed in a derivative of the expression host, *Bacillus subtilis* BW366-2prsA, deficient in alkaline protease (aprE), neutral protease (nprE), alpha-amylase (amyE), pectate lyase (pel), xylanase (xynA), minor extracellular serine protease (epr), cell wall associated protease (wprA), bacillo peptidase (bpr), metalloprotease (mpr), minor extracellular protease (vpr), major intracellular protease (ispA). Site-saturation libraries were generated by the method known as "Mega PCR" approach in each mentioned position in the Mannanase gene with NNS doping in the reverse mutagenic primer. NNS is a well-known method, where the "N" designates any of the four nucleotide bases and "S" designates the nucleotides "C" and "G".

Two PCR reactions were performed, wherein 1) was generation of N-terminal fragment with the reverse mutagenic primer and the flanking forward primer and 2) was generation of Mega PCR product using the N-terminal fragment as the forward mega-primer and the flanking C-terminal reverse primer to give the full-length cassette. The Mega PCR product was then transformed in to the *Bacillus* host, where site-specific homologous recombination in the *Bacillus* chromosome took place.

After 18-20 hours of growth in LB agar media with chloramphenicol for antibiotic selection, the transformed colonies were picked and inoculated in to the aqueous growth media, i.e. TB-Gly media. After 1 day growth, cultures from different plates were pooled and sent to NGS for sequencing. The unique positions based on the sequencing results were hit picked and delivered for screening assays.

Example 5: Variant Generation by Site-Directed Mutagenesis

The gene of Mannanase (SEQ ID NO: 45) was cloned into the *Bacillus subtilis* expression cassette and transformed in the expression host, *Bacillus subtilis* as described in Example 4. A Mega PCR-based site-directed mutagenesis (SDM) was carried out to generate variants of the Mannanase gene by introducing mutations at specific sites (as described in Example 4). SDM was carried out using a single mutagenic primer of 20-30 base pairs with the desired amino acid change (substitution/deletion/insertion) lying in the middle of the oligonucleotide with sufficient flanking residues (9-15 base pairs). Two PCR reactions were involved 1) generation of N-terminal fragment with the flanking N-terminal mutagenic primer and the forward flanking primer 2) generation of Mega PCR product using the N-terminal fragment as the forward mega-primer and the flanking C-terminal reverse primer to give the full-length cassette. The Mega PCR product was then transformed in to the *Bacillus* host, where site-specific homologous recombination in the *Bacillus* chromosome takes place.

After 18-20 hours of growth in LB agar media with appropriate antibiotic, the transformed colonies were picked and inoculated into the aqueous expression media and given for screening assays. The hits from the screening assays were subjected to culture PCR and sent for sequence confirmation. The polymerase used for the PR reaction was Phusion DNA polymerase (obtained from ThermoScientific, Cat. No.: F530L).

Example 6: Detergent Stability Determination

Variants generated as described above were tested for detergent stability at pH 8 under the conditions as indicated in Table 4. Stability test was performed by incubating the variants in detergent for different length of time and temperature depending on the stability of wild-type (WrT) or backbone and comparing the activity against control plate which was incubated at 4C for the same duration.

The residual activity was measured by using the Mannanase enzyme assay using insoluble Azo-carob-galactomannan substrate from Megazyme. Substrate was incubated with enzyme at 3000 for 30 min, shaking at 800 rpm. After this, the reaction mixture was kept static for 10 min to allow insoluble substrate to settle. Enzyme activity was measured by reading the optical density of supernatant at 590 nm. The residual activity was calculated by taking the ratio of Stress response to Un-stress response and expressing in terms of % RA, which is then used to calculate the improvement factor by comparing to residual activity of the wild type.

TABLE 4

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| Q168D + L454I | 30° C. | 30 | 90% Model A | 1.1 |
| Q168D + L413A | 30° C. | 30 | 90% Model A | 1.3 |
| K26E + Q168D + N296A | 30° C. | 30 | 90% Model A | 1.5 |

TABLE 4-continued

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| Q168D + D385P + L413A | 30° C. | 30 | 90% Model A | 1.4 |
| Q168D + E249Q + N283Y + L413A | 30° C. | 30 | 90% Model A | 3.8 |
| Q168D + A210E + N283Y + L413A + R489K | 30° C. | 30 | 90% Model A | 2.8 |
| Q168D + Q183E + L413A | 30° C. | 30 | 90% Model A | 1.3 |
| K26E + Q168D | 30° C. | 40 | 90% Model A | 2.1 |
| K26E + Q168D + S181T + K408C + K482Q | 30° C. | 30 | 90% Model A | 1.6 |
| K26E + Q168D + N283Y + N296A | 30° C. | 70 | 70% Model A | 4.2 |
| K26E + Q168D + A210E + S260C + N283Y + N296A + K482Q | 30° C. | 70 | 70% Model A | 7.0 |
| K26E + Q168D + A210E + S260C + S271G + N283Y + N296A | 30° C. | 70 | 70% Model A | 3.1 |
| K26E + Q168D + A210E + S271G + N283Y + N296A | 30° C. | 70 | 70% Model A | 3.6 |
| K26E + Q168D + A210Q + S239A + E249Q + S271Y + N296A | 30° C. | 70 | 70% Model A | 4.1 |
| K26E + Q168D + A210Q + E249Q + S271Y + N296A | 30° C. | 70 | 70% Model A | 2.5 |
| K26E + Q168D + A184T + N242T + N296A + E380D + T438A | 30° C. | 70 | 70% Model A | 3.5 |
| K26E + Q168D + A184T + N296A + E322D + H323A + E380D + T438A | 30° C. | 70 | 70% Model A | 6.0 |
| K26E + Q168D + A184T + N242T + N296A + E322D + H323A + E380D + T438A | 30° C. | 70 | 70% Model A | 3.4 |
| K26E + Q168D + A184T + N242T + N296A + E322D + H323A + K364Y + E380D + T438A | 30° C. | 70 | 70% Model A | 3.6 |
| K26E + R164A + Q168D + S181T + N296A + Q321W + K408S + L413V | 30° C. | 70 | 70% Model A | 4.2 |
| K26E + R164A + Q168D + S181T + N296A + K408S + L413V | 30° C. | 70 | 70% Model A | 4.0 |
| K26E + R164A + Q168D + S181T + N296A | 30° C. | 70 | 70% Model A | 3.0 |
| K26E + R164A + Q168D + S181T + N296A + Q321W + K408S | 30° C. | 70 | 70% Model A | 7.9 |
| K26E + Q168D + Y213K + K252E + E285D + N296A + D385P | 30° C. | 70 | 70% Model A | 5.2 |
| K26E + Q168D + K252E + E285D + N296A + A344C + G366H + D385P | 30° C. | 70 | 70% Model A | 6.4 |
| K26E + Q168D + T192A + Y213K + N296A + A344C + D385P | 30° C. | 70 | 70% Model A | 3.5 |
| K26E + Q168D + K252E + N296A + A344C + D385P | 30° C. | 70 | 70% Model A | 2.9 |
| K26E + R164H + Q168D + F190Y + S271G + N296A | 30° C. | 70 | 70% Model A | 3.3 |
| K26E + Q168D + S271G + N296A + Y354W + V377E + K408A | 30° C. | 70 | 70% Model A | 3.7 |
| K26E + Q168D + F190Y + S239A + S271G + N296A | 30° C. | 70 | 70% Model A | 2.6 |
| K26E + Q168D + N283Y + N296A + S403Q | 30° C. | 70 | 70% Model A | 8.6 |
| K26E + Q168D + N283Y + N296A + D385S + S403Q + K408C | 30° C. | 70 | 70% Model A | 5.6 |
| K26E + Q168D + N283Y + N296A + S403Q + L413T | 30° C. | 70 | 70% Model A | 5.3 |
| K26E + Q168D + N283Y + N296A + D385S + S403Q + K408C + L413T | 30° C. | 70 | 70% Model A | 7.2 |
| K26E + Q168D + N283Y + N296A + S403Q + K408C + L413T | 30° C. | 70 | 70% Model A | 12.3 |
| K26E K36N Q168D K198N L413A N473F | 30° C. | 70 | 30% Model A | 3.7 |
| R38Q Q168D D385F | 30° C. | 30 | 90% Model A | 3.4 |
| Q168D + Q183E + K252E + R253W + K408T + L413A | 30° C. | 30 | 90% Model A | 1.6 |
| K169P + Q183E + S260C + N283Y + L413A | 30° C. | 30 | 90% Model A | 4.3 |
| K26E + Q168D + Q183E + L413A | 30° C. | 30 | 90% Model A | 3.2 |
| K26E + Q168D + S181T + E249Q + N283Y + D385A + L413A | 33° C. | 35 | 90% Model A | 4.5 |
| K26E + Q168D + S181T + K197F + V235L + E249Q + N283Y + L413A | 33° C. | 35 | 90% Model A | 3.7 |
| K26E + Q168D + N296A + D385F + K482Q | 30° C. | 30 | 90% Model A | 2.9 |
| E64P + Q168D | 30° C. | 30 | 90% Model A | 1.6 |
| K26E + Q168D + A210Q + S239A + E249Q + K364Y | 33° C. | 30 | 90% Model A | 2.3 |
| K26E + Q168D + S271Y + L454I | 33° C. | 30 | 90% Model A | 2.3 |
| K26E + Q168D + A210Q + S271Y + V377E | 33° C. | 30 | 90% Model A | 2.3 |

TABLE 4-continued

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| K26E + Q168D + A210Q + S271Y + L454I | 33° C. | 30 | 90% Model A | 2.4 |
| K26E + Q168D + A184T + F190Y + N242T + E322D + H323A | 33° C. | 30 | 90% Model A | 2.6 |
| K26E + Q168D + F190Y + N242T + T315A | 33° C. | 30 | 90% Model A | 2.3 |
| K26E + Q168D + A184T + F190Y + N242T + T315A + E380D | 33° C. | 30 | 90% Model A | 2.7 |
| K26E + Q168D + A184T + F190Y + N242T + T315A | 33° C. | 30 | 90% Model A | 2.6 |
| K26E + Q168D + F190Y + N242T + N283Y + E322D + H323A | 33° C. | 30 | 90% Model A | 3.0 |
| K26E + Q168D + Y213K + S260C + G366H | 33° C. | 30 | 90% Model A | 2.8 |
| K26E + Q168D + E249L + P347D | 33° C. | 30 | 90% Model A | 3.7 |
| K26E + Q168D + K252E + R253W + K378H | 33° C. | 30 | 90% Model A | 3.0 |
| K26E + Q168D + K197N + K252E + R253W + K408T | 33° C. | 30 | 90% Model A | 3.1 |
| K26E + Q168D + K197N + K252E + R253W + K378H | 33° C. | 30 | 90% Model A | 2.9 |
| K26E + Q168D + A210E + N283Y + D385A + L413A + R489K | 33° C. | 30 | 90% Model A | 8.6 |
| K26E + Q168D + S181T + A210E + N283Y + L413A + R489K | 33° C. | 30 | 90% Model A | 9.1 |
| K26E + Q168D + A210E + S271G + N283Y | 33° C. | 30 | 90% Model A | 4.7 |
| K26E + Q168D + L259F + S271G | 33° C. | 30 | 90% Model A | 2.3 |
| K26E + Q168D + N283Y | 33° C. | 30 | 90% Model A | 3.0 |
| K26E + Q168D + A210E + L259F + S271G | 33° C. | 30 | 90% Model A | 2.3 |
| K26E + Q168D + A210E + L259F + S271G + N283Y + R489K | 33° C. | 30 | 90% Model A | 3.0 |
| K26E + Q168D + L259F + N283Y | 33° C. | 30 | 90% Model A | 3.0 |
| R38Q + Q168D + L413T | 30° C. | 30 | 90% Model A | 2.8 |
| R38Q + Q168D + T192V | 30° C. | 30 | 90% Model A | 1.7 |
| R38Q Q168D S239A | 30° C. | 30 | 90% Model A | 1.9 |
| K26E + Q168D + K408T | 33° C. | 30 | 90% Model A | 3.4 |
| K26E Q168D K197F | 33° C. | 30 | 90% Model A | 2.7 |
| K26E + Q168D + L413T | 33° C. | 30 | 90% Model A | 2.8 |
| K26E + Q168D + D385A | 30° C. | 90 | 90% Model A | 3.1 |
| K26E + Q168D + R355Q | 33° C. | 30 | 90% Model A | 2.7 |
| K26E + Q168D + P347D | 33° C. | 30 | 90% Model A | 2.6 |
| K26E + Q168D + G483D | 33° C. | 30 | 90% Model A | 3.3 |
| K26E + Q168D + T192V | 33° C. | 30 | 90% Model A | 3.7 |
| K26E Q168D A210E | 33° C. | 30 | 90% Model A | 3.3 |
| K26E + Q168D + N193S | 33° C. | 30 | 90% Model A | 2.3 |
| K26E + Q168D + S239A | 33° C. | 30 | 90% Model A | 3.5 |
| K26H + Q168D | 30° C. | 40 | 90% Model A | 1.4 |
| K26E + Q69P + Q168D | 33° C. | 30 | 90% Model A | 2.9 |
| K26E E61D Q168D | 33° C. | 30 | 90% Model A | 2.7 |
| K26E + T53E + E61D + Q168D | 33° C. | 30 | 90% Model A | 2.4 |
| K26E + T53E + E64P + Q168D | 33° C. | 30 | 90% Model A | 3.1 |
| K26E + T53E + K65N + Q168D | 33° C. | 30 | 90% Model A | 2.7 |
| K26E + K36E + Q168D | 33° C. | 30 | 90% Model A | 3.6 |
| K26E + R38M + Q168D | 33° C. | 30 | 90% Model A | 3.2 |
| K26E + K36T + Q168D | 33° C. | 30 | 90% Model A | 3.8 |
| Q17A + Q168D | 30° C. | 30 | 90% Model A | 1.1 |
| A23M + Q168D | 30° C. | 30 | 90% Model A | 1.1 |
| S103V + Q168D | 30° C. | 30 | 90% Model A | 1.6 |
| S103E + Q168D | 30° C. | 30 | 90% Model A | 2.0 |
| Q69P + Q168D | 30° C. | 30 | 90% Model A | 1.3 |
| H12A + Q168D | 30° C. | 40 | 90% Model A | 1.2 |
| K65S + Q168D | 30° C. | 30 | 90% Model A | 1.2 |
| N97Y + Q168D | 30° C. | 30 | 90% Model A | 1.1 |
| Q168D + K304F | 30° C. | 30 | 90% Model A | 1.1 |
| Q168D + K179V | 30° C. | 30 | 90% Model A | 1.1 |
| K26E + E64P + Q168D | 33° C. | 30 | 90% Model A | 3.3 |
| H12D K26E Q168D | 33° C. | 30 | 90% Model A | 2.7 |
| K26E + K70E + Q168D | 33° C. | 30 | 90% Model A | 2.5 |
| K26E + T42E + Q168D | 33° C. | 30 | 90% Model A | 2.8 |
| K26E + T53C + Q168D | 33° C. | 30 | 90% Model A | 2.6 |
| K26E + T53P + Q168D | 33° C. | 30 | 90% Model A | 2.7 |
| K26E + K70M + Q168D | 33° C. | 30 | 90% Model A | 2.8 |
| K26E + K70P + Q168D | 33° C. | 30 | 90% Model A | 3.2 |
| K26E S72F Q168D | 33° C. | 30 | 90% Model A | 2.7 |
| K26E A101I Q168D | 33° C. | 30 | 90% Model A | 2.4 |
| K26E + A101L + Q168D | 33° C. | 30 | 90% Model A | 3.2 |
| K26E S103E Q168D | 33° C. | 30 | 90% Model A | 3.3 |

TABLE 4-continued

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| K26E + S103I + Q168D | 33° C. | 30 | 90% Model A | 2.7 |
| K26E + Q168D + Y354W | 33° C. | 30 | 90% Model A | 2.6 |
| K26E + Q168D + L413V | 33° C. | 30 | 90% Model A | 2.3 |
| K26E + Q168D + E249L | 33° C. | 30 | 90% Model A | 2.5 |
| K26E + R38L + Q168D | 33° C. | 30 | 90% Model A | 2.3 |
| K26E + R38L + K70P + A101L + Q168D | 33° C. | 30 | 90% Model A | 4.1 |
| K26E + K36E + Q168D + D385A | 33° C. | 45 | 90% Model A | 40.0 |
| K26E + R38T + Q168D + D385A | 33° C. | 45 | 90% Model A | 17.3 |
| K26E + S103V + Q168D + D385A | 33° C. | 45 | 90% Model A | 20.6 |
| K26E + K36T + Q168D + D385A | 33° C. | 45 | 90% Model A | 19.7 |
| K26E + R38M + Q168D + D385A | 33° C. | 45 | 90% Model A | 24.0 |
| K26E + K36A + Q168D + D385A | 33° C. | 45 | 90% Model A | 13.2 |
| K26E + S103E + Q168D + D385A | 33° C. | 45 | 90% Model A | 17.1 |
| K26E + R38C + A126S + Q168D + D385A | 33° C. | 45 | 90% Model A | 14.9 |
| K26E + R38L + Q168D + D385A | 33° C. | 45 | 90% Model A | 20.9 |
| K26E + S103C + Q168D + D385A | 33° C. | 45 | 90% Model A | 10.7 |
| K26E + K70M + Q168D + D385A | 33° C. | 45 | 90% Model A | 17.6 |
| K26E + S103I + Q168D + D385A | 33° C. | 45 | 90% Model A | 15.1 |
| K26E + K70P + Q168D + D385A | 33° C. | 45 | 90% Model A | 19.0 |
| K26E + A101V + S103Y + Q168D + D385A | 33° C. | 45 | 90% Model A | 11.0 |
| K26E + K70I + Q168D + D385A | 33° C. | 45 | 90% Model A | 14.3 |
| K26E + R38F + Q168D + D385A | 33° C. | 45 | 90% Model A | 9.3 |
| K26E + S103Q + Q168D + D385A | 33° C. | 45 | 90% Model A | 11.4 |
| K26E + A101C + Q168D + D385A | 33° C. | 45 | 90% Model A | 7.3 |
| K26E + K70E + Q168D + D385A | 33° C. | 45 | 90% Model A | 10.8 |
| K26E + A101L + Q168D + D385A | 33° C. | 45 | 90% Model A | 9.3 |
| K26E + K36C + Q168D + D385A | 33° C. | 45 | 90% Model A | 11.0 |
| K26E + S103D + Q168D + D385A | 33° C. | 45 | 90% Model A | 8.2 |
| K26E + K70T + Q168D + D385A | 33° C. | 45 | 90% Model A | 10.6 |
| K26E + A101Q + Q168D + D385A | 33° C. | 45 | 90% Model A | 9.2 |
| K26E + K65N + Q168D + D385A | 33° C. | 45 | 90% Model A | 8.2 |
| K26E + K100R + Q168D + D385A | 33° C. | 45 | 90% Model A | 10.8 |
| K26E + S103L + Q168D + D385A | 33° C. | 45 | 90% Model A | 7.7 |
| K26E + K36M + Q168D + D385A | 33° C. | 45 | 90% Model A | 6.6 |
| K26E + T53P + Q168D + D385A | 33° C. | 45 | 90% Model A | 9.8 |
| K26E + A101N + Q168D + D385A | 33° C. | 45 | 90% Model A | 10.4 |
| K26E + K36D + Q168D + D385A | 33° C. | 45 | 90% Model A | 7.9 |
| K26E + T53C + Q168D + D385A | 33° C. | 45 | 90% Model A | 8.0 |
| K26E + K65T + Q168D + D385A | 33° C. | 45 | 90% Model A | 13.9 |
| K26E + Q168D + R489P | 33° C. | 30 | 90% Model A | 2.4 |
| K26E + Q168D + L477F | 33° C. | 30 | 90% Model A | 2.4 |
| K26E + Q168D + K491P | 33° C. | 30 | 90% Model A | 2.3 |
| K26E + R38L + K70P + Q168D | 33° C. | 30 | 90% Model A | 3.6 |
| K26E + T42E + Q69P + Q168D | 33° C. | 30 | 90% Model A | 2.8 |
| V4D + K26E + K65T + K120P + Q168D | 33° C. | 30 | 90% Model A | 3.0 |
| H12D + Q17A + K26E + E64P + Q168D | 33° C. | 30 | 90% Model A | 2.9 |
| K26E + Q168D + N283Y + D385A + K408S + D452N + K466Q | 33° C. | 30 | 90% Model A | 7.3 |
| K26E + A101E + Q168D + K197A + K408S | 33° C. | 30 | 90% Model A | 3.8 |
| K26E Q168D N283M | 33° C. | 30 | 90% Model A | 4.0 |
| K26E Q168D Y195H | 33° C. | 30 | 90% Model A | 3.2 |
| K26E + T42E + Q69P + Q168D + D385A | 33° C. | 45 | 90% Model A | 18.2 |
| V4D + K26E + T53P + K65Q + K120P + Q168D + D385A | 33° C. | 45 | 90% Model A | 12.7 |
| V4D + K26E + T53P + K120P + Q168D + D385A | 33° C. | 45 | 90% Model A | 9.5 |
| H12D + Q17A + K26E + E64P + A111L + Q168D + D385A | 33° C. | 45 | 90% Model A | 15.8 |
| K26E + Q168D + N283Y + D385A + K408S | 33° C. | 30 | 90% Model A | 7.3 |
| K26E + Q168D + N283Y + K408S | 33° C. | 30 | 90% Model A | 4.3 |
| K26E + Q168D + K197A + N283Y + K408S | 33° C. | 30 | 90% Model A | 7.6 |
| K26E + K70P + Q168D + D385A | 33° C. | 35 | 90% Model A | 24.1 |
| K26E K70P Q168D E249L | 33° C. | 35 | 90% Model A | 5.1 |
| K26E K70P Q168D Y354W | 33° C. | 35 | 90% Model A | 12.9 |
| K26E + K70P + Q168D + L413V | 33° C. | 35 | 90% Model A | 9.0 |
| K26E + S103E + Q168D + D385A | 33° C. | 35 | 90% Model A | 16.2 |
| K26E + S103E + Q168D + L413V | 33° C. | 35 | 90% Model A | 7.2 |
| H12D + Q17A + K26E + E64P + V68T + Q168D + D385A | 33° C. | 45 | 90% Model A | 11.0 |
| H12D + Q17A + K26E + E64P + V68T + A111L + Q168D + D385A | 33° C. | 45 | 90% Model A | 14.3 |
| K26E + Q168D + N283Y + D385A | 33° C. | 45 | 90% Model A | 8.7 |
| K26E + K36E + E64P + Q168D + D385A | 35° C. | 135 | 90% Model A | 30.7 |

TABLE 4-continued

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| K26E + K36E + S72F + Q168D + D385A + W443G | 35° C. | 135 | 90% Model A | 25.7 |
| K26E + K36E + S103V + Q168D + D385A | 30° C. | 1080 | 90% Model A | 43.0 |
| K26E + K36E + Q168D + D385A | 30° C. | 300 | 90% Model A | 30.4 |
| K26E + K36E + Q168D + D385A + K417Q | 35° C. | 135 | 90% Model A | 33.8 |
| K26E + K36E + S103V + Q168D + D385A | 30° C. | 300 | 90% Model A | 35.1 |
| K26E K70A S103V Q168D D385A | 35° C. | 90 | 90% Model A | 41.2 |
| K26E K70M S103V Q168D D385A | 35° C. | 90 | 90% Model A | 41.9 |
| K26E + K70I + S103V + Q168D + D385A | 35° C. | 90 | 90% Model A | 26.5 |
| K26E + S103V + K120P + Q168D + D385A | 35° C. | 90 | 90% Model A | 23.7 |
| M130V + Q168D | 30° C. | 30 | 90% Model A | 1.1 |
| K26E + K36E + T53P + Q168D + D385A | 35° C. | 135 | 90% Model A | 34.9 |
| K26E + K36E + A101L + Q168D + D385A | 35° C. | 135 | 90% Model A | 41.2 |
| K26E + K36T + S103V + Q168D + D385A | 35° C. | 90 | 90% Model A | 51.0 |
| K26E + R38M + S103V + Q168D + D385A | 35° C. | 90 | 90% Model A | 36.5 |
| K26E + T42E + S103V + Q168D + D385A | 35° C. | 90 | 90% Model A | 23.5 |
| K26E + T53P + S103V + Q168D + D385A | 35° C. | 90 | 90% Model A | 23.1 |
| H12D + K26E + K36E + T42E + E64P + K70P + A101L + Q168D + D385A | 35° C. | 135 | 90% Model A | 31.6 |
| K26E + K36E + K70P + K120P + Q168D + D385A | 35° C. | 135 | 90% Model A | 107.4 |
| K26E + T42E + Q69P + S103V + Q168D + D385A | 35° C. | 90 | 90% Model A | 34.4 |
| K26E + K36E + K70P + S103V + K120P + Q168D + D385A | 35° C. | 90 | 90% Model A | 85.0 |
| H12D + K26E + T42E + E64P + K70P + S103V + Q168D + D385A | 35° C. | 90 | 90% Model A | 105.8 |
| F25Y + K36E + T53P + S103V + Q168D + T192V + D385A | 37° C. | 160 | 90% Model A | 95.5 |
| K26E K36E S103V Q168D F190Y D385A | 37° C. | 160 | 90% Model A | 59.5 |
| K26E + K36E + S103V + Q168D + S271G + D385A | 30° C. | 1440 | 90% Model A | 75.4 |
| K26E + K36E + S103V + Q168D + D385A + L413V | 37° C. | 160 | 90% Model A | 96.6 |
| K26E + K36E + S103V + Q168D + D385A + K417Q | 37° C. | 160 | 90% Model A | 78.6 |
| K26E + K36E + S103V + Q168D + D385A + K462L | 37° C. | 160 | 90% Model A | 53.5 |
| K26E + K36E + S103V + Q168D + D385A + K408T | 37° C. | 160 | 90% Model A | 54.5 |
| K26E + K36E + S103V + K120P + Q168D + D385A | 37° C. | 160 | 90% Model A | 48.4 |
| K26E + K36E + K70A + Q168D + D385A | 37° C. | 90 | 90% Model A | 43.4 |
| K26E + K36E + K70P + Q168D + D385A | 37° C. | 90 | 90% Model A | 49.2 |
| K26E + K36E + S72F + Q168D + D385A | 37° C. | 90 | 90% Model A | 34.7 |
| K26E + K36E + A101L + Q168D + D385A | 37° C. | 90 | 90% Model A | 48.6 |
| K26E + R38L + K70P + A101L + Q168D + N283Y | 33° C. | 45 | 90% Model A | 9.6 |
| K26E + R38L + K70P + A101L + Q168D + K408D | 33° C. | 45 | 90% Model A | 10.2 |
| K26E + R38L + K70P + A101L + Q168D + L413A | 33° C. | 45 | 90% Model A | 11.7 |
| K26E + R38L + K70P + A101L + Q168D + L413T | 33° C. | 45 | 90% Model A | 12.5 |
| K26E + R38L + K70P + A101L + S109D + Q168D | 33° C. | 45 | 90% Model A | 6.2 |
| K26E + R38L + K70P + A101L + Q168D + D385A | 33° C. | 45 | 90% Model A | 19.7 |
| K26E + R38L + K70P + A101L + A126T + Q168D + E379P | 33° C. | 45 | 90% Model A | 10.9 |
| K26E + K70P + Q168D + K197A + K408S + K462L + K466Q | 33° C. | 35 | 90% Model A | 9.1 |
| K26E + K70P + Q168D + K197F + N283Y + K408S + L413T | 33° C. | 35 | 90% Model A | 16.2 |
| K26E + K70P + Q168D + K197F + N283Y | 33° C. | 35 | 90% Model A | 12.3 |
| K26E + K70P + Q168D + N283Y + K408S + L413T | 33° C. | 35 | 90% Model A | 21.5 |
| K26E + K70P + Q168D + N283Y + D385A + S403Q | 33° C. | 35 | 90% Model A | 17.3 |
| H12D + K26E + R38L + T42E + K70P + A101L + Q168D | 33° C. | 35 | 90% Model A | 5.8 |

TABLE 4-continued

Variants of the present invention having an improved half-life Improvement Factor (HIF) measured as improved stability compared to the wild type mannanase (SEQ ID NO: 1)

| Mutations in SEQ ID NO: 1 | Incubation Temp | Incubation Time(min) | Detergent in stress | HIF over WT (SEQ ID NO: 1) |
|---|---|---|---|---|
| K26E + K70A + S103V + Q168D + K197A + D385A | 37° C. | 160 | 90% Model A | 48.5 |
| K26E + K70A + S103V + Q168D + D385A + K462P | 37° C. | 160 | 90% Model A | 66.9 |
| K26E + E64P + K70A + S103V + Q168D + D385A | 37° C. | 160 | 90% Model A | 64.3 |
| K26E + K36T + K70A + S103V + Q168D + D385A | 37° C. | 160 | 90% Model A | 75.5 |
| K26E + K70A + S103V + Q168D + K304R + D385A | 37° C. | 160 | 90% Model A | 43.0 |
| K26E + K70P + S103V + Q168D + D385A | 37° C. | 160 | 90% Model A | 58.9 |
| K26E + K36E + T53P + K65Q + Q168D + F190Y + K197A + D385A | 37° C. | 90 | 90% Model A | 43.6 |
| K26E + K36E + E64P + K70P + S103V + Q168D + N283Y + D385A | 30° C. | 3030 | 90% Model A | 105.4 |
| K26E + K36E + E64P + K70P + S103V + Q168D + F190Y + N283Y + D385A + W443G | 30° C. | 3030 | 90% Model A | 148.5 |
| K26E + K36E + E64P + K70P + S103V + Q168D + T192V + N283Y + D385A | 30° C. | 3030 | 90% Model A | 185.2 |
| K26E + K36E + E64P + K70P + S103V + S109D + Q168D + N283Y + D385A | 35° C. | 960 | 90% Model A | 229.1 |
| K26E + K36E + E64P + K70P + S103V + Q168D + K197Y + N283Y + D385A | 35° C. | 960 | 90% Model A | 198.2 |
| K26E + K36E + S103V + Q168D + D385A + L413V + K462L | 37° C. | 240 | 90% Model A | 116.2 |
| K26E + K36E + S103V + Q168D + K197D + D385A + K462L | 37° C. | 240 | 90% Model A | 80.6 |
| K26E + K36E + T53P + E64P + K70P + A101I + Q168D + N283Y + D385A + K408S + L413T | 30° C. | 30 | 90% Model A | 5.1 |
| K26E + K36E + E64P + K70P + S103V + Q168D + N283Y + D385A + L413T | 35° C. | 930 | 90% Model A | 182.8 |
| K26E + K36E + E64P + K70P + S103V + E162D + Q168D + N283Y + D385A | 35° C. | 930 | 90% Model A | 282.5 |
| K26E + K36E + E64P + K70P + S103V + Q168D + F190Y + N283Y + D385A + L413T | 37° C. | 960 | 90% Model A | 351.7 |
| K26E + K36E + E64P + K70P + S103V + Q168D + S271G + N283Y + D385A + L413T | 37° C. | 960 | 90% Model A | 287.9 |
| K26E + K36E + E64P + K70P + S103V + Q168D + N283Y + D385A + K408T + L413T | 37° C. | 960 | 90% Model A | 547.6 |
| K26E + K36E + E64P + K70P + S103V + Q168D + T192V + N283Y + D385A + L413T | 37° C. | 960 | 90% Model A | 595.6 |
| K26E + K36E + E64P + K70P + S103V + Q168D + N283Y + D385A + L413T + K462P | 37° C. | 960 | 90% Model A | 497.1 |
| K26E + K36E + E64P + K70P + S103V + Q168D + N283Y + D385A + L413T + K466Q | 37° C. | 960 | 90% Model A | 399.1 |
| V4Y + K26E + K36E + E64P + K70P + S103V + Q168D + N283Y + D385A + L413T | 37° C. | 960 | 90% Model A | 280.6 |
| K26E + K36E + D48A + E64P + K70P + S103V + Q168D + N283Y + D385A + L413T | 37° C. | 960 | 90% Model A | 296.6 |
| K26E + K36E + E64P + K70P + S103V + P163E + Q168D + N283Y + D385A + L413T | 37° C. | 960 | 90% Model A | 479.0 |
| K26E + K36E + E64P + K70P + S103V + Q168D + K197D + N283Y + D385A + L413T | 37° C. | 960 | 90% Model A | 493.1 |
| K26E + K36E + E64P K70P S103V Q168D N283Y + D385A + L413T + K417E | 37° C. | 960 | 90% Model A | 609.1 |
| K26E + K36E + E64P + K70P + S103V Q168D + N283Y + D385A + L413T + L477F | 37° C. | 960 | 90% Model A | 797.7 |
| K26E + K36E + T53P + E64P + K70P + S103V + Q168D + T192V + N283Y + D385A | 35° C. | 960 | 90% Model A | 253.2 |
| F25Y + K26E + K36E + T53P + S103V + Q168D + T192V + D385A + K462L | 37° C. | 240 | 90% Model A | 52.9 |
| K26E + K36E + E64P + S103V + K120P + Q168D + N283Y + D385A + K462L | 37° C. | 240 | 90% Model A | 116.3 |

Example 7: Protease Stability of Mannanase Variants

Variants generated as described above were tested for detergent stability at pH 8 under the conditions as indicated in Tables 5-6. To the model detergent was added a variant of SEQ ID NO: 14 with the following modifications: Y161A+R164S+A188P in 0.8% (w/w) concentration.

Stability test was performed by incubating the variants in detergent for different length of time and temperature depending on the stability of wild-type (WT) or backbone and comparing the activity against control plate which was incubated at 4° C. for the same duration.

The residual activity was measured by using the Mannanase enzyme assay using insoluble Azo-carob-galacto-mannan substrate from Megazyme. Substrate was incubated with enzyme at 3000 for 30 min, shaking at 800 rpm. After this, the reaction mixture was kept static for 10 min to allow insoluble substrate to settle. Enzyme activity was measured by reading the optical density of supernatant at 590 nm. The residual activity was calculated by taking the ratio of Stress response to Un-stress response and expressing in terms of % RA, which is then used to calculate the improvement factor by comparing to residual activity of the wild type.

TABLE 5

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| K26E + K36E + E64P + K70P + S103V + Q168D + N283Y + D385A | 30° C. | 300 | 90% Model A | 8.9 | — |
| K26E + K36E + E64P + K70P + S103V + Q168D + N283Y + D385A + L413T | 30° C. | 900 | 90% Model A | 43.4 | — |
| K26E + K36E + E64P + K70P + S103V + E162D + Q168D + N283Y + D385A | 30° C. | 240 | 90% Model A | 12.2 | — |
| K26E + K36E + E64P + K70P + S103V + Q168D + N283Y + D385A + L477F | 30° C. | 240 | 90% Model A | 17.3 | — |
| K26E + K36E + E64P + K70P + S103V + E162D + Q168D + N283Y + D385A + L413T | 30° C. | 870 | 90% Model A | 27.4 | — |
| K26E + K36E + E64P + K70P + S103V + S109D + Q168D + N283Y + D385A + L413T | 30° C. | 870 | 90% Model A | 43.1 | — |
| F25Y + K36E + T53P + E64P + K70P + S103V + Q168D + T192V + N283Y + D385A | 30° C. | 240 | 90% Model A | 16.4 | — |
| F25Y K36E T53P E64P K70P S103V Q168D T192V K197N N283Y D385A | 33° C. | 120 | 90% Model A | 12.7 | — |
| F25Y + K36E + T53P + E64P + K70P + S103V + E162D + Q168D + T192V + N283Y + D385A | 33° C. | 120 | 90% Model A | 11.9 | — |
| S14N + K26E + K36E + E64P + K70P + S103V + Q168D + K197D + N283Y + D385A + L413T | 30° C. | 870 | 90% Model A | 29.3 | — |
| K26E + K36E + E64P + K70P + S103V + Q168D + M172I + K197D + N283Y + D385A + L413T | 33° C. | 240 | 90% Model A | 22.7 | — |
| K26E + K36E + E64P + K70P + S103V + T167K + Q168D + K197D + N283Y + D385A + L413T | 33° C. | 240 | 90% Model A | 16.6 | — |
| K26E + K36E + E64P + K70P + S103V + I165L + Q168D + K197D + N283Y + D385A + L413T | 33° C. | 240 | 90% Model A | 27.3 | — |
| K26E + K36E + E64P + K70P + S103V + T166P + Q168D + K197D + N283Y + D385A + L413T | 33° C. | 240 | 90% Model A | 107.9 | — |
| K26E + K36E + E64P + K70P + S103V + P163N + Q168D + K197D + N283Y + D385A + L413T | 33° C. | 240 | 90% Model A | 20.5 | — |
| K26E + K36E + E64P + K70P + S103V + Q168D + K197D + N283Y + D385P + L413T | 33° C. | 240 | 90% Model A | 17.3 | — |
| K26E + K36E + E64P + K70P + S103V + R164H + Q168D + K197D + N283Y + D385A + L413T | 33° C. | 240 | 90% Model A | 19.1 | — |
| K26E + K36E + E64P + K70P + S103V + Q168F + K197D + N283Y + D385A + L413T | 33° C. | 240 | 90% Model A | 28.9 | — |
| K26E + K36E + E64P + K70P + S103V + Q168M + K197D + N283Y + D385A + L413T | 33° C. | 240 | 90% Model A | 40.4 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| K26E + K36E + E64P + K70P + S103V + K169V + K197D + N283Y + D385A + L413T | 33° C. | 240 | 90% Model A | 46.2 | — |
| K26E + K36E + E64P + K70P + S103V + T166P + Q168D + N283Y + D385A + L477F | 30° C. | 2460 | 90% Model A | 344.3 | — |
| S14N + K26E + K36E + E64P + K70P + S103V + Q168D + K197D + N283Y + D385A + D410M + L413T | 30° C. | 270 | 90% Model A | 14.3 | — |
| S14N + K26E + K36E + E64P + Q69S + S103V + Q168D + K197D + N283Y + D385A + L413T | 35° C. | 120 | 90% Model A | 16.3 | — |
| S14N + K26E + K36E + E64P + K70P + S103V + Q168D + K169Q + K197D + N283Y + D385A + L413T | 35° C. | 120 | 90% Model A | 34.6 | — |
| S14N + K26E + K36E + E64P + K70P + S103V + K169P + K197D + N283Y + D385A + L413T | 35° C. | 120 | 90% Model A | 27.5 | — |
| K26E + K36E + E64P + Q69P + N97Y + S103V + T123R + Q168D + K197D + N283Y + D385A + L413T | 33° C. | 240 | 90% Model A | 31.6 | — |
| K26E + K36E + E64P + K70P + S103V + K169T + N283Y + D385A + L413T + L477F | 30° C. | 2460 | 90% Model A | 145.3 | — |
| K26E + K36E + E64P + K70P S103V + Q168D + K169Q + N283Y + D385A + L413T + L477F | 35° C. | 90 | 90% Model A | 35.5 | — |
| H12P + K26E + K36E + E64P + K70P + S103V + Q168D + N283Y + D385A + L413T + L477F | 35° C. | 90 | 90% Model A | 13.1 | — |
| K26E + K36E + E64P + Q69T S103V + Q168D + N283Y + D385A + L413T + L477F | 35° C. | 90 | 90% Model A | 17.6 | — |
| K26E + K36E + E64P + Q69R S103V Q168D N283Y D385A L413T L477F | 35° C. | 90 | 90% Model A | 18.4 | — |
| K26E + K36E + E64P + K70P + S103V + T166L + Q168D + N283Y + D385A + L413T + L477F | 35° C. | 90 | 90% Model A | 17.0 | — |
| K26E + K36E + E64P + K70P + S103V + T166Q + Q168D + N283Y + D385A + L413T + L477F | 35° C. | 90 | 90% Model A | 17.5 | — |
| K26E + K36E + E64P + K70P + S103V + T166V + Q168D + N283Y + D385A + L413T + L477F | 35° C. | 90 | 90% Model A | 19.0 | — |
| K26E + K36E + E64P + K70P + S103V + T166G + Q168D + N283Y + D385A + L413T + L477F | 35° C. | 90 | 90% Model A | 30.5 | — |
| K26E + K36E + E64P + K70P + S103V + T166N + Q168D + N283Y + D385A + L413T + L477F | 35° C. | 90 | 90% Model A | 14.0 | — |
| K26E + K36E + E64P + K70P + S103V + T166I + Q168D + N283Y + D385A + L413T + L477F | 35° C. | 90 | 90% Model A | 38.9 | — |
| K26E + K36E + E64P + K70P + S103V + T166W + Q168D + N283Y + D385A + L413T + L477F | 35° C. | 90 | 90% Model A | 19.3 | — |
| K26E + K36E + E64P + K70P + S103V + T166R + Q168D + N283Y + D385A + L413T + L477F | 35° C. | 90 | 90% Model A | 32.3 | — |
| K26E + K36E + E64P + K70P + S103V + T166E + Q168D + N283Y + D385A + L413T + L477F | 35° C. | 90 | 90% Model A | 30.5 | — |
| K26E + K36E + E64P + K70P + S103V + Q168P + N283Y + D385A + L413T + L477F | 35° C. | 90 | 90% Model A | 50.5 | — |
| K26E + K36E + E64P + K70P + S103V + Q168P + N283Y + D385A + L413T + L477F | 35° C. | 90 | 90% Model A | 79.8 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| K26E + K36E + S57R + E64P + K70P + S103V + Q168D + N283Y + D385A + L413T + L477F | 35° C. | 90 | 90% Model A | 22.8 | — |
| K26E + K36E + S57P + E64P + K70P + S103V + Q168D + N283Y + D385A + L413T + L477F | 35° C. | 90 | 90% Model A | 65.4 | — |
| S14N + K26E + K36E + E64P + K70P + S103V + I165A + Q168D + K197D + N283Y + D385A + D410M + L413T | 35° C. | 120 | 90% Model A | 36.0 | — |
| S14N + K26E + K36E + E64P + K70P + S103V + I165L + Q168D + K197D + N283Y + D385A + D410M + L413T | 35° C. | 120 | 90% Model A | 99.1 | — |
| S14N + K26E + K36E + E64P + K70P + S103V + T166P + Q168D + K197D + N283Y + D385A + D410M + L413T | 30° C. | 5250 | 90% Model A | 268.6 | — |
| V4D + S14N + K26E + K36E + E64P + K70P + S103V + Q168D + K197D + N283Y + D385A + D410M + L413T | 35° C. | 120 | 90% Model A | 27.1 | — |
| S14N + K26E + K36E + E64P + K70P + S103V + P163N + Q168D + K197D + N283Y + D385A + D410M + L413T | 35° C. | 120 | 90% Model A | 60.5 | — |
| K26E + K36E + E64P + K70P + S103V + T166P + Q168D + K197D + N283Y + D385A + D410L + L413T | 40° C. | 270 | 90% Model A | 479.1 | — |
| K26E + K36E + E64P + K70P + S103V + T166P + Q168D + K197D + N283Y + D385A + D410M + L413T | 40° C. | 270 | 90% Model A | 461.2 | — |
| K26E + K36E + E64P + K70P + S103V + E162D + T166P + Q168D + K197D + N283Y + D385A + L413T | 30° C. | 5250 | 90% Model A | 402.6 | — |
| K26E + K36E + E64P + K70P + S103V + T166P + Q168D + K197D + N283Y + D385A + K408M + L413T | 40° C. | 270 | 90% Model A | 522.2 | — |
| S15Q + K26E + K36E + E64P + K70P + S103V + G112V + T166P + Q168D + K197D + N283Y + D385A + L413T | 40° C. | 270 | 90% Model A | 378.8 | — |
| H12V + K26E + K36E + E64P + K70P + S103V + T166P + Q168D + K197D + N283Y + D385A + L413T | 40° C. | 270 | 90% Model A | 382.1 | — |
| S14N + K26E + K36E + E64P + K70P + S103V + T166P + Q168D + K197D + N283Y + D385A + L413T | 40° C. | 270 | 90% Model A | 403.6 | — |
| K26E + K36E + E64P + K70P + S103V + T166P + Q168D + K197Y + N283Y + D385A + L413T | 37° C. | 300 | 90% Model A | — | 13.3 |
| F25Y + K26E + K36E + E64P + K70P + S103V + T166P + Q168D + K197D + N283Y + D385A + L413T + L477F | 35° C. | 90 | 90% Model A | 111.7 | — |
| K26E + K36E + E64P + K70P + S103V + T166P + Q168D + N283Y + D385A + L413T + L477F | 30° C. | 3960 | 90% Model A | 399.7 | — |
| V4Y + K26E + K36E + E64P + K70P + S103V + I165L + Q168D + N283Y + D385A + L413T + L477F | 35° C. | 90 | 90% Model A | 15.7 | — |
| S14N + K26E + K36E + T53P + E64P + K70P + S103V + R160N + T166P + Q168D + K197D + N283Y + D385A + L413T | 40° C. | 270 | 90% Model A | 406.6 | — |
| K26E + K36E + E64P + K70P + S103V + E162D + T166P + Q168D + K197D + N283Y + D385A + L413T | 40° C. | 270 | 90% Model A | 537.2 | — |
| K26E + K36E + E64P + K70P + S103V + I165D + Q168D + K197D + N283Y + D385A + L413T | 40° C. | 270 | 90% Model A | 438.8 | — |
| K26E + K36E + E64P + K70P + S103V + T166P + Q168D + M171N + K197D + N283Y + D385A + L413T | 40° C. | 270 | 90% Model A | 477.0 | — |
| K26E + K36E E64P K70P S103V T166P Q168D M171Q K197D N283Y D385A L413T | 40° C. | 270 | 90% Model A | 607.4 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| K26E K36E E64P K70P S103V T166P Q168D M171E K197D N283Y D385A L413T | 40° C. | 270 | 90% Model A | 466.8 | — |
| K26E + K36E + E64P + K70P + S103V + T166P + Q168D + T170H + K197D + N283Y + D385A + D410M + L413T | 30° C. | 4320 | 90% Model A | 332.0 | — |
| S15Q + K26E + K36E + E64P + K70P + S103V + T166P + Q168D + K197D + N283Y + D385A + D410M + L413T | 30° C. | 5250 | 90% Model A | 518.8 | — |
| K26E + K36E + E64P + K70P + S103V + E162D + T166P + Q168D + K197D + N283Y + T315V + D385A + L413T | 37° C. | 960 | 90% Model A | 670.8 | — |
| K26E + K36E + E64P + K70P + S103V + E162D + T166P + Q168D + K197D + N283Y + D385H + L413T | 37° C. | 960 | 90% Model A | 20.3 | — |
| K26E + K36E + E64P + K70P + S103V + E162D + T166P + Q168D + K197D + N283Y + D385A + K408A + L413T | 37° C. | 960 | 90% Model A | 1215.8 | — |
| K26E + K36E + E64P + K70P + S103V + E162D + T166P + Q168D + K197D + N283Y + D385A + K408Q + L413T | 37° C. | 960 | 90% Model A | 869.3 | — |
| H12E + K26E + K36E + E64P + K70P + S103V + E162D + T166P + Q168D + K197D + N283Y + D385A + L413T | 37° C. | 960 | 90% Model A | 549.7 | — |
| H12R + K26E + K36E + E64P + K70P + S103V + E162D + T166P + Q168D + K197D + N283Y + D385A + L413T | 37° C. | 960 | 90% Model A | 591.0 | — |
| H12V + K26E + K36E + E64P + K70P + S103V + E162D + T166P + Q168D + K197D + N283Y + D385A + L413T | 30° C. | 4320 | 90% Model A | 446.9 | — |
| S14N + K26E + K36E + E64P + K70P + S103V + E162D + T166P + Q168D + K197D + N283Y + D385A + L413T | 37° C. | 960 | 90% Model A | 693.2 | — |
| K26E + K36E + E64P + Q69P + K70P + S103V + E162D + T166P + Q168D + K197D + N283Y + D385A + L413T | 37° C. | 960 | 90% Model A | 681.3 | — |
| K26E + K36E + E64P + K70P + S103V + T166P + Q168D + S178D + K197D + N283Y + D385A + L413T | 40° C. | 270 | 90% Model A | 472.9 | — |
| K26E + K36E + E64P + K70P + S103V + T166P + Q168D + S178P + K197D + N283Y + D385A + D410M + L413T | 40° C. | 270 | 90% Model A | 550.1 | — |
| K26E + K36E + E64P + K70P + S103V + T166P + Q168D + S178D + K197D + N283Y + D385A + L413T | 40° C. | 270 | 90% Model A | 435.6 | — |
| K26E + K36E + E64P + K70P + S103V + T166P + Q168D + K179N + K197D + N283Y + D385A + L413T | 40° C. | 270 | 90% Model A | 602.6 | — |
| K26E + K36E + E64P + K70P + S103V + E162D + T166P + Q168D + K197D + S271G + N283Y + D385A + L413T | 37° C. | 960 | 90% Model A | 636.3 | — |
| S15Q + K26E + K36E + E64P + K70P + S103V + E162D + T166P + Q168D + K197D + N283Y + D385A + L413T | 37° C. | 960 | 90% Model A | 539.4 | — |
| K26E + K36E + E64P + K70P + S103V + T166P + Q168D + M171Q + K197D + N283Y + D385A + K408Q + L413T | 30° C. | 5250 | 90% Model A | 474.3 | — |
| H12R + K26E + K36E + E64P + K70P + S103V + T166P + Q168D + M171Q + K197D + N283Y + D385A + L413T | 30° C. | 4200 | 90% Model A | 339.0 | — |
| K26E + K36E + E64P + K70P + S103V + T166P + Q168D + F190Y + N283Y + D385A + L477F | 40° C. | 270 | 90% Model A | 404.2 | — |
| K26E + K36E + E64P + K70P + S103V + T166P + Q168D + T192V + N283Y + D385A + L477F | 33° C. | 2370 | 90% Model A | 472.2 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| V4D + K26E + K36E + E64P + K70P + S103V + T166P + Q168D + N283Y + D385A + L477F | 33° C. | 2370 | 90% Model A | 368.2 | — |
| S15Q + K26E + K36E + E64P + K70P + S103V + T166P + Q168D + K197D + S271G + N283Y + D385A + D410M + L413T | 38° C. | 1080 | 90% Model A | 1082.1 | — |
| S15Q + K26E + K36E + E64P + K70P + S103V + T166P + Q168D + K197D + M248I + N283Y + D385A + D410M + L413T | 38° C. | 1080 | 90% Model A | 564.2 | — |
| S15Q + K26E + K36E + T53P + E64P + K70P + S103V + T166P + Q168D + K197D + N283Y + D385A + D410M + L413T | 33° C. | 2790 | 90% Model A | 570.4 | — |
| S15Q + K26E + K36E + E64P + K70P + S103V + P163N + T166P + Q168D + K197D + N283Y + D385A + D410M + L413T | 38° C. | 1080 | 90% Model A | 589.6 | — |
| K26E + K36E + E64P + K70P + S103V + E162D + T166P + Q168D + K197D + S271G + N283Y + D385H + L413T | 30° C. | 3960 | 90% Model A | 476.6 | — |
| K26E + K36E + E64P + K70P + S103V + E162D + T166P + Q168D + M172I + K197D + N283Y + D385H + L413T | 38° C. | 840 | 90% Model A | 664.8 | — |
| K26E + K36E + E64P + K70P + S103V + E162D + T166P + Q168D + K197D + M248I + N283Y + D385H + L413T | 38° C. | 840 | 90% Model A | 740.6 | — |
| F25Y + K26E + K36E + E64P + K70P + S103V + E162D + T166P + Q168D + K197D + N283Y + D385H + L413T | 38° C. | 840 | 90% Model A | 598.0 | — |
| V4N + K26E + K36E + E64P + K70P + S103V + E162D + T166P + Q168D + K197D + N283Y + D385H + L413T | 38° C. | 840 | 90% Model A | 718.3 | — |
| S15Q + K26E + K36E + E64P + K70P + S103V + E162D + T166P + Q168D + K197D + N283Y + D385H + L413T | 38° C. | 840 | 90% Model A | 686.5 | — |
| K26E + K36E + E64P + K70P + S103V + R164* + I165* + Q168D + K197D + N283Y + D385H + L413T | 30° C. | 4260 | 90% Model A | 381.7 | — |
| H12R + K26E + K36E + E64P + K70P + S103V + T166P + Q168D + M171Q + K197D + A210E + N283Y + E322D + D385A + L413T | 30° C. | 5400 | 90% Model A | 435.3 | — |
| H12R + K26E + K36E + E64P + K70P + S103V + T166P + Q168D + M171Q + K197D + S271G + N283Y + D385A + L413T | 30° C. | 5400 | 90% Model A | 637.0 | — |
| H12R + K26E + K36E + E64P + K70P + S103V + E162D + T166P + Q168D + M171Q + K197D + N283Y + D385A + L413T | 30° C. | 5400 | 90% Model A | 412.3 | — |
| S15Q + K26E + K36E + E64P + K70P + S103V + T166P + Q168D + K197D + M248I + S271G + N283Y + D385A + D410M + L413T | 37° C. | 960 | 90% Model A | — | 38.9 |
| S14N + K26E + K36E + L49M + E64P + K70P + S103V + E162D + T166P + Q168D + K197D + N283Y + D385A + K408A + L413T | 30° C. | 7170 | 90% Model A | 226.7 | — |
| K26E + K36E + E64P + K70P + S103V + T166P + Q168D + T170H + S178P + K197D + N283Y + D385A + D410M + L413T | 33° C. | 2280 | 90% Model A | 403.1 | — |
| H12R + K26E + K36E + E64P + K70P + S103V + T166P + Q168D + M171Q + F190Y + K197D + S271G + N283Y + D385A + L413T | 30° C. | 5640 | 90% Model A | 753.9 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| H12R + K26E + K36E + E64P + K70P + S103V + K129M + E162D + T166P + Q168D + M171Q + K197D + S271G + N283Y + D385A + L413T | 30° C. | 7170 | 90% Model A | 750.1 | — |
| H12R + K26E + K36E + E64P + K70P + S103V + T166P + Q168D + M171Q + K197D + M248I + S271G + N283Y + D385A + L413T | 33° C. | 3000 | 90% Model A | 818.3 | — |
| H12R + K26E + K36E + E64P + K70P + S103V + T166P + Q168D + M171Q + K197D + S271G + N283Y + D385A + K408M + L413T | 30° C. | 5640 | 90% Model A | 658.6 | — |
| H12R + K26E + K36E + K65H + K70P + S103V + T166P + Q168D + M171Q + K197D + S271G + N283Y + D385A + L413T | 30° C. | 5640 | 90% Model A | 626.0 | — |
| H12R + K26E + K36E + E46Y + E64P + K70P + S103V + T166P + Q168D + M171Q + K197D + S271G + N283Y + D385A + L413T | 30° C. | 7200 | 90% Model A | 661.4 | — |
| S15Q + K26E + K36E + E64P + K70P + S103V + E162D + T166P + Q168D + K197D + M248I + S271G + N283Y + D385A + D410M + L413T | 30° C. | 8670 | 90% Model A | 958.7 | — |
| S15Q + K26E + K36E + E64P + K70P + S103V + T166P + Q168D + S178P + K197D + M248I + S271G + N283Y + D385A + D410M + L413T | 30° C. | 7170 | 90% Model A | 606.6 | — |
| S15Q + K26E + K36E + E64P + K70P + S103V + T166P + Q168D + K197D + M248I + S271G + N283Y + D385A + K408M + D410M + L413T | 30° C. | 10080 | 90% Model A | 934.4 | — |
| S15Q + K26E + K36E + D48S + E64P + K70P + S103V + T166P + Q168D + K197D + M248I + S271G + N283Y + D385A + D410M + L413T | 30° C. | 3120 | 90% Model A | 828.3 | — |
| S15Q + K26E + K36E + E64P + K70P + S103V + P163E + T166P + Q168D + K197D + M248I + S271G + N283Y + D385A + D410M + L413T | 30° C. | 7200 | 90% Model A | 958.8 | — |
| S15Q + K26E + K36E + E64P + K70P + S103V + I165D + Q168D + K197D + M248I + S271G + N283Y + D385A + D410M + L413T | 30° C. | 3120 | 90% Model A | 874.4 | — |
| S14N + K26E + K36E + L49M + E64P + K70P + S103V + E162D + T166P + Q168D + K197D + S258G + N283Y + D385A + K408A + L413T | 30° C. | 7170 | 90% Model A | 477.9 | — |
| S14N + K26E + K36E + L49M + E64P + K70P + S103V + E162D + T166P + Q168D + K197D + N283Y + D385A + K408E + L413T | 30° C. | 4260 | 90% Model A | 190.8 | — |
| S14N + K26E + K36E + L49M + E64P + K70P + S103V + E162D + T166P + Q168D + K197D + N283Y + D385A + K408M + L413T | 30° C. | 5760 | 90% Model A | 653.8 | — |
| V4G + S14N + K26E + K36E + L49M + E64P + K70P + S103V + E162D + T166P + Q168D + K197D + N283Y + D385A + K408A + L413T | 30° C. | 5760 | 90% Model A | 577.3 | — |
| H12R + K26E + K36E + K65H + K70P + S103V + E162D + T166P + Q168D + M171Q + K197D + S271G + N283Y + D385A + L413T | 30° C. | 7170 | 90% Model A | 494.3 | — |
| H12R + K26E + K36E + K65H + K70P + S103V + T166P + Q168D + T170H + K197D + S271G + N283Y + D385A + L413T | 30° C. | 7170 | 90% Model A | 492.4 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q + K26E + K36E + E46Y + E64P + K70P + S103V + T166P + Q168D + K197D + M248I + S271G + N283Y + D385A + K408M + D410M + L413T | 30° C. | 9840 | 90% Model A | 932.3 | — |
| H12R + K26E + K36E + E46Y + E64P + K70P + S103V + T166P + Q168D + M171Q + K197D + S271G + N283Y + D385A + L413T + G483D | 30° C. | 7200 | 90% Model A | 770.1 | — |
| H12R + K26E + K36E + E46Y + E64P + K70P + S103V + T166P + Q168D + M171Q + K197D + S271G + N283Y + K378Q + D385A + L413T | 30° C. | 10080 | 90% Model A | 1023.9 | — |
| H12R + K26E + K36E + E46Y + E64P + K70P + S103V + T166P + Q168D + M171Q + K197D + S271G + N283Y + D385A + K408A + L413T | 30° C. | 8640 | 90% Model A | 802.4 | — |
| H12R + K26E + K36E + E46Y + E64P + K70P + S103V + E162D + T166P + Q168D + M171Q + K197D + S271G + N283Y + D385A + L413T | 30° C. | 8640 | 90% Model A | 885.7 | — |
| H12R + K26E + K36E + E46Y + E64P + K70P + S103E + T166P + Q168D + M171Q + K197D + S271G + N283Y + D385A + L413T | 30° C. | 5760 | 90% Model A | 836.9 | — |
| S14N + K26E + K36E + L49M + E64P + K70P + S103V + E162D + T166P + Q168D + K197D + S239A + S258G + N283Y + D385A + K408A + L413T | 30° C. | 10080 | 90% Model A | 1219.5 | — |
| H12R + K26E + K36E + E46Y + E64P + K70P + S103D + T166P + Q168D + M171Q + K197D + S271G + N283Y + D385A + L413T | 30° C. | 6720 | 90% Model A | 486.7 | — |
| H12R + K26E + K36E + E46Y + E64P + K70P + S103V + T166P + Q168D + M171Q + K197D + S271G + N283Y + K304R + D385A + L413T | 30° C. | 6960 | 90% Model A | 756.5 | — |
| H12R + K26E + K36E + E46Y + E64P + K70P + S103V + T166P + Q168D + M171Q + K197D + S271G + N283Y + K304S + D385A + L413T | 30° C. | 6720 | 90% Model A | 577.2 | — |
| F7P + H12R + K26E + K36E + E46Y + E64P + K70P + S103V + T166P + Q168D + M171Q + K197D + S271G + N283Y + D385A + L413T | 30° C. | 6720 | 90% Model A | 626.4 | — |
| F7I + H12R + K26E + K36E + E46Y + E64P + K70P + S103V + T166P + Q168D + M171Q + K197D + S271G + N283Y + D385A + V391L + D410M + L413T | 30° C. | 8400 | 90% Model A | 916.9 | — |
| S15Q + K26E + K36E + E64P + K70P + S103V + P163N + T166P + Q168D + K197D + S271G + N283Y + D385A + D410M + L413T | 30° C. | 8400 | 90% Model A | 721.5 | — |
| S15Q + K26E + K36E + E64P + K70P + S103V + T166P + Q168D + K197D + S271G + N283Y + D385A + S403R + D410M + L413T | 30° C. | 5520 | 90% Model A | 678.5 | — |
| H12R + K26E + K36E + E64P + K70P + S103V + G110S + T166P + Q168D + M171Q + K197D + S271G + N283Y + D385A + K408M + L413T | 30° C. | 9660 | 90% Model A | 925.5 | — |
| H12R + K26E + K36E + E64P + K70P + S103V + G110C + T166P + Q168D + M171Q + K197D + S271G + N283Y + D385A + K408M + L413T | 30° C. | 9840 | 90% Model A | 1221.0 | — |
| V4D + H12R + S14N + A23S + F25W + K26E + K36E + E46Y + E64P + K70P + S103V + T166P + Q168D + M171Q + K197D + S271G + N283Y + D385A + L413T | 30° C. | 6720 | 90% Model A | 516.0 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| H12R + S15Q + A23S + F25W + K26E + K36E + E46Y + E64P + K70P + S103V + T166P + Q168D + M171Q + K197D + S271G + N283Y + D385A + L413T | 30° C. | 8400 | 90% Model A | 871.4 | — |
| H12R + K26E + K36E + E46Y + E64P + K70P + S103V + T166P + Q168D + M171Q + K197D + S258G + S271G + N283Y + D385A + L413T | 30° C. | 9660 | 90% Model A | 915.6 | — |
| H12R + A23S + F25W + K26E + K36E + E46Y + E64P + K70P + S103V + T166P + Q168D + M171Q + K197D + S271G + N283Y + D385A + L413T | 30° C. | 6720 | 90% Model A | 702.8 | — |
| S15Q + K26E + K36E + E46Y + E64P + K70P + S103V + P163A + T166P + Q168D + K197D + M248I + S271G + N283Y + D385A + K408M + D410M + L413T | 30° C. | 8640 | 90% Model A | 1140.9 | — |
| S15Q + K26E + K36E + E46Y + E64P + K70P + S103V + Y155H + T166P + Q168D + K197D + M248I + S271G + N283Y + D385A + K408M + D410M + L413T | 30° C. | 11100 | 90% Model A | 1094.0 | — |
| S15Q + K26E + K36E + E46Y + E64P + K70P + S103V + R160N + T166P + Q168D + K197D + M248I + S271G + N283Y + D385A + K408M + D410M + L413T | 30° C. | 11100 | 90% Model A | 1237.3 | — |
| H12R + K26E + K36E + E46Y + E64P + K70P + S103V + T166P + Q168D + M171Q + K197D + A210S + S271G + N283Y + D385A + L413T | 30° C. | 6960 | 90% Model A | 610.6 | — |
| H12R + K26E + K36E + E46Y + E64P + K70P + S103V + T166P + Q168D + M171Q + K197D + S271G + N283Y + D385A + K408E + L413T | 30° C. | 9660 | 90% Model A | 1026.0 | — |
| H12R + K26E + K36E + E46Y + E64P + K70P + S103V + T166P + Q168D + M171Q + K197D + S271G + N283Y + D385A + K408V + L413T | 30° C. | 9600 | 90% Model A | 853.3 | — |
| S15Q + K26E + K36E + E46Y + E64P + K70P + S103V + T166P + Q168D + K197D + M248I + S271G + N283Y + D385A + K408M + D410M + L413T + D472Y | 30° C. | 9600 | 90% Model A | 839.1 | — |
| S15Q + K26E + K36E + E46Y + E64P + K70P + S103V + T166P + Q168D + K197D + M248I + S271G + N283Y + D385A + K408M + D410M + L413T + K482G | 30° C. | 6720 | 90% Model A | 735.6 | — |
| S15Q + K26E + K36E + E46Y + E64P + K70P + S103V + T166P + Q168D + K197D + M248I + S271G + N283Y + D385A + K408M + D410M + L413T + D486V | 30° C. | 11400 | 90% Model A | 1245.9 | — |
| S15Q + K26E + K36E + E46Y + E64P + K70P + S103V + T166P + Q168D + K197D + M248I + S271G + N283Y + D385A + K408M + D410M + L413T + N470Y | 30° C. | 9660 | 90% Model A | 971.7 | — |
| S15Q + K26E + K36E + E46Y + E64P + K70P + S103V + T166P + Q168D + K197D + M248I + S271G + N283Y + D385A + K408M + D410M + L413T + P488L | 30° C. | 9600 | 90% Model A | 1096.5 | — |
| H12R + K26E + K36E + E46Y + E64P + K70P + S103E + T166P + Q168D + M171Q + K197D + S271G + N283Y + K378Q + D385A + L413T | 30° C. | 6720 | 90% Model A | 742.8 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| H12R + K26E + K36E + E46Y + E64P + K70P + S103V + E162D + I165L + T166P + Q168D + M171Q + K197D + S271G + N283Y + K378Q + D385A + L413T | 30° C. | 11400 | 90% Model A | 1126.3 | — |
| H12R + K26E + K36E + E46Y + E64P + K70P + S103V + T166P + Q168D + M171Q + K197D + M248I + E249L + S271G + N283Y + K378Q + D385A + L413T | 30° C. | 9660 | 90% Model A | 1206.1 | — |
| H12R + K26E + K36E + E46Y + E64P + K70P + S103V + T166P + Q168D + M171Q + K197D + Q214R + S271G + N283Y + K378Q + D385A + L413T | 30° C. | 11400 | 90% Model A | 1341.8 | — |
| S15Q + K26E + K36E + E46Y + E64P + K70P + S103V + T166P + Q168D + K197D + M248I + S271G + N283Y + D385A + K408M + D410M + L413T + L484Q | 30° C. | 8640 | 90% Model A | 695.3 | — |
| S15Q + K26E + K36E + E46Y + E64P + K70P + S103V + P163A + T166P + Q168D + S178P + K197D + M248I + S271G + N283Y + D385A + K408M + D410M + L413T | 30° C. | 8160 | 90% Model A | 970.0 | — |
| S15Q + K26E + K36E + E46Y + E64P + K70P + S103V + R160N + P163A + T166P + Q168D + K197D + M248I + S271G + N283Y + D385A + K408M + D410M + L413T | 30° C. | 11100 | 90% Model A | 1273.3 | — |
| S15Q + K26E + K36E + E46Y + E64P + K70P + S103V + P163A + T166P + Q168D + M171N + K197D + M248I + S271G + N283Y + D385A + K408M + D410M + L413T | 30° C. | 11100 | 90% Model A | 1277.2 | — |
| S15Q + K26E + K36E + E46Y + E64P + K70P + S103V + P163A + T166P + Q168D + M171Q + K197D + M248I + S271G + N283Y + D385A + K408M + D410M + L413T | 30° C. | 11100 | 90% Model A | 1559.8 | — |
| S15Q + K26E + K36E + E46Y + E64P + K70P + S103V + P163A + T166P + Q168D + K197D + M248I + S258G + S271G + N283Y + D385A + K408M + D410M + L413T | 30° C. | 17280 | 90% Model A | 1921.4 | — |
| H12R + K26E + K36E + E46Y + E64P + K70P + S103V + T166P + Q168D + M171Q + K197D + S271G + N283Y + D385A + L413T + Q437A | 30° C. | 6720 | 90% Model A | 844.9 | — |
| H12R + K26E + K36E + E46Y + E64P + K70P + S103V + T166P + Q168D + M171Q + K197D + E249H + S271G + N283Y + D385A + L413T | 30° C. | 6720 | 90% Model A | 1003.7 | — |
| S15Q + K26E + K36E + E46Y + E64P + K70P + S103V + R160L + T166P + Q168D + K197D + M248I + S271G + N283Y + D385A + K408M + D410M + L413T + N470Y | 30° C. | 8160 | 90% Model A | 837.8 | — |
| S15Q + K26E + K36E + E46Y + E64P + K70P + S103V + R160N + T166P + Q168D + K197D + M248I + S271G + N283Y + D385A + K408M + D410M + L413T + N470Y | 30° C. | 11040 | 90% Model A | 1320.5 | — |
| S15Q + K26E + K36E + E46Y + E64P + K70P + S103V + P163A + T166P + Q168D + M172I + K197D + M248I + S258G + S271G + N283Y + D385A + K408M + D410M + L413T | 30° C. | 18720 | 90% Model A | 2291.7 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q K26E K36E E46Y E64P K70P S103V P163A T166P Q168D M172I K197D M248I S258G S271G N283Y D385A K408M D410M L413T | 30° C. | 16830 | 90% Model A | 1757.5 | — |
| V4N + S15Q + K26E + K36E + E46Y + E64P + K70P + S103V + P163A + T166P + Q168D + S178E + K197D + M248I + S258G + S271G + N283Y + D385A + K408M + D410M + L413T | 30° C. | 11520 | 90% Model A | 1098.4 | — |
| S15Q + K26E + K36E + E46Y + E64P + K70P + S103V + P163A + T166P + Q168D + M171Q + K197D + M248I + S258G + S271G + N283Y + D385A + K408M + D410M + L413T | 30° C. | 11520 | 90% Model A | 1303.0 | — |
| A1Y + V4G + S15Q + K26E + K36E + E46Y + E64P + K70P + S103V + P163A + T166P + Q168D + K197D + M248I + S258G + S271G + N283Y + D385A + K408M + D410M + L413T | 30° C. | 12480 | 90% Model A | 1187.0 | — |
| S15Q + K26E + K36E + E46Y + E64P + K70P + S103V + P163A + T166P + Q168D + K197D + M248I + S258G + S271G + N283Y + D385A + K408M + D410M + L413T + K491R | 30° C. | 10080 | 90% Model A | 1122.0 | — |
| S15Q + K26E + K36E + E46Y + E64P + K70P + S103V + P163A + T166P + Q168D + K197D + M248I + S258G + S271G + N283Y + D385A + K408M + D410M + L413T + K482R | 30° C. | 10080 | 90% Model A | 1118.5 | — |
| S15M + K26E + K36E + E46Y + E64P + K70P + S103V + P163A + T166P + Q168D + K197D + M248I + S258G + S271G + N283Y + D385A + K408M + D410M + L413T | 30° C. | 11520 | 90% Model A | 1088.5 | — |
| S15Q + K26E + K36E + E46Y + E64P + K70P + S103V + P163A + T166P + Q168D + K197D + M248I + S258G + S271G + N283Y + D385A + K408M + D410M + L413T + K482D | 30° C. | 11520 | 90% Model A | 1095.4 | — |
| S15Q + K26E + K36E + E46Y + E64P + K70P + S103V + P163A + T166P + Q168D + S178P + K197D + M248I + S258G + S271G + N283Y + D385A + K408M + D410M + L413T | 30° C. | 16860 | 90% Model A | 1831.2 | — |
| S15Q + F25Y + K26E + K36E + E46Y + E64P + K70P + S103V + P163A + T166P + Q168D + K197D + M248I + S258G + S271G + N283Y + D385A + K408M + D410M + L413T | 30° C. | 11520 | 90% Model A | 1233.4 | — |
| S15Q + K26E + K36E + E46Y + E64P + K70P + S103V + P163A + T166P + Q168D + K197D + M248I + S258G + S271G + N283Y + K304Q + D385A + K408M + D410M + L413T | 30° C. | 10080 | 90% Model A | 1093.9 | — |
| S15Q + K26E + K36E + E46Y + E64P + K70P + S103V + P163A + T166P + Q168D + K197D + M248I + S258G + S271G + N283Y + D385A + K408M + D410M + L413T + R489N | 30° C. | 10080 | 90% Model A | 1036.8 | — |
| S15Q + K26E + K36E + E46Y + E64P + K70P + S103V + P163A + T166P + Q168D + K197D + M248I + S258G + S271G + N283Y + K378D + D385A + K408M + D410M + L413T | 30° C. | 11520 | 90% Model A | 1076.9 | — |
| S15Q + K26E + K36E + E46Y + E64P + K70P + S103V + P163A + T166P + Q168D + M171E + K197D + M248I + S258G + S271G + N283Y + D385A + K408M + D410M + L413T | 30° C. | 11520 | 90% Model A | 1219.2 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| A1Y + S15Q + K26E + K36E + E46Y + E64P + K70P + S103V + P163A + T166P + Q168D + K197D + M248I + S258G + S271G + N283Y + D385A + K408M + D410M + L413T | 30° C. | 10080 | 90% Model A | 893.4 | — |
| S15Q + K26E + K36E + E46Y + E64P + K70P + S103V + P163A + T166P + Q168D + S178H + K197D + M248I + S258G + S271G + N283Y + D385A + K408M + D410M + L413T | 30° C. | 10080 | 90% Model A | 945.6 | — |
| S15Q + K26E + K36E + E46Y + E64P + K70P + S103V + P163A + T166P + Q168D + S178T + K197D + M248I + S258G + S271G + N283Y + D385A + K408M + D410M + L413T | 30° C. | 17280 | 90% Model A | 1733.2 | — |
| F7G + S15Q + K26E + K36E + E46Y + E64P + K70P + S103V + P163A + T166P + Q168D + S178P + K197D + M248I + S258G + S271G + N283Y + D385A + K408M + D410M + L413T | 30° C. | 17280 | 90% Model A | 1554.0 | — |
| S15Q + K26E + K36E + E46Y + E64P + K70P + S103V + P163A + T166P + Q168D + S178P + K197D + M248I + S258G + S271G + N283Y + T315V + D385A + K408M + D410M + L413T | 30° C. | 17280 | 90% Model A | 1671.3 | — |
| S15Q + K26E + K36E + E46Y + E64P + K70P + S103V + P163A + T166P + Q168D + M172I + S178P + K197D + M248I + S258G + S271G + N283Y + D385A + K408M + D410M + L413T | 30° C. | 19860 | 90% Model A | 2338.3 | — |
| S15Q + K26E + K36E + E46Y + T53P + E64P + K70P + S103V + P163A + T166P + Q168D + S178P + K197D + M248I + S258G + S271G + N283Y + D385A + K408M + D410M + L413T | 30° C. | 11520 | 90% Model A | 1314.4 | — |
| S15Q + K26E + K36E + E46Y + T53H + E64P + K70P + S103V + P163A + T166P + Q168D + K197D + M248I + S271G + N283Y + D385A + K408M + D410M + L413T | 37° C. | 3840 | 90% Model A | 66.6 | — |
| S15Q + K26E + K36E + E46Y + E64P + K70P + S103V + P163A + T166P + Q168D + M188Y + K197D + M248I + S271G + N283Y + D385A + K408M + D410M + L413T | 37° C. | 1440 | 90% Model A + 6% LAS | — | 1.5 |
| S15Q + K26E + K36E + E46Y + E64P + K70P + S103V + P163A + T166P + Q168D + K197D + M248I + S271G + N283Y + Y358W + D385A + K408M + D410M + L413T | 37° C. | 1440 | 90% Model A + 6% LAS | | 1.6 |
| S15Q + K26E + K36E + E46Y + E64P + K70P + S103V + P163N + T166P + Q168D + M172I + S178P + K197D + M248I + S258G + S271G + N283Y + D385A + K408M + D410M + L413T | 30° C. | 18720 | 90% Model A + 6% LAS | 2088.5 | — |
| S15Q + K26E + K36E + E46Y + E64P + K70P + S103V + P163E + T166P + Q168D + M172I + S178P + K197D + M248I + S258G + S271G + N283Y + D385A + K408M + D410M + L413T | 30° C. | 18720 | 90% Model A + 6% LAS | 1965.0 | — |
| S15Q + K26E + K36E + E46Y + E64P + K70P + S103V + P163A + T166P + Q168D + M172I + S178P + K197D + M248I + S258G + S271G + N283Y + D385A + K408M + D410M + L413T + K466F | 30° C. | 18720 | 90% Model A + 6% LAS | 1678.8 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| F7A + S15Q + K26E + K36E + E46Y + T53Q + E64P + K70P + S103V + P163A + T166P + Q168D + M172I + S178P + K197D + M248I + S258G + S271G + N283Y + D385A + K408M + D410M + L413T | 30° C. | 18720 | 90% Model A + 6% LAS | 1771.6 | — |
| S15Q + K26E + K36E + E46Y + E64P + K70P + S103V + P163A + T166P + Q168D + M172I + S178P + K197D + M248I + S258G + S271G + N283Y + D385A + K408M + D410M + L413T + D472G + W490A | 30° C. | 18720 | 90% Model A + 6% LAS | 2178.3 | — |
| V9P + S15Q + K26E + K36E + E46Y + T53Q + E64P + K70P + S103V + P163A + T166P + Q168D + M172I + K197D + M248I + S258G + S271G + N283Y + D385A + K408M + D410M + L413T | 30° C. | 16860 | 90% Model A | 2069.6 | — |
| V9P + S15Q + K26E + K36E + E46Y + E64P + K70P + S103V + P163A + T166P + Q168D + M172I + K197D + M248I + S258G + S271G + N283Y + D385A + K408M + D410M + L413T | 30° C. | 21180 | 90% Model A | 2208.5 | — |
| S15Q + K26E + K36E + E46Y + E64P + K70P + S103V + P163A + T166P + Q168D + M172I + K179R + K197D + M248I + S258G + S271G + N283Y + D385A + K408M + D410M + L413T | 30° C. | 6660 | 90% Model A | 134.8 | — |
| S15Q + K26E + K36E + E46Y + E64P + K70P + S103V + P163A + T166P + Q168D + M172I + S178P + F190Y + K197D + Y213R + M248I + S258G + S271G + N283Y + D385A + K408M + D410M + L413T | 30° C. | 5280 | 90% Model A | 120.5 | — |
| S15Q + K26E + K36E + E46Y + E64P + K70P + S103V + Q143R + P163A + T166P + Q168D + M172I + S178P + K197D + M248I + S258G + S271G + N283Y + D385A + K408M + D410M + L413T | 30° C. | 16980 | 90% Model A | 2001.7 | — |
| T3E + V8W + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 30° C. | 16980 | 90% Model A | 1903.4 | — |
| V8W + S15Q + K26E + K36E + E46Y + E64P + K70P + S103V + P121A + P163A + T166P + Q168D + M172I + S178P + K197D + M248I + S258G + S271G + N283Y + D385A + K408M + D410M + L413T | 37° C. | 6660 | 90% Model A | 144.4 | — |
| V8W + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 5280 | 90% Model A | 106.4 | — |
| S15Q + K26E + K36E + E46Y + E64P + K70P + S103V + P163A + T166P + Q168D + M172I + S178P + M188I + K197D + M248I + S258G + S271G + N283Y + K378R + D385A + K408M + D410M + L413T | 37° C. | 5280 | 90% Model A | 116.0 | — |
| S15Q + K26E + K36E + E46Y + E64P + K70P + S103V + P163A + T166P + Q168D + M172I + S178P + K197D + Y213Q + M248I + S258G + S271G + N283Y + D385A + K408M + D410M + L413T | 37° C. | 5490 | 90% Model A | 103.4 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q + K26E + K36E + E46Y + E64P + K70P + S103V + P163A + T166P + Q168D + M172I + S178P + F190Y + K197D + Y213R + S239A + M248I + S258G + S271G + N283Y + D385A + K408M + D410M + L413T | 30° C. | 22680 | 90% Model A | 2687.9 | — |
| A1Y + F7G + S15Q + K26E + K36E + E46Y + E64P + K70P + S103V + I165E + T166P + Q168D + M172I + S178P + K197D + M248I + S258G + S271G + N283Y + D385A + K408M + D410M + L413T | 37° C. | 5490 | 90% Model A | 116.7 | — |
| S15Q + K26E + K36E + E46Y + E64P + K70P + S103V + I165E + T166P + Q168D + M172I + S178H + K197D + M248I + S258G + S271G + N283Y + D385A + K408M + D410M + L413T | 37° C. | 5280 | 90% Model A | 81.6 | — |
| S15Q + K26E + K36E + E46Y + E64P + K70P + S103V + E162D + T166P + Q168D + M172I + S178P + F190Y + K197D + M248I + S258G + S271G + N283Y + D385A + K408M + D410M + L413T | 37° C. | 6720 | 90% Model A | 115.3 | — |
| S15Q + K26E + K36E + E46Y + E64P + K70P + S103V + P163A + T166P + Q168D + M172I + S178P + A184T + F190Y + K197D + M248I + S258G + S271G + N283Y + D385A + K408M + D410M + L413T | 37° C. | 6720 | 90% Model A | 116.3 | — |
| T3E + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 6720 | 90% Model A | 116.4 | — |
| V9P + S15Q + K26E + K36E + E46Y + E64P + K70P + S103V + E162D + T166P + Q168D + M172I + S178P + K197D + M248I + S258G + S271G + N283Y + D385A + K408M + D410M + L413T | 37° C. | 6720 | 90% Model A | 100.1 | — |
| T3E + V9P + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 6720 | 90% Model A | 100.9 | — |
| V9P + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 6720 | 90% Model A | 107.1 | — |
| S15Q + K26E + K36E + E46Y + E64P + K70P + S103V + P163A + T166P + Q168D + M172I + S178P + K197D + M248I + S258G + S271G + N283Y + K378Q + D385A + K408M + D410M + L413T | 37° C. | 6720 | 90% Model A | 152.4 | — |
| A1T + V8W + S15Q + K26E + K36E + E46Y + E64P + K70P + S103V + E162D + T166P + Q168D + M172I + S178P + K197D + M248I + S258G + S271G + N283Y + D385A + K408M + D410M + L413T | 37° C. | 6720 | 90% Model A | 122.2 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q + K26E + K36E + E46Y + E64P + K70P + S103V + P163A + T166P + Q168D + M172I + S178P + K197D + M248I + S258G + S271G + N283Y + D385A + K408M + D410M + L413T + N473Y | 37° C. | 6720 | 90% Model A | 137.0 | — |
| V9P + S15Q + K26E + K36E + E46Y + E64P + K70P + S103V + P163A + T166P + Q168D + M172I + S178P + K197D + S239A + M248I + S258G + S271G + N283Y + D385A + K408M + D410M + L413T | 37° C. | 8160 | 90% Model A | 157.0 | — |
| V4M + S15Q + K26E + K36E + E46Y + E64P + K70P + S103V + P163A + T166P + Q168D + M172I + S178P + K197D + S239A + M248I + S258G + S271G + N283Y + D385A + K408M + D410M + L413T | 30° C. | 27000 | 90% Model A | 2707.5 | — |
| S15Q + K26E + K36E + E46Y + T53P + E64P + K70P + S103V + P163A + T166P + Q168D + M172I + S178P + K197D + S239A + M248I + S258G + S271G + N283Y + D385A + K408M + D410M + L413T | 30° C. | 27000 | 90% Model A | 2508.1 | — |
| S15Q + K26E + K36E + E46Y + E64P + K70P + S103V + P163A + T166P + Q168D + M172I + S178P + K197D + S239A + M248I + S258G + S271G + N283Y + K378Q + D385A + K408M + D410M + L413T | 30° C. | 27000 | 90% Model A | 3205.8 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + D385A + K408M + D410M + L413T | 30° C. | 29760 | 90% Model A | 2845.6 | — |
| A1Y + F7P + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 3960 | 90% Model A | 89.3 | — |
| F7P + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 3960 | 90% Model A | 95.8 | — |
| S15Q + K26E + K36E + E46Y + E64P + K70P + S103V + P163A + T166P + Q168D + M172I + S178P + K197D + M248I + S258G + S271G + N283Y + D385A + K408M + D410M + L413T + K417Q + K462P | 37° C. | 5280 | 90% Model A | 210.3 | — |
| A1T + F7G + S15Q + K26E + K36E + E46Y + T53Q + E64P + K70P + S103V + P163A + T166P + Q168D + M172I + S178P + K197D + M248I + S258G + S271G + N283Y + D385A + K408M + D410M + L413T | 37° C. | 3960 | 90% Model A | 112.8 | — |
| A1T + S15Q + K26E + K36E + E46Y + E64P + K70P + S103V + P163A + T166P + Q168D + M172I + S178P + K197D + M248I + S258G + S271G + N283Y + D385A + K408M + D410M + L413T | 37° C. | 3960 | 90% Model A | 104.7 | — |
| S15Q + K26E + K36E + E46Y + E64P + K70P + S103V + E162D + T166P + Q168D + M172I + S178P + K197D + | 37° C. | 3960 | 90% Model A | 93.6 | — |

TABLE 5-continued

| Protease stability at pH 8. The protease is a variant of SEQ ID NO: 14 with the following modifications: Y161A + R164S + A188P added in 0.8% (w/w) concentration | | | | | |
|---|---|---|---|---|---|
| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
| M248I + S258G + S271G + N283Y + D385A + K408M + D410M + L413T | | | | | |
| A1T + F7G + S15Q + K26E + K36E + E46Y + E64P + K70P + S103V + I165E + T166P + Q168D + M172I + S178P + K197D + M248I + S258G + S271G + N283Y + D385A + K408M + D410M + L413T | 30° C. | 18420 | 90% Model A | 2124.5 | — |
| A1Y + F7G + S15Q + K26E + K36E + E46Y + E64P + K70P + S103V + I165E + T166P + Q168D + M172I + S178P + K197D + M248I + S258G + S271G + N283Y + K378Q + D385A + K408M + D410M + L413T | 30° C. | 21180 | 90% Model A | 2381.4 | — |
| A1Y + F7G + S15Q + K26E + K36E + E46Y + E64P + K70P + S103V + I165E + T166P + Q168D + M172I + S178P + K197D + M248I + S258G + S271G + N283Y + K378Q + D385A + K408M + D410M + L413T + P488L | 30° C. | 19860 | 90% Model A | 1874.5 | — |
| A1Y + F7G + S15Q + K26E + K36E + E46Y + E64P + K70P + S103V + I165E + T166P + Q168D + M172I + S178P + K197N + M248I + S258G + S271G + N283Y + D385A + K408M + D410M + L413T | 30° C. | 19860 | 90% Model A | 1994.7 | — |
| A1Y + F7G + S15Q + K26E + K36E + E46Y + E64P + K70P + S103V + I165E + T166P + Q168D + M172I + S178P + K197N + M248I + S258G + S271G + N283Y + K364R + D385A + K408M + D410M + L413T | 37° C. | 3960 | 90% Model A | 69.7 | — |
| A1Y + F7G + S15Q + K26E + K36E + E46Y + E64P + K70P + S103V + I165E + T166P + Q168D + M172I + S178P + K197D + N242T + M248I + S258G + S271G + N283Y + D385A + K408M + D410M + L413T | 30° C. | 18420 | 90% Model A | 1924.0 | — |
| S15Q + K26E + K36E + E46Y + E64P + K70P + S103V + P121A + Q143R + P163A + T166P + Q168D + M172I + S178P + F190Y + K197D + Y213Q + M248I + S258G + S271G + N283Y + D385A + K408M + D410M + L413T | 37° C. | 3960 | 90% Model A | 87.8 | — |
| S15Q + K26E + K36E + E46Y + E64P + K70P + S103V + P163A + T166P + Q168D + M172I + S178P + K197D + Q214R + M248I + S258G + S271G + N283Y + T315V + D385A + K408M + D410M + L413T | 30° C. | 21180 | 90% Model A | 2235.7 | — |
| F7G + S15Q + K26E + K36E + E46Y + E64P + K70P + S103V + P163A + T166P + Q168D + M172I + S178P + K197D + Y213Q + M248I + S258G + S271G + N283Y + D385A + K408M + D410M + L413T | 37° C. | 3960 | 90% Model A | 77.0 | — |
| S15Q + K26E + K36E + E46Y + E64P + K70P + S103V + P163A + T166P + Q168D + M172I + S178P + K197D + Q214R + M248I + S258G + S271G + N283Y + D385A + K408M + D410M + L413T | 37° C. | 3960 | 90% Model A | 76.1 | — |
| S15Q + K26E + K36E + E46Y + E64P + K70P + S103V + I165E + T166P + Q168D + M172I + S178P + K197D + Y213Q + M248I + S258G + S271G + N283Y + D385A + K408M + D410M + L413T | 37° C. | 3960 | 90% Model A | 67.2 | — |
| V4N + S15Q + K26E + K36E + E46Y + E64P + K70P + S103V + P163A + | 37° C. | 3960 | 90% Model A | 96.0 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| T166P + Q168D + M172I + S178P + K197D + Y213Q + M248I + S258G + S271G + N283Y + D385A + K408M + D410M + L413T | | | | | |
| S15Q + K26E + K36E + E46Y + E64P + K70P + S103V + P163A + T166P + Q168D + M172I + S178P + K197D + Y213Q + M248I + S258G + S271G + N283Y + K378Q + D385A + K408M + D410M + L413T | 30° C. | 21180 | 90% Model A | 2023.2 | — |
| S15Q + K26E + K36E + E46Y + E64P + K70P + S103V + P163A + T166P + Q168D + M172I + S178P + K197D + Q215E + M248I + S258G + S271G + N283Y + D385A + K408M + D410M + L413T | 37° C. | 3960 | 90% Model A | 87.9 | — |
| M172I + K197D + M248I + S258G + S271G + N283Y + D385A + K408M + D410M + L413T | 30° C. | 12720 | 90% Model A | 630.7 | — |
| V4M + S15Q + K26E + K36E + E46Y + T53Q + E64P + K70P + S103V + P163A + T166P + Q168D + M172I + S178P + K197D + Y213Q + M248I + S258G + S271G + N283Y + D385A + K408M + D410M + L413T | 37° C. | 5490 | 90% Model A | 80.5 | — |
| A1Y + F7G + S15Q + K26E + K36E + E46Y + E64P + K70P + S103V + I165E + T166P + Q168D + M172I + S178P + K197D + M248I + S258G + S271G + N283Y + T315V + K378Q + D385A + K408M + D410M + L413T | 37° C. | 5490 | 90% Model A | 95.7 | — |
| A1Y + F7G + S15Q + K26E + K36E + E46Y + E64P + K70P + S103V + Q143R + I165E + T166P + Q168D + M172I + S178P + K197D + M248I + S258G + S271G + N283Y + D385A + K408M + D410M + L413T | 37° C. | 5490 | 90% Model A | 106.6 | — |
| A1Y + F7G + S15Q + K26E + K36E + E46Y + E64P + K70P + S103V + I165E + T166P + Q168D + M172I + S178P + K197D + Q214R + M248I + S258G + S271G + N283Y + D385A + K408M + D410M + L413T | 37° C. | 5490 | 90% Model A | 108.0 | — |
| A1Y + F7G + S15Q + K26E + K36E + E46Y + E64P + K70P + S103V + I165E + T166P + Q168D + M172I + S178P + K197D + Q214R + M248I + S258G + S271G + N283Y + T315V + D385A + K408M + D410M + L413T | 30° C. | 18360 | 90% Model A | 2430.9 | — |
| A1Y + F7G + S15Q + K26E + K36E + E46Y + E64P + K70P + S103V + I165E + T166P + Q168D + M172I + S178P + K197D + M248I + S258G + S271G + N283Y + K304Q + T315V + D385A + K408M + D410M + L413T | 37° C. | 5490 | 90% Model A | 119.0 | — |
| A1Y + F7G + S15Q + K26E + K36E + E46Y + T53P + E64P + K70P + S103V + I165E + T166P + Q168D + M172I + S178P + K197D + M248I + S258G + S271G + N283Y + D385A + K408M + D410M + L413T | 37° C. | 5490 | 90% Model A | 126.3 | — |
| A1Y + F7G + S15Q + K26E + K36E + E46Y + E64P + K70P + S103V + E162D + I165E + T166P + Q168D + M172I + S178P + K197D + M248I + S258G + S271G + N283Y + D385A + K408M + D410M + L413T | 37° C. | 5490 | 90% Model A | 96.2 | — |
| A1Y + F7G + S15Q + K26E + K36E + E46Y + E64P + K70P + S103V + P121A + I165E + T166P + Q168D + | 37° C. | 5490 | 90% Model A | 86.6 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| M172I + S178P + K197D + M248I + S258G + S271G + N283Y + D385A + K408M + D410M + L413T | | | | | |
| A1Y + F7G + S15Q + K26E + K36E + E46Y + T53K + E64P + K70P + S103V + I165E + T166P + Q168D + M172I + S178P + K197D + M248I + S258G + S271G + N283Y + D385A + K408M + D410M + L413T | 37° C. | 5490 | 90% Model A | 84.7 | — |
| S15Q + K26E + K36E + E46Y + E64P + K70P + S103V + P163A + T166P + Q168D + M172I + S178P + K197D + S239A + M248I + S258G + S271G + N283Y + K378Q + D385A + K408M + D410M + L413T + P488I | 37° C. | 7050 | 90% Model A | 147.0 | — |
| S15Q + K26E + K36E + E46Y + E64P + K70P + S103V + P163A + T166P + Q168D + M172I + S178P + K197D + S239A + M248I + S258G + S271G + N283Y + K378Q + D385A + K408M + D410M + L413T + P488L | 37° C. | 5280 | 90% Model A | 124.8 | — |
| S15Q + K26E + K36E + E46Y + E64P + K70P + S103V + P163A + T166P + Q168D + M172I + S178P + M188Y + K197D + S239A + M248I + S258G + S271G + N283Y + K378Q + D385A + K408M + D410M + L413T | 37° C. | 5280 | 90% Model A | 257.0 | — |
| S15Q + K26E + K36E + E46Y + E64P + K70P + S103V + P163A + T166P + Q168D + M172I + S178P + F190Y + K197D + S239A + M248I + S258G + S271G + N283Y + K378Q + D385A + K408M + D410M + L413T | 30° C. | 31320 | 90% Model A | 2976.1 | — |
| S15Q + K26E + K36E + E46Y + E61D + E64P + K70P + S103V + P163A + T166P + Q168D + M172I + S178P + K197D + S239A + M248I + S258G + S271G + N283Y + K378Q + D385A + K408M + D410M + L413T | 37° C. | 5280 | 90% Model A | 217.1 | — |
| S15Q + K26E + K36E + E46Y + K65N + K70P + S103V + P163A + T166P + Q168D + M172I + S178P + K197D + S239A + M248I + S258G + S271G + N283Y + K378Q + D385A + K408M + D410M + L413T | 30° C. | 28440 | 90% Model A | 2602.1 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + D385A + K408M + D410M + L413T + R489N | 37° C. | 7050 | 90% Model A | 113.8 | — |
| S15Q + K26E + K36E + E46Y + K65N + K70P + S103V + A126T + P163A + T166P + Q168D + M172I + S178P + K197D + Y213R + S239A + M248I + S258G + S271G + N283Y + D385A + K408M + D410M + L413T | 37° C. | 7050 | 90% Model A | 132.6 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + D385A + K408M + D410M + L413T + K482D | 37° C. | 7050 | 90% Model A | 106.8 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + D385A + K408M + D410M + L413T + S487G | 37° C. | 7050 | 90% Model A | 152.5 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q + K26E + K36E + E46Y + E64P + K70P + S103V + A126T + P163A + T166P + Q168D + M172I + S178P + K197D + Y213R + S239A + M248I + S258G + S271G + N283Y + K378D + D385A + K408M + D410M + L413T | 37° C. | 5280 | 90% Model A | 234.5 | — |
| S15Q + K26E + K36E + E46Y + E64P + K70P + S103V + A126T + P163A + T166P + Q168D + M172I + S178P + K197D + Q214R + S239A + M248I + S258G + S271G + N283Y + K378D + D385A + S403Q + K408M + D410M + L413T + K482D | 37° C. | 5280 | 90% Model A | 154.6 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + K378D + D385A + K408M + D410M + L413T + K482D | 37° C. | 5280 | 90% Model A | 162.3 | — |
| S15T + K26E + K36E + E46Y + T53Q + E64P + K70P + S103V + P121A + P163A + T166P + Q168D + M172I + S178P + K197D + S239A + M248I + S258G + S271G + N283Y + K378Q + D385A + K408M + D410M + L413T | 37° C. | 5280 | 90% Model A | 131.3 | — |
| S15Q + K26E + K36E + E46Y + E64P + K70P + S103V + P163A + T166P + Q168D + M172I + S178P + K197D + Y213Q + S239A + M248I + S258G + S271G + N283Y + K378Q + D385A + K408M + D410M + L413T | 37° C. | 8160 | 90% Model A | 161.5 | — |
| S15Q + K26E + K36E + E46Y + E64P + K70P + S103V + P163A + T166P + Q168D + M172I + S178P + F190Y + K197D + Y213Q + S239A + M248I + S258G + S271G + N283Y + K378Q + D385A + K408M + D410M + L413T | 37° C. | 5280 | 90% Model A | 310.4 | — |
| S15Q + K26E + K36E + E46Y + E64P + K70P + S103V + A126T + L134T + E162D + P163E + T166P + Q168D + M172I + S178P + K197D + Y213R + S239A + M248I + S258G + S271G + N283Y + D385A + K408M + D410M + L413T | 37° C. | 5280 | 90% Model A | 161.1 | — |
| S15Q + K26E + K36E + E46Y + E64P + K70P + S103V + A126T + E162D + P163E + T166P + Q168D + M172I + S178P + K197D + Y213R + S239A + M248I + S258G + S271G + N283Y + D385A + K408M + D410M + L413T | 37° C. | 5280 | 90% Model A | 199.0 | — |
| S15Q + K26E + K36E + E46Y + E64P + K70P + S103V + A126T + P163A + T166P + Q168D + M172I + S178P + K197D + Y213R + S239A + M248I + S258G + S271G + N283Y + D385A + K408M + D410M + L413T + N473Y | 37° C. | 5280 | 90% Model A | 230.3 | — |
| V9P + S15Q + K26E + K36E + E46Y + E64P + K70P + S103V + Q143R + P163A + T166P + Q168D + M172I + S178P + K197D + S239A + M248I + S258G + S271G + N283Y + K378Q + D385A + K408M + D410M + L413T | 37° C. | 5280 | 90% Model A | 287.2 | — |
| V9P + S15Q + K26E + K36E + E46Y + E64P + K70P + S103V + P163A + T166P + Q168D + M172I + S178P + K197D + S239A + M248I + S258G + S271G + N283Y + K378Q + D385A + K408M + D410M + L413T | 37° C. | 5280 | 90% Model A | 217.5 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| V9P + S15Q + K26E + K36E + E46Y + E64P + K70P + S103V + P163A + T166P + Q168D + M172I + S178P + K197D + S239A + M248I + S258G + S271G + N283Y + K378Q + D385A + K408M + D410M + L413T | 37° C. | 5280 | 90% Model A | 270.9 | — |
| V8W + S15Q + K26E + K36E + E46Y + E64P + K70P + S103V + P163E + T166P + Q168D + M172I + S178P + F190Y + K197D + Y213R + S239A + M248I + S258G + S271G + N283Y + D385A + K408M + D410M + L413T | 30° C. | 26910 | 90% Model A | 2884.8 | — |
| V8W + S15Q + K26E + K36E + E46Y + E64P + K70P + S103V + P121A + P163E + T166P + Q168D + M172I + S178P + F190Y + K197D + Y213R + S239A + M248I + S258G + S271G + N283Y + D385A + K408M + D410M + L413T | 37° C. | 5280 | 90% Model A | 187.8 | — |
| T3E + S15Q + K26E + K36E + E46Y + E64P + K70P + S103V + P163A + T166P + Q168D + M172I + S178P + F190Y + K197D + Y213R + S239A + M248I + S258G + S271G + N283Y + D385A + K408M + D410M + L413T | 37° C. | 5280 | 90% Model A | 217.3 | — |
| F7G + S15Q + K26E + K36E + E46Y + E64P + K70P + S103V + P163A + T166P + Q168D + M172I + S178P + F190Y + K197D + Y213R + S239A + M248I + S258G + S271G + N283Y + D385A + K408M + D410M + L413T | 37° C. | 5280 | 90% Model A | 195.7 | — |
| A1Y + F7G + S15Q + K26E + K36E + E46Y + E64P + K70P + S103V + I165E + T166P + Q168D + M172I + S178P + K197D + S239A + M248I + S258G + S271G + N283Y + K378Q + D385A + K408M + D410M + L413T | 30° C. | 31320 | 90% Model A | 3910.7 | — |
| S15Q + K26E + K36E + E46Y + E64P + K70P + S103V + P163A + T166P + Q168D + M172I + S178P + F190Y + K197D + Q214R + S239A + M248I + S258G + S271G + N283Y + K378Q + D385A + K408M + D410M + L413T | 37° C. | 6780 | 90% Model A | 163.0 | — |
| S15Q + K26E + K36E + E46Y + E64P + K70P + S103V + P163A + T166P + Q168D + M172I + S178P + F190Y + K197D + Q214R + S239A + M248I + S258G + S271G + N283Y + K378Q + D385A + K408M + D410M + L413T + P488L | 37° C. | 6780 | 90% Model A | 167.9 | — |
| S15Q + K26E + K36E + E46Y + E64P + K70P + S103V + P163A + T166P + Q168D + M172I + S178P + F190Y + K197D + S239A + M248I + S258G + S271G + N283Y + K378Q + D385A + K408M + D410M + L413T + N473Y | 30° C. | 35640 | 90% Model A | 3244.2 | — |
| S15Q + K26E + K36E + E46Y + T53P + E64P + K70P + S103V + P121A + P163A + T166P + Q168D + M172I + S178P + K197D + Y213Q + S239A + M248I + S258G + S271G + N283Y + K378Q + D385A + K408M + D410M + L413T | 37° C. | 5340 | 90% Model A | 164.0 | — |
| S15Q + K26E + K36E + E46Y + E64P + K70P + S103V + P121A + Q143R + P163A + T166P + Q168D + M172I + S178P + K197D + Q214R + S239A + M248I + S258G + S271G + N283Y + K378Q + D385A + K408M + D410M + L413T | 30° C. | 29760 | 90% Model A | 3399.0 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| S15Q + K26E + K36E + E46Y + E64P + K70P + S103V + P121A + Q143R + P163A + T166P + Q168D + M172I + S178P + K197D + Y213Q + S239A + M248I + S258G + S271G + N283Y + K378Q + D385A + K408M + D410M + L413T | 37° C. | 5340 | 90% Model A | 195.2 | — |
| S15Q + K26E + K36E + E46Y + E64P + K70P + S103V + E162D + T166P + Q168D + M172I + S178P + K197D + Q214R + S239A + M248I + S258G + S271G + N283Y + K378Q + D385A + K408M + D410M + L413T + R489N | 30° C. | 29760 | 90% Model A | 3431.1 | — |
| S15Q + K26E + K36E + E46Y + E64P + K70P + S103V + P163A + T166P + Q168D + M172I + S178P + K197D + Q214R + S239A + M248I + S258G + S271G + N283Y + K378Q + D385A + K408M + D410M + L413T | 37° C. | 5340 | 90% Model A | 166.0 | — |
| A1Y + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 30° C. | 35640 | 90% Model A | 3658.1 | — |
| A1Y + F7G + S15Q + K26E + K36E + E46Y + E64P + K70P + S103V + P121A + I165E + T166P + Q168D + M172I + S178P + K197D + S239A + M248I + S258G + S271G + N283Y + K378Q + D385A + K408M + D410M + L413T | 30° C. | 31320 | 90% Model A | 3483.3 | — |
| A1Y + F7G + S15Q + K26E + K36E + E46Y + E64P + K70P + S103V + Q143R + I165E + T166P + Q168D + M172I + S178P + K197D + Q214R + S239A + M248I + S258G + S271G + N283Y + K378Q + D385A + K408M + D410M + L413T | 37° C. | 8160 | 90% Model A | 182.5 | — |
| S15Q + K26E + K36E + E46Y + E64P + K70P + S103V + Q143R + P163A + T166P + Q168D + M172I + S178P + K197D + Y213Q + S239A + M248I + S258G + S271G + N283Y + K378Q + D385A + K408M + D410M + L413T | 37° C. | 8160 | 90% Model A | 164.8 | — |
| S15Q + K26E + K36E + E46Y + E64P + K70P + S103V + P163A + T166P + Q168D + M172I + S178P + F190Y + K197D + S239A + M248I + S258G + S271G + N283Y + K378Q + D385A + K408M + D410M + L413T + H442N + N473Y | 30° C. | 31200 | 90% Model A | 2830.6 | — |
| S15Q + K26E + K36E + E46Y + E64P + K70P + S103V + P163A + T166P + Q168D + M172I + S178P + F190Y + K197D + S239A + M248I + S258G + S271G + N283Y + E299W + K378Q + D385A + K408M + D410M + L413T + N473Y | 30° C. | 31200 | 90% Model A | 3368.7 | — |
| S15Q + K26E + K36E + E46Y + E64P + K70P + S103V + P163A + T166P + Q168D + M172I + S178P + F190Y + K197D + S239A + M248I + S258G + S271G + N283Y + K378Q + D385A + K408M + D410M + L413T + N473Y + K482R + K491E | 30° C. | 31200 | 90% Model A | 3610.2 | — |
| V4D + V8D + S15Q + K26E + K36E + E46Y + E64P + K70P + S103V + P163A + T166P + Q168D + M172I + | 30° C. | 31200 | 90% Model A | 2768.8 | — |

TABLE 5-continued

| Protease stability at pH 8. The protease is a variant of SEQ ID NO: 14 with the following modifications: Y161A + R164S + A188P added in 0.8% (w/w) concentration | | | | | |
|---|---|---|---|---|---|
| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
| S178P + F190Y + K197D + S239A + M248I + S258G + S271G + N283Y + K378Q + D385A + K408M + D410M + L413T + N473Y | | | | | |
| A1Y + F7G + S15Q + K26E + K36E + E46Y + E64P + K70P + S103V + P121A + Q143R + I165E + T166P + Q168D + M172I + S178P + K197D + Q214R + S239A + M248I + S258G + S271G + N283Y + K378Q + D385A + K408M + D410M + L413T + H442N + K466N + K482G | 30° C. | 31200 | 90% Model A | 3147.7 | — |
| A1Y + F7G + S15Q + K26E + K36E + E46Y + E64P + K70P + S103V + P121A + Q143R + 165E + T166P + Q168D + M172I + S178P + K197D + Q214R + S239A + M248I + S258G + S271G + N283Y + K378Q + D385A + K408M + D410M + L413A | 30° C. | 31200 | 90% Model A | 3111.4 | — |
| A1Y + F7G + S15Q + K26E + K36E + E46Y + E64P + K70P + S103V + P121A + I165E + T166P + Q168D + M172I + S178P + K197D + S239A + M248I + S258G + S271G + N283Y + E380D + D385A + K408M + D410M + L413T + G440Q | 37° C. | 7200 | 90% Model A | 176.3 | — |
| A1Y + F7G + S15Q + K26E + K36E + E46Y + E64P + K70P + S103V + P121A + I165E + T166P + Q168D + M172I + S178P + K197D + S239A + M248I + S258G + S271G + N283Y + K378Q + D385A + K408M + D410M + L413T + H442N | 37° C. | 7200 | 90% Model A | 178.6 | — |
| A1Y + F7G + S15Q + K26E + K36E + E46Y + E64P + K70P + S103V + P121A + I165E + T166P + Q168D + M172I + S178P + K197D + S239A + M248I + R253A + S258G + S271G + N283Y + K378Q + D385A + K408M + D410M + L413T + H442N | 30° C. | 31320 | 90% Model A | 3138.5 | — |
| T3E F7G S15Q K26E K36E E46Y E64P K70P S103V P163A T166P Q168D M172I S178P F190Y K197D Q214R S239A M248I S258G S271G N283Y E299W K378Q D385A K408M D410M L413T N473Y | 30° C. | 45960 | 90% Model A | 6221.2 | — |
| S15Q + K26E + K36E + E46Y + E64P + K70P + S103V + P163A + T166P + Q168D + M172I + S178P + F190Y + K197D + S239A + M248I + S258G + S271G + N283Y + G366H + K378Q + D385A + K408M + D410M + L413T + N473Y | 37° C. | 7200 | 90% Model A | 250.0 | — |
| A1Y + F7G + S15Q + K26E + K36E + E46Y + E64P + K70P + S103V + P121A + R160N + I165E + T166P + Q168D + M172I + S178P + K197D + Y219W + S239A + M248I + S258G + S271G + N283Y + K378Q + D385A + K408M + D410M + L413T | 37° C. | 7200 | 90% Model A | 193.8 | — |
| A1Y + F7G + S15Q + K26E + K36E + E46Y + E64P + K70P + S103V + P121A + Q143R + I165E + T166P + Q168D + M172I + S176N + S178P + K197D + S239A + M248I + S258G + S271G + N283Y + K378Q + D385A + K408M + D410M + L413T | 37° C. | 8160 | 90% Model A | 127.8 | — |
| A1Y + F7G + S15Q + K26E + K36E + E46Y + E64P + K70P + S103V + P121A + Q143R + I165E + T166P + | 37° C. | 8160 | 90% Model A | 166.6 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| Q168D + M172I + S178P + K197D + S239A + M248I + S258G + S271G + N283Y + K378Q + D385A + K408M + D410M + L413T + H442D + S487R | | | | | |
| A1Y + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + H442D + K482D + S487R | 37° C. | 8160 | 90% Model A | 172.4 | — |
| A1Y + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 30° C. | 39900 | 90% Model A | 4198.1 | — |
| A1Y + F7G + S15Q + K26E + K36E + E46Y + E64P + K70P + S103V + P121A + R160K + P163A + I165E + T166P + Q168D + M172I + S178P + K197D + S239A + M248I + S258G + S271G + N283Y + K378Q + D385A + K408M + D410M + L413T | 37° C. | 8160 | 90% Model A | 165.0 | — |
| A1Y + F7G + S15Q + K26E + K36E + E46Y + E64P + K70P + S103V + P121A + R160V + P163A + I165E + T166P + Q168D + M172I + S178P + K197D + S239A + M248I + S258G + S271G + N283Y + K378Q + D385A + K408M + D410M + L413T | 37° C. | 8160 | 90% Model A | 149.1 | — |
| A1Y + F7G + S15Q + K26E + K36E + E46Y + E64P + K70P + S103V + P121A + E162G + P163A + I165E + T166P + Q168D + M172I + S178P + K197D + S239A + M248I + S258G + S271G + N283Y + K378Q + D385A + K408M + D410M + L413T | 37° C. | 8160 | 90% Model A | 174.3 | — |
| A1* + I2* + T3* + V4* + P5* + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 8160 | 90% Model A | 198.7 | — |
| A1Y + G6* + F7* + V8* + V9* + E10* + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 8160 | 90% Model A | 184.5 | — |
| E10* + V9* + V8* + F7* + G6* + P5* + V4* + T3* + I2* + A1* + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 8160 | 90% Model A | 178.1 | — |
| T3E + F7G + S15Q + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 10080 | 90% Model A | 428.6 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378D + D385A + K408M + D410M + L413T + N473Y + K482Q | 37° C. | 10080 | 90% Model A | 410.5 | — |
| T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378D + D385A + K408M + D410M + L413T + N473Y | 37° C. | 10080 | 90% Model A | 255.5 | — |
| A1S + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 8100 | 90% Model A | 224.0 | — |
| A1Y + F7D + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 8100 | 90% Model A | 215.0 | — |
| A1Y + F7D + S15Q + K26E + K36E + E46Y + E64P + K70P + S103V + P121A + L134P + Q143R + I165E + T166P + Q168D + M172I + S178P + K197D + S239A + M248I + S258G + S271G + N283Y + K378Q + D385A + K408M + D410M + L413T | 37° C. | 8100 | 90% Model A | 181.9 | — |
| A1Y + F7D + S15Q + K26E + K36E + E46Y + E64P + K70P + S103V + P121A + Q143R + I165E + T166P + Q168D + M172I + S178P + K197D + S239A + M248I + S258G + 269 + S271G + N283Y + K378Q + D385A + K408M + D410M + L413T | 37° C. | 8100 | 90% Model A | 212.0 | — |
| A1Y + F7G + Q17A + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 8100 | 90% Model A | 243.3 | — |
| A1Y + F7G + S15Q + N18S + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 8100 | 90% Model A | 203.8 | — |

TABLE 5-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time(min) | Detergent in stress | HIF over WT (SEQ ID NO: 1) | HIF over WT (SEQ ID NO: 1 + K26E + K36E + E64P + K70P + S103V Q168D + N283Y + D385A + L413T + L477F) |
|---|---|---|---|---|---|
| A1Y + F7G + S15Q + K26E + K36E + E46Y + E64P + K70P + S103V + P121A + P163A + I165E + T166P + Q168D + M172I + S178P + K197D + S239A + M248I + S258G + S271G + N283Y + K378Q + D385A + K408M + D410M + L413T | 37° C. | 9660 | 90% Model A | 173.9 | — |
| A1Y + F7G + S15Q + K26E + K36E + E46Y + E64P + K70P + S103V + P121A + A126T + P163A + I165E + T166P + Q168D + M172I + S178P + K197D + S239A + M248I + S258G + S271G + N283Y + K378Q + D385A + K408M + D410M + L413T | 37° C. | 9660 | 90% Model A | 161.7 | — |
| A1Y + F7G + S14N + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 9660 | 90% Model A | 210.6 | — |
| A1Y + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 9660 | 90% Model A | 222.7 | — |
| A1Y + F7G + S15Q + A23S + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T | 37° C. | 9660 | 90% Model A | 182.5 | — |
| A1Y + F7G + S15Q + 122V + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 9660 | 90% Model A | 267.2 | — |

TABLE 6

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over SEQ ID NO: 1 |
|---|---|---|---|---|
| T3E + F7G + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 30° C. | 14160 | 90% Model A | 759 |

TABLE 7

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + A1Y + F7G + S15Q + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q) |
|---|---|---|---|---|
| A1Y + F7G + S15Q + K26E + I30L + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 2460 | 90% Model A2 | 0.92 |
| A1Y + F7G + S15D + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 2460 | 90% Model A2 | 0.81 |
| A1Y + F7G + S15C + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q | 37° C. | 2460 | 90% Model A2 | 0.99 |

TABLE 8

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + T3E + F7G + S15Q + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R) |
|---|---|---|---|---|
| T3E + F7G + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + G366H + K378Q + D385A + K408M + D410M + L413T + H442N + N473Y + K491R | 37° C. | 2460 | 90% Model A2 | 1.10 |

TABLE 9

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + A1Y + F7G ++ S15Q + I22V + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q) |
|---|---|---|---|---|
| A1Y + F7G + S15Q + I22V + K26E + K36E + E46Y + E64P + K70P + S103V + P121A + Q143R + I165E + T166P + Q168D + M172I + S178P + K197D + Q214R + G217Q + S239A + M248I + S258G + S271G + R280K + N283Y + K378Q + D385A + K408M + D410M + L413T + G440Q | 37° C. | 2520 | 90% Model A2 | 1.77 |
| A1Y + F7G + S15Q + I22V + K26E + K36E + E46Y + E64P + K70P + S103V + P121A + Q143R + I165E + T166P + Q168D + M172I + S178P + K197D + Q214W + S239A + M248I + S258G + S271G + R280K + N283Y + K378Q + D385A + K408M + D410M + L413T + G440Q | 37° C. | 2520 | 90% Model A2 | 1.38 |
| A1Y + F7G + S15Q + I22V + K26E + K36E + E46Y + E64P + K70P + S103V + P121A + Q143R + I165E + T166P + Q168D + M172I + S178P + K197D + Q214R + G217Q + S239A + M248I + S258G + S271G + R280K + N283Y + W342G + K378Q + D385A + K408M + D410M + L413T + G440Q | 30° C. | 14160 | 90% Model A2 | 1.72 |
| A1Y + F7G + S15Q + I22V + K26E + K36E + E46Y + E64P + K70P + S103V + P121A + Q143R + I165E + T166P + Q168D + M172I + S178P + K197D + Q215E + S239A + M248I + S258G + S271G + R280K + N283Y + K378Q + D385A + K408M + D410M + L413T + G440Q | 37° C. | 2520 | 90% Model A2 | 1.49 |
| A1Y + F7G + S15Q + I22V + K26E + K36E + E46Y + E64P + K70P + S103V + P121A + Q143R + I165E + T166P + Q168D + M172I + S178P + K197D + Q214R + S239A + M248I + S258G + S271G + R280K + N283Y + K378Q + D385A + K408M + D410M + L413T + G440Q | 30° C. | 14160 | 90% Model A2 | 1.74 |
| A1Y + F7G + S15Q + I22V + K26E + K36E + E46Y + E64P + K70P + S103V + P121A + Q143R + I165E + T166P + Q168D + M172I + S178P + K197D + Q214W + G217Q + S239A + M248I + S258G + S271G + R280K + N283Y + K378Q + D385A + K408M + D410M + L413T + G440Q | 37° C. | 2520 | 90% Model A2 | 1.67 |
| A1Y + F7G + S15Q + I22V + K26E + K36E + E46Y + E64P + K70P + S103V + P121A + Q143R + I165E + T166P + Q168D + M172I + S178P + K197D + S239A + M248I + S258G + S271G + R280K + N283Y + K378Q + D385A + K408M + D410M + L413T + G440Q | 30° C. | 14160 | 90% Model A2 | 1.76 |
| A1Y + F7G + S15Q + I22V + K26E + K36E + E46Y + T53K + E64P + K70P + S103V + P121A + Q143R + I165E + T166P + Q168D + M172I + K179N + K197D + S239A + M248I + S258G + S271G + R280K + N283Y + K378Q + D385A + K408M + D410M + L413T + G440Q | 37° C. | 2760 | 90% Model A2 | 1.47 |
| A1Y + F7G + S15Q + I22V + K26E + K36E + E46Y + T53K + E64P + K70P + S103V + P121A + Q143R + I165E + T166P + Q168D + M171Q + K179N + | 37° C. | 2520 | 90% Model A2 | 2.09 |

TABLE 9-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + A1Y + F7G ++ S15Q + I22V + K26E + K36E + E46Y + E64P + K70P + S103V + P121A + Q143R + I165E + T166P + Q168D + M172I + S178P + K197D + S239A + M248I + S258G + S271G + N283Y + K378Q + D385A + K408M + D410M + L413T + G440Q) |
|---|---|---|---|---|
| K197D + S239A + M248I + S258G + S271G + R280K + N283Y + K378Q + D385A + K408M + D410M + L413T + G440Q | | | | |
| A1Y + F7G + S15Q + I22V + K26E + K36E + E46Y + E64P + K70P + S103V + P121A + Q143R + I165E + T166P + Q168D + M172I + S178P + M188Y + K197N + G217Q + S239A + M248I + S258G + S271G + N283Y + K378Q + D385A + K408M + D410M + L413T + G440Q | 37° C. | 2520 | 90% Model A2 | 1.31 |

TABLE 10

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + T3E + F7G + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R) |
|---|---|---|---|---|
| T3E + F7G + S15Q + A20G + K26D + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2760 | 90% Model A2 | 1.08 |
| T3E + F7G + S15Q + A20G + K26E + K36E + E46Y + E64P + K70P + S103V + K120A + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2760 | 90% Model A2 | 1.24 |
| T3E + F7G + S15Q + A20G + K26E + K36E + E46Y + E64P + K70P + S103A + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2760 | 90% Model A2 | 0.95 |
| T3E + V9G + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2760 | 90% Model A2 | 0.93 |
| T3E + V9M + S15Q + A20G + K26E + K36E + E46Y + E64P + K70P + S103V + S141R + P163A + T166P + Q168D + M172I + S178P + F190Y + K197D + | 37° C. | 2760 | 90% Model A2 | 1.02 |

TABLE 10-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | HIF over WT (SEQ ID NO: 1 + T3E + F7G + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R) |
| Q214R + S239A + M248I + S258G + S271G + N283Y + E299W + K378Q + D385A + K408M + D410M + L413T + N473Y + K491R | | | | |
| T3E + V9A + S15Q + A20G + K26E + K36E + E46Y + E64P + K70P + S103V + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2760 | 90% Model A2 | 1.26 |

TABLE 11

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | HIF over WT (SEQ ID NO: 1 + A1Y + F7G + S15Q + I22V + K26E + K36E + E46Y + E64P + K70P + S103V + P121A + Q143R + I165E + T166P + Q168D + M172I + S178P + K197D + Q214R + S239A + M248I + S258G + S271G + R280K + N283Y + K378Q + D385A + K408M + D410M + L413T + G440Q) |
| A1Y + F7G + S15Q + I22V + K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 2460 | 90% Model A2 | 1.26 |

TABLE 12

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | HIF over WT (SEQ ID NO: 1 + A1Y + F7G + S15Q + I22V + K26E + K36E + E46Y + T53K + E64P + K70P + S103V + P121A + Q143R + I165E + T166P + Q168D + M171Q + K179N + K197D + S239A + M248I + S258G + S271G + R280K + N283Y + K378Q + D385A + K408M + D410M + L413T + G440Q) |
| A1Y + F7G + S15Q + I22V + K26E + K36E + E46Y + T53K + E64P + K70P + S103V + P121A + Q143R + I165E + T166P + Q168D + M171Q + K179N + K197D + S239A + M248I + S258G + S271G + R280K + N283Y + | 37° C. | 2460 | 90% Model A2 | 1.20 |

TABLE 12-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + A1Y + F7G + S15Q + I22V + K26E + K36E + E46Y + T53K + E64P + K70P + S103V + P121A + Q143R + I165E + T166P + Q168D + M171Q + K179N + K197D + S239A + M248I + S258G + S271G + R280K + N283Y + K378Q + D385A + K408M + D410M + L413T + G440Q) |
|---|---|---|---|---|
| K378Q + D385A + K408M + D410M + L413T + T438A | | | | |
| A1Y + F7G + S15Q + I22V + K26E + K36E + E46Y + T53K + E64P + K70P + S103V + P121A + Q143R + I165E + T166P + Q168D + M171Q + K179N + K197D + S239A + M248I + S258G + S271G + R280K + N283Y + K378Q + D385A + K408M + D410M + L413T + T438A | 37° C. | 2460 | 90% Model A2 | 1.12 |

TABLE 13

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ ID NO: 1 + A1Y + F7G + S15Q + I22V + K26E + K36E + E46Y + T53K + E64P + K70P + S103V + P121A + Q143R + I165E + T166P + Q168D + M171 + K179N + K197D + S239A + M248I + S258G + S271G + R280K + N283Y + K378Q + D385A + K408M + D410M + L413T + T438A) |
|---|---|---|---|---|
| A1V + F7G + S15Q + I22V + K26E + K36E + E46Y + T53K + E64P + K70P + S103V + P121A + M130I + Q143R + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.33 |
| A1Y + F7G + S15Q + I22V + K26E + K36E + E46Y + T53K + E64P + K70P + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 4080 | 90% Model A2 | 1.33 |

TABLE 14

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ IDNO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| F7G + T3* + G6* + P5* + V4* + I2* + A1* + S15Q + K26E + K36E + E46Y + | 37° C. | 2640 | 90% Model | 0.86 |

TABLE 14-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | HIF over WT (SEQ IDNO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y | | | A2 | |
| T3* + V9* + V8* + G7* + G6* + P5* + V4* + I2* + A1* + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y | 37° C. | 2640 | 90% Model A2 | 0.97 |

TABLE 15

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3E + F7G + S15Q + A20G + K26E + I30L + K36E + E46M + E64P + K70P + S103V + K120A + S141R + P163A + T166P + Q168D + M172I + S178P + F190Y + K197D + Q214R + S239A + M248I + S258G + S271G + N283Y + E299W + K378Q + D385A + K408M + D410M + L413T + N473Y + K491R | 37° C. | 2700 | 90% Model A2 | 1.08 |
| A1V + F7G + T13I + S15Q + I22V + K26E + K36E + E46Y + T53K + E64P + K70P + S103V + P121A + M130I + Q143R + I165E + T166P + Q168D + M171Q + K179N + K197D + S239A + M248I + S258G + S271G + R280K + N283Y + K378Q + D385A + K408M + D410M + L413T + T438A | 37° C. | 4020 | 90% Model A2 | 1.10 |
| A1V + V8A + S15Q + I22V + K26E + K36E + E46Y + T53K + E64P + K70P + S103V + P121A + M130I + Q143R + I165E + T166P + Q168D + M171Q + K179N + K197D + S239A + M248I + S258G + S271G + R280K + N283Y + K378Q + D385A + K408M + D410M + L413T + T438A | 37° C. | 4020 | 90% Model A2 | 1.38 |
| A1Y + F7G + S15Q + I22V + K26E + K36E + E46Y + T53K + E64P + K70P + Q76T + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.58 |
| A1Y + F7G + S15Q + I22V + K26E + K36E + E46Y + T53K + E64P + Q69P + | 37° C. | 4020 | 90% Model A2 | 1.46 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| Q76T + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | | | | |
| A1Y + F7G + S15Q + I22V + K26E + K36E + E46Y + T53K + E64P + K70P + Q76T + S103V + P121A + Q143R + E162D + I165E + T166P + Q168D + M171Q + K179N + F190Y + K197D + Q214R + S239A + M248I + S258G + S271G + R280K + N283Y + K378Q + D385A + K408M + D410M + L413T + T438A | 37° C. | 2640 | 90% Model A2 | 1.66 |
| A1Y + F7G + T13I + S15Q + I22V + K26E + K36E + E46Y + T53K + E64P + K70P + Q76T + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.55 |
| A1V + F7G + P11A + S15Q + I22V + K26E + K36E + E46Y + T53K + E64P + K70P + S103V + P121A + M130I + Q143R + E162D + I165E + T166P + Q168D + M171Q + K179N + K197D + Y219W + S239A + M248I + S258G + S271G + R280K + N283Y + K378Q + D385A + K408M + D410M + L413T + T438A | 37° C. | 2640 | 90% Model A2 | 1.35 |
| A1Y + F7G + S15Q + I22V + K26E + K36E + E46Y + T53K + E64P + K70P + Q76T + S103V + P121A + M130I + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.21 |
| T3G + F7G + T13I + S15Q + A20G + K26E + I30L + K36E + E46Y + E64P + K70P + S103V + S141R + P163A + T166P + Q168D + M172I + S178P + F190Y + K197N + Q214R + Y219W + S239A + M248I + S258G + S271G + N283Y + E299W + K378Q + D385A + K408M + D410M + L413T + N473Y + K491R | 37° C. | 2640 | 90% Model A2 | 1.19 |
| A1V + F7G + T13I + S15Q + A20G + K26E + I30L + K36E + E46Y + E64P + K70P + S103V + S141R + P163A + T166P + Q168D + M172I + S178P + F190Y + K197N + Q214R + Y219W + S239A + M248I + S258G + S271G + N283Y + E299W + K378Q + D385A + K408M + D410M + L413T + N473Y + K491R | 37° C. | 2640 | 90% Model A2 | 1.53 |
| T3G + F7G + T13I + S15Q + A20G + K26E + K36E + E46Y + E64P + K70P + S103V + K120A + S141R + P163A + T166P + Q168D + M172I + S178P + F190Y + K197N + Q214R + Y219W + S239A + M248I + S258G + S271G + N283Y + E299W + K378Q + D385A + K408M + D410M + L413T + N473Y + K491R | 37° C. | 2640 | 90% Model A2 | 1.19 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + S15Q + A20G + K26E + K36E + E46M + E64P + K70P + S103V + K120A + S141A + P163A + T166P + Q168D + M172I + S176N + S178P + F190Y + K197D + A210E + Q214R + S239A + M248I + R253A + S258G + S271G + R280K + N283Y + K378Q + D385A + K408M + D410M + L413T + V422I + N473Y + K491R | 37° C. | 2640 | 90% Model A2 | 1.33 |
| A1V + F7G + T13I + S15Q + A20G + K26E + I30L + K36E + E46Y + E64P + K70P + S103V + S141R + P163T + T166P + Q168D + M172I + S178P + F190Y + K197D + Q214R + Y219W + S239A + M248I + S258G + S271G + N283Y + E299W + K378Q + D385A + K408M + D410M + L413T + N473Y + K491R | 37° C. | 3840 | 90% Model A2 | 1.09 |
| A1Y + F7G + P11E + S15Q + I22V + K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 3840 | 90% Model A2 | 1.18 |
| A1Y + F7G + P11I + S15Q + I22V + K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 3840 | 90% Model A2 | 1.18 |
| A1Y + F7G + S14Q + S15Q + I22V + K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 3840 | 90% Model A2 | 1.09 |
| A1Y + F7G + S14R + S15Q + I22V + K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 3840 | 90% Model A2 | 1.21 |
| A1Y + F7G + S15Q + I22V + K26E + K36E + A45M + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | 37° C. | 3840 | 90% Model A2 | 1.18 |
| A1V + F7G + P11A + S15Q + I21L + K26E + K36E + E46Y + T53K + E64P + K70P + Q76T + S103V + P121A + M130I + Q143R + E162D + I165E + T166P + Q168D + M171Q + K179N + K197D + Y219W + S239A + M248I + S258G + S271G + R280K + N283Y + K378Q + D385A + K408M + D410M + L413T + T438A | 37° C. | 2400 | 90% Model A2 | 1.34 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| A1V + F7G + P11A + S15Q + I21L + K26E + K36E + E46Y + T53K + E64P + K70P + Q76T + S103V + P121A + M130I + Q143R + Y155H + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.20 |
| A1V + F7G + P11A + S15Q + I21L + K26E + K36E + E46Y + T53K + E64P + K70P + Q76T + S103V + S109D + P121A + M130I + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.11 |
| T3G + F7G + S15Q + A20G + K26E + K36E + E46M + E64P + K70P + N82A + S103V + K120A + S141R + P163A + T166P + Q168D + M172I + S176N + S178P + F190Y + K197D + Q214R + Y219W + S239A + M248I + R253A + S258G + S271G + N283Y + E299W + K378Q + K408M + D410M + L413T + N473Y + K491R | 37° C. | 2640 | 90% Model A2 | 1.12 |
| A1V + F7G + P11A + S15Q + I21L + K26E + K36E + E46Y + T53K + E64P + K70P + Q76T + S103V + P121A + M130I + Q143R + I165E + T166P + Q168D + M171Q + K179N + T192V + K197D + S239A + M248I + S258G + S271G + R280K + N283Y + T315V + K378Q + D385A + K408M + D410M + L413T + T438A | 37° C. | 2400 | 90% Model A2 | 1.12 |
| T3G + F7G + S15Q + A20G + K26E + K36E + E46M + E64P + K70P + S103V + K120A + S141R + P163A + T166P + Q168D + M172I + S176N + S178P + F190Y + K197D + Q214R + Y219W + S239A + M248I + R253A + S258G + S271G + R280K + N283Y + E299W + K304Q + T315V + K378Q + K408M + D410M + L413T + N473Y + K491R | 37° C. | 2400 | 90% Model A2 | 1.14 |
| T3G + F7G + S15Q + A20G + K26E + I30L + K36E + E46M + K70P + S103V + K120A + S141R + P163A + T166P + Q168D + M172I + S176N + S178P + F190Y + K197D + Q214R + Y219W + S239A + M248I + R253A + S258G + S271G + N283Y + E299W + K378Q + K408M + D410M + L413T + N473Y + K491R | 37° C. | 2400 | 90% Model A2 | 1.84 |
| T3G + F7G + S15Q + A20G + K26E + I30L + K36E + E46M + E64P + K70P + Q76T + A101R + S103V + G110R + M130I + S141R + P163A + T166P + Q168D + M172I + S176N + S178P + F190Y + K197D + Q214R + Y219W + S239A + M248I + R253A + S258G + S271G + N283Y + E299W + K378Q + D385A + K408M + D410M + L413T + N473Y + K491R | 37° C. | 2400 | 90% Model A2 | 1.29 |
| A1V + F7G + T13I + S15Q + A20G + K26E + I30L + K36E + E46Y + E64P + K70P + S103E + S109D + S141R + | 37° C. | 2640 | 90% Model A2 | 2.09 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| E162D + T166P + Q168D + M172I + S178P + F190Y + K197N + Q214R + Y219W + S239A + M248I + S258G + S271G + N283Y + E299W + K378Q + D385A + K408M + D410M + L413T + N473Y + K491R | | | | |
| A1V + F7G + T13I + S15Q + A20G + K26E + I30L + K36E + E46Y + E64P + K70P + S103A + S141R + W148Q + E162D + T166P + Q168D + M172I + S178P + F190Y + K197N + Q214R + Y219W + S239A + M248I + S258G + S271G + N283Y + E299W + K378Q + D385A + K408M + D410M + L413T + N473Y + K491R | 37° C. | 2760 | 90% Model A2 | 1.25 |
| A1V + F7G + P11A + S15Q + I21L + K26E + K36E + E46Y + T53K + E64P + K70P + Q76T + S103V + P121A + M130I + Q143R + E162D + I165E + T166P + Q168D + M171Q + K179N + K197D + Y219W + S239A + M248I + S258G + S271G + H276Y + R280K + N283Y + E299D + K378Q + D385A + K408M + D410M + L413T + T438A | 37° C. | 2760 | 90% Model A2 | 1.18 |
| T3G + F7G + S15Q + A20G + K26E + K36E + E46M + E64P + K70P + N82T + S103E + K120A + S141R + P163A + T166P + Q168D + M172I + S176N + S178P + F190Y + K197D + Q214R + Y219W + S239A + M248I + R253A + S258G + S271G + N283Y + E299W + K378Q + K408M + D410M + L413T + N473Y + K491R | 37° C. | 2760 | 90% Model A2 | 1.59 |
| A1V + F7G + P11A + S15Q + I21L + K26E + K36E + E46Y + T53K + E64P + Q69P + K70P + Q76T + S103V + P121A + M130I + Q143R + E162D + I165E + T166P + Q168D + M171Q + K179N + K197D + Y219W + S239A + M248I + S258G + S271G + R280K + N283Y + K378Q + D385A + K408M + D410M + L413T + T438A | 37° C. | 2640 | 90% Model A2 | 1.29 |
| A1V + F7G + T13I + S15Q + A20G + K26E + I30L + K36E + E46Y + E61D + E64P + Q69P + K70P + Q76T + S141R + E162D + T166P + Q168D + M172I + S178P + F190Y + K197N + Q214R + Y219W + S239A + M248I + S258G + S271G + R280K + N283Y + E299W + K378Q + D385A + K408M + D410M + L413T + N473Y + K491R | 37° C. | 3840 | 90% Model A2 | 2.19 |
| T3G + F7G + S15Q + A20G + K26E + I30L + K36E + E46M + K70P + Q76T + A101R + S103V + G110R + M130I + S141Q + P163A + T166P + Q168D + M172I + S176N + S178P + F190Y + K197D + Q214R + Q215E + Y219W + S239A + M248I + R253A + S258G + S271G + N283Y + E299W + K378Q + D385A + K408M + D410M + L413V + N473Y + D486K + K491R | 30° C. | 14160 | 90% Model A2 | 1.05 |
| A1V + F7G + T13I + S15Q + A20G + K26E + I30L + K36E + E46Y + E61D + E64P + Q69P + K70P + Q76T + S103R + G122P + S141R + E162D + T166P + Q168D + M172I + S178P + F190Y + K197N + Q214R + Y219W + S239A + | 30° C. | 14160 | 90% Model A2 | 1.15 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| M248I + S258G + S271G + R280K + N283Y + E299W + K378Q + D385A + K408M + D410M + L413T + N473Y + K491R | | | | |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Y219W + S239A + M248I + R253A + S258G + S271G + N283Y + E299W + K378Q + K408M + D410M + L413T + N473Y + K491R | 37° C. | 4080 | 90% Model A2 | 1.69 |
| T3G + F7G + V9A + S15Q + A20G + K26E + K36E + E46M + E61D + E64P + Q69P + K70P + N82T + S103E + K120A + S141R + P163A + T166P + Q168D + M172I + S176N + S178P + F190Y + K197D + Q214R + Y219W + S239A + M248I + R253A + S258G + S271G + N283Y + E299W + K378Q + K408M + D410M + L413T + N473Y + K491R | 37° C. | 4080 | 90% Model A2 | 1.59 |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + K408M + D410M + L413T + N473Y + K491R | 37° C. | 4080 | 90% Model A2 | 2.33 |
| A1V + F7G + P11N + S15Q + I21L + K26E + K36E + E46Y + T53K + E64P + Q69P + K70P + Q76T + N82T + S103V + S109D + K120A + P121A + M130I + Q143R + E162D + I165E + T166P + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4080 | 90% Model A2 | 1.42 |
| A1V + F7G + P11A + S15Q + I21L + K26E + K36E + E46Y + T53K + E64P + Q69P + K70P + Q76T + N82T + S103V + S109D + K120A + P121A + M130I + Q143R + E162D + I165E + T166P + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4080 | 90% Model A2 | 1.40 |
| A1V + F7G + P11A + S15Q + I21L + K26E + K36E + E46Y + T53K + E64P + Q69P + K70P + Q76T + N82T + S103V + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4080 | 90% Model A2 | 1.53 |
| A1V + F7G + T13I + S15Q + A20G + K26E + I30L + K36E + E46Y + E64P + K70P + S103E + S109D + S141R + E162D + T166P + Q168D + M172I + S178P + F190Y + K197N + Q214R + | 37° C. | 4080 | 90% Model A2 | 1.73 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q215E + Y219W + S239A + M248I + S258G + S271G + R280K + N283Y + E299W + K378Q + D385A + K408M + D410M + L413T + N473Y + K491R | | | | |
| T3G + F7G + V9A + S15Q + A20G + K26E + K36E + E46M + E61D + E64P + Q69P + K70P + N82T + S103E + K120A + S141R + P163T + T166P + Q168D + M172I + S176N + S178P + F190Y + K197D + Q214R + Y219W + S239A + M248I + R253A + S258G + S271G + R280K + N283Y + E299W + K378Q + K408M + D410M + L413T + N473Y + K491R | 37° C. | 4110 | 90% Model A2 | 1.57 |
| T3G + F7G + V9A + S15Q + A20G + K26E + K36E + E46M + E61D + E64P + Q69P + K70P + N82T + S103E + K120A + S141R + P163A + T166P + Q168D + M172I + S176N + S178P + F190Y + K197D + Q214R + Y219W + S239A + M248I + R253A + S258G + S271G + R280K + N283Y + E299W + K378Q + K408M + D410M + L413T + N473Y + K491R | 37° C. | 4110 | 90% Model A2 | 1.79 |
| T3G + F7G + V9A + S15Q + A20G + K26E + K36E + E46M + E64P + Q69P + K70P + N82T + S103E + K120A + S141R + P163A + T166P + Q168D + M171Q + M172I + S176N + S178R + F190Y + K197D + Q214R + Q215E + Y219W + S239A + M248I + R253A + S258G + S271G + R280K + N283Y + E299W + K378Q + K408M + D410M + L413T + N473Y + K491R | 37° C. | 4080 | 90% Model A2 | 2.80 |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4080 | 90% Model A2 | 2.17 |
| A1V + F7G + P11A + S15Q + I21L + K26E + K36E + E46Y + T53K + E64P + Q69P + K70P + Q76T + N82T + S103V + S109D + P121A + M130I + Q143R + E162D + I165E + T166P + T167A + Q168D + M171Q + K179N + M188F + K197D + Y219W + S239A + M248I + S258G + S271G + R280K + N283Y + K304Q + E363H + K378Q + D385A + K408M + D410M + L413T + T438A | 37° C. | 4080 | 90% Model A2 | 1.69 |
| A1V + F7G + P11A + S15Q + I21L + K26E + K36E + E46Y + T53K + E64P + Q69P + K70P + T74E + Q76T + N82T + S103V + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.13 |
| A1V + F7G + P11A + S15Q + I21L + K26E + K36E + E46Y + T53K + E64P + Q69P + K70P + Q76T + N82T + S103V + | 37° C. | 4080 | 90% Model A2 | 1.24 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A + K462R | | | | |
| A1V + F7G + P11A + T13I + S15Q + Q19N + A20G + K26E + K36E + E46Y + T53K + E64P + Q69P + K70P + Q76T + N82T + S103V + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.08 |
| A1V + F7G + P11A + S15Q + I21L + K26E + K36E + E46Y + T53K + E64P + Q69P + K70P + Q76T + N82T + S103E + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.24 |
| A1V + F7G + P11A + S15Q + I21L + K26E + K36E + E46Y + T53K + E64P + Q69P + K70P + T74E + Q76T + N82T + S103E + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.29 |
| A1V + F7G + P11A + S15Q + I21L + K26E + I30L + K36E + E46Y + T53K + E64P + Q69P + K70P + Q76T + N82T + S103V + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.11 |
| A1V + F7G + T13I + S15Q + I21L + K26E + I30L + K36E + E46Y + T53K + E64P + Q69P + K70P + Q76T + N82T + S103V + S109D + P121A + M130I + Q143R + E162D + I165E + T166P + T167A + Q168D + M171Q + K179N + K197D + Y219W + S239A + M248I + S258G + S271G + R280K + N283Y + K304Q + E363H + K378Q + D385A + K408M + D410M + L413T + T438A | 37° C. | 4110 | 90% Model A2 | 1.06 |
| T3G + F7G + V9A + S15Q + I22Q + K26E + K36E + E46M + E64P + Q69P + K70P + N82T + A101V + K120A + S141R + P163A + T166P + Q168D + M172I + S176N + S178P + F190Y + K197D + Q214R + Q215E + Y219W + | 37° C. | 4080 | 90% Model A2 | 1.22 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| S239A + M248I + R253A + S258G + S271G + R280K + N283Y + E299W + K378Q + K408M + D410M + L413T + N473Y + K491R | | | | |
| T3G + F7G + V9A + S15Q + A20G + K26E + K36E + E46M + E64P + Q69P + K70P + N82T + S103E + K120A + S141A + P163A + T166P + Q168D + M172I + S176N + S178P + F190Y + K197D + Q214R + Q215E + Y219W + S239A + M248I + R253A + S258G + S271G + R280K + N283Y + E299W + H324N + K378Q + K408M + D410M + L413T + N473Y + K491R | 37° C. | 4080 | 90% Model A2 | 2.53 |
| T3G + F7G + V9A + S15Q + A20G + K26E + K36E + E46M + E64P + Q69P + K70P + N82T + S103E + K120A + S141R + P163A + T166P + Q168D + K169P + M172I + S176N + S178P + F190Y + K197A + Q214R + Q215E + Y219W + S239A + M248I + R253A + S258G + S271G + R280K + N283Y + E299W + K378Q + K408M + D410M + L413T + N473Y + K491R | 37° C. | 5640 | 90% Model A2 | 2.18 |
| T3G + F7G + V9A + S15Q + A20G + K26E + K36E + E46M + E64P + Q69P + K70P + N82T + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 8640 | 90% Model A2 | 2.39 |
| T3G + F7G + T13N + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.80 |
| T3G + F7G + V9A + S15Q + A20G + K26E + K36E + E46Y + T53K + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 2.17 |
| T3G + F7G + V9A + S15Q + A20G + K26E + K36E + E46Y + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.76 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + T13I + S14N + S15Q + A20G + K26E + K36E + E46M + E64P + Q69P + K70P + N82T + S103E + K120A + S141R + P163A + I165D + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.60 |
| T3G + F7G + T13I + S14N + S15Q + A20G + K26E + K36E + E46M + E64P + Q69P + K70P + N82T + S103E + K120A + S141R + P163A + I165D + T166P + Q168D + M172I + S176N + S178P + F190Y + K197D + Q214R + Q215E + Y219W + S239A + M248I + R253A + S258G + S271G + R280K + N283Y + E299W + K378Q + D385H + P399A + K408M + D410M + L413T + N473Y + K491R | 37° C. | 4110 | 90% Model A2 | 1.85 |
| T3G + F7G + V9A + S15Q + A20G + K26E + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + R280K + N283Y + E299W + H324N + K378Q + D385H + K408M + D410M + L413T + N473Y + K491R | 37° C. | 4110 | 90% Model A2 | 2.42 |
| T3G + F7G + T13I + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.98 |
| T3G + F7G + V9A + S15Q + A20G + K26E + I30L + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + S403R + K408M + D410M + L413T + N473Y + K491R | 37° C. | 5640 | 90% Model A2 | 1.71 |
| T3G + F7G + V9A + S15Q + I22V + K26E + I30L + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 5640 | 90% Model A2 | 1.44 |
| T3G + F7G + V9A + S15Q + A20G + K26E + E31Q + K36E + E46M + E64P + Q69P + K70P + N82T + S103E + K120A + S141R + P163A + T166P + Q168D + M172I + S176N + S178P + F190Y + | 37° C. | 4110 | 90% Model A2 | 1.76 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| K197D + Q214R + Q215E + Y219W + S239A + M248I + R253A + S258G + S271G + R280K + N283Y + E299W + K378Q + D385H + K408M + D410M + L413T + N473Y + K491R | | | | |
| T3G + F7G + V9A + S15Q + A20G + K26E + E31Q + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + Q321K + K378Q + D385H + K408M + D410M + L413T + N473Y + K491R | 37° C. | 4110 | 90% Model A2 | 1.88 |
| T3G + F7G + V9A + S15Q + A20G + K26E + K36E + E46M + E64P + Q69P + K70P + N82T + S103E + K120A + S141R + P163A + T166P + Q168D + M171K + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 2.35 |
| T3G + F7G + V9A + S15Q + A20G + K26E + K36E + E46M + E64P + Q69P + K70P + K78E + N82T + S103E + K120A + N139K + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.52 |
| A1V + G6P + F7G + T13I + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.69 |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + E299W + K378Q + D385H + K408M + D410M + L413T + N473Y + K491R | 37° C. | 4110 | 90% Model A2 | 1.81 |
| T3G + F7G + V9A + S15Q + A20G + K26E + K36E + E46M + E64P + Q69P + K70P + N82T + S103E + K120A + S141I + P163A + T166P + Q168D + K169P + M172I + S176N + S178P + F190Y + K197A + Q214R + Q215E + Y219W + S239A + M248I + R253A + S258G + S271G + R280K + N283Y + E299W + K378Q + K408M + D410M + L413T + N473Y + K491R | 37° C. | 5640 | 90% Model A2 | 1.72 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + V9A + S15Q + A20G + K26E + K36E + E46M + E64P + Q69P + K70P + N82T + S103E + K120A + S141R + P163A + T166P + Q168D + K169P + M172I + S176N + S178P + F190Y + K197A + Q214R + Q215E + Y219W + S239A + M248I + R253W + S258G + S271G + H276N + R280K + N283Y + E299W + A312V + K378Q + K408M + D410M + L413T + N473Y + K491R | 37° C. | 5640 | 90% Model A2 | 2.02 |
| T3G + F7G + V9A + S15Q + A20G + K26E + K36E + E46M + E64P + Q69P + K70P + N82T + S103N + S109E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5640 | 90% Model A2 | 2.49 |
| T3G + F7G + V9A + S15Q + A20G + K26E + K36E + E46M + E64P + Q69P + K70P + K78E + N82A + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5640 | 90% Model A2 | 2.24 |
| T3G + F7G + V9A + S15Q + A20G + K26E + K36E + E46M + E64P + Q69P + K70P + K78E + N82A + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5115 | 90% Model A2 | 2.74 |
| T3G + F7G + V9A + S15Q + A20G + K26E + I30L + K36E + E46M + E64P + Q69P + K70P + N82T + S103E + S109E + K120A + S141R + P163A + T166P + Q168D + M171Q + M172I + S176N + S178P + K189S + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5640 | 90% Model A2 | 2.81 |
| T3G + F7G + V9A + S15Q + A20G + K26E + K36E + E46M + E64P + Q69P + K70P + N82T + S103E + S109E + K120A + S141R + P163A + T166P + Q168D + M171Q + M172I + S176N + S178P + K189S + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5640 | 90% Model A2 | 2.41 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 5640 | 90% Model A2 | 4.15 |
| T3G + F7G + V9A + S15Q + A20G + K26E + K36E + E46M + E64P + Q69P + K70P + N82T + S103E + S109D + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5550 | 90% Model A2 | 3.64 |
| T3G + F7G + V9A + S15Q + A20G + K26E + K36E + E46M + E64P + Q69P + K70P + Q76T + N82T + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5550 | 90% Model A2 | 1.92 |
| T3G + F7G + T13I + S14H + S15Q + A20G + K26E + K36E + E46M + E64P + Q69P + K70P + Q76T + N82T + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5550 | 90% Model A2 | 2.10 |
| T3G + F7G + V9A + S15Q + A20G + K26E + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5115 | 90% Model A2 | 2.14 |
| T3G + F7G + E10Y + T13I + S15Q + A20G + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 8025 | 90% Model A2 | 3.12 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + V9A + S15Q + A20G + K26E + K36E + E46M + E64P + Q69P + K70P + K78E + N82T + S103E + K120A + N139K + S141R + P163A + T166P + Q168D + M172I + S176N + S178P + K179H + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.19 |
| T3G + F7G + T13I + S14N + S15Q + A20G + K26E + I30L + K36E + E46Y + E64P + Q69P + K70P + K78E + N82T + S103E + K120A + N139K + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 2.04 |
| T3G + F7G + T13I + S14N + S15Q + A20G + K26E + K36E + E46Y + E64P + Q69P + K70P + K78E + N82T + S103E + K120A + N139K + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.30 |
| T3G + F7G + V9A + S15Q + A20G + K26E + K36E + E46M + E64P + Q69P + K70P + K78E + N82T + S103E + K120A + N139K + S141R + P163A + I165T + T166P + Q168D + M171K + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.58 |
| T3G + F7G + H12Q + T13I + S15Q + A20G + K26E + K36E + E46M + E64P + K65Q + Q69P + K70P + K78E + N82T + S103E + K120A + N139K + S141R + P163A + T166P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 4110 | 90% Model A2 | 1.39 |
| T3G + F7G + V9A + S15Q + A20G + K26E + K36E + E46M + E64P + Q69P + K70P + K78E + N82A + S103E + K120A + S141R + R160F + E162D + T166P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 2.70 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + T13E + S15Q + A20G + K26E + K36E + E46M + E64P + Q69P + K70P + K78E + N82A + S103E + S109D + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 3.33 |
| T3G + F7G + E10Y + T13I + S15Q + A20G + K26E + K36E + E46M + E64P + Q69P + K70P + K78E + N82A + S103E + K120A + S141R + R160F + E162D + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 2.85 |
| T3G + F7G + V9A + S15Q + A20G + K26E + K36E + E46M + E64P + Q69P + K70P + K78E + N82A + S103E + S109D + K120A + S141R + P163A + T166P + T167P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 3.44 |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 8640 | 90% Model A2 | 3.70 |
| T3G + F7G + V9A + S15Q + A20G + K26E + K36E + E46M + E64P + Q69P + K70P + N82A + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8640 | 90% Model A2 | 5.14 |
| T3G + F7G + T13I + S14H + S15Q + A20G + K26E + K36E + E46M + E64P + Q69P + K70P + Q76T + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8025 | 90% Model A2 | 2.72 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + V9A + S15Q + A20G + K26E + I30L + K36E + E46Y + E64P + Q69P + K70P + N82T + S103E + S109E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8640 | 90% Model A2 | 5.73 |
| T3G + F7G + V9A + S15Q + A20G + K26E + E31Q + K36E + E46Y + E64P + Q69P + K70P + N82T + S103E + K120A + S141R + P163A + T166P + Q168D + M171K + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8640 | 90% Model A2 | 6.49 |
| T3G + F7G + V9A + S15Q + A20G + K26E + E31Q + K36E + E46M + E64P + Q69P + K70P + N82T + S103E + S109E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8025 | 90% Model A2 | 3.40 |
| T3G + F7G + V9A + S15Q + A20G + K26E + K36E + E46M + E64P + Q69P + K70P + N82T + S103E + S109E + K120A + S141R + P163A + T166P + Q168D + M171K + M172I + S176N + S178P + K189S + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8640 | 90% Model A2 | 7.66 |
| T3G + F7G + V9A + S15Q + A20G + K26E + K36E + E46M + E64P + Q69P + K70P + N82T + S103E + K120A + S141R + P163A + I165D + T166P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8025 | 90% Model A2 | 3.30 |
| T3G + F7G + V9A + S15Q + K26E + K36E + E46M + E64P + Q69P + K70P + N82T + S103E + K120A + S141R + R160F + E162D + T166P + T167P + Q168D + M172I + S176N + S178P + F190Y + K197D + Q214R + Q215E + Y219W + S239A + M248I + R253A + S258G + S271G + H276C + R280K + | 37° C. | 8025 | 90% Model A2 | 13.41 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| N283Y + F286C + E299W + K378Q + D385H + K408M + D410M + L413T + N473Y + K491R | | | | |
| T3G + F7G + V9A + S15Q + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 8025 | 90% Model A2 | 19.16 |
| T3G + F7G + V9A + S15Q + A20G + K26E + K36E + A45M + E46Y + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5700 | 90% Model A2 | 2.26 |
| T3G + F7G + V8A + T13I + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5700 | 90% Model A2 | 2.34 |
| T3G + F7G + P11A + T13I + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5700 | 90% Model A2 | 1.90 |
| T3G + F7G + V9A + S15Q + A20G + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413V + N473Y + D486E + K491R | 37° C. | 7200 | 90% Model A2 | 6.59 |
| T3G + F7G + V8A + T13I + S15Q + I22V + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + | 37° C. | 5700 | 90% Model A2 | 2.53 |

TABLE 15-continued

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Protease stability at pH 8. The protease is a variant of SEQ ID NO: 14 with the following modifications: Y161A + R164S + A188P added in 0.8% (w/w) concentration | | | | |
| D385H + K408M + D410M + L413T + N473Y + D486E + K491R | | | | |
| T3G + F7G + V9A + S15Q + A20G + A23T + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 7200 | 90% Model A2 | 2.72 |
| T3G + F7G + V9A + S15Q + A20G + A23T + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 3.33 |
| T3G + F7G + V9A + S15Q + A20G + K26E + K36E + E46M + E64P + Q69P + K70P + K78E + N82A + S103E + K120A + S141R + P163A + T166P + Q168D + M171Q + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + R489F + K491R | 37° C. | 8640 | 90% Model A2 | 1.62 |
| T3G + F7G + V9A + S15Q + A20G + K26E + I30L + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5700 | 90% Model A2 | 1.87 |
| T3G + F7G + V9A + S15Q + A20G + K26E + K36E + E46M + E64P + Q69P + K70P + E86D + S103E + K120A + S141R + V161S + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5700 | 90% Model A2 | 2.76 |
| T3G + F7G + V9A + S15Q + I22T + K26E + I30L + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + | 37° C. | 5700 | 90% Model A2 | 2.29 |

TABLE 15-continued

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Protease stability at pH 8. The protease is a variant of SEQ ID NO: 14 with the following modifications: Y161A + R164S + A188P added in 0.8% (w/w) concentration | | | | |
| N283Y + E299W + A312V + K378Q + K408M + D410M + L413T + N473Y + K491R | | | | |
| T3G + F7G + V9A + S15Q + A20G + K26E + K36E + E46M + E64P + Q69P + K70P + Q76E + S103E + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 4.33 |
| T3G + F7G + V9A + S15Q + A20G + K26E + K36E + E46M + E64P + Q69P + K70P + Q76E + S103E + K120A + N139K + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 7200 | 90% Model A2 | 5.15 |
| S-17G + T3G + F7G + V9A + S15Q + A20G + K26E + K36E + E46M + E64P + Q69P + K70P + K78E + N82T + S103E + K120A + N139K + S141R + P163A + T166P + Q168D + M172I + S176N + S178P + F190Y + K197D + Q214R + Q215E + Y219W + S239A + M248I + R253A + S258G + S271G + R280L + N283Y + E299W + K378Q + D385H + K408M + D410M + L413T + N473Y + K491R | 37° C. | 7200 | 90% Model A2 | 1.63 |
| S-17G + T3G + F7G + V9A + S15Q + A20G + K26E + K36E + E46M + E64P + Q69P + K70P + K78E + N82T + S103E + K120A + N139K + S141R + P163A + T166P + T167P + Q168D + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 37° C. | 7200 | 90% Model A2 | 3.56 |
| T3G + F7G + V8A + T13I + S15Q + I22V + K26E + K36E + E46M + E64P + Q69P + K70P + N82T + S103E + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 10860 | 90% Model A2 | 4.52 |
| T3G + F7G + V9A + S15Q + A20G + K26E + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + H276N + R280K + | 37° C. | 11160 | 90% Model A2 | 2.11 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| N283Y + E299W + K304Q + A312V + K378Q + K408M + D410M + L413T + N473Y + K491R | | | | |
| T3G + F7G + V9A + S15Q + A20G + K26E + K36E + E46M + E64P + Q69P + K70P + N82T + S103E + K120A + K129R + S141R + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 11160 | 90% Model A2 | 2.01 |
| T3G + F7G + V9A + S15Q + A20G + K26E + K36E + E46M + E64P + Q69P + K70P + N82T + S103E + K120A + S141R + P163E + T166P + Q168D + K169P + M172I + S176N + S178P + F190Y + K197D + Q214R + Q215E + Y219W + S239A + M248I + R253A + S258G + S271G + H276N + R280K + N283Y + E299W + K304Q + A312V + K378Q + K408M + D410M + L413T + N473Y + K491R | 37° C. | 11160 | 90% Model A2 | 1.79 |
| T3G + F7G + V8A + T13I + S15Q + A20P + K26E + K36E + E46M + E64P + Q69P + K70P + N82T + S103E + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 4.54 |
| T3G + F7G + V8A + T13I + S15Q + K26E + K36E + E46M + E64P + Q69P + K70P + N82T + S103E + K120A + S141R + Y155H + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 8.92 |
| T3G + F7G + V8A + T13I + S15Q + I22V + K26E + K36E + E46M + E64P + Q69P + K70P + N82T + S103E + K120A + S141R + Y155H + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 10.33 |
| T3G + F7G + V8A + T13I + S15Q + I22V + K26E + K36E + E46M + E64P + Q69P + K70P + N82T + S103E + K120A + S141R + Y155H + P163A + T166P + Q168D + K169P + M172I + S178P + P182R + F190Y + K197D + Q214R + | 37° C. | 11160 | 90% Model A2 | 4.99 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + I22V + K26E + K36E + E46M + E64P + Q69P + K70P + N82T + S103E + K120A + S141R + R160N + P163A + T166P + Q168D + M171K + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 4.21 |
| T3G + F7G + V8A + T13I + S15Q + I22V + K26E + K36E + E46M + E64P + Q69P + K70P + N82T + S103E + K120A + S141R + Y155H + P163A + I165D + T166P + Q168D + M171K + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 8.79 |
| T3G + F7G + V8A + T13I + S15Q + I22V + K26E + K36E + E46M + E64P + Q69P + K70P + N82T + S103E + K120A + S141R + P163A + I165D + T166P + Q168D + M171K + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 10.36 |
| T3G + F7G + V8A + T13I + S15Q + I22V + K26E + K36E + E46M + E64P + Q69P + K70P + N82T + S109D + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 10860 | 90% Model A2 | 2.77 |
| T3G + F7G + V8A + T13I + S15Q + I22V + K26E + K36E + E46M + E64P + Q69P + K70P + N82T + S103E + S109D + K120A + S141R + R160L + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + | 37° C. | 11160 | 90% Model A2 | 7.14 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| E299W + G366N + K378Q + D385H + K408M + D410M + L413T + K462A + N473Y + D486E + K491R | | | | |
| T3G + F7G + V9A + T13I + S15Q + I22V + K26E + K36E + E46M + E64P + Q69P + K70P + N82T + A101R + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 10860 | 90% Model A2 | 5.41 |
| T3G + F7G + V8A + T13I + S15Q + I22V + K26E + K36E + E46M + E64P + Q69P + K70P + N82T + A101R + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 10860 | 90% Model A2 | 5.05 |
| A1V + G6P + F7G + T13I + S15Q + I22V + K26E + K36E + E46M + E64P + Q69P + K70P + N82T + A101R + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + K462A + N473Y + D486E + K491R | 37° C. | 10860 | 90% Model A2 | 4.41 |
| T3G + F7G + V8A + T13I + S15Q + I22V + K26E + K36E + E46M + E64P + Q69P + K70P + N82T + A101R + K120A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + K462A + N473Y + D486E + K491R | 37° C. | 10860 | 90% Model A2 | 6.81 |
| T3G + F7G + V8A + T13I + S15Q + I22V + K26E + K36E + E46M + E64P + Q69P + K70P + N82T + S103E + T115V + K120A + S137A + S141R + Y155H + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11160 | 90% Model A2 | 5.35 |
| T3G + F7G + V9A + S15Q + A20G + A23T + K26E + K36E + E46M + E64P + Q69P + K70P + N82T + S103E + T115Y + K120A + S141R + P163A + T166P + | 37° C. | 5460 | 90% Model A2 | 3.13 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V9A + S15Q + A20G + A23T + K26E + K36E + E46M + E64P + Q69P + K70P + N82T + S103E + S109D + T115Y + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 3.37 |
| T3G + F7G + V9A + S15Q + A20G + A23T + K26E + K36E + E46M + E64P + Q69P + K70P + N82T + S103E + S109E + K120A + S141R + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11160 | 90% Model A2 | 5.89 |
| T3G + F7G + E10G + T13I + S15Q + A20G + A23T + K26E + K36E + E46M + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 3.10 |
| T3G + F7G + V9A + S15Q + A20G + A23T + K26E + K36E + E46M + T53K + E64P + Q69P + K70P + N82T + S103E + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 2.91 |
| T3G + F7G + V9A + S15Q + A20G + A23T + K26E + K36E + E46M + E64P + Q69P + K70P + N82T + S103E + T115Y + K120A + S141R + V161T + P163A + T166P + Q168D + M171K + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 3.26 |
| T3G + F7G + V9A + S15Q + A20G + A23T + K26E + K36E + E46M + E64P + | 37° C. | 5460 | 90% Model A2 | 2.99 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q69P + K70P + N82T + S103E + T115W + K120A + S141R + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V9A + S15Q + A20G + A23T + K26E + K36E + E46M + E64P + Q69P + K70P + N82T + S103E + T115W + K120A + S141R + V161T + P163A + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 5460 | 90% Model A2 | 2.77 |
| T3G + F7G + V9A + S15Q + A20G + K26E + K36E + E46M + T53K + E64P + Q69P + K70P + Q76E + S103E + K120A + S141R + P163A + T166P + Q168D + K169P + M172I + S176N + S178P + K179Q + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 5460 | 90% Model A2 | 2.25 |
| T3G + F7G + V8A + T13I + S15Q + I22V + K26E + I30L + E31Q + K36E + E46M + E64P + Q69P + K70P + N82T + S103E + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 6.45 |
| T3G + F7G + V8A + T13I + S15Q + I22V + K26E + K36E + E46M + E64P + Q69P + K70P + N82T + S103E + K120A + S141R + Q143R + V161T + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 17.52 |
| T3G + F7G + V8A + T13I + S15Q + I22V + K26E + K36E + E46M + E64P + Q69P + K70P + N82T + S103E + K120A + S141R + Q143R + V161T + P163A + T166P + T167P + Q168D + M172I + S178P + P182R + F190Y + K197D + Q214R + Q215E + Y219W + S239A + M248I + R253A + S258G + S271G + H276C + R280K + N283Y + F286C + E299W + G366N + K378Q + D385H + | 37° C. | 12720 | 90% Model A2 | 8.19 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| K408M + D410M + L413T + N473Y + D486E + K491R | | | | |
| T3G + F7G + V8A + T13I + S15Q + I22V + K26E + K36E + E46M + E64P + Q69P + K70P + N82T + S103E + K120A + S141R + Y155H + E162D + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 6.77 |
| T3G + F7G + V8A + T13I + S15Q + I22V + K26E + K36E + E46M + E64P + Q69P + K70P + N82T + S103E + K120A + S141R + R160I + P163A + T166P + Q168D + K169P + M172I + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 5.51 |
| T3G + F7G + V8A + T13I + S15Q + I22V + K26E + K36E + E46M + E64P + Q69P + K70P + N82T + A101R + K120A + S141R + Y155H + E162G + P163A + T166P + Q168D + K169P + M172I + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 3.81 |
| T3G + F7G + V8A + T13I + S15Q + I22V + K26E + K36E + E46M + E64P + Q69P + K70P + N82T + A101R + K120A + S141R + E162G + P163A + T166P + Q168D + K169P + M172I + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 3.90 |
| T3G + F7G + V9A + T13I + S15Q + I22V + K26E + K36E + E46M + E64P + Q69P + K70P + N82T + S103E + K120A + S141R + R160F + E162D + T166P + Q168D + K169P + M172I + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 12720 | 90% Model A2 | 5.97 |
| T3G + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + | 37° C. | 12720 | 90% Model A2 | 10.98 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V9A + S15Q + A20G + K26E + K36E + E46M + E64P + Q69P + K70P + Q76E + S103E + K120A + S141R + V161S + P163A + T166P + Q168D + K169P + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 40° C. | 9840 | 90% Model A2 | 2.40 |
| T3G + F7G + P11A + T13I + S15Q + A20G + A23T + K26E + K36E + E46M + E64P + Q69P + K70P + N82T + S103E + K120A + S141R + P163A + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 3.10 |
| T3G + F7G + P11A + T13I + S15Q + A20G + A23T + K26E + K36E + E46M + E64P + Q69P + K70P + N82T + S103E + K120A + S141R + P163A + I165E + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 3.36 |
| T3G + F7G + P11A + T13I + S15Q + A20G + A23T + K26E + K36E + E46M + E64P + Q69P + K70P + N82T + S103E + K120A + S141R + P163A + I165E + T166P + Q168D + K169P + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 3.10 |
| T3G + F7G + V9A + S15Q + A20G + A23T + K26E + K36E + E46M + E64P + Q69P + K70P + N82T + S103E + K120A + S141R + P163A + I165E + T166P + Q168D + M172I + S176N + S178P + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 2.98 |
| T3G + F7G + V9A + S15Q + K26E + K36E + E46M + E64P + Q69P + K70P + | 40° C. | 9840 | 90% Model A2 | 3.66 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + R489F + K491R | | | | |
| T3G + F7G + V9A + S15Q + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + K491R | 37° C. | 12720 | 90% Model A2 | 9.88 |
| T3G + F7G + V9A + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 12720 | 90% Model A2 | 5.50 |
| T3G + F7G + V8A + T13I + S15Q + A20P + K26E + K36E + E46M + E64P + Q69P + K70P + N82T + A101R + T115Y + K120A + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 39.48 |
| T3G + F7G + V8A + T13I + S15Q + A20P + K26E + K36E + E46M + E64P + Q69P + K70P + N82T + A101R + K120A + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 4.00 |
| T3G + F7G + V8A + T13I + S15Q + A20P + K26E + K36E + E46M + E64P + Q69P + K70P + N82T + A101R + T115Y + K120A + K129R + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + | 40° C. | 9840 | 90% Model A2 | 13.82 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| R280K + N283Y + F286C + E299W + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + S109D + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 20.34 |
| T3G + F7G + V8A + T13I + S15Q + A20P + K26E + K36E + E46M + E64P + Q69P + K70P + N82T + A101R + S109D + K120A + S141R + Y155H + P163A + T166P + T167P + Q168D + M171K + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 16.60 |
| T3G + F7G + V8A + T13I + S15Q + A20P + K26E + K36E + E46M + E64P + Q69P + K70P + N82T + A101R + S109D + T115V + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 21.72 |
| T3G + F7G + V8A + T13I + S15Q + A20P + K26E + K36E + E46M + E64P + Q69P + K70P + N82T + A101R + S109D + T115V + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 22.95 |
| T3G + F7G + V8A + T13I + S15Q + A20P + K26E + K36E + E46M + E64P + Q69P + K70P + N82T + A101R + K120A + S137A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 18.86 |
| T3G + F7G + V8A + T13I + S15Q + A20P + K26E + K36E + E46M + E64P + | 40° C. | 9840 | 90% Model A2 | 8.33 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q69P + K70P + N82T + A101R + K120P + S137A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + A20T + K26E + K36E + E46M + E64P + Q69P + K70P + N82T + A101R + K120P + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 11280 | 90% Model A2 | 21.57 |
| T3G + F7G + V8A + T13I + S15Q + A20P + K26E + K36E + E46M + E64P + Q69P + K70P + N82T + A101R + K120P + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 40° C. | 9840 | 90% Model A2 | 62.34 |
| T3G + F7G + V9A + S15Q + A20G + K26E + K36E + E46M + E64P + Q69P + K70P + N82T + S103E + K120A + S141R + P163A + T166P + Q168D + T170E + M172I + S176N + S178P + F190Y + K197D + Q214R + Q215E + Y219W + S239A + M248I + R253A + S258G + S271G + R280K + N283Y + E299W + K378Q + D385H + K408M + D410M + L413T + N473Y + K491R | 40° C. | 5460 | 90% Model A2 | 1.48 |
| T3G + F7G + E10Y + T13I + S15Q + A20G + K26E + K36E + E46M + E64P + Q69P + K70P + Q76T + K78R + S103E + K120A + S141R + P163A + T166P + T167P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 11280 | 90% Model A2 | 4.18 |
| T3G + F7G + E10Y + T13I + S15Q + A20G + K26E + K36E + E46M + E64P + Q69P + K70P + N82T + S103E + K120A + S141R + P163A + R164Q + T166P + Q168D + M171K + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 42° C. | 5610 | 90% Model A2 | 2.03 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T3G + F7G + P11A + T13I + S15Q + A20G + I22V + K26E + I30L + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 40° C. | 5460 | 90% Model A2 | 2.45 |
| T3G + F7G + E10Y + T13I + S15Q + A20G + I22V + K26E + I30L + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276N + R280K + N283Y + E299W + A312V + K378Q + K408M + D410M + L413T + N473Y + K491R | 37° C. | 11280 | 90% Model A2 | 3.56 |
| T3G + F7G + V9A + S15Q + K26E + K36E + E46Y + D48A + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + K252G + R253A + S258G + S271G + H276C + R280K + N283Y + F286C + E299W + K378Q + D385H + K408M + D410M + L413T + N473Y + K491R | 37° C. | 11280 | 90% Model A2 | 13.02 |
| T3G + F7G + V9A + S15Q + K26E + K36E + E46Y + D48A + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 40° C. | 9840 | 90% Model A2 | 7.56 |
| T3G + F7G + V8A + T13I + S15Q + A20P + K26E + K36E + E46M + E64P + Q69P + K70P + N82T + A101R + S109D + T115V + K120P + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 7095 | 90% Model A2 | 8.11 |
| T3G + F7G + V8A + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + | 42° C. | 7095 | 90% Model A2 | 7.93 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + G110R + T115V + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 7095 | 90% Model A2 | 7.50 |
| A1V + V4M + F7G + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 7095 | 90% Model A2 | 4.75 |
| A1V + V4M + F7G + V9A + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 7095 | 90% Model A2 | 5.58 |
| T3G + F7G + V9A + S15Q + A20G + A23V + K26E + K36E + E46M + E64P + Q69P + K70P + N82A + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 7095 | 90% Model A2 | 5.33 |
| T3G + F7G + V9A + S15Q + A20G + A23V + K26E + K36E + E46M + E64P + Q69P + K70P + N82A + A101R + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 7095 | 90% Model A2 | 5.14 |
| T3G + F7G + V9A + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253W + | 42° C. | 7095 | 90% Model A2 | 4.45 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S258G + S271G + H276C + R280K + N283Y + F286C + E299W + K378Q + D385H + K408M + D410M + L413T + N473Y + K491R | | | | |
| T3G + F7G + V8A + T13I + S15Q + A20P + K26E + K36E + E46M + E64P + Q69P + K70P + N82T + L89F + A101R + S109D + T115Y + K120A + S141R + Y155H + P163A + T166P + T167P + Q168D + M171I + M172I + S176N + S178P + P182R + F190Y + K197D + Q214R + Q215E + Y219W + M228I + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 6.60 |
| T3G + F7G + V8A + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + E380T + D385H + K408M + D410M + L413T + N473Y + D486E + K491R | 42° C. | 11460 | 90% Model A2 | 13.83 |
| T3G + F7G + H12E + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 10.33 |
| T3G + F7G + V8A + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + N272D + H276C + R280K + N283Y + F286C + E299W + G366N + K378Q + D385H + K408M + D410M + L413T + N473Y + D486E + K491R | 42° C. | 11460 | 90% Model A2 | 9.08 |
| A1V + V4N + F7G + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + | 42° C. | 11460 | 90% Model A2 | 9.55 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| D410M + L413T + N473Y + D486E + K491R | | | | |
| T3G + F7G + V8A + T13I + S15Q + A20P + K26E + K36E + E46M + E64P + Q69P + K70P + N82T + A101R + S109D + T115Y + K120A + S141R + W148Q + P163A + T166P + T167P + Q168D + M171I + M172I + S176N + S178P + P182R + F190Y + K197D + Q214R + Q215E + Y219W + S239A + M248I + R253A + S258G + 268/ + G270C + 271/ + S271G + N272D + H276C + R280K + N283Y + F286C + E299W + G366N + K378Q + D385H + K408M + D410M + L413T + N473Y + D486E + K491R | 42° C. | 11460 | 90% Model A2 | 14.76 |
| T3G + F7G + V9A + S15Q + K26E + K36E + E46M + E64P + Q69P + K70P + N82T + A101R + K120A + S141R + R160F + E162D + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + K491R | 42° C. | 11460 | 90% Model A2 | 11.01 |
| T3G + F7G + V9A + T13I + S15Q + A20P + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + K491R | 42° C. | 11460 | 90% Model A2 | 11.04 |
| T3G + F7G + V9A + S15Q + K26E + K36E + E46M + E64P + Q69P + K70P + N82T + S103E + K120P + S141R + R160F + E162D + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + K491R | 42° C. | 11460 | 90% Model A2 | 13.27 |
| T3G + F7G + V9A + S15Q + K26E + K36E + E46M + E64P + Q69P + K70P + N82T + S103E + S109E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K364D + K378Q + D385H + K408M + D410M + L413T + N473Y + K491R | 42° C. | 11460 | 90% Model A2 | 12.07 |
| A1V + T3E + F7G + V9A + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + | 42° C. | 11460 | 90% Model A2 | 10.12 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| R280K + N283Y + F286C + E299W + K378Q + D385H + K408M + D410M + L413T + N473Y + K491R | | | | |
| T3G + F7G + T13I + S15Q + A20G + A23V + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 11460 | 90% Model A2 | 9.83 |
| T3G + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + A210F + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 10.60 |
| T3G + F7G + P11A + T13I + S15Q + A20P + K26E + K36E + E46M + T53P + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 21.39 |
| T3G + F7G + V8D + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 12.90 |
| T3G + F7G + S15Q + A20P + K26E + K36E + E46M + E64P + Q69P + K70P + N82A + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 12.16 |
| T3G + F7G + V8A + T13I + S15Q + A20P + K26E + K36E + E64P + Q69P + K70P + N82T + A101R + K120A + S141R + Y155H + P163A + T166P + T167P + Q168D + M172I + S176N + | 42° C. | 11460 | 90% Model A2 | 4.40 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S178P + P182R + F190Y + N193W + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + S103V + K120A + S141R + Y155H + P163A + T166P + T167P + Q168D + M172I + S176N + S178P + P182R + F190Y + K197D + Q214R + Q215E + Y219W + S239A + N242T + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 10.56 |
| T3G + F7G + V8A + T13I + S15Q + A20P + K26E + K36E + E46M + E64P + Q69P + K70P + A101R + K120A + S141R + Y155H + P163A + T166P + T167P + Q168D + M172I + S176N + S178P + P182R + F190Y + K197F + Q214R + Q215E + Y219W + S239A + M248I + R253A + S258G + S271G + H276C + R280K + N283Y + F286C + E299W + G366N + K378Q + D385H + P398E + K408M + D410M + L413T + N473Y + D486E + K491R | 42° C. | 11460 | 90% Model A2 | 7.75 |
| T3G + F7G + V8A + T13I + S15Q + A20P + K26E + K36E + E46M + E64P + Q69P + K70P + N82T + A101R + G110R + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 9.99 |
| T3G + F7A + T13I + S15Q + A20P + K26E + K36E + E46M + E64P + Q69P + K70P + N82A + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 11.00 |
| A1V + V4N + F7G + V9P + T13I + S15Q + A20P + K26E + K36E + E46M + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + | 42° C. | 11460 | 90% Model A2 | 15.93 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| G366N + K378Q + D385H + K408M + D410M + L413T + N473Y + D486E + K491R | | | | |
| A1V + V4N + F7G + T13I + S15Q + A20P + K26E + K36E + E46M + E64P + Q69P + K70P + N82T + A101R + S109D + T115Y + K120A + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 20.84 |
| A1V + V4N + F7G + T13I + S15Q + A20P + K26E + K36E + E46M + E64P + Q69P + K70P + N82T + A101R + S109D + T115Y + K120A + N139I + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 12.67 |
| A1V + V4N + F7G + T13I + S15Q + A20P + K26E + K36E + A45M + E46Y + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 12.88 |
| A1V + V4N + F7G + T13I + S15Q + A20P + K26E + K36E + E46M + E64P + Q69P + K70P + N82T + A101R + S109D + T115Y + K120A + A126T + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 11.03 |
| T3G + F7G + V8A + T13I + S15Q + A20P + K26E + K36E + E46M + E64P + Q69P + K70P + N82T + A101R + S109D + T115V + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + | 42° C. | 11460 | 90% Model A2 | 18.09 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| H324K + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + S109D + T115V + K120A + S141R + Y155H + P163* + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 8.92 |
| T3G + F7G + V8A + S15K + A20P + K26E + K36E + E46M + E64P + Q69P + K70P + N82T + A101R + S109D + T115V + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 11.23 |
| T3G + F7G + V8A + T13I + S15Q + A20P + K26E + K36E + E46M + E64P + Q69P + K70P + N82T + A101R + S109D + T115V + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + E379K + D385H + K408M + D410M + L413T + N473Y + D486E + K491R | 42° C. | 11460 | 90% Model A2 | 20.14 |
| A1V + V4D + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + K304A + G366N + K378Q + D385H + K408M + D410M + L413T + N473Y + D486E + K491R | 42° C. | 15840 | 90% Model A2 | 10.23 |
| A1V + V4D + F7G + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 14.28 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| A1T + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 13.02 |
| T3G + F7G + P11A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + E322R + G366N + K378Q + D385H + K408M + D410M + L413T + N473Y + D486E + K491R | 42° C. | 15840 | 90% Model A2 | 11.01 |
| T3G + F7G + P11A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 11460 | 90% Model A2 | 12.19 |
| T3G + F7G + V9A + S15Q + A20G + A23V + K26E + K36E + E46M + E64P + Q69P + K70P + N82T + S103E + K120A + S141R + V161S + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + K378Q + D385H + K408M + D410M + L413T + N473Y + K491R | 42° C. | 15840 | 90% Model A2 | 11.88 |
| T3G + F7G + V9A + S15Q + A20G + A23V + K26E + K36E + E46M + E64P + Q69P + K70P + N82T + S103E + K120A + S141I + R160I + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + K378Q + D385H + K408M + D410M + L413T + N473Y + K491R | 42° C. | 15840 | 90% Model A2 | 10.56 |
| T3G + F7G + V9A + S15Q + A20G + A23V + K26E + K36E + E46M + E64P + Q69P + K70P + N82T + S103E + K120A + S141R + R160I + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + | 42° C. | 15840 | 90% Model A2 | 9.99 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| K378Q + D385H + K408M + D410M + L413T + N473Y + K491R | | | | |
| T3G + F7G + V9A + S15Q + A20G + A23I + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 42° C. | 11460 | 90% Model A2 | 9.58 |
| T3G + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + N272D + H276C + R280K + N283Y + F286C + E299W + G366N + K378Q + D385H + K408M + D410M + L413T + N473Y + D486E + K491R | 42° C. | 15840 | 90% Model A2 | 14.39 |
| T3G + F7G + V8A + T13I + S15Q + A20P + K26E + K36E + E46M + E64P + Q69P + K70P + N82T + A101R + S109D + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 15.65 |
| T3G + F7G + V8A + T13I + S15Q + A20P + K26E + E31Q + K36E + E46Y + T53K + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 12960 | 90% Model A2 | 15.69 |
| T3G + F7G + V8A + T13I + S15Q + A20P + K26E + K36E + E46M + E64P + Q69P + K70P + N82A + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 16.94 |
| T3G + F7G + V8A + T13I + S15Q + A20P + K26E + K36E + E46M + E64P + Q69P + K70P + N82T + A101R + T115Y + K120P + S141R + Y155H + P163A + T166P + T167P + Q168D + M172I + S176N + S178P + P182R + F190Y + | 42° C. | 15840 | 90% Model A2 | 15.48 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + G110R + T115Y + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 13.19 |
| T3G + F7G + V8A + T13I + S15Q + A20P + K26E + K36E + E46M + E64P + Q69P + K70P + N82T + A101R + S109E + T115Y + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 42° C. | 15840 | 90% Model A2 | 13.77 |
| T3G + F7G + V9A + S15Q + A20G + A23V + K26E + K36E + E46M + E64P + Q69P + K70P + N82T + S103I + T115I + K120A + S141R + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + K378Q + D385H + K408M + D410M + L413T + N473Y + K491R | 42° C. | 15840 | 90% Model A2 | 20.91 |
| T3G + F7G + V9A + S15Q + A20G + A23V + K26E + K36E + E46M + E64P + Q69P + K70P + N82T + S103E + T115I + K120A + A126T + S141R + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + K378Q + D385H + K408M + D410M + L413T + N473Y + K491R | 42° C. | 15840 | 90% Model A2 | 11.69 |
| T3G + F7G + V9A + S15Q + A20G + A23V + K26E + K36E + E46M + E64P + Q69P + K70P + N82T + S103E + A118V + K120A + L134I + S141R + P163A + T166P + T167P + Q168D + M172I + S176N + S178P + F190Y + K197D + Q214R + Q215E + Y219W + S239A + M248I + R253W + S258G + S271G + H276C + R280K + N283Y + F286C + E299W + K378Q + D385H + K408M + D410M + L413T + N473Y + K491R | 42° C. | 15840 | 90% Model A2 | 5.43 |
| A1V + V4N + F7G + T13I + S15Q + A20P + K26E + K36E + A45M + E46Y + T53P + E64P + K65N + Q69P + K70P + | 37° C. | 40320 | 90% Model A2 | 122.69 |

TABLE 15-continued

| Protease stability at pH 8. The protease is a variant of SEQ ID NO: 14 with the following modifications: Y161A + R164S + A188P added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| N82A + A101L + S109E + T115Y + K120A + S141R + Y155H + E162G + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| A1V + V4N + F7G + T13I + S15Q + A20P + K26E + K36E + E46M + E64P + Q69P + K70P + N82T + A101R + S109E + T115Y + K120P + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 88.15 |
| T3G + F7G + V8A + T13I + S15Q + A20P + K26E + K36E + A45M + E46Y + T53P + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 59.60 |
| A1V + V4N + F7G + T13I + S15Q + A20P + K26E + K36E + E46M + E64P + K65N + Q69P + K70P + N82A + A101R + S109E + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 52.56 |
| A1V + V4N + F7G + T13I + S15Q + A20P + K26E + K36E + E46M + E64P + Q69P + K70P + N82T + N97E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 31.95 |
| T3G + F7G + V8A + T13I + S15Q + A20P + K26E + K36E + A45M + E46Y + E64P + K65N + Q69P + K70P + N82A + A101R + S109E + K120A + A126T + L134I + S141R + Y155H + P163A + | 37° C. | 40320 | 90% Model A2 | 22.77 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V9D + T13I + S15Q + A20P + K26E + K36E + E46M + T53K + E64P + Q69P + K70P + N82T + A101R + S109D + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 21.37 |
| T3G + F7G + V8A + T13I + S15Q + A20P + K26E + K36E + A45M + E46Y + E64P + V68M + Q69P + K70P + N82T + A101R + S109D + T115V + K120A + S141R + Y155H + P163A + T166P + T167P + Q168D + M172I + S176N + S178P + P182E + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 21.36 |
| T3G + F7G + V8A + T13I + S15Q + A20P + K26E + K36E + A45M + E46Y + E64P + Q69P + K70P + N82T + A101R + S109D + T115V + K120A + S141R + Y155H + P163A + T166P + T167P + Q168D + M172I + S176N + S178P + P182E + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 20.65 |
| A1V + V4N + F7G + T13I + S15Q + A20P + K26E + K36E + E46M + E64P + K65N + Q69P + K70P + N82T + A101R + S109E + T115Y + K120A + S141R + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 19.71 |
| A1V + V4N + F7G + T13I + S15Q + A20P + K26E + K36E + E46M + E64P + Q69P + K70P + N82T + A101R + S109E + T115Y + K120P + S141R + Y155H + P163A + T166P + T167P + Q168D + M171I + M172I + S176N + S178P + P182R + F190Y + K197D + Q214R + | 37° C. | 40320 | 90% Model A2 | 16.98 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| A1V + V4N + F7G + T13I + S15Q + A20P + K26E + K36E + A45M + E46Y + E64P + Q69P + K70P + N82T + A101R + S109D + T115Y + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 15.79 |
| A1D + T3G + F7G + V8A + T13I + S15Q + A20P + K26E + K36E + A45M + E46Y + E64P + Q69P + K70P + A101R + K120A + S141R + Y155H + P163A + T166P + T167P + Q168D + M172I + S176N + S178P + P182R + F190Y + K197F + Q214R + Q215E + Y219W + S239A + M248I + R253A + S258G + S271G + H276C + R280K + N283Y + F286C + E299W + G366N + K378Q + D385H + P398E + K408M + D410M + L413T + N473Y + D486E + K491R | 37° C. | 40320 | 90% Model A2 | 14.16 |
| S-6P + A1V + V4N + F7G + T13I + S15Q + A20P + K26E + K36E + E46M + E64P + Q69P + K70P + N82T + N97E + S109D + T115Y + K120A + A126D + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 40320 | 90% Model A2 | 12.94 |
| A1D + F7G + V8A + T13I + S15Q + A20P + K26E + K36E + A45M + E46Y + E64P + Q69P + K70P + A101R + K120A + S141R + Y155H + P163A + T166P + T167P + Q168D + M172I + S176N + S178P + P182R + F190Y + K197F + Q214R + Q215E + Y219W + S239A + M248I + R253A + S258G + S271G + H276C + R280K + N283Y + F286C + E299W + G366N + K378Q + D385H + P398E + K408M + D410M + L413T + N473Y + D486E + K491R | 37° C. | 40320 | 90% Model A2 | 12.49 |
| A1Y + F7G + S15Q + I22V + K26E + K36E + E46Y + E64P + K70P + S103V + P121A + Q143R + I165E + T166P + Q168D + M172I + S178P + K197D + Q214R + S239A + M248I + S258G + S271G + R280K + N283Y + K378Q + D385A + K408M + D410M + L413T + G440Q | 37° C. | 2460 | 90% Model A2 | 1.39 |
| A1Y + F7G + S15Q + I22V + K26E + K36E + E46Y + T53K + E64P + K70P + S103V + P121A + Q143R + I165E + T166P + | 37° C. | 2460 | 90% Model A2 | 1.76 |

TABLE 15-continued

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q168D + M172I + S178P + K197D + Q214R + S239A + M248I + S258G + S271G + R280K + N283Y + K304Q + K378Q + D385A + K408M + D410M + L413T + G440Q | | | | |
| A1Y + F7G + S15Q + I22V + K26E + K36E + E46Y + T53K + E64P + K70P + S103V + P121A + Q143R + I165E + T166P + Q168D + M171Q + K179N + K197D + S239A + M248I + S258G + S271G + R280K + N283Y + K378Q + D385A + K408M + D410M + L413T + T438A | 37° C. | 2460 | 90% Model A2 | 1.46 |
| A1V + F7G + S15Q + I22V + K26E + K36E + E46Y + T53K + E64P + K70P + S103V + P121A + M130I + Q143R + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 1.63 |
| A1Y + F7G + S15Q + I22V + K26E + K36E + E46Y + T53K + E64P + K70P + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | 37° C. | 2640 | 90% Model A2 | 2.57 |
| T3G + F7G + T13I + S15Q + A20V + K26E + K36E + E46Y + E64P + K70P + S103V + S141R + P163A + T166P + Q168D + M172I + S178P + F190Y + K197N + Q214R + S239A + M248I + S258G + S271G + N283Y + E299W + K378Q + D385A + K408M + D410M + L413T + N473Y + K491R | 37° C. | 2520 | 90% Model A2 | 1.09 |
| T3E + F7G + T13I + S15Q + A20G + K26E + K36E + E46Y + E64P + K70P + S103V + S141R + P163A + T166P + Q168D + M172I + S178P + F190Y + K197N + Q214R + S239A + M248I + S258G + S271G + N283Y + E299W + K378Q + D385A + K408M + D410M + L413T + V422I + N473Y + K491R | 37° C. | 2520 | 90% Model A2 | 1.07 |

TABLE 16

Protease stability at pH 8. The protease is a variant of SEQ ID NO: 14 with the following modifications: Y161A + R164S + A188P added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S15Q + K26E + K36E + E46Y + E64P + K70P + S103V + P163A + T166P + Q168D + M188Y + K197D + M248I + S271G + N283Y + D385A + K408M + D410M + L413T | 37° C. | 1440 | 90% Model A + 6% LAS | 1.54 |

TABLE 16-continued

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Protease stability at pH 8. The protease is a variant of SEQ ID NO: 14 with the following modifications: Y161A + R164S + A188P added in 0.8% (w/w) concentration | | | | |
| S15Q + K26E + K36E + E46Y + E64P + K70P + S103V + P163A + T166P + Q168D + K197D + M248I + S271G + N283Y + Y358W + D385A + K408M + D410M + L413T | 37° C. | 1440 | 90% Model A + 6% LAS | 1.56 |

TABLE 17

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration | | | | |
| T3G + F7G + V8A + T13I + S15Q + A20P + K26E + E31Q + K36E + E46Y + E64P + Q69P + K70P + N82T + A101R + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 10.72 |
| T3G + F7G + V8A + T13I + S15Q + A20P + K26E + K36E + E46M + E64P + Q69P + K70P + N82T + A101R + S109D + T115I + K120A + K129L + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 10.12 |
| T3G + F7G + V8A + T13I + S15Q + A20P + K26E + K36E + E46M + E64P + Q69P + K70P + N82T + A101R + S109D + K120A + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 8.60 |
| T3G + F7G + V8A + T13I + S15Q + A20P + K26E + K36E + E46M + E64P + Q69P + K70P + N82T + A101R + S109D + K120A + S141R + Y155H + P163A + T166P + T167P + Q168D + M172I + S176N + S178P + P182R + F190Y + K197D + A210T + Q214R + | 37° C. | 2640 | 90% Model A2 | 7.51 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + S109D + K120A + S141R + R160I + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.99 |
| T3G + F7G + V8A + T13I + S15Q + A20P + K26E + K36E + E46M + E64P + Q69P + K70P + N82T + A101R + S109D + T115I + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 8.85 |
| T3G + F7G + V8A + T13I + S15Q + A20P + K26E + K36E + E46M + E64P + Q69P + K70P + N82T + A101R + S109D + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.76 |
| T3G + F7G + V8A + T13I + S15Q + A20P + K26E + K36E + E46M + E64P + Q69P + K70P + N82T + A101R + S109D + K120A + A126T + L134V + S141R + Y155H + P163A + T166P + T167P + Q168D + M172 + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.46 |
| T3G + F7G + V8A + T13I + S15Q + A20P + K26E + K36E + E46M + E64P + Q69P + K70P + N82A + A101R + G110R + K120A + S141R + Y155H + P163A + T166P + T167P + Q168D + M172I + S176N + S178P + P182R + F190Y + K197D + Q214R + Q215E + Y219W + S239A + M248I + R253A + | 37° C. | 2640 | 90% Model A2 | 8.69 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S258G + S271G + H276C + R280K + N283Y + F286C + E299W + G366N + K378Q + D385H + K408M + D410M + L413T + N473Y + D486E + K491R | | | | |
| T3G + F7G + V8A + T13I + S15Q + A20P + K26E + K36E + E46M + E64P + Q69P + K70P + N82T + A101R + K120A + S141R + Y155H + P163A + T166P + T167P + Q168D + M172I + S176N + S178P + P182R + F190Y + N193W + K197D + Q214R + Q215E + Y219W + S239A + M248I + R253A + S258G + S271G + N272D + H276C + R280K + N283Y + F286C + E299W + G366N + K378Q + D385H + K408M + D410M + L413T + N473Y + D486E + K491R | 37° C. | 2640 | 90% Model A2 | 8.76 |
| A1V + V4N + F7G + T13I + S15Q + A20P + K26E + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 8.89 |
| A1V + V4N + F7G + T13I + S15Q + A20P + K26E + K36E + E46M + E64P + Q69P + K70P + N82T + A101R + S109D + T115Y + K120A + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + L259V + S271G + H276C + R280K + N283Y + F286C + E299W + G366N + K378Q + D385H + K408M + D410M + L413T + N473Y + D486E + K491R | 37° C. | 2610 | 90% Model A2 | 9.88 |
| T3G + F7G + V9A + S15Q + A20G + A23I + K26E + K36E + E46M + E64P + Q69P + K70P + N82T + S103E + K120A + S141R + Q143R + V161T + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 2610 | 90% Model A2 | 8.02 |
| T3G + F7G + V9A + S15Q + A20G + A23I + K26E + K36E + E46M + E64P + Q69P + K70P + N82T + S103E + K120A + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + E379K + D385H + K408M + D410M + L413T + N473Y + K491R | 37° C. | 2610 | 90% Model A2 | 7.67 |
| T3G + F7G + V9A + S15Q + A20G + A23I + K26E + K36E + E46M + E64P + | 37° C. | 2610 | 90% Model A2 | 7.72 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| Q69P + K70P + N82T + S103E + K120P + S141R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | | | | |
| T3G + F7G + V9A + S15Q + A20G + A23I + K26E + K36E + E46M + E64P + Q69P + K70P + N82T + S103E + K120P + S141R + Q143R + P163A + T166P + T167P + Q168D + M172I + S176N + S178P + F190Y + K197D + Q214R + Q215E + Y219W + S239A + M248I + R253A + S258G + S271G + H276C + R280K + N283Y + F286C + E299W + K378Q + D385H + K408M + D410M + L413T + N473Y + K491R | 37° C. | 2610 | 90% Model A2 | 8.77 |
| T3G + F7G + V8A + T13I + S15Q + A20P + K26E + K36E + E46M + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 10.27 |
| T3G + F7G + P11A + T13I + S15Q + A20P + K26E + K36E + E46M + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 8.41 |
| T3G + F7G + V8A + T13I + S15Q + A20P + K26E + K36E + A45L + E46Y + E64P + Q69P + K70P + N82T + A101R + S109D + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 18.05 |
| T3G + F7G + V8A + T13I + S15Q + Q17K + A20G + K26E + K36E + A45L + E46Y + E64P + Q69P + K70P + N82T + A101R + S109D + K120A + A126T + L134I + S141R + Y155H + P163A + T166P + T167P + Q168D + M172I + P174K + S176N + S178P + P182R + F190Y + K197D + Q214R + Q215E + Y219W + S239A + M248I + R253A + | 37° C. | 2610 | 90% Model A2 | 10.57 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S258G + S271G + H276C + R280K + N283Y + F286C + E299W + G366N + K378Q + D385H + K408M + D410M + L413T + N473Y + D486E + K491R | | | | |
| T3G + F7G + P11A + T13I + S15Q + A20P + K26E + K36E + E46M + E64P + K65N + Q69P + K70P + N82T + A101R + S109E + K120A + A126T + L134I + S141R + Q143T + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 6.47 |
| T3G + F7G + P11A + T13I + S15Q + A20P + K26E + K36E + E46M + E64P + Q69P + K70P + N82A + A101R + G110D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 7.26 |
| T3G + F7G + P11A + T13I + S15Q + A20P + K26E + K36E + E46M + E64P + Q69P + K70P + N82T + G96D + A101R + S109D + K120A + A126T + L134I + N139I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 7.21 |
| T3G + F7G + P11A + T13I + S15Q + A20P + K26E + K36E + E46M + E64P + Q69P + K70P + N82T + A101R + S109D + K120A + A126T + L134I + N139I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 7.31 |
| T3G + F7G + P11A + T13I + S15Q + A20P + K26E + K36E + E46M + E64P + Q69P + K70P + N82T + P94M + A101R + S109D + K120A + A126T + L134I + S141R + Q143R + Y155H + P163A + T166P + T167P + Q168D + M172I + S176N + S178P + P182R + F190Y + | 37° C. | 2580 | 90% Model A2 | 8.09 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | | | | |
| T3G + F7G + P11A + T13I + S15Q + A20P + K26E + K36E + E46M + T53K + E64P + Q69P + K70P + N82T + A101R + S109D + K120A + A126T + L134I + N139I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 6.50 |
| T3G + F7G + P11A + T13I + S15Q + A20P + K26E + K36E + E46M + T53K + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 7.21 |
| T3G + F7G + P11A + T13I + S15Q + A20P + K26E + K36E + E46M + T53K + E64P + Q69P + K70P + N82T + A101R + S109D + K120A + A126T + L134I + N139I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 6.24 |
| T3G + F7G + P11A + T13I + S15Q + A20P + K26E + K36E + E46M + E64P + K65N + Q69P + K70P + N82T + A101R + S109E + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 8.40 |
| T3G + F7G + P11A + T13I + S15Q + A20P + K26E + K36E + E46M + E64P + Q69P + K70P + N82T + A101R + S109E + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + | 37° C. | 2610 | 90% Model A2 | 5.81 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| F286C + E299W + G366N + K378Q + D385H + K408M + D410M + L413T + N473Y + D486E + K491R | | | | |
| T3G + F7G + P11A + T13I + S15Q + A20P + K26E + K36E + E46M + E64P + Q69P + K70P + N82T + A101R + G110D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 8.48 |
| T3G + F7G + P11A + T13I + S15Q + A20P + K26E + K36E + E46M + E64P + Q69P + K70P + N82A + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 6.30 |
| T3G + F7G + V8A + T13I + S15Q + A20P + K26E + I30L + K36E + E46M + E64P + Q69P + K70P + N82T + A101R + S109D + T115V + K120A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2610 | 90% Model A2 | 7.80 |
| A1V + V4N + F7G + T13I + S15Q + A20P + K26E + I30L + K36E + E46M + T53K + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 10.47 |
| A1V + V4N + F7G + T13I + S15Q + K26E + I30L + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + | 37° C. | 2640 | 90% Model A2 | 9.91 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S258G + S271G + H276C + R280K + N283Y + F286C + E299W + G366N + K378Q + D385H + K408M + D410M + L413T + N473Y + D486E + K491R | | | | |
| A1V + V4N + F7G + T13I + S15Q + A20P + K26E + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + V422I + Q437I + N473Y + D486E + K491R | 37° C. | 2580 | 90% Model A2 | 9.88 |
| A1V + V4N + F7G + T13I + S15Q + A20P + K26E + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + H324N + G366N + K378Q + D385H + K408M + D410M + L413T + N473Y + D486E + K491R | 37° C. | 2580 | 90% Model A2 | 8.80 |
| A1V + V4N + F7G + T13I + S15Q + A20P + K26E + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253W + S258G + S271G + H276C + R280K + N283Y + F286C + E299W + G366N + K378Q + D385H + K408M + D410M + L413T + N473Y + D486E + K491R | 37° C. | 2580 | 90% Model A2 | 7.70 |
| A1V + V4N + F7G + T13I + S15Q + A20P + K26E + K36E + E46M + E64P + Q69P + K70P + N82T + G96E + A101R + S109D + T115Y + K120P + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + T438A + N473Y + D486E + K491R | 37° C. | 2580 | 90% Model A2 | 7.61 |
| T3G + F7G + P11A + T13I + S15Q + A20P + K26E + K36E + E46M + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + | 37° C. | 2610 | 90% Model A2 | 8.43 |

TABLE 17-continued

| Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| S271G + H276C + R280K + N283Y + F286C + E299W + E301K + G366N + K378Q + D385H + K408M + D410M + L413T + N473Y + D486E + K491R | | | | |
| T3G + F7G + P11A + T13I + S15Q + A20P + K26E + K36E + E46M + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + E301K + G366N + K378Q + D385H + K408M + D410M + L413T + F414T + N473Y + D486E + K491R | 37° C. | 2580 | 90% Model A2 | 9.29 |
| T3G + F7G + P11A + T13I + S15Q + A20P + K26E + K36E + E46M + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + L480I + D486E + K491R | 37° C. | 2610 | 90% Model A2 | 5.64 |
| T3G + F7G + P11A + T13I + S15Q + A20P + K26E + K36E + E46M + E64P + Q69P + K70P + N82T + A101R + S109D + K120A + A126T + L134I + S141R + Q143R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + K417G + N473Y + L480I + D486E + K491R | 37° C. | 2580 | 90% Model A2 | 7.79 |
| A1V + V4N + F7G + T13I + S15Q + A20P + K26E + K36E + E46M + E64P + Q69P + K70P + N82T + A101L + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 8.36 |
| A1V + V4N + F7G + T13I + S15Q + A20P + K26E + K36E + E46M + E64P + Q69P + K70P + N82T + A101L + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + | 37° C. | 2640 | 90% Model A2 | 8.57 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| N283Y + F286C + E299W + H324K + G366N + K378Q + D385H + K408M + D410M + L413T + N473Y + D486E + K491R | | | | |
| A1V + V4N + F7G + T13E + S15Q + A20P + K26E + K36E + E46M + T53P + E64P + Q69P + K70P + N82A + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.64 |
| A1V + V4N + F7G + T13I + S15Q + A20P + K26E + K36E + E46M + E64P + Q69P + K70P + N82T + N97E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 10.18 |
| A1V + V4N + F7G + T13I + S15Q + A20P + K26E + K36E + E46M + E64P + Q69P + K70P + N82T + N97E + A101R + S109D + T115Y + K120A + A126D + L134V + S141R + Q143T + Y155H + P163A + T166P + T167P + Q168D + M171I + M172I + S176N + S178P + P182R + F190Y + K197D + Q214R + Q215E + Y219W + S239A + M248I + E249H + S258G + S271G + H276C + R280K + N283Y + F286C + E299W + G366N + K378Q + D385H + K408M + D410M + L413T + N473Y + D486E + K491R | 37° C. | 2640 | 90% Model A2 | 10.10 |
| A1V + V4N + F7G + T13I + S15Q + A20P + K26E + K36E + E46M + E64P + Q69P + K70P + N82T + N97E + S109D + T115Y + K120A + A126D + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 9.77 |
| A1V + V4N + F7G + T13I + S15Q + A20P + K26E + K36E + E46M + E64P + Q69P + K70P + N82T + A101L + S109D + T115Y + K120A + K129L + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + | 37° C. | 2640 | 90% Model A2 | 8.66 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| N283Y + F286C + E299W + G366N + K378Q + D385H + K408M + D410M + L413T + N473Y + D486E + K491R | | | | |
| A1V + V4N + F7G + T13I + S15Q + A20P + K26E + K36E + E46M + E64P + Q69P + K70P + N82T + A101L + S109D + T115Y + K120A + K129L + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 6.71 |
| A1V + V4N + F7G + T13I + S15Q + A20P + K26E + D27N + K36E + E46M + E64P + Q69P + K70P + N82T + G96E + A101R + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 5.97 |
| A1V + V4N + F7G + T13I + S15Q + A20P + K26E + D27N + K36E + E46M + E64P + Q69P + K70P + N82T + G96E + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 5.39 |
| A1V + V4N + F7G + T13I + S15Q + A20P + K26E + D27N + K36E + E46M + E64P + Q69P + K70P + N82T + S109D + T115Y + K120A + L134V + S141R + Q143T + Y155H + P163A + T166P + T167P + Q168D + M171I + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.57 |
| T3G + F7G + P11A + T13I + S15Q + A20P + K26E + K36E + E46M + T53K + E64P + Q69P + K70P + N82T + A101R + S109D + K120A + A126T + L134I + N139I + S141R + Y155H + E162G + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + | 37° C. | 2580 | 90% Model A2 | 6.04 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| K378Q + D385H + K408M + D410M + L413T + N473Y + D486E + K491R | | | | |
| T3G + F7G + P11A + T13I + S15Q + A20P + K26E + K36E + E46M + T53K + E64P + Q69P + K70P + N82T + A101R + S109D + K120A + A126T + L134I + N139I + S141R + E162G + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 5.31 |
| T3G + F7G + P11A + T13I + S15Q + A20P + K26E + K36E + E46M + T53K + E64P + Q69P + K70P + N82T + A101R + S109D + K120A + A126T + L134I + N139I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + A423G + N473Y + E479R + D486E + K491R | 37° C. | 2580 | 90% Model A2 | 5.24 |
| A1V + T3E + F7G + P11A + T13I + S15Q + A20P + K26E + K36E + E46M + T53K + E64P + Q69P + K70P + N82T + N97E + A101R + S109D + K120A + A126T + L134I + N139I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 7.65 |
| A1V + T3E + F7G + P11A + T13I + S15Q + A20P + K26E + K36E + E46M + T53K + E64P + Q69P + K70P + N82T + A101R + S109D + K120A + A126T + L134I + N139I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 6.13 |
| T3G + F7G + V8A + T13I + S15Q + A20P + K26E + K36E + A45M + E46Y + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + | 37° C. | 2580 | 90% Model A2 | 15.73 |

TABLE 17-continued

Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration

| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
|---|---|---|---|---|
| S239A + M248I + R253A + S258G + S271G + H276C + R280K + N283Y + F286C + E299W + E363H + G366N + K378Q + D385H + K408M + D410M + L413T + N473Y + D486E + K491R | | | | |
| T3G + F7G + V8A + T13I + S15Q + Q17K + A20G + K26E + K36E + E46M + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 6.50 |
| T3G + F7G + V8A + T13I + S15Q + Q17K + A20G + K26E + K36E + E46M + T53P + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 5.39 |
| T3G + F7G + V8A + T13I + S15Q + Q17K + A20G + K26E + K36E + E46M + E61D + E64P + K65N + Q69P + K70P + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2640 | 90% Model A2 | 6.82 |
| T3G + F7G + V8A + T13I + S15Q + A20P + K26E + K36E + E46M + E64P + K65N + Q69P + K70P + N82A + A101R + S109E + K120A + A126T + N139A + S141R + Y155H + P163A + T166P + T167P + Q168D + M172I + S176N + S178P + P182R + F190Y + K197D + Q214R + Q215E + Y219W + S239A + M248I + R253A + S258G + S271G + H276C + R280K + N283Y + F286C + E299W + G366N + K378Q + D385H + K408M + D410M + L413T + N473Y + D486E + K491R | 37° C. | 2580 | 90% Model A2 | 6.43 |
| T3G + F7G + V8A + T13I + S15Q + A20P + K26E + K36E + E46M + E64P + K65N + Q69P + K70P + Q76T + N82A + A101R + S109E + K120A + A126T + L134I + S141R + Y155H + P163A + T166P + T167P + Q168D + M172I + S176N + S178P + P182R + F190Y + K197D + Q214R + Q215E + Y219W + | 37° C. | 2580 | 90% Model A2 | 6.67 |

TABLE 17-continued

| Protease stability at pH 8. The protease is a variant of SEQ ID NO: 14 with the following modifications: S9E + N43R + N76D + V205I + Q206L + Y209W + S259D + N261W + L262E added in 0.8% (w/w) concentration | | | | |
|---|---|---|---|---|
| Mutations in SEQ ID NO: 1 | Incubation Temp | Incubation Time (min) | Detergent in stress | IF over WT (SEQ ID NO: 1 + T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y) |
| S239A + M248I + R253A + S258G + S271G + H276C + R280K + N283Y + F286C + E299W + G366N + K378Q + D385H + K408M + D410M + L413T + N473Y + D486E + K491R | | | | |

Example 8: Wash Performance of Mannanase Variants Using Terg-O-Tometer Washing Trial Variants were evaluated for wash performance using the TOM washing trial method as described above, with any adjustments as noted below. Wash trials are conducted with GH26 mannanase variants alone, compared to and/or in combination with a GH5 mannanase (SEQ ID NO: 38 having mutations A3T, Y93Q, S95D, +118K, A136P, D139R, N200T, S202R, R21G, W260F, N283H, L288I, L294P, S295V).

Total enzyme performance was calculated as the average of individual Delta REM and is shown in Table 18 below.

TABLE 18

| TOM wash Assay results | | | | | | | |
|---|---|---|---|---|---|---|---|
| Sample | Dose (ppm) | Detergent | Detergent conc. (g/L) | Temp (° C.) | Time (min) | Stains | Sum of Delta REM |
| Blank | 0 | Model A | 3.33 | 20 | 20 | CS-43, CS-73, DN-33 & DN-34 | 0.0 |
| GH5 mannanase | 0.02 | | | | | | 10.0 |
| SEQ ID NO: 1 having mutations K26E + K36E + E64P + K70P + S103V + Q168D + K197D + N283Y + D385A + L413T | 0.02 | | | | | | 15.6 |
| GH5 mannanase + SEQ ID NO: 1 having mutations K26E + K36E + E64P + K70P + S103V + Q168D + K197D + N283Y + D385A + L413T | 0.02 | | | | | | 20.7 |
| Blank | | Model A | 3.33 | 20 | 20 | CS-43, CS-73, DN-33, DN-34, CS-05S, CS-06, CS-68, CS-69 CS-70, CS-71 & CS-72 | 0.0 |
| GH5 mannanase | 0.02 | | | | | | 30.0 |
| SEQ ID NO: 1 having mutations S15Q + K26E + K36E + E46Y + E64P + K70P + S103V + P163A + T166P + Q168D + M172I + K197D + M248I + S258G + S271G + N283Y + D385A + K408M + D410M + L413T | 0.02 | | | | | | 67.2 |
| SEQ ID NO: 1 having mutations S15Q + K26E + K36E + E46Y + K65N + K70P + S103V + P163A + T166P + Q168D + M172I + S178P + K197D + S239A + M248I + S258G + S271G + N283Y + K378Q + D385A + K408M + D410M + L413T | 0.02 | | | | | | 55.7 |
| GH5 mannanase + SEQ ID NO: 1 having mutations S15Q + K26E + K36E + E46Y + E64P + K70P + S103V + P163A + | 0.02 | | | | | | 74.0 |

TABLE 18-continued

| TOM wash Assay results | | | | | | | |
|---|---|---|---|---|---|---|---|
| Sample | Dose (ppm) | Detergent | Detergent conc. (g/L) | Temp (° C.) | Time (min) | Stains | Sum of Delta REM |
| T166P + Q168D + M172I + K197D + M248I + S258G + S271G + N283Y + D385A + K408M + D410M + L413T | | | | | | | |
| GH5 mannanase + SEQ ID NO: 1 having mutations S15Q + K26E + K36E + E46Y + K65N + K70P + S103V + P163A + T166P + Q168D + M172I + S178 + K197D + S239A + M248I + 258G + S271G + N283Y + K378Q + D385A + K408M + D410M + L413T | 0.02 | | | | | | 57.2 |
| Blank | | Model A | 3.33 | 20 | 20 | CS-43, CS-73, DN-33, DN-34, CS-05S, CS-06 & CS-68 | 0.0 |
| GH5 mannanase | 0.02 | | | | | | 35.1 |
| SEQ ID NO: 1 having mutations T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y | 0.02 | | | | | | 57.4 |
| Blank | | Model A2 | 3.33 | 20 | 20 | CS-43, CS-73, DN-33, DN-34, CS-05S, CS-06 & CS-68 | 0.0 |
| GH5 mannanase | 0.02 | | | | | | 35.3 |
| SEQ ID NO: 1 having mutations T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y | 0.02 | | | | | | 54.1 |
| Blank | | Model J | 0.79 | 30 | 20 | CS-43, CS-73, DN-33, DN-34, CS-05S, CS-06, CS-68 & CS-69 | 0 |
| GH5 mannanase | 0.02 | | | | | | 32.2 |
| SEQ ID NO: 1 having mutations T3E + F7G + S15Q + K26E + K36E + E46Y + E64P + K70P + S103V + P163A + T166P + Q168D + M172I + S178P + F190Y + K197D + Q214R + S239A + M248I + S258G + S271G + N283Y + E299W + K378Q + D385A + K408M + D410M + L413T + N473Y | 0.02 | | | | | | 54.0 |
| Blank | | Model A2 | 3.33 | 20 | 20 | CS-43, CS-73, DN-33, DN-34, CS-05S, CS-06, CS-68 & CS-69 | 0 |
| GH5 mannanase | 0.02 | | | | | | 28.6 |
| SEQ ID NO: 1 having mutations A1Y + F7G + S15Q + I22V + | 0.02 | | | | | | 38.0 |

TABLE 18-continued

| TOM wash Assay results | | | | | | | |
|---|---|---|---|---|---|---|---|
| Sample | Dose (ppm) | Detergent | Detergent conc. (g/L) | Temp (° C.) | Time (min) | Stains | Sum of Delta REM |
| K26E + K36E + E46Y + T53K + E64P + K70P + S103V + P121A + Q143R + I165E + T166P + Q168D + M172I + S178P + K197D + Q214R + S239A + M248I + S258G + S271G + R280K + N283Y + K304Q + K378Q + D385A + K408M + D410M + L413T + G440Q | | | | | | | |
| SEQ ID NO: 1 having mutations A1V + F7G + S15Q + I22V + K26E + K36E + E46Y + T53K + E64P + K70P + S103V + P121A + M130I + Q143R + I165E + T166P + Q168D + M171Q + K179N + K197D + S239A + M248I + S258G + S271G + R280K + N283Y + K378Q + D385A + K408M + D410M + L413T + T438A | 0.02 | | | | | | 47.4 |
| SEQ ID NO: 1 having mutations A1Y + F7G + S15Q + I22V + K26E + K36E + E46Y + T53K + E64P + K70P + S103V + P121A + Q143R + E162D + I165E + T166P + Q168D + M171Q + K179N + K197D + S239A + M248I + S258G + S271G + R280K + N283Y + K378Q + D385A + K408M + D410M + L413T + T438A | 0.02 | | | | | | 58.7 |
| Blank | | Model A2 | 3.33 | 20 | 20 | CS-43, CS-73, DN-33, DN-34, CS-05S, CS-06, CS-68 & CS-69 | |
| GH5 mannanase | 0.02 | | | | | | 28.9 |
| SEQ ID NO: 1 having mutations A1Y + F7G + S15Q + I22V + K26E + K36E + E46Y + E64P + K70P + S103V + P121A + Q143R + I165E + T166P + Q168D + M172I + S178P + K197D + Q214R + S239A + M248I + S258G + S271G + R280K + N283Y + K378Q + D385A + K408M + D410M + L413T + G440Q | 0.02 | | | | | | 46.2 |
| SEQ ID NO: 1 having mutations A1Y + F7G + S15Q + I22V + K26E + K36E + E46Y + T53K + E64P + K70P + S103V + P121A + Q143R + I165E + T166P Q168D + M171Q + K179N + K197D + S239A + M248I + S258G + S271G + R280K + N283Y + K378Q D385A + K408M + D410M + L413T + G440Q | 0.02 | | | | | | 43.9 |
| SEQ ID NO: 1 having mutations A1Y + F7G + S15Q + I22V + K26E + K36E + E46Y + T53K + E64P + K70P + S103V + P121A + Q143R + I165E + T166P + Q168D + M171Q + K179N + K197D + S239A + M2481 + S258G + S271G + R280K + N283Y + K378Q + D385A + K408M + D410M + L413T + T438A | 0.02 | | | | | | 41.0 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A variant of a parent mannanase, which comprises (a) a substitution with A, R, D, N, C, E, G, H, I, L, K, M, F, P, S, T or W or a deletion of Q, at the position corresponding to position 168 of SEQ ID NO: 1; and (b) a second substitution or a second deletion at one or more positions corresponding to positions selected from the group consisting of 1, 2, 3, 4, 5, 6, 7, 8, 9, 10, 11, 12, 13, 14, 15, 17, 18, 19, 20, 21, 22, 23, 25, 26, 30, 35, 36, 37, 38, 42, 45, 46, 48, 49, 53, 57, 61, 63, 64, 65, 68, 69, 70, 72, 74, 76, 78, 82, 83, 86, 89, 94, 96, 97, 100, 101, 103, 105, 109, 110, 111, 112, 115, 117, 118, 120, 121, 122, 123, 126, 129, 130, 134, 137, 139, 141, 142, 143, 148, 155, 160, 161, 162, 163, 164, 165, 166, 167, 169, 170, 171, 172, 174, 176, 178, 179, 181, 182, 183, 184, 185, 188, 189, 190, 192, 193, 195, 197, 198, 210, 213, 214, 215, 217, 218, 219, 228, 235, 239, 242, 248, 249, 252, 253, 254, 258, 259, 260, 267, 270, 271, 272, 276, 280, 283, 286, 296, 299, 301, 304, 312, 315, 321, 322, 323, 324, 342, 344, 347, 351, 352, 354, 355, 358, 363, 366, 368, 377, 378, 379, 380, 385, 391, 398, 403, 408, 410, 413, 414, 417, 419, 422, 423, 437, 438, 440, 442, 443, 452, 454, 462, 463, 466, 467, 470, 472, 473, 477, 479, 480, 482, 483, 484, 486, 487, 488, 489, 490, and 491 of SEQ ID NO: 1;

wherein the variant has mannanase activity and has at least 85% sequence identity to the amino acid sequence of SEQ ID NO: 1.

2. The variant of claim 1, which comprises the substitution with A, R, D, N, C, E, G, H, I, L, K, M, F, P, S, T or W at the position corresponding to position 168 of SEQ ID NO: 1.

3. The variant of claim 2, which has at least 90% sequence identity to the amino acid sequence of SEQ ID NO: 1.

4. The variant of claim 2, which has at least 95% sequence identity to the amino acid sequence of SEQ ID NO: 1.

5. The variant of claim 2, wherein the substitution at the position corresponding to position 168 is 168D, 168F, 168M, or 168P.

6. The variant of claim 5, wherein the substitution at the position corresponding to position 168 is Q168D, Q168F, Q168M, or Q168P.

7. The variant of claim 3, wherein the substitution at the position corresponding to position 168 is 168D, 168F, 168M, or 168P.

8. The variant of claim 7, wherein the substitution at the position corresponding to position 168 is Q168D, Q168F, Q168M, or Q168P.

9. The variant of claim 4, wherein the substitution at the position corresponding to position 168 is 168D, 168F, 168M, or 168P.

10. The variant of claim 9, wherein the substitution at the position corresponding to position 168 is Q168D, Q168F, Q168M, or Q168P.

11. The variant of claim 2, wherein the second substitution or second deletion is at one or more positions corresponding to positions selected from the group consisting of 7, 13, 15, 20, 26, 36, 46, 64, 69, 70, 82, 101, 103, 109, 120, 141, 155, 162, 163, 166, 167, 172, 176, 178, 182, 190, 197, 214, 215, 219, 239, 248, 253, 258, 271, 276, 280, 283, 286, 299, 366, 378, 385, 408, 410, 413, 473, 486 and 491 of SEQ ID NO: 1.

12. The variant of claim 11, wherein the second substitution is a substitution at the position corresponding to position 26 of SEQ ID NO: 1.

13. The variant of claim 11, wherein the second substitution or second deletion is selected from the group consisting of:

T13I, T13M, T13N, T13W, T13Y, or T13E:
S15K, S15C, S15D, S15M, S15Q, or S15T;
A20S, A20P, A20T, A20G, or A20V;
K26D, K26E, or K26H;
K36A, K36C, K36D, K36E, K36M, or K36T;
E46I, E46F, E46M, or E46Y;
E64P;
Q69P, Q69R, Q69S, or Q69T;
K70A, K70E, K70I, K70M, K70P, or K70T;
N82T or N82A;

A101R, A101C, A101E, A101I, A101L, A101N, A101Q, or A101V;
S109E or S109D;
K120S, K120A, K120G, K120I, or K120P;
S141R, S141I, S141Q, or S141A;
Y155H;
E162D, E162G, or E162Q;
P163*, P163T, P163A, P163E, or P163N;
T166E, T166G, T166I, T166L, T166N, T166P, T166Q, T166R, T166V, or T166W;
T167P, T167A, T167R, or T167K;
M172I;
S176N;
S178R, S178E, S178H, S178P, or S178T;
P182R or P182E;
F190Y;
K197A, K197D, K197F, K197M, K197N, or K197Y;
Q214R or Q214W;
Q215E;
Y219W:
S239A;
M248I;
R253A or R253W;
S258G;
S271G or S271Y;
H276C, H276N, or H276Y;
R280L or R280K;
N283M or N283Y;
F286C;
E299K, E299D, or E299W;
G366N;
K378D, K378H, K378Q, or K378R;
D385A, D385F, D385H, D385P, or D385S;
K408A, K408C, K408D, K408E, K408M, K408Q, K408S, K408T, or K408V;
D410L or D410M;
L413Q, L413A, L413T, or L413V;
N473Y;
D486E, or D486K;
K491E, K491P, or K491R; and
combinations thereof.

14. The variant of claim 1, wherein the second substitution or second substitution is selected from the group consisting of:
A1*, A1S, A1T, A1V, A1G, A1D, A1I, or A1Y;
I2*;
T3*, T3A, T3E, or T3G;
V4*, V4N, V4D, V4G, V4M, or V4Y;
P5*;
G6* or G6P;
V8*, V8A, V8Q, V8F, V8D, or V8W;
V9*, V9D, V9A, V9G, V9M, or V9P;
E10*, E10Y, or E10G;
P11A, P11L, P11E, P11I, or P11N;
H12A, H12D, H12E, H12G, H12L, H12P, H12Q, H12R, or H12V;
S14Q, S14R, S14E, S14H, S14N, or S14V;
Q17K or Q17A;
N18S;
Q19N;
I21L;
I22V, I22Q, or I22T;
A23I, A23T, A23V A23M, or A23S;
F25W or F25Y;
I35*;
K37V;
R38C, R38F, R38L, R38M, or R38T;
T42E;
A45L, A45M, or A45R;
D48A, D48P, or D48S;
L49M;
T53C, T53E, T53H, T53K, T53P, or T53Q;
S57P or S57R;
E61D;
D63C;
E64P;
K65C, K65F, K65H, K65N, K65Q, K65S, or K65T;
V68M or V68T;
S72F;
T74A, T74Q, or T74E;
Q76T or Q76E;
G83E or G83S;
E86D;
L89F;
P94M;
G96E, G96D, or G96R;
N97E, N97D, or N97Y;
K100R;
S103R, S103A, S103C, S103D, S103E, S103I, S103L, S103N, S103Q, S103V, or S103Y;
Q105V;
G110R, G110D, G110P, G110C, or G110S;
A111L;
G112E or G112V;
T115W, T115Y, T115V, or T115I;
S117P;
A118V;
P121A;
G122P;
T123R;
A126D, A126S, or A126T;
K129R, K129L, or K129M;
M130I or M130V;
L134I, L134V, L134P, or L134T;
S137A, S137D, or S137W;
N139I, N139K, or N139A;
Q143T, Q143S, or Q143R;
Y155H;
R160I, R160F, R160K, R160L, R160N, or R160V;
V161S or V161T;
R164* or R164Q;
I165E, I165D, I165T, or I165L;
K169P, K169Q, K169T, or K169V;
T170E or T170H;
M171E, M171N, M171I, M171K, or M171Q;
M172I;
P174K;
S176N;
K179S, K179H, K179Q, K179N, or K179R;
S181T;
Q183E;
A184T;
K185N or K185Q;
M188F, M188I, or M188Y;
K189S;
F190Y;
T192A or T192V;
N193W or N193S;
Y195H;
A210E, A210Q, A210F, A210T, or A210S;
Y213K, Y213Q, or Y213R;
Q214R or Q214W;
Q215E;
G217Q;

K218R;
Y219W;
M228I;
V235L;
S239A;
N242T;
M248I;
E249H, E249L, or E249Q;
K252G or K252E;
R253A or R253W;
G254S;
L259V;
S260C;
K267L;
G270C;
N272D;
E285D;
F286C;
N296A;
E301K;
K304A, K304F, K304Q, K304R, or K304S;
A312V;
T315A or T315V;
Q321K or Q321W;
E322R, E322A, or E322D;
H323A;
H324N;
W342G;
A344C;
P347D;
K351V;
K352Q;
Y354W;
R355Q;
Y358W;
E363H;
K364D, K364R, or K364Y;
G366N;
N368D;
V377E;
E379K or E379P;
E380T or E380D;
V391L;
P398F or P398E;
S403Q or S403R;
F414T, F414S, or F414P;
K417G, K417E, or K417Q;
K419V;
V422R or V422I;
A423G;
Q4371 or Q437A;
T438A;
G440Q;
H442N;
W443G;
D452N;
L454I;
K462A, K462R, K462L, or K462P;
E463Q;
K466F, K466H, K466N, or K466Q;
K467H or K467Y;
N470Y;
D472G or D472Y;
N473Y;
L477F;
E479R;
L480I;
K482A, K482P, K482D, K482G, K482Q, or K482R;
G483A, G483D, or L484Q;
S487R;
P488I or P488L;
R489F, R489K, R489N, or R489P;
W490A;
K491E, K491P, or 491R, and combinations thereof.

15. A detergent composition comprising the variant of claim 1 and at least one detergent component.

16. A method of cleaning a textile or surface, comprising contacting a variant of claim 1 with the textile or surface to be cleaned.

17. The method of claim 16, wherein the method of cleaning comprises laundering, washing, cleaning and/or deep cleaning.

* * * * *